US010386373B2

(12) United States Patent
Daugherty et al.

(10) Patent No.: US 10,386,373 B2
(45) Date of Patent: Aug. 20, 2019

(54) METHODS AND COMPOSITIONS FOR ASSESSING ANTIBODY SPECIFICITIES

(71) Applicant: SERIMMUNE INC., Goleta, CA (US)

(72) Inventors: Patrick Sean Daugherty, Goleta, CA (US); Kathryn Vinaya Louise Kamath, Santa Barbara, CA (US); Jack Ryan Reifert, Santa Barbara, CA (US)

(73) Assignee: Serimmune Inc., Goleta, CA (US)

( * ) Notice: Subject to any disclaimer, the term of this patent is extended or adjusted under 35 U.S.C. 154(b) by 0 days.

(21) Appl. No.: 15/991,982

(22) Filed: May 29, 2018

(65) Prior Publication Data

US 2018/0267056 A1    Sep. 20, 2018

Related U.S. Application Data

(63) Continuation of application No. 15/775,363, filed as application No. PCT/US2016/061929 on Nov. 14, 2016.

(60) Provisional application No. 62/339,644, filed on May 20, 2016, provisional application No. 62/253,926, filed on Nov. 11, 2015.

(51) Int. Cl.
| | |
|---|---|
| *C12N 9/10* | (2006.01) |
| *G01N 33/68* | (2006.01) |
| *A61K 38/00* | (2006.01) |
| *C12Q 1/689* | (2018.01) |
| *G01N 33/558* | (2006.01) |
| *C07K 14/195* | (2006.01) |
| *C07K 14/315* | (2006.01) |
| *C07K 14/285* | (2006.01) |
| *C07K 14/435* | (2006.01) |
| *C07K 14/44* | (2006.01) |
| *C07K 14/45* | (2006.01) |
| *C12N 15/10* | (2006.01) |

(52) U.S. Cl.
CPC ....... *G01N 33/6854* (2013.01); *C07K 14/195* (2013.01); *C07K 14/285* (2013.01); *C07K 14/315* (2013.01); *C07K 14/43554* (2013.01); *C07K 14/44* (2013.01); *C07K 14/45* (2013.01); *G01N 33/6842* (2013.01); *C12N 15/1037* (2013.01); *C12Q 1/689* (2013.01); *G01N 2800/26* (2013.01); *Y02A 50/57* (2018.01)

(58) Field of Classification Search
CPC .... C12N 15/1037; A61K 38/00; C12Q 1/689; G01N 33/558
See application file for complete search history.

(56) References Cited

U.S. PATENT DOCUMENTS

| | | |
|---|---|---|
| 3,970,518 A | 7/1976 | Giaever |
| 4,230,685 A | 10/1980 | Senyei et al. |
| 4,554,088 A | 11/1985 | Whitehead et al. |
| 5,348,867 A | 9/1994 | Georgiou et al. |
| 6,274,345 B1 | 8/2001 | Lee et al. |
| 6,441,140 B1 | 8/2002 | Comb et al. |
| 6,623,982 B1 | 9/2003 | Liberti et al. |
| 6,686,164 B1 | 2/2004 | Olsen et al. |
| 7,129,060 B1 | 10/2006 | Maurer et al. |
| 7,198,896 B2 | 4/2007 | Rush et al. |
| 7,256,038 B2 | 8/2007 | Daugherty et al. |
| 7,587,281 B2 | 9/2009 | Gershoni et al. |
| 7,612,019 B2 | 11/2009 | Daugherty et al. |
| 7,657,378 B1 | 2/2010 | Brahmachari et al. |
| 7,666,817 B2 | 2/2010 | Daugherty et al. |
| 7,863,004 B2 | 1/2011 | Tainsky et al. |
| 8,293,685 B2 | 10/2012 | Daugherty et al. |
| 8,361,933 B2 | 1/2013 | Daugherty et al. |
| 8,513,390 B2 | 8/2013 | Stagliano et al. |
| 8,841,104 B2 | 9/2014 | Dryga et al. |
| 9,121,828 B2 | 9/2015 | Daugherty et al. |
| 9,234,847 B2 | 1/2016 | Daugherty et al. |
| 9,309,510 B2 | 4/2016 | La Porte et al. |
| 9,428,547 B2 | 8/2016 | Dryga et al. |
| 9,562,896 B2 | 2/2017 | Esch et al. |
| 9,632,078 B2 | 4/2017 | Reidt et al. |
| 9,670,485 B2 | 6/2017 | Bustamante et al. |
| 9,671,395 B2 | 6/2017 | Dryga et al. |
| 9,672,324 B1 | 6/2017 | Kasak et al. |
| 9,770,504 B2 | 9/2017 | Vitetta |
| 2002/0098503 A1 | 7/2002 | Kamb |
| 2004/0014028 A1 | 1/2004 | Lopez et al. |
| 2004/0048243 A1 | 3/2004 | Arap et al. |
| 2005/0255464 A1 | 11/2005 | Hagen et al. |
| 2007/0003954 A1 | 1/2007 | Kodadek |
| 2007/0207976 A1 | 9/2007 | Doucette Stamm et al. |
| 2010/0184620 A1 | 7/2010 | Rychlewski et al. |
| 2011/0262989 A1 | 10/2011 | Clarizia et al. |
| 2014/0087963 A1 | 3/2014 | Johnston et al. |
| 2015/0153354 A1 | 6/2015 | Trost et al. |
| 2016/0131662 A1 | 5/2016 | Kodadek |
| 2016/0349248 A1 | 12/2016 | Dryga et al. |
| 2016/0370380 A1 | 12/2016 | Mandecki et al. |
| 2017/0131276 A1 | 5/2017 | Johnston |
| 2017/0145406 A1 | 5/2017 | Esch et al. |
| 2017/0153247 A1 | 6/2017 | Chen |
| 2017/0233832 A1 | 8/2017 | Jain et al. |

FOREIGN PATENT DOCUMENTS

| | | |
|---|---|---|
| WO | WO 2016/083874 A1 | 6/2016 |
| WO | WO 2017/145128 A1 | 8/2017 |

OTHER PUBLICATIONS

Bowie et al. (Science, 1990, 257:1306-1310) (Year: 1990).*
Amstutz, P., et al., In vitro display technologies: novel developments and applicat+Al:A47ions. Curr Opin Biotechnol, 2001. 12(4): p. 400-5.

(Continued)

*Primary Examiner* — Misook Yu
*Assistant Examiner* — Lakia J Jackson-Tongue
(74) *Attorney, Agent, or Firm* — Goodwin Procter LLP

(57) ABSTRACT

The present invention provides compositions and methods that can be used to determine a peptide signature for an antibody repertoire in a sample comprising multiple antibodies. The method can be used to characterize a phenotype in a sample, such as providing a diagnosis, prognosis or theranosis of a medical condition.

28 Claims, 26 Drawing Sheets

Specification includes a Sequence Listing.

(56) References Cited

OTHER PUBLICATIONS

Anderson, K.S., et al., Protein microarray signature of autoantibody biomarkers for the early detection of breast cancer. J Proteome Res, 2011. 10(1): p. 85-96.
Andreatta, M., O. Lund, and M. Nielsen, Simultaneous alignment and clustering of peptide data using a Gibbs sampling approach. Bioinformatics, 2013. 29(1): p. 8-14.
Bailey, T.L. and C. Elkan, Fitting a mixture model by expectation maximization to discover motifs in biopolymers. Proc Int Conf Intell Syst Mol Biol, 1994. 2: p. 28-36.
Bailey, T.L. and C. Elkan, The value of prior knowledge in discovering motifs with MEME. Proc Int Conf Intell Syst Mol Biol, 1995. 3: p. 21-9.
Ballew, J.T., et al., Antibody biomarker discovery through in vitro directed evolution of consensus recognition epitopes. Proc Natl Acad Sci US A, 2013. 110(48): p. 19330-5.
Carmona, S.J., et al., Towards high-throughput immunomics for infectious diseases: use of next-generation peptide microarrays for rapid discovery and mapping of antigenic determinants. Mol Cell Proteomics, 2015, pp. 1871-1884.
Cima-Cabal et al., "Immunodetection of Pneumolysin in Human Urine by ELISA," Journal of Microbiological Methods, Feb. 27, 2003, vol. 54, Iss. 1, pp. 47-55.
Daugherty, P.S., Protein engineering with bacterial display. Curr Opin Struct Biol, 2007. 17(4): p. 474-80.
Fleisher G & Bolognese R (1983) Persistent Epstein-Barr virus infection and pregnancy. J Infect Dis 147(6):982-986.
Georgiou, G., et al., The promise and challenge of high-throughput sequencing of the antibody repertoire. Nat Biotechnol, 2014. 32(2): p. 158-68.
Getz, J.A., T.D. Schoep, and P.S. Daugherty, Peptide discovery using bacterial display and flow cytometry. 2012, Methods Enzymol. 503: p. 75-97.
Griffiths, P. and S. Lumley, Cytomegalovirus. Curr Opin Infect Dis, 2014. 27(6): p. 554-9.
Hadker, N., et al., Financial impact of a novel pre-eclampsia diagnostic test versus standard practice: a decision-analytic modeling analysis from a UK healthcare payer perspective. Dec. 7, 2010, J Med Econ. 13(4): p. 728-37.
Haeri S, Baker AM, & Boggess KA (2010) Prevalence of Epstein-Barr virus reactivation in pregnancy. Am J Perinatol 27(9):715-719.
Halenius, A. and H. Hengel, Human cytomegalovirus and autoimmune disease. Biomed Res Int, 2014. 2014: 15 pages.
Hall SS & Daugherty PS (2009) Quantitative specificity-based display library screening identifies determinants of antibody-epitope binding specificity. Protein Sci 18(9):1926-1934.
Herse, F., et al., Prevalence of agonistic autoantibodies against the angiotensin 11 type 1 receptor and soluble fins-like tyrosine kinase 1 in a gestational age-matched case study. Hypertension, 2009. 53(2): p. 393-8.
Icart J, Didier J, Dalens M, Chabanon G, & Boucays A (1981) Prospective study of Epstein Barr virus (EBV) infection during pregnancy. Biomedicine / [publiee pour l'A.A.I.C.I.G.] 34(3):160-163.
Kleinrouweler, C.E., et al., Accuracy of circulating placental growth factor, vascular endothelial growth factor, soluble fms-like tyrosine kinase 1 and soluble endoglin in the prediction of pre-eclampsia: a systematic review and meta-analysis. BJOG, 2012. 119(7): p. 778-87.
Lain, K.Y. and J.M. Roberts, Contemporary concepts of the pathogenesis and management of preeclampsia. JANIA, 2002. 287(24): p. 3183-6.
Larman, H.B., et al., PhIP-Seq characterization of autoantibodies from patients with multiple sclerosis, type 1 diabetes and rheumatoid arthritis. J Autoimmun, 2013. 43: p. 1-9.
Levine, R.J., et al., Circulating angiogenic factors and the risk of preeclampsia. N Engl J Med, 2004. 350(7): p. 672-83.

MacKay, AP., C.J. Berg, and H.K. Atrash, Pregnancy-related mortality from preeclampsia and eclampsia. Obstet Gynecol, 2001. 97(4): p. 533-8.
Masoura, S., et al., Biomarkers in pre-eclampsia: a novel approach to early detection of the disease. J Obstet Gynaecol, 2012. 32(7): p. 609-16.
Mintz PJ, et al. (2003) Fingerprinting the circulating repertoire of antibodies from cancer patients. Nat Biotechnol 21(1):57-63.
Ohkuchi, A., et al., Evaluation of a new and automated electrochemiluminescence immunoassay for plasma sFlt-1 and PlGF levels in women with preeclampsia. Hypertens Res. 2010. 33(5): p. 422-7.
Pantazes et al., "Identification of Disease-Specific Motifs in the Antibody Specificity Repertoire via Next-Generation Sequencing," Scientific Reports, Aug. 2, 2016, vol. 6, No. 30312, pp. 1-11.
Parrish, M.R., et al., The effect of immune factors, tumor necrosis factor-alpha, and agonistic autoantibodies to the angiotensin II type I receptor on soluble fma-like tyrosine-I and soluble endoglin production in response to hypertension during pregnancy. Aug. 2010. Am J Hypertens. 23(8): p. 911-6.
PCT International Search Report and Written Opinion, PCT Application No. PCT/US2016/061929, dated Apr. 6, 2017, 17 pages.
Plebani, Jvi., et al., Recent advances in diagnostic technologies for autoimmune diseases. Autoimmun Rev, 2009. 8(3): p. 238-43.
Rice, J.J. and P.S. Daugherty, Directed evolution of a biterminal bacterial display scaffold enhances the display of diverse peptides. Protein Eng Des Sel, 2008. 21(7): p. 435-42.
Roberts, J. M., Angiotensin-1 receptor autoantibodies: A role in the pathogenesis of preeclampsia? Circulation, 2000. 101(20): p. 2335-7.
Rossitto, G., et al., Elevation of Angiotensin-II Type-I-Receptor Autoantibodies Titer in Primary Aldosteronism as a Result of Aldosterone-Producing Adenoma. Hypertension, 2013. 61(2): p. 526-33.
Samadi, A.R., et al., Maternal hypertension and associated pregnancy complications among African-American and other women in the United States. Obstet Gynecol, 1996. 87(4): p. 557-63.
Schiettecatte, J., et al., Multicenter evaluation of the first automated Elecsys sFlt-1 and PlGF assays in normal pregnancies and preeclampsia. Clin Biochem. 2010. 43(9): p. 768-70.
Spatola, B.N., et al., Antibody Repertoire Profiling Using Bacterial Display Identifies Reactivity Signatures of Celiac Disease. Analytical Chemistry, 2012. 85(2): p. 1215-1222.
Wagner, L.K., Diagnosis and management of preeclampsia. Am Fam Physician, 2004. 70(12): p. 2317-24.
Wallis, A.B., et al., Secular trends in the rates of preeclampsia, eclampsia, and gestational hypertension, United States, 1987-2004. Am J Hypertens, 2008. 21(5): p. 521-6.
Wallukat, G., et al., Patients with preeclampsia develop agonistic autoantibodies against the angiotensin ATJ receptor. J Clin Invest, 1999. 103(7): p. 945-52.
Wallukat, G., et al., Spontaneously beating neonatal rat heart myocyte culture-a model to characterize angiotensin 11 at(I) receptor autoantibodies in patients with preeclampsia. In Vitro Cell Dev Biol Anim, 2002. 38(7): p. 376-7.
Walther, T., et al., Angiotensin 11 type 1 receptor agonistic antibodies reflect fundamental alterations in the uteroplacental vasculature. Hypertension, 2005. 46(6): p. 1275-9.
Wang, X., et al., Autoantibody signatures in prostate cancer. N Engl J Med, 2005. 353(12): p. 1224-35.
Xu, G.J., et al., Viral immunology. Comprehensive serological profiling of human populations using a synthetic human virome. Science, 2015. 348(6239): p. aaa0698. 23 pages.
Zhang et al., "A Method for De Novo Nucleic Acid Diagnostic Target Discovery," Bioinformatics, Aug. 7, 2014, vol. 30, No. 22, pp. 3174-3180.
Zhou, C.C., et al., Angiotensin receptor agonistic autoantibodies induce pre-eclampsia in pregnant mice. Nat Med, 2008. 14(8): p. 855-62.
Zhou, C.C., et al., Autoantibody from women with preeclampsia induces soluble Fms-like tyrosine kinase-1 production via angiotensin type 1 receptor and calcineurin/nuclear factor of activated T-cells signaling. Hypertension, 2008. 51(4): p. 1010-9.

\* cited by examiner

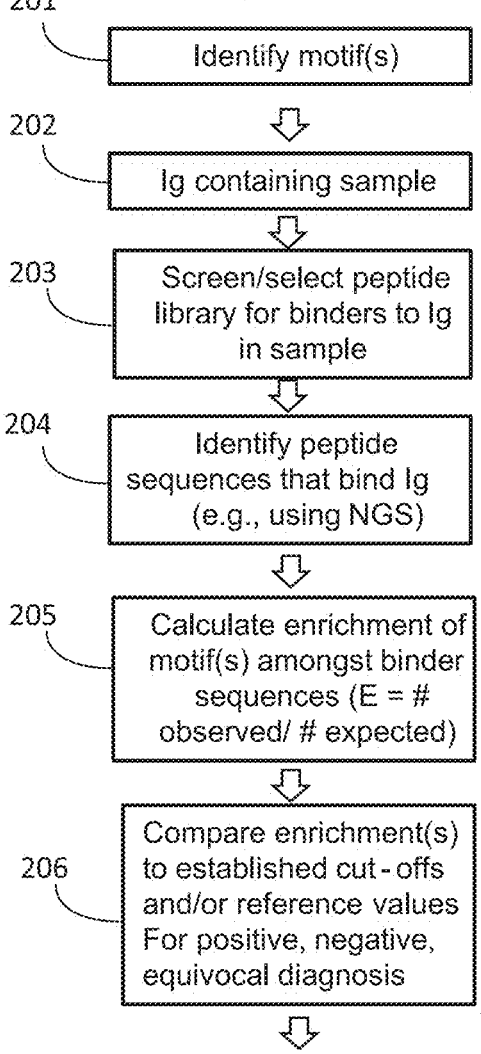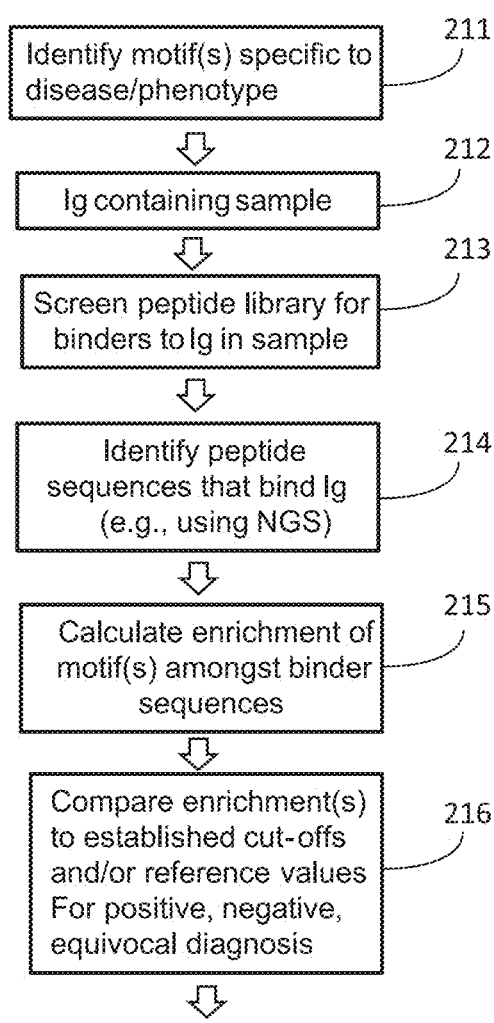

FIG 4B

"Patient epitope repertoire"
>1 Million unique peptides

Peptide Display- NGS

```
SARQPEFRGSLP (SEQ ID NO: 872)
VAGLGTVPEFAG (SEQ ID NO: 873)
LNAQVPEFNGAF (SEQ ID NO: 874)
VGLSLSGMGDLR (SEQ ID NO: 915)
DVLTYGARRPFW (SEQ ID NO: 916)
CSEVNGRRPFFG (SEQ ID NO: 917)
RLAGCDGGSRSA (SEQ ID NO: 918)
DFVGKPEYASLL (SEQ ID NO: 919)
NAWSLTGRRPFW (SEQ ID NO: 920)
GPARDHGRRPWF (SEQ ID NO: 921)
KPPVKPATRGSE (SEQ ID NO: 922)
SSGRRPFFGYQS (SEQ ID NO: 923)
...
KRTSSGGAGPLM (SEQ ID NO: 924)
GGPAITLAGMAD (SEQ ID NO: 925)
SGFLKPVEFYGS (SEQ ID NO: 876)
KTLFFAEDYTMN (SEQ ID NO: 926)
IDDNGGAGTRWW (SEQ ID NO: 927)
RREQQASTAGGA (SEQ ID NO: 928)
```

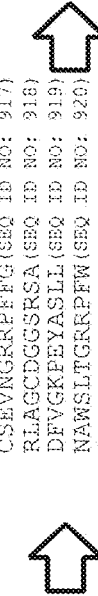

Dx Motif Panels

Lyme
```
[IVM]XLXGMXD    (SEQ ID NO: 895)
RGLXX[TVS][ED]  (SEQ ID NO: 896)
GEXEDK          (SEQ ID NO: 897)
ALXLXEXVI       (SEQ ID NO: 898)
...
[RK]NC]C[GA]    (SEQ ID NO: 899)
```

Babesia
```
KDRXXDE         (SEQ ID NO: 900)
TT[LV][MLF]XXXG (SEQ ID NO: 901)
DLDXXXLE        (SEQ ID NO: 902)
RXXXRCRGC       (SEQ ID NO: 903)
...
TEEDQ           (SEQ ID NO: 904)
```

Erlichia
```
MMHXXEHK        (SEQ ID NO: 905)
[LE]RITXXMXE    (SEQ ID NO: 906)
LAXXAXXXR       (SEQ ID NO: 907)
DESTK           (SEQ ID NO: 908)
...
F[FY]LXX[I]ER   (SEQ ID NO: 909)
```

Anaplasma
```
D[ED]QJRXT      (SEQ ID NO: 910)
E[LV][LVP]I     (SEQ ID NO: 911)
GGXGTXAG        (SEQ ID NO: 912)
RXXXRXXXITXE    (SEQ ID NO: 913)
...
[FY][LIV]GXXHG  (SEQ ID NO: 914)
```

Computational Processing

1. Calculate all motif enrichment values
2. Standardize enrichment values (i.e., z-scores)
3. Sum z-scores for each disease
4. Output sum of z-scores, Dx results

Dx Test Report

| Disease | Range | | Result |
|---|---|---|---|
| Lyme IgG | -6.3–10.9 | 45 | POS |
| Lyme IgM | -18–22 | 107 | POS |
| Babesia IgG | -8.8–16.7 | -1.6 | NEG |
| Erlichia IgG | -22–34 | 89 | POS |
| Anaplasma IgG | -10 – 18 | 54 | POS |
| ... | | | |
| Bartonella IgG | -9.3 – 14.2 | 1.2 | NEG |
| Francisella IgG | -11.7 – 19 | -2.4 | NEG |

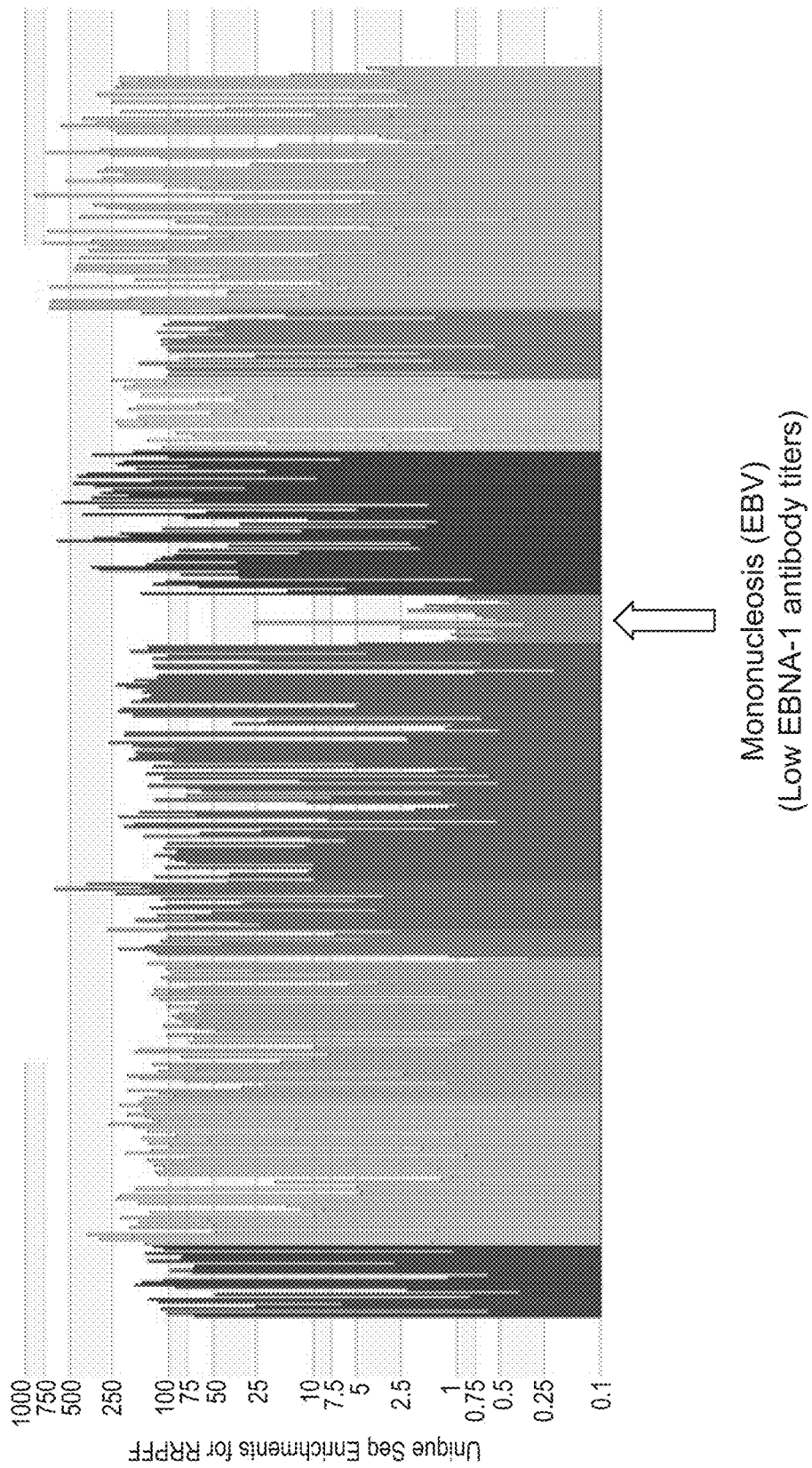

KPXFXGXK (SEQ ID NO: 929)

METHODS AND COMPOSITIONS FOR ASSESSING ANTIBODY SPECIFICITIES

CROSS REFERENCE TO RELATED APPLICATIONS

This application is a continuation of U.S. application Ser. No. 15/775,363, which is the National Stage of International Application No. PCT/US2016/061929, filed Nov. 14, 2016, which claims the benefit of U.S. Provisional Application Nos. 62/339,644, filed May 20, 2016, and 62/253,926, filed Nov. 11, 2015, each of which is herein incorporated in its entirety by reference.

SEQUENCE LISTING

The instant application contains a Sequence Listing which has been submitted via EFS-Web and is hereby incorporated by reference in its entirety. Said ASCII copy, created on Dec. 11, 2018, is named 40692US_CRF_sequencelisting.txt, and is 269,735 bytes in size.

FIELD OF INVENTION

In various embodiments, the invention relates to compositions and methods for diagnosing disease by detecting antibodies in a sample.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art Antibodies present in human specimens serve as the primary analyte and disease biomarker for a large and broad group of infectious, bacterial, viral, allergic, parasitic, and autoimmune diseases. As such, hundreds of distinct antibody detecting tests (collectively referred to as "immunoassays", have been developed to diagnose human disease using tissue samples that include but are not limited to whole blood, serum, plasma, saliva, urine, and tissue aspirates. Immunoassays remain essential to the diagnosis of autoimmune diseases including, but not limited to, Grave's disease, Sjogren's syndrome Celiac disease, Crohn's disease, Rheumatoid arthritis. Immunoassay are also widely used to diagnosis infectious diseases including for example viral infections (e.g. HIV, Hepatitis C, HSV-1, Zika virus, Epstein Barr virus, and others), bacterial infections include for example (*Streptococcus* sp., *Helicobacter pylori, Borrellia burdorferi* (Lyme), and others), fungal infections (e.g. Valley Fever), parasitic infections (e.g., *Trypanosoma cruzi, Toxoplasma gondii, Taenia solium, Toxocara canis*, and others). Furthermore, Immunoassays are often used to identify and monitor allergies (e.g. peanut allergy, milk, pollen, and others. Beyond these areas, immunoassays have demonstrated utility for the diagnosis of neurodegenerative disease, cardiovascular disease, and cancers.

Methods to detect antibodies include radio immunoassay (MA), enzyme linked immunosorbant assays (ELISA), chemiluminescent assays, and protein and peptide arrays. These assay formats share in common the requirement to develop a molecular chemical reagent that binds to the analyte antibody in a sample in the majority of individuals with disease, to provide sensitivity, but not to any of the many distinct antibodies present in individuals without disease, to provide diagnostic specificity. Such reagents include antibodies, peptides, human proteins, nucleic acid aptamers, and other molecular binding entities [1, 2] [3, 4]. Such reagents are often highly optimized (Ballew J et al., PNAS, 2014) in order to achieve high sensitivity and specificity. Such optimization has been the subject of much research and development. Individual reagents, however, often possess insufficient affinity and specificity for the analytes of interest.

Present method used to develop diagnostic immunoassays limit the overall sensitivity and specificity that can be obtained from the assay, and thus the utility, because they include extraneous antigen matter (i.e., large proteins, peptides, lipids, whole cell lysates) that can result in cross-reactive binding from unrelated antibodies. For example, Lyme disease (infection with *Borrelia burgdorferi*) tests use whole cell lysates that contain a large number of distinct molecular compositions that are not targeted by the immune response *Borrelia*, but capture or detect antibodies generated in response to other infections such as infectious mononucleosis. Thus there is an unmet need for diagnostic technologies that can identify and present only those antigen components that are most specifically recognized by the immune response in individuals with a given phenotype.

Because individual reagents often do not capture or react with a sufficient number of samples from individuals with the disease (i.e. insufficient sensitivity), two or more reagents can be combined into a diagnostic test or used in parallel as an antigen panel. Nevertheless, combining sets of peptides into a single assay to increase the sensitivity of diagnosis is challenging since their non-specific binding, that limits specificity, is generally additive thereby limiting the overall diagnostic specificity of the assay. Experimental identification of the optimal combination of biochemical reagents is difficult given the combinatorial complexity of combining and weighting the antibody reactivities to each antigen in a panel [5, 6].

An important limitation associated with existing immunoassay formats is that they cannot be readily combined or aggregated together. Consequently, performing a large number of tests is additive in terms of cost and labor, thereby decrease the probability of making a correct diagnosis. For example, if an individual is bit by a tick, they may be infected with multiple tick-borne pathogens (there are more than 10 known tick-transmitted infectious agents). In many cases, physicians will only a test for *Borrelia burgdorferi*, even though any of 10s of other organisms may have infected that individual. Thus, there is a need for low cost multiplexed test that can diagnosis any or all of the tick-borne infections. Similarly, if a patient presents with a common symptom (e.g. fever, fatigue, headache), it can be difficult to identify which tests should be ordered to identify potential causes of the presenting symptoms. Thus, there is a need for methods and compositions that can integrate many tests into a single standardized assay, and thus simultaneously test for many different diseases or infections. The present invention provides solution to this problem.

The use of massively parallel DNA sequencing, also known as next-generation sequencing (hereafter referred to as "NGS"), high throughput sequencing, or deep sequencing, has been applied to enable the diagnosis of human diseases [7]. These collective approaches may be referred to generally as "NGS" throughout.

The prospect of analyzing entire human antibody repertoires has been a goal for at least several decades. Reported methods include human proteome arrays, phage display/immunoprecipitation (Ph-IP), peptide and peptoid arrays, and NGS analysis of antibody genes (Ig-Seq) [9][8]. One challenge associated with repertoire characterization is identifying particular peptide sequences to populate arrays limited to ~$10^6$ fields. Hence, prior methods have used small arrays of random peptides, typically having fewer than 300,000 peptides, or peptoids unlikely to closely mimic antigens. Array based approaches are presently limited to small collections of organisms with small proteomes (e.g., viruses) [10]. For peptide arrays, their relatively low peptide sequence diversity limits their ability to find individual sequences and motifs that mimic the bona-fide antigen targeted by an antibody.

A principle advantage of the invention provided herein is that it is unbiased—that is, it does not assume which organisms are antigenic. The method claimed can identify epitopes in any organisms in the rapidly growing protein database, not just pre-specified viruses [10], allowing antigen identification within even the largest proteomes (e.g., wheat genome=17 GB). Thus, the wheat genome alone is 100-1000× larger than the combined genomes of all known human viruses.

SUMMARY

The following embodiments and aspects thereof are described and illustrated in conjunction with systems, compositions and methods which are meant to be exemplary and illustrative, not limiting in scope.

In an aspect, the invention provides a method of identifying a plurality of peptides, comprising: a) providing a biological sample comprising a plurality of antibodies; b) contacting the biological sample with a plurality of peptides; and c) identifying members of the plurality of peptides that form complex members of the plurality of antibodies.

The biological sample may comprise a bodily fluid. Antibodies may be found in any bodily fluid. In some embodiments of the invention, the bodily fluid comprises peripheral blood, plasma, serum lymphatic fluid, sweat, saliva, mucus, or a derivative of any thereof.

In an embodiment, identifying members of the plurality of peptides that form a complex with members of the plurality of antibodies comprises sequencing a nucleic acid that encodes the peptide. Any useful sequencing method may be employed. For example, the sequencing may comprise next generation sequencing (NGS), Sanger sequencing, real-time PCR, or pyrosequencing. However, NGS can provide billions of sequences encoding peptides in a single experiment. The nucleic acid and peptide can be coupled physically, thereby allowing sequencing of the nucleic acid to determine the sequence of the peptide encoded by the nucleic acid. Any useful DNA construct can be used. For example, the nucleic acid molecule may comprise deoxyribonucleic acid (DNA), ribonucleic acid (RNA), or a derivative of any thereof.

In some embodiments, each peptide is directly coupled to its corresponding nucleic acid molecule. For example, the nucleic acid may be bound to a protein complex that comprises the peptide, including without limitation a ribosome display system. In another embodiment, each peptide is indirectly coupled to its corresponding nucleic acid molecule. For example, the corresponding nucleic acid molecule may be contained within a vector that encodes the peptide. As desired, the vector may be configured to express the peptide. The vector can also be comprised in a host cell. In an embodiment, the host cell expresses the peptide. The peptide may be expressed on the surface of the host cell. Appropriate display systems are available in the art or are provided herein. For example, the host cell can be a microbial cell, a bacterial cell, an *E. coli* cell, a eukaryotic cell, a yeast cell, or a mammalian cell.

The method of the invention may further comprise capturing members of the plurality of peptides that form a complex with members of the plurality of antibodies prior to identifying members of the plurality of peptides that form complex members of the plurality of antibodies (step c). In an embodiment, the capturing comprises capturing the peptide-bound members of the plurality of antibodies. The peptide-bound members of the plurality of antibodies may be captured to a substrate. Any useful substrate can be used. For example, the substrate can be a planar surface, e.g., a plate well, or a plurality of microbeads (also referred to as microparticles). The plurality of microbeads may be configured to facilitate capture as desired. For example, the microbeads may be magnetic or carry a label, including without limitation a fluorescent label. The bound members of the plurality of antibodies can be captured using a reagent that binds an antibody constant region. For example, the reagent can be Protein A, Protein G, Protein L and/or an anti-immunoglobulin antibody or aptamer. As desired, the reagent is coupled to the substrate, thereby allowing capture of peptide-bound antibodies to the substrate.

In some embodiments, the method of the invention further comprises filtering the plurality of antibodies prior to contacting the biological sample with a plurality of peptides (step b). The filtering may comprise contacting the plurality of antibodies with at least one reagent configured to deplete antibodies that bind to assay components other than the plurality of peptides. In an embodiment, the at least one reagent comprises a host cell as described herein, e.g., a host cell that is configured to display members of the plurality of peptides. The step allows removal of antibodies that bind to the host cell itself instead of members of the plurality of peptides.

In another embodiment, the method of the invention further comprises filtering the plurality of peptides prior to contacting the biological sample with a plurality of peptides (step b). The filtering of the plurality of peptides may comprise contacting the plurality of peptides with at least one reagent configured to deplete peptides that form a complex with assay components other than the plurality of antibodies. In an embodiment, the at least one reagent configured to deplete peptides comprises Protein A, Protein G, Protein L, and/or an anti-immunoglobulin antibody or aptamer.

As desired, filtering or depletion of both the plurality of antibodies and the plurality of peptides can be performed.

In some embodiments, the methods of the invention further comprise determining at least one peptide motif from the members of the plurality of peptides identified in c) above. The determining may comprise aligning the sequences of the members of the plurality of peptides identified in c) above. The aligning may comprise using a computational alignment algorithm. Such algorithms are known in the art or provided herein. For example, the MEME program may be used as described further below.

In an aspect, the invention provides a method of identifying at least one peptide indicative of a phenotype in a biological sample comprising: a) identifying a plurality of peptides in the biological sample according to the method of the invention as described above; b) comparing the presence or level of members of the plurality of peptides identified in (a) to a reference value; and c) identifying a peptide with a presence or level that differs from the reference based on the comparison in b), thereby identifying the at least peptide indicative of the phenotype. The reference value for each member of the plurality of peptides may comprise a presence or level of that member of the plurality of peptides in a control sample.

In another aspect, the invention provides a method of identifying at least one peptide motif indicative of a phenotype in a biological sample comprising: a) identifying at least one peptide motif in the biological sample according to the method of the invention as described above; b) comparing the presence or level of the at least one peptide motif identified in step a) to a reference value; and c) identifying at least one peptide motif with a presence or level that differs from the reference based on the comparison in b), thereby identifying the at least one peptide motif indicative of the phenotype. The reference value may comprise a presence or level of the same peptide motif in a control sample.

In still another aspect, the invention provides a method of characterizing a phenotype in a biological sample comprising: a) identifying a plurality of peptides in the biological sample according to the method of the invention as described above; b) comparing the presence or level of each member of the plurality of peptides identified in a) to a reference value; and c) identifying a peptide with a presence or level that differs from the reference based on the comparison in b), thereby characterizing the phenotype. The reference value for each member of the plurality of peptides may comprise a presence or level of that member of the plurality of peptides in a control sample. In an embodiment, the biological sample is from a subject and the method is used to characterize the phenotype in the subject.

In yet another aspect, the invention provides a method of characterizing a phenotype in a biological sample comprising: a) identifying at least one peptide motif in the biological sample according to the method of the invention as described above; b) comparing the presence or level of the at least one peptide motif identified in step a) to a reference value; and c) identifying at least one peptide motif with a presence or level that differs from the reference based on the comparison in b), thereby identifying the at least one peptide motif indicative of the phenotype. In an embodiment, the reference value comprises a presence or level of the same peptide motif in a control sample. In an embodiment, the biological sample is from a subject and the method is used to characterize the phenotype in the subject.

The control sample in the aspects above may have a different phenotype than the biological sample. One of skill will appreciate that the control sample can be chosen to facilitate identification of peptides indicative of a phenotype or useful for characterizing a phenotype. For example, if the phenotype of interest is a medical condition, the control may be a sample that does not have the same condition. Or if the phenotype of interest is a state of a medical condition, the control may be a sample that has a different state of the condition. As still another example, if the phenotype of interest is exposure to an environmental insult or pathogen, the control may be a sample that has not been exposed to the environmental insult or pathogen.

In some embodiments of the methods of the invention, the phenotype comprises a medical condition, e.g., a disease or disorder. The characterizing may comprise a diagnosis, prognosis or theranosis of the disease or disorder. The characterizing may comprise determining a stage, grade, progression, severity, treatment regimen likely to be beneficial or not, and/or treatment response of the disease or disorder.

The disease or disorder can be any disease or disorder having an immune component. For the example, the disease or disorder may comprise an infectious, autoimmune, parasitic, allergic, oncological, neurological, cardiovascular, pregnancy-related or endocrine disease or disorder. In some embodiments, the disease or disorder comprises an infectious disease or an autoimmune disease. The disease, disorder, or infection can be celiac disease (CD), Sjogren's Syndrome (SS), systemic lupus erythematosus (SLE), Epstein-Barr virus (EBV), rhinovirus, cytomegalovirus (CMV), *Streptococcus* sp., human immunodeficiency virus (HIV), *Haemophilus influenza, Borrelia burgdorferi, Babesia microti, Ehrlichia* sp., *Anaplasma* sp., *Trypanosoma cruzi, Leishmania* sp., *Taenia solium, Toxocara canis*, or *Toxoplasma gondii*. The disease or disorder may comprise a microbial infection, viral infection, bacterial infection, protozoan infection, parasitic infection, or fungal infection.

In one embodiment, the disease or disorder comprises celiac disease (CD) and the at least one peptide motif is selected from QXXXPF[PS]E (SEQ ID NO: 6), PFSEM (SEQ ID NO: 7), PFSEX[FW] (SEQ ID NO: 8), QPXXPFX [ED] (SEQ ID NO: 4) or combinations thereof.

In another embodiment, the disease or disorder comprises Chagas disease and the at least one peptide motif is selected from Table. 1

In another embodiment, the disease or disorder comprises Lyme disease and the at least one peptide motif is selected from Table 2.

In another embodiment, the disease or disorder comprises Toxoplasmosis and the at least one peptide motif is selected from Table 3.

In another embodiment, the disease or disorder comprises Cysticercosis and the at least one peptide motif is selected from Table 4.

In another embodiment, the disease or disorder comprises primary Epstein-Barr virus (EBV) infection (mononucleosis) and the at least one peptide motif is selected from Table 5.

In another embodiment, the disease or disorder comprises Zika virus infection and the at least one peptide motif is selected from Table 6 or Table 7.

In another embodiment, the disease or disorder comprises Human Immunodeficiency virus (HIV) infection and the at least one peptide motif is selected from Table 8.

In another embodiment, the disease or disorder comprises latent Epstein-Barr virus (EBV) infection and the at least one peptide motif is selected from Table 9.

In still another embodiment, the disease or disorder comprises rhinovirus and the at least one peptide motif is selected from Table 10.

In yet another embodiment, the disease or disorder comprises cytomegalovirus (CMV) and the at least one peptide motif is selected from Table 11.

In an embodiment, the disease or disorder comprises *Streptococcus* infection and the at least one peptide motif is selected from Table 12.

In an embodiment, the disease or disorder comprises *Leishmania* infection and the at least one peptide motif is selected from Table 13.

In an embodiment, the disease or disorder comprises *Babesia* infection and the at least one peptide motif is selected from Table 14.

In an embodiment, the disease or disorder comprises *Ehrlichia* infection and the at least one peptide motif is selected from Table 15.

In an embodiment, the disease or disorder comprises *Anaplasma* infection and the at least one peptide motif is selected from Table 16.

In an embodiment, the disease or disorder comprises *Toxocara canis* infection and the at least one peptide motif is selected from Table 17.

In another aspect, the invention provides a peptide comprising a sequence in any of Tables 1-18. In a related aspect, the method comprises a composition comprising at least one such peptide.

One of skill will appreciate that the methods of the invention can be used to assess peptides and/or motifs characteristic of multiple phenotypes in a single experiment or assay.

In an aspect, the invention provides the use of at least one reagent to carry out the method of the invention described herein. In a related aspect, the invention provides a kit comprising at least one reagent to carry out the method. The at least one reagent can be any useful reagent that can be used to carry out the subject methods. In some embodiments, the at least one reagent comprises at least one of: at least one peptide provided by the invention; a composition provided by the invention; a peptide library display system; an antibody binding agent; a primer set; or a depletion reagent. The peptide library display system may comprise an *E. coli* display system. In one embodiment, the peptide library display system comprises a naïve or random peptide library. Such a naïve library can be used to screen a sample for peptides, motifs and patterns. See, for example, FIG. 1 and related discussion. In other embodiments, the peptide library display system is configured to characterize a phenotype. See, e.g., FIG. 2A and FIG. 2B and related discussion.

Provided herein are methods for treating a disease in a subject in need thereof. In various embodiments, the methods include identifying a disease comprising identifying at least one peptide, at least one peptide motif or a combination of one or more peptides and peptide motifs indicative of a phenotype (for example, a disease or disorder) in a biological sample by the methods described herein and treating the disease. In exemplary embodiments, treatments include but are not limited to administration of effective amounts of therapeutic agents, prescribing life style changes (such as dietary changes and/or exercise) or combinations thereof.

In exemplary embodiments, the diseases include but are not limited to an infectious, autoimmune, parasitic, allergic, oncological, neurological, cardiovascular, pregnancy-related or endocrine disease or disorder. In some embodiments, the disease or disorder comprises an infectious disease or an autoimmune disease. The disease, disorder, or infection can be celiac disease (CD), Sjogren's Syndrome (SS), systemic lupus erythematosis (SLE), Epstein-Barr virus (EBV), rhinovirus, cytomegalovirus (CMV), *Streptococcus* sp., human immunodeficiency virus (HIV), *Haemophilus influenza, Borrelia burgdorferi, Babesia microti, Ehrlichia* sp., *Anaplasma* sp., *Trypanosoma cruzi, Leishmania* sp., *Taenia solium, Toxocara canis*, or *Toxoplasma gondii*. The disease or disorder may comprise a microbial infection, viral infection, bacterial infection, protozoan infection, parasitic infection, or fungal infection. Treatments for each of the diseases and the effective amounts for the treatments will be apparent to a person of skill in the art.

In one embodiment, the disease is celiac disease and exemplary treatments include but are not limited to recommending gluten-free diet to the subject. Further treatments and effective dosages will be apparent to a person of skill in the art.

In another embodiment, the disease is Chagas disease and treatment include but are not limited to administering an effective amount of benznidazole, nifurtimox or combinations thereof. For heart-related complications of Chagas disease, treatments may include medications, a pacemaker or other devices to regulate your heart rhythm, surgery, or even a heart transplant. For digestive-related complications of Chagas disease, treatments may include diet modification, medications, corticosteroids or, in severe cases, surgery. Further treatments and effective dosages will be apparent to a person of skill in the art.

In a further embodiment the disease is Lyme disease. In some embodiments, the subject diagnosed with Lyme disease is treated with therapeutically effective amounts of appropriate antibiotics (for example, doxycycline, amoxicillin, or cefuroxime axetil). Patients with certain neurological or cardiac forms of Lyme disease may require intravenous treatment with drugs such as ceftriaxone or penicillin. Further treatments and effective dosages will be apparent to a person of skill in the art.

In an embodiment, the disease is *Toxoplasma gondii* infection. In some embodiments, the subjects diagnosed with *Toxoplasma gondii* are treated with pyrimethamine and sulfadiazine, plus folinic acid. Further treatments and effective dosages will be apparent to a person of skill in the art.

In one embodiment, the disease is a *Taenia solium* infection (Cysticercosis). In some embodiments, the subjects diagnosed with Cysticercosis are treated with praziquantel (Biltricide), niclosamide, albendazole (Albenza) or combinations thereof. Further treatments and effective dosages will be apparent to a person of skill in the art.

In another embodiment, the disease is mononucleosis by EBV infection. In some embodiments, treatments for mononucleosis by EBV infection include rest, fluid and anti-viral agents such including acyclovir, ganciclovir and/or foscarnet. Further treatments and effective dosages will be apparent to a person of skill in the art.

In an embodiment, the disease is a Zika virus infection. In exemplary embodiments, treatment for Zika virus infection includes rest and fluids and acetaminophen or paracetamol. Further treatments and effective dosages will be apparent to a person of skill in the art.

In one embodiment, the disease is an HIV infection. In exemplary embodiments, the treatment for HIV includes antiretroviral therapy. Further treatments and effective dosages will be apparent to a person of skill in the art.

In an embodiment, the disease is Sjogren's syndrome. In exemplary embodiments, the treatment for Sjogren's syndrome includes pilocarpine, cevimeline, NSAIDS, Hydroxychloroquine or combinations thereof. Further treatments and effective dosages will be apparent to a person of skill in the art.

In one embodiment, the disease is a Rhinovirus infection. In exemplary embodiments, the treatment for rhinovirus infections include rest, hydration, antihistamines, and nasal decongestants and in case of further bacterial infection, antibacterial agents. Further treatments and effective dosages will be apparent to a person of skill in the art.

In an embodiment, the disease is a Cytomegalovirus infection. In exemplary embodiments, treatments for Cytomegalovirus infections include valganciclovir ganciclovir foscarnet, cidofovir or maribavir. Further treatments and effective dosages will be apparent to a person of skill in the art.

In some embodiments, the disease is a bacterial infections (for example, *Streptococcus* sp. infection, *Borrelia* infection, *Ehrlichia* infection, *Anaplasma* infection, *Haemophilus influenza* infection or *Babesia* infection). In exemplary embodiments, treatment for bacterial infections include antibacterial agents such a antibiotics, cephalosporin antibiotics, macrolide antibiotics, penicillin antibiotics, quinolone antibiotics, sulphonamide antibiotics, tetracycline antibiotics or combinations thereof. Further treatments and effective dosages will be apparent to a person of skill in the art.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Exemplary embodiments are illustrated in referenced figures. It is intended that the embodiments and figures disclosed herein are to be considered illustrative rather than restrictive. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustrates an overview of a method of determining an antibody specificity in a subject or individual. FIG. 2B illustrates an overview of a method of characterizing a phenotype in a subject or individual, e.g., to provide a diagnosis of a condition such as a disease or infection in the individual.

FIG. 3 also discloses SEQ ID NOS 877-894, respectively, in order of appearance.

FIG. 4B illustrates the how multiple motif panels can be used to simultaneously diagnose multiple different diseases (SEQ ID NOS 872-874, 915-925, 876, 926-928, and 895-914, respectively, in order of columns.

FIG. 11B illustrates the utility of the absence of motif enrichment in a sample, that is specific for Epstein Barr virus infection. "RRPFF" is disclosed as SEQ ID NO: 937.

DETAILED DESCRIPTION OF THE INVENTION

Figure 1:
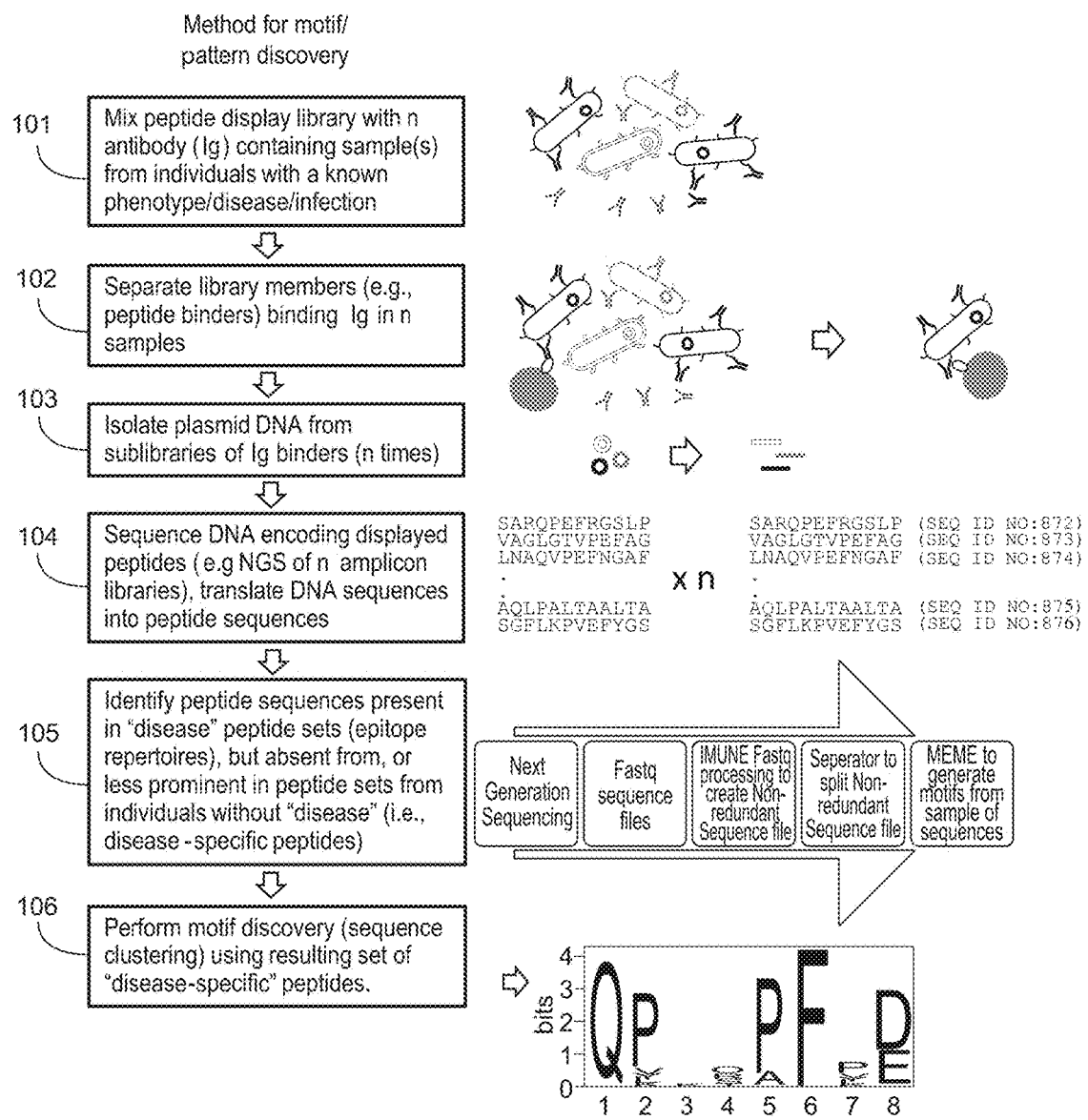
FIG. 1 illustrates an overview of a method of identifying in a sample, which can be used for peptide motif or pattern discovery (SEQ ID NOS 872-876 and 872-876, respectively, in order of columns).

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, N.Y. 2006); Smith, March's Advanced Organic Chemistry Reactions, Mechanisms and Structure 7th ed., J. Wiley & Sons (New York, N.Y. 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2nd ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 Jul. 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The invention provides compositions and methods that can be used to detect the presence of an antibody specificity in a biological sample containing a mixture of antibodies. The method may comprise measuring the enrichment of specific peptide motifs in a set of thousands or more, e.g., at least $10^5$ peptides, that bind to antibodies present in the sample. The method of the invention may be referred to herein as "Display-seq."

As used herein, "specificity" can refer to an antibody species that binds to particular antigen, or a peptide motif, pattern, or sequence containing an antibody's preferred amino acid contact residues.

The invention further provides a method to discover amino acid sequence motifs ("motifs"), which, when enriched within a sample dataset, can be used to characterize a phenotype. As an example, the phenotype may be a disease or disorder and the characterization can include a diagnosis, prognosis or theranosis for the disease or disorder. In an embodiment, the method is used to detect a disease in an individual by determining motifs present in the individual. The invention enables the facile discovery of synthetic peptide compositions that enable detection of antibodies in a mixture.

The invention further provides amino acid sequence motifs and synthetic peptide compositions useful for detecting antigen-specific antibodies present within a sample. The presence of antigen specific antibodies can be indicative or diagnostic of disease or disorder, e.g., an infection. Thus, in various embodiments, the compositions and methods of the invention are used for diagnosing human disease, for assessing vaccine efficacy and safety, or for monitoring changes in immune status. The invention may overcome limitations of diagnostic methods utilizing isolated biochemical reagents. For example, the invention does not require experimental optimization of a single reagent, it allows for arbitrary combinations of motifs to be used to make diagnostic decisions, and it allows for measurement of a large number of motif enrichments with a single data set, thereby seamlessly integrating many different biological assays into one process.

The compositions and methods of the invention are described further below. Briefly, a random peptide library is co-incubated with a sample that contains a mixture of different antibodies. Peptide library members that capture antibodies are then recovered. The sequences of all peptides in the enriched library of binders are then determined, thereby providing a signature of antibody specificities in the sample. The peptide library may be displayed on the surface of a biological entity that comprises a nucleic acid sequence encoding the peptide. The identity of peptides that were bound by antibodies can be determined by sequencing the nucleic acids. In some embodiments, the sequencing comprises massively parallel DNA sequencing or next generation sequencing (NGS). Analysis of peptide signatures and antibody specificities in a sample can be used to characterize a phenotype, such as providing a diagnosis, prognosis or theranosis of a disease or disorder.

Definitions

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. Beneficial or desired clinical results include, but are not limited to, alleviation of one or more symptom(s), diminishment of extent of the deficit, stabilized (i.e., not worsening) state of progression, delay or slowing of progression or invasiveness, and amelioration or palliation of symptoms associated with the brain insulin resistance. Treatment also includes a decrease in mortality or an increase in the lifespan of a subject as compared to one not receiving the treatment.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder described herein. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment), As used herein, the term "administering," refers to the placement an agent as disclosed herein into a subject by a method or route which results in at least partial localization of the agents at a desired site.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, -carboxyglutamate, and O-phosphoserine. Amino acid analogs refers to compounds that have the same basic chemical structure as a naturally occurring amino acid, i.e., an carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A protein refers to any of a class of nitrogenous organic compounds that consist of large molecules composed of one or more long chains of amino acids and are an essential part of all living organisms. A protein may contain various modifications to the amino acid structure such as disulfide bond formation, phosphorylations and glycosylations. A linear chain of amino acid residues may be called a "polypeptide." A protein contains at least one polypeptide. Short polypeptides, e.g., containing less than 20-30 residues, are sometimes referred to as "peptides." The terms protein, polypeptide and peptide may be used interchangeably herein to refer to molecules comprised of amino acid residues.

An antibody (Ab), also known as an immunoglobulin (Ig), is a large, Y-shape protein produced by plasma cells that is used by the immune system to identify and neutralize pathogens such as bacteria and viruses. The antibody recognizes a unique molecule of the agent, called an antigen, via the antibody's so-called variable region[11].

The term "autoantibody" as used herein refers to an antibody produced by the immune system in an organism in response to, and directed against, a constituent of its own tissues. Many autoimmune diseases and disorders, e.g., lupus erythematosus, celiac disease and type 1 diabetes, are caused by such autoantibodies wherein the immune system fails to properly distinguish between "self" and "non-self."

Figure 3:
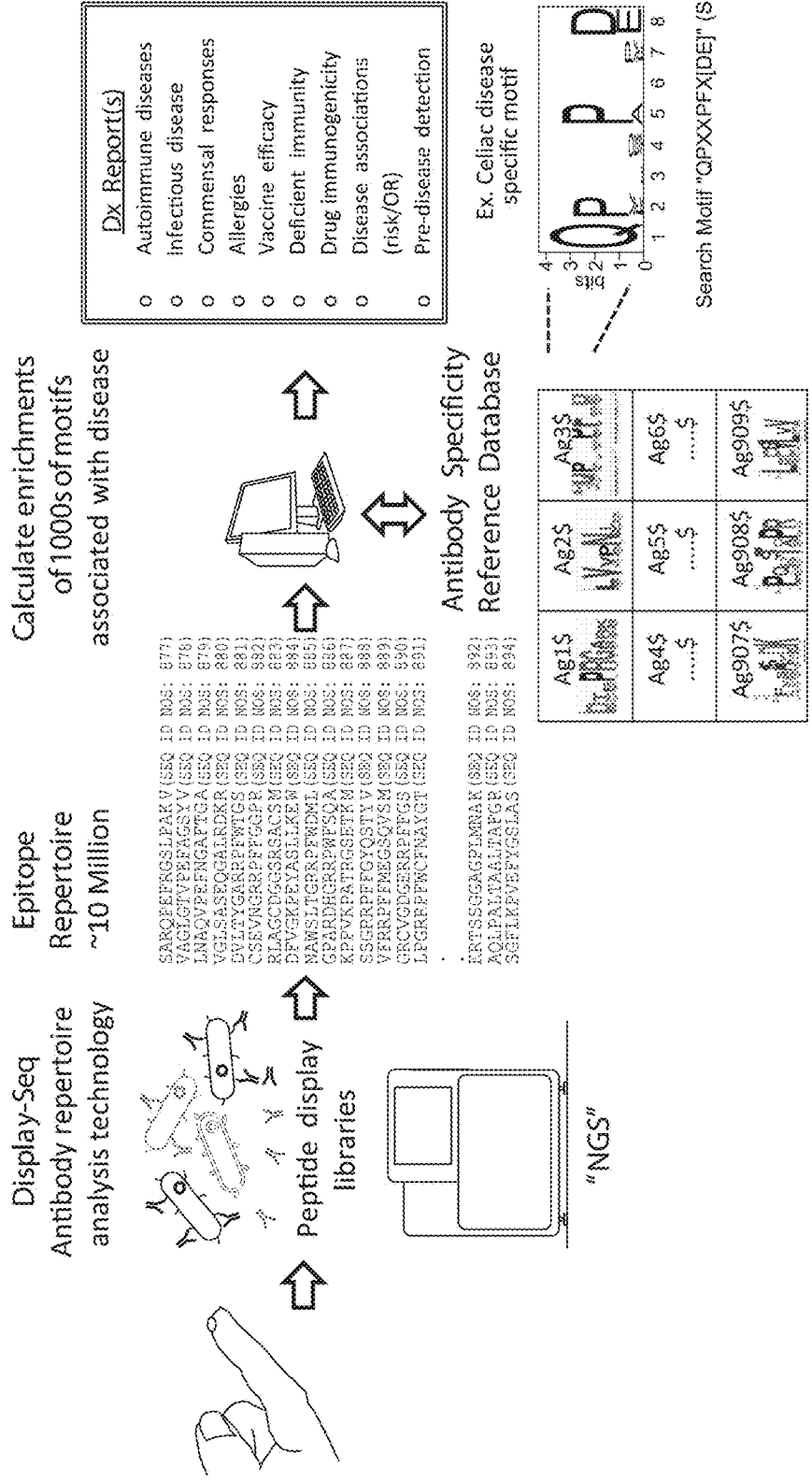
FIG. 3 illustrates a method of diagnosing a subject as having Celiac disease. The method includes i) enriching a collection of antibody binding peptides from a random peptide library of 6-60 amino acids for binding to a biological sample, ii) isolating plasmid DNA from the enriched library, iii) subjecting the amplicon library to sequencing (NGS), iii) counting the enrichment of a motif previously validated to be both sensitive and specific for celiac disease (e.g. QPXXPFX[DE] (SEQ ID NO: 4)), and comparing this enrichment to a reference value or threshold value.
Figure 4A:
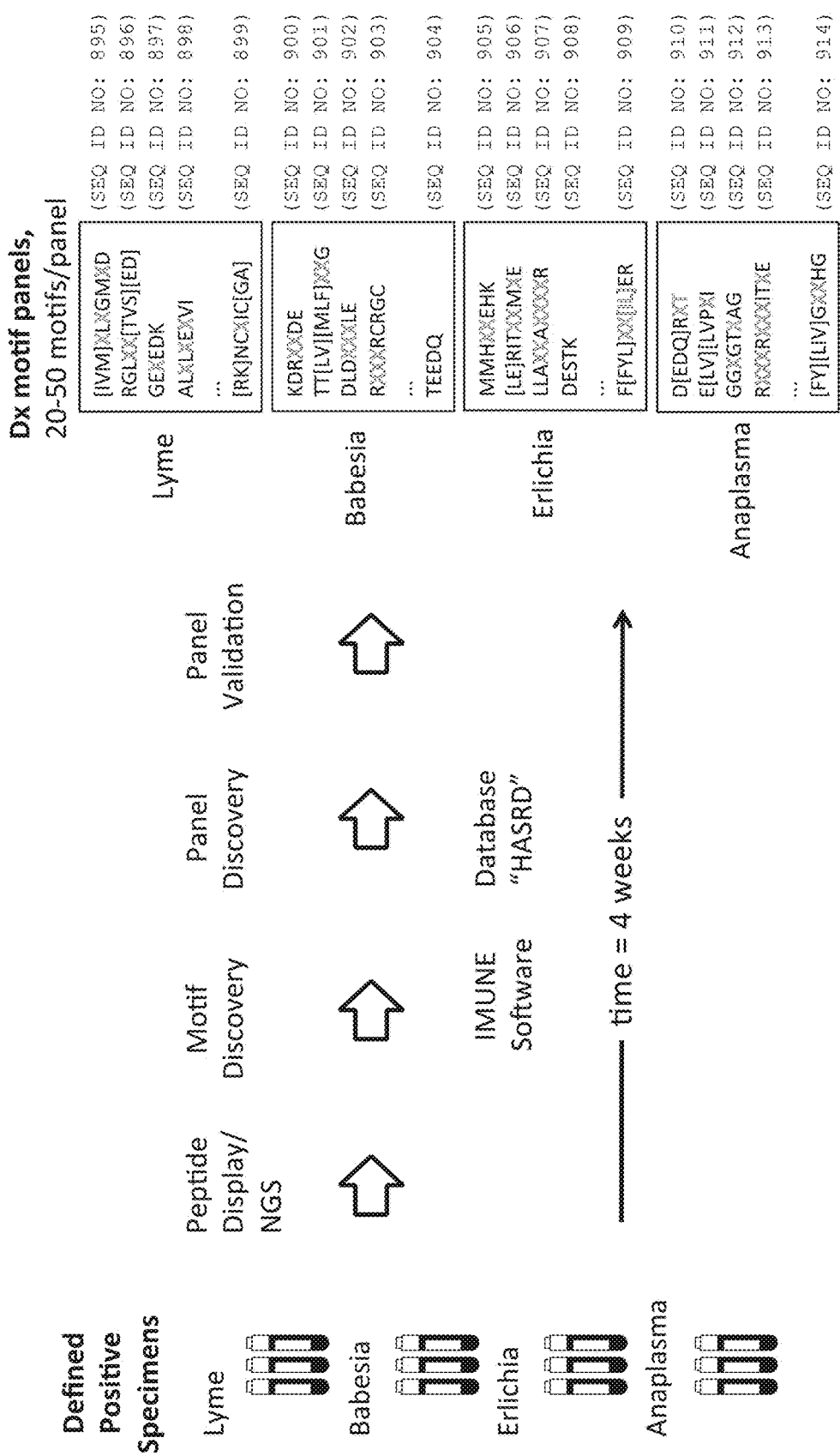
FIG. 4A illustrates the method and workflow to develop multiplexed diagnostic motif panels (SEQ ID NOS 895-914, respectively, in order of appearance).

The term "motif" as used herein comprises an amino acid sequence pattern, which comprises preferred amino acids at each position of a peptide sequence. For example, [DE]TX[FYL]K (SEQ ID NO: 1) where "X" is any amino acid and each letter corresponds to the conventional one-letter amino acid code. The notation [XYZ] within a motif means that the indicated position comprises one amino acid that is selected from "X or Y or Z". Motifs may alternatively be presented graphically as a sequence "logo," wherein the frequencies of occurrence of individual amino acids at each position in a motif are represented by the height of the character (e.g. one letter amino acid code) at that position. A larger letter indicates a higher frequency of occurrence. Examples are shown in FIG. 1 and FIG. 3 herein.

The term "pattern" refers to a sequence of amino acids, wherein the sequence may vary in length and may have intervening random amino acids. For example, DTXFK (SEQ ID NO: 2) and DXTXFXXK (SEQ ID NO: 3) are patterns.

The term "specificity repertoire" as used herein comprises the set of all binding specificities, (e.g. motifs, peptides, or patterns) comprised within an antibody repertoire.

The term "epitope" refers to the part of an antigen molecule/s to which an antibody attaches itself. For example, in the case of a protein antigen, the epitope can be the amino acid sequence or protein structural region to which an antibody binds.

The term "epitope repertoire" as used herein comprises the set of all antigens recognized, or bound by, by antibodies within a sample, or group of samples. For example, the epitope repertoire may refer to the set of all peptides or antigens recognized, or bound by, by antibodies within a sample, or group of samples.

The term "enrichment" as used herein refers to the number of observations of a peptide, pattern, or motif within an epitope repertoire divided by the number expected within a random dataset of equivalent size. For example, in a hypothetical 9-mer peptide library (-XXXXXXXXX-), where X is any amino acid, the pattern QPXXPFX[ED] (SEQ ID NO: 4) is expected to occur once in every 800,000 ((1aa/20aa)$^4$×(2aa/20aa)×2) random sequences (aa=amino acid). If 4 million sequences were determined, then one would expect to observe five (5) occurrences (i.e., once in every 800,000 sequences). As an example, if the pattern was actually observed in 50 unique peptides sequences (i.e. 50 observations) in an epitope repertoire, then the pattern would be "enriched" by 10-fold versus random.

The term "threshold" as used herein refers to the magnitude or intensity that must be exceeded for a certain reaction, phenomenon, result, or condition to occur or be considered relevant. For example, the threshold can be a numerical value above which enrichment is considered relevant. The relevance can depend on context, e.g., it may refer to a positive, reactive or statistically significant relevance.

The term "peptide display library" as used herein refers to any one of a family of methods wherein a sequence of amino acids is physically associated with a nucleic acid sequence that encodes that peptide. See [12].

The term "peptide signature" as used herein refers to the antigenic peptide repertoire detected in a sample. A peptide signature may comprise the enrichment of various peptides and/or common motifs observed in the sample The term "ELISA" as used herein refers to an enzyme-linked immunosorbent assay, which is a wet-lab test that uses antibodies and color change to identify a substance. Methods of performing ELISA assays are known to those of skill in the art. Typically, antigens from a sample are attached to a surface, such as the well of an ELISA plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate. The amount of color produced can correlate with the amount of antigen in the sample. The immunoassay format may be modified to use detection systems other than enzyme-mediated color change, e.g., radioactivity or fluorescence. The term "RIA" as used herein refers to a radioimmunoassay, "MIA" as used herein refers to a magneticimmunoassay, and "ECL" as used herein refers to enzymatic chemiluminescence.

The term "depleted sample" as used herein refers to specimen containing a mixture of antibodies wherein certain species of antibodies have been removed from the sample, for example by affinity capture. Depleted samples include those that have been incubated with a subset of the display library (e.g., phage/bacteria/yeast) to remove antibody species that bind to members of the library subset. The library subset could be a single clone that displays the scaffold used to present the peptide on the particle/cell surface or a mixture of two or more cell types that display different peptides that bind to antibodies of known specificity in the sample.

The term "computational depletion" as used herein refers to the removal of peptides from a set of peptides sequences that contain one or more specified motifs. For example, the motif QPXXPFX[DE] (SEQ ID NO: 4), as specified, would remove all instances of peptides in a large set of peptides that contain this motif, thereby computationally depleting the set of peptides carrying an instance of this motif. Many known or abundant motifs can be used to define a set of motifs for depletion. Depletion of common motifs has the effect of enriching rare motifs.

The term "clustering algorithm" as used herein refers to a computational algorithm used to perform "cluster analysis." Cluster analysis or clustering is the task of grouping a set of objects in such a way that objects in the same group (called a cluster) are more similar (in some sense or another) to each other than to those in other groups (clusters). A variety of clustering algorithms are known to those of skill in the art. See, e.g., [13-15].

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, e.g., 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a computational alignment algorithm. Such sequences are then said to be "substantially identical." For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. A common example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990).

A "comparison window," as used herein, includes reference to a segment of any one of the number of contiguous positions may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

The term "triplet-phosphoramidite" refers to a synthetic molecule of deoxyribonucleic acid (DNA) composed of three nucleotide bases. See, e.g., (Onto A, 1995), (Kayushin et al., 1996).

The term "surface display" as used herein refers to the presentation of heterologous peptides and proteins on the outer surface of a biological particle such as living cell, virus, or bacteriophage. See [16].

The terms "body fluid" or "bodily fluids" are liquids originating from inside the bodies of organisms. Bodily fluids include amniotic fluid, aqueous humour, vitreous humour, bile, blood (e.g., serum), breast milk, cerebrospinal fluid, cerumen (earwax), chyle, chyme, endolymph and perilymph, exudates, feces, female ejaculate, gastric acid, gastric juice, lymph, mucus (e.g., nasal drainage and phlegm), pericardial fluid, peritoneal fluid, pleural fluid, pus, rheum, saliva, sebum (skin oil), serous fluid, semen, smegma, sputum, synovial fluid, sweat, tears, urine, vaginal secretion, and vomit. Extracellular bodily fluids include intravascular fluid (blood plasma), interstitial fluids, lymphatic fluid and transcellular fluid. Immunoglobulin G (IgG), the most abundant antibody subclass, may be found in all body fluids. "Biological sample" also includes a mixture of the above-mentioned body fluids. "Biological samples" may be untreated or pretreated (or pre-processed) biological samples.

The term "disease" refers to an abnormal condition affecting the body of an organism. The term "disorder" refers to a functional abnormality or disturbance. The terms disease or disorder are used interchangeably herein unless otherwise noted or clear given the context in which the term is used. The terms disease and disorder may also be referred to collectively as a "condition."

The term "phenotype" as used herein comprises the composite of an organism's observable characteristics or traits, such as its morphology, development, biochemical or physiological properties, phenology, behavior, and products of behavior.

The term "diagnosis," or "dx," refers to the identification of the nature and cause of a certain phenomenon. As used herein, a diagnosis typically refers to a medical diagnosis, which is the process of determining which disease or condition explains a symptoms and signs. A diagnostic procedure, often a diagnostic test or assay, can be used to provide a diagnosis. A diagnosis can comprise detecting the presence of a disease or disorder, or The term "prognosis," or "px," as used herein refers to predicting the likely outcome of a current standing. For example, a prognosis can include the expected duration and course of a disease or disorder, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

As used here, the terms "massively parallel signature sequencing" (MPSS) or "next generation sequencing" (NGS) and the like are used interchangeably to refer to high throughput nucleic acid sequencing (HTS) approaches. Platforms for NGS that rely on different sequencing technologies are commercially available from a number of vendors such as Pacific Biosciences, Ion Torrent from Thermo Fisher, 454 Life Sciences, Illumina, Inc. (e.g., MiSeq, NextSeq, HiSeq) and Oxford Nanopore. For review of NGS technologies, see, e.g., van Dijk E L et al. Ten years of next-generation sequencing technology. Trends Genet. 2014 September; 30(9):418-26. [17]

General molecular biology terminology and techniques are known to those of skill in the art. See, e.g., Sambrook et al., Molecular Cloning: A Laboratory Manual, Cold Spring Harbor Press, N.Y., (3.sup.rd ed., 2000); and Brent et al., Current Protocols in Molecular Biology, John Wiley & Sons, Inc. (ringbou ed., 2003).

Phenotypes

As described herein, the compositions and methods of the invention may be used to characterize a phenotype in a sample of interest. The phenotype can be any phenotype of interest that may be characterized using the subject compositions and methods. Consider a non-limiting example wherein the phenotype comprises a disease or disorder. In such cases, the characterizing may be providing a diagnosis, prognosis or theranosis for the disease or disorder. In an illustrative embodiment, a sample from a subject is analyzed using the compositions and methods of the invention. The analysis is then used to predict or determine the presence, stage, grade, outcome, or likely therapeutic response of a disease or disorder in the subject. The analysis can also be used to assist in making such prediction or determination.

The repertoire of antibodies present in an organism can be indicative of various antigens that the organism has encountered. Such antigens may be derived from external insults, e.g., viral particles or microorganisms such as bacterial cells or fungi. External insults may also be allergens such as pollen or gluten, or environmental factors such as toxins. An organism may also generate antibodies specific to internal antigens. For example, autoimmune disorders are caused by the formation of antibodies that recognize antigens of the host organism. Autoantibodies to various cancer antigens have been observed. In sum, a host organism can comprise antibodies to numerous external and internal antigens indicative of a multitude of diseases, disorders and other environmental factors. Thus, the compositions and methods of the invention can be used to characterize any number of phenotypes in an organism, including without limitation determining environmental exposures and/or providing a diagnosis, prognosis or theranosis for various medical conditions. These conditions include without limitation infectious, autoimmune, parasitic, allergic, neoplastic, genetic, oncological, neurological, cardiovascular, and endocrine diseases and disorders.

Method to Discover Epitopes and Motifs Recognized by a Mixture of Antibodies in a Sample The present invention enables the discovery and identification of amino acid sequence motifs and peptide epitopes that are bound by antibodies within a sample that contains a mixture of antibodies. Thus, the method can provide a peptide signature for the sample. In an embodiment, the sample comprises a bodily fluid as a source of the mixture of antibodies.

An outline of one embodiment of the method is shown in FIG. 1. A peptide library is contacted with a desired number (n) of antibody (Ig) containing sample(s) 101. Each member of the peptide library can be displayed on the surface of a host cell. The sample(s) can be from one or more individual with a known phenotype of interest, including without limitation a disease or infection. This can allow the identification of peptides in the individuals indicative of the phenotype. In a next step 102, library members binding Ig (e.g., peptide binders) in the n samples are separated from non-binders. In this step, the peptides which are bound by antibodies from the sample are identified. The identity of the bound peptides is determined by isolating DNA encoding each peptide from the separated sublibraries of Ig binders (n times) 103. The DNA can be within a vector, e.g., a plasmid, which encodes the peptide. The sequences of the DNAs encoding the displayed peptides (e.g NGS of n amplicon libraries) are translated into the encoded peptide sequences 104. This step thereby provides the peptide signature of the sample. As desired, the peptide sequences present in the peptide sets (epitope repertoires), but absent from, or less prominent in peptide sets from control samples are determined 105. As an example, the individual/s may have a certain disease whereas the control samples are from individuals without the disease. This arrangement may be used to identify disease-specific peptide sets. Further as desired, motif discovery (sequence clustering) is performed using resulting set of the peptides 106. Following the above example, these motifs may comprise disease specific motifs that can be used to characterize (e.g., provide a diagnosis, prognosis or theranosis) of the disease. The Examples herein provide a number of such motifs identified using the methods of the invention for various disease settings.

In an aspect, the invention provides a method of identifying a plurality of peptides, comprising: a) providing a biological sample comprising a plurality of antibodies; b) contacting the biological sample with a plurality of peptides; and c) identifying members of the plurality of peptides that form a complex members of the plurality of antibodies.

The biological sample may comprise a bodily fluid. Antibodies may be found in any bodily fluid. In some embodiments of the invention, the bodily fluid comprises peripheral blood, lymphatic fluid, sweat, saliva, mucus, or a derivative of any thereof.

In an embodiment, identifying members of the plurality of peptides that form a complex with members of the plurality of antibodies comprises sequencing a nucleic acid that encodes the peptide. Any useful sequencing method may be employed. For example, the sequencing may comprise next generation sequencing (NGS), Sanger sequencing, real-time PCR, or pyrosequencing. Next generation sequencing can allow screening a vast number of sequencing in a single experiment. The nucleic acid and peptide can be coupled, thereby allowing sequencing of the nucleic acid to be converted to the sequence of the peptide. Any useful DNA construct can be used. For example, the nucleic acid molecule may comprise deoxyribonucleic acid (DNA), ribonucleic acid (RNA), or a derivative of any thereof.

In some embodiments, each peptide is directly coupled to its corresponding nucleic acid molecule. For example, the nucleic acid may be bound to a protein complex that comprises the peptide, including without limitation a ribosome, mRNA, or DNA display system. In another embodiment, each peptide is indirectly coupled to its corresponding nucleic acid molecule. For example, the corresponding nucleic acid molecule may be contained within a vector that encodes the peptide. As desired, the vector may be configured to express the peptide. The vector can also be comprised in a host cell. In an embodiment, the host cell expresses the peptide. The peptide may be expressed on the surface of the host cell. Appropriate display systems are available in the art or are provided herein. For example, the host cell can be a microbial cell, a bacterial cell, an *E. coli* cell, a eukaryotic cell, a yeast cell, or a mammalian cell.

The method of the invention may further comprise capturing members of the plurality of peptides that form a complex with members of the plurality of antibodies prior to step c). In an embodiment, the capturing comprises capturing the peptide-bound members of the plurality of antibodies. The peptide-bound members of the plurality of antibodies may be captured to a substrate. Any useful substrate can be used. For example, the substrate can be a planar surface, e.g., a plate well, or a plurality of microbeads (also referred to as microparticles). The plurality of microbeads may be configured to facilitate capture as desired. For example, the microbeads may be magnetic or carry a label, including without limitation a fluorescent label. The bound members of the plurality of antibodies can be captured using a reagent that binds an antibody constant region. For example, the reagent can be Protein A, Protein G, Protein L and/or an anti-immunoglobulin antibody or aptamer. As desired, the reagent is coupled to the substrate, thereby allowing capture of peptide-bound antibodies to the substrate.

In some embodiments, the method of the invention further comprises filtering the plurality of antibodies prior to step b). The filtering may comprise contacting the plurality of antibodies with at least one reagent configured to deplete antibodies that bind to assay components other than the plurality of peptides. In an embodiment, the at least one reagent comprises a host cell as described herein, e.g., a host cell that is configured to display members of the plurality of peptides. The step allows removal of antibodies that bind to the host cell itself instead of members of the plurality of peptides.

In another embodiment, the method of the invention further comprises filtering the plurality of peptides prior to step b). The filtering of the plurality of peptides may comprise contacting the plurality of peptides with at least one reagent configured to deplete peptides that form a complex with assay components other than the plurality of antibodies. In an embodiment, the at least one reagent configured to deplete peptides comprises Protein A, Protein G, Protein L, and/or an anti-immunoglobulin antibody or aptamer.

As desired, filtering of both the plurality of antibodies and the plurality of peptides can be performed.

In some embodiments, the methods of the invention further comprise determining at least one peptide motif from the members of the plurality of peptides identified in c). The determining may comprise aligning the sequences of the members of the plurality of peptides identified in c). The aligning may comprise using a computational alignment algorithm. Such algorithms are known in the art or provided herein. For example, the MEME program may be used as described further below.

The following paragraphs provide an exemplary protocol when performing the methods of the invention using peptide libraries displayed on *E. coli* cells to identify antibody specificities in blood (serum) samples. One of skill will appreciate that these methods can use alternate display configurations and/or alternate sample sources. Various useful alternatives are described elsewhere herein. Certain steps would then be altered or perhaps skipped accordingly.

1) Serum Depletion Step:

Antibodies in the starting sample that bind to assay components are first removed to favor recovery of antibodies which bind displayed peptides. For example, antibodies targeting *E. coli* cells can be removed by incubating serum with an *E. coli* strain expressing the library scaffold alone (i.e., no peptides). After the incubation, the bacteria along with any bound antibodies are removed using centrifugation and collection of the supernatant (unbound antibodies).

2) Library Clearing Step:

The peptide display libraries can also be cleared of peptides that may form a complex with particular assay components. For example, peptide libraries can be cleared of protein A and protein G binders by incubating the induced library with magnetic beads coated with protein A and protein G. Magnetic separation captures the beads along with any cells that are bound to the protein coating the beads. The unbound fraction is collected for screening for serum antibody binders.

3) Antibody Binding Step:

The Serum and Peptide Display Libraries are Contacted to allow antibodies present in the serum sample to bind to peptides displayed on the *E. coli* cells.

For example, the depleted serum sample can be incubated with Protein A and G cleared cells expressing the peptide library. Antibodies from serum bound to expressed peptides on the cells are harvested using centrifugation followed by washing to remove non-specific interactions.

4) Library Enrichment Step:

The above step allowed formation of complexes between the antibodies and displayed peptides. These complexes are now recovered. Washed cells are then incubated with magnetic beads coated with protein A and protein G to capture antibodies from the serum, which will also capture the cells expressing peptides that are bound by antibodies. The beads are washed several times while magnetized to remove cells captured non-specifically.

6) Growth Step:

The final enriched display library (i.e., cells displaying peptides that remain bound to washed beads) is recovered. The cells can be resuspended in growth broth (e.g., LB) and allowed to replicate. Alternatively, one can proceed directly to step 9 or step 10a.

7) Repeat Enrichment Step:

The above steps can be repeated as desired. For example, a second round can further enrich for peptide members of the library that interact with antibodies from serum and reduce non-specific binding cells that may have come through the first round of the screen.

8) Enrichment Analysis Step:

After the one or more rounds of enrichment are completed, the final enriched library is analyzed to confirm and quantify binding of library members to patient serum antibodies (quality control for enrichment). Such analysis can use flow cytometry methodology (FACS).

9) DNA Isolation from Enriched Library Step:

Each cell contains DNA encoding the peptide that cell displays on its surface. An *E. coli* cell may contain a plasmid vector encoding the peptide. The plasmid is isolated from the enriched library from each serum sample for preparation for sequencing analysis.

NGS technology can be used sequence large numbers of plasmid in a single reaction. Various platforms exist for NGS analysis. Below are alternative methods using the Illumina, Inc. or Life Technologies (Thermo Fisher) platforms. Unless otherwise specified herein, the methods of the invention may employ any appropriate NGS technology.

10a) Amplicon Preparation Step:

(For sequencing using the Illumina platform—MySeq, NextSeq, HiSeq) The "region of interest" (random/peptide region from the library) is amplified using the plasmid as template with forward and reverse primers that flank the random region. The primers contain adaptors specific for use on the Illumina NextSeq. The PCR product is cleaned using magnetic beads that bind DNA and the resulting product is subjected to a second PCR using primers specific to the adaptors from the first PCR. The second PCR primers are provided by an Illumina (Nextra XT) indexing kit. The second PCR primers contain 8 nucleotide indices to provide a unique index combination specific to the amplicon from each sample for tracking of the sample during the sequencing.

10b) Amplicon Preparation Step:

(For sequencing using the Ion platform (Life Technologies)—Personal Genome Machine, Proton) The "region of interest" (random/peptide region from the library) is amplified using the plasmid as template with forward and reverse primers that flank the random region. The primers contain adaptors specific for use on the Ion Proton along with a unique barcode for each sample that will be pooled for sequencing. The PCR product is cleaned using magnetic beads that bind DNA.

11) Amplicon Quality Control Step:

After cleaning the second PCR product, the purity is confirmed using gel electrophoresis or a Bioanalyzer 2100 and the quantity of the DNA is determined. Amplicons specific for the enriched libraries from all serum samples screened are normalized and pooled at equal molar concentrations for running on the sequencer.

12a) Sequencing Step:

The amplicon pool is run on the Illumina NGS instrument per instructions from the manufacturer. Using the NextSeq instrument, a 75 cycle high-output flow cell is used with single read and dual indexing settings. These specifications allow for approximately 400 million total sequences, are sequenced once in the "forward" direction for a length of 75 base pairs (fully covering the 12 amino acid random region in the library), and are also read for both 5 prime and 3 prime indices.

12b) The amplicon pool is run on the Ion Proton instrument per instructions from the manufacturer (Life Technologies).

13) Sequence De-Multiplexing Step:

If required, the resulting sequences are de-multiplexed using the index codes to identify which serum samples the sequences originated from. Indexed sequences are sorted for each sample and subjected to bioinformatics analysis. This analysis may comprise identifying peptide sequences from their respective DNA sequences as determined above. Thus, the peptide signatures or epitope repertoires of the sample/s are determined.

A peptide display library is enriched for library members that bind antibodies within a sample. The library of peptides can be displayed on any useful biological entity, e.g., microbial cells such as bacteria, phage, synthetic beads, yeast cells, or ribosomes. The library may have a high diversity of more than $10^5$ unique library members, e.g., more than $10^6$, $10^7$, $10^8$, $10^9$, $10^{10}$, or more than $10^{11}$ members. Various peptide library compositions can be used including fully random peptide libraries of 3-30 random positions, or using libraries with one or more positions fixed to cysteine to favor the formation of disulfide bonds. Disulfide bonds may increase the affinity of some antibody binding peptide epitopes. Additionally, libraries derived from structural scaffolds can be used including for example, helix-turn-helix (i.e., alpha-alpha), beta-hairpins, alpha-beta, beta-alpha, beta-sheets, zinc fingers, or protein interaction modules including SH2, SH3, and other domains. In some embodiments, the length of random region is chosen to be 10-20 amino acids, e.g., 10, 11, 12, 13, 14, 15, 16, 17, 18, 19 or 20 amino acids. The random region can have more than 20 amino acids if desired. A peptide library may be configured to i) possess a minimum number of stop codons (that prevent peptide display), and ii) minimizes bias towards certain amino acids that are more abundant in libraries constructed using NNS or NNK codons. One method to accomplish this is prepare synthetic oligonucleotides for PCR reactions, using 20 triplet-phosphoramidites (DNA molecules composed of three bases) that uniquely encode one of the 20 amino acids. Preparation of such libraries is a method known to those skilled in the art of peptide and protein library construction. See, e.g., Directed Evolution Library Creation: Methods and Protocols (Methods in Molecular Biology) Softcover reprint of hardcover 1st ed. 2003 Edition by Frances H. Arnold (Editor), George Georgiou (Editor); ISBN-13: 978-1617374715.

In some embodiments of the invention, the sample to be analyzed is first depleted of antibodies that bind to the biological entity displaying the peptide (e.g., phage, bacteria, yeast, ribosomes, cells), by incubating a mixture of sample containing the antibodies with an excess of the biological entity that does not display a peptide. The entities bound to antibodies are then separated using centrifugation, filtration, sedimentation, or other separation method, and the unbound antibodies are recovered to generate a "depleted sample." The depleted sample is then mixed with, and allowed to contact the library to allow complexes to form between the antibodies and displayed peptides. The mixture can be allowed to incubate for any desired time, e.g., 1, 2, 3, 4, 5, 6, 7, 8, 9, 10 or more than 10 h. Antibodies that are not bound to library peptides are removed from the mixture, e.g., using centrifugation or sedimentation, and recovered antibody-peptide complexes are resuspended into a buffered salt solution. Library members with bound antibodies can be captured using Protein A and/or Protein G to bind to the constant regions of the peptide-bound antibodies, or with anti-human Ig antibodies. The Protein A, Protein G or anti-human antibodies can be bound to a substrate to facilitate capture. For example, the substrate can be a planar surface or bead. In an embodiment, the Protein A, Protein G or anti-human antibodies are coupled to magnetic beads. Labeled cells are then separated using magnetic separation or magnetic activated cell sorting (MACS), and recovered into growth media to amplify the population of selected cells. This process typically results an enrichment of antibody binders in the library from an initial frequency of 0.5-5% to about 50-60% binders. To increase the fraction of binders in the population, and the quality of useable data, the sorting process above can be repeated one or more times to increase the purity of binders within the enriched library, typically to >85%.

Sample preparation for sequencing: As described herein, the amino acid sequence of the bound peptides can be determined by sequencing DNA encoding the peptides. In an embodiment, the peptides are encoded on plasmid DNA comprised in a host cell. The plasmid DNA can be isolated from the cells and the sequence of the DNA encoding the peptides is determined. In some embodiments, the plasmids are used as a template for polymerase chain reaction PCR to create an amplicon library. As desired, each amplicon library enriched against a distinct sample can be given a unique nucleic acid sequence identifier or "bar code" embedded within the amplicon library. This step allows many amplicon libraries to be pooled together and analyzed in a single NGS run.

Sequencing of the samples is then performed. In some embodiments, NGS sequencing is used. The raw DNA sequences are translated into amino acid sequences. If necessary peptide variants arising from sequencing errors are identified as sequences exhibiting identity beyond what is statistically probable. For example, for a 12-mer random peptide library with 12 random amino acid positions, sequences having 10 or 11 identities are unlikely to be unique, since the library contains 10'10 members. The probability of finding two sequences with 10 identities in a library of this size constructed using triplet phosphoramidites is low.

In one embodiment of the invention, a listing of all unique peptides, along with the number of observations (counts) observed in each sample analyzed is generated. From this unique sequence listing, peptides occurring two or more samples obtained from individuals having a given phenotype are enumerated and motifs occurring in those peptides are identified using one or more established motif discovery algorithms, e.g., sequence clustering algorithms such as MEME, available at www.meme-suite.org [13-15]. This step identifies the commonalties between antibody specificities directed towards the same antigens from different individuals. One benefit of finding commonalties in a plurality of samples is that this may more accurately identify a specific motif that can be used to search the epitope repertoires from many different samples. And, the motif will more closely match the corresponding epitope sequence of the antigen that gave rise to the antibody.

The above approach has been applied to serum samples from healthy donors to identify hundreds of motifs. See the Examples herein for details.

For sequence clustering algorithms whose computation time scales as $\sim N^2$, the number of sequences accessed can be reduced to facilitate efficient computations. For example, with current computing power, a size of about 5000 sequences may restrain computation time to a period of less than 12 hrs. However, greater computer power and efficiency and longer computer time can increase the number of sequences used for clustering along with quality and number of motifs generated.

Increasing the Number of Motifs by Computational Depletion.

In order to identify a larger number of distinct antibody specificities within the epitope repertoire, peptides containing motifs constructed from the largest number of representative sequences (e.g. the motifs with the largest number of "sites" from MEME) are removed from a set of peptides most specific to a sample or set of samples. The set of peptides should be large enough that after performing computational depletion the file is approximately the same size as the file used for the first round of clustering. See, e.g., [13-15]. The resulting depleted file is then used for a new run of sequence clustering for motif discovery. The process can be iterated as desired to identify motifs corresponding to less abundant antibodies within the repertoire whose presence may be important for diagnosis. Computational depletion can identify new motifs, and improve the quality of motifs identified without depletion.

To identify common motifs within the NGS dataset of a single sample, the set of peptides that are present in the sample and also present in one or more other samples selected from a group of samples is determined. This reduced set of peptides can be analyzed using peptide sequence clustering algorithms.

Method to Discover Disease-Specific Epitopes and Motifs

In another embodiment of the invention a listing containing all unique peptides, along with the number of observations (counts) observed in each sample analyzed is generated. The listing is contained in a computer file. From this file, peptides that exhibit the highest specificity and sensitivity for the disease can be identified as those occurring in the largest number of samples from individuals with disease, but the smallest number of samples from individuals without disease. For example, if epitope repertoires are determined for 20 samples from individuals with disease and 20 from age and gender matched controls, then peptides present in more than 10 of 20 disease samples and in none of 20 controls samples (or e.g., <2/20 controls) can be used as input for motif discovery via clustering (e.g., MEME). All peptides present in 1-20 disease samples (e.g., 20/20, 19/20, 18/20/17/20, 16/20, 15/20, 14/20, 13/20, . . . 1/20 etc.) can analyzed by sequence clustering algorithms (e.g., MEME). For peptides present in exactly N samples out of a total of M samples, a threshold number of N can be determined such that the number of peptides within N/M samples can be analyzed using peptide sequence clustering algorithms.

Alternatively, individual peptides that occur in the largest number of disease samples and the fewest (or none) control samples can be aligned. In some embodiments, to identify diagnostic compositions, individual peptides exhibiting the highest disease sample specificity (present in the largest number of disease samples, and fewest control samples) are assayed for reactivity with new samples from individual samples with and without disease to validate their diagnostic utility, and estimate their diagnostic sensitivity and specificity.

To identify those motifs with the most utility for diagnostic use, the enrichment of individual motifs can be calculated in an arbitrary number of samples from healthy controls or other disease controls to identify motifs with the highest specificity. For example, if a motif appears in fewer than 5% of many samples from individuals without CD, or untested controls, but more than 10% of CD cases the significance of enrichment can be calculated using statistical methods to determine a p-value.

Calculating Enrichment

As described herein, the compositions and methods of the invention can be used for determining or measuring an antibody specificity in a sample by determining enrichment of antibodies against various peptide or peptide motifs of interest. An exemplary flow diagram is shown in FIG. 2A. Peptide signatures and/or motif(s) specific to a phenotype of interest are determined as described herein 201. See, e.g., FIG. 1 and related discussion above. A sample comprising antibodies (Ig) is collected from a subject 202. The sample is contacted with a peptide library as described herein and the library is screened for peptide binders to the antibodies in the sample 203. Peptide sequences that are bound by antibodies in the sample are determined as described herein, e.g., using NGS 204. The enrichment of given peptides is calculated amongst the determined peptide sequences 205. This step may also comprise determining peptide motif(s) present in the sample as described herein. The calculated enrichment(s) of the peptides and/or motifs of interest may be used for further analysis as desired, e.g., to compare to established thresholds in order to characterize the sample 216.

In order to detect a given antibody directed towards a predefined amino acid sequence, pattern, or motif, the number of sequence, patterns, or motifs occurring within a sample NGS dataset can be counted, motif enrichment can measured as the number of observations of that sequence/pattern/or motif divided by the number of instances expected by random chance. For example, if one million unique 12-mer peptide sequences from a library constructed using 20 triplet phosphoramidates (i.e., one codon per amino acid) were obtained for a sample, and the distribution of amino acids within the sample was assumed to be approximately random one would expect the pattern QPXXPF (SEQ ID NO: 5) to occur about $[(1/20)^4$ instances/frame$\times$(7 frames)$\times 10^6$=43.74 by random chance.

If the number of instances of this motif/pattern is larger than this number, e.g., 272, one can calculate the enrichment as 272/43.75=6.2-fold and the significance value for the level of enrichment observed can be calculated using an appropriate statistical test (e.g. t-test, z-test, U-test, rank-sum test, etc).

Characterization of Phenotypes

As described herein, the compositions and methods of the invention can be used for characterizing a phenotype of interest, e.g., to provide a diagnosis, prognosis, or theranosis of a condition such as an infection or autoimmune disorder. An exemplary flow diagram is shown in FIG. 2B, FIG. 3. Peptide signatures and/or motif(s) specific to a phenotype of interest are determined as described herein 211. See, e.g., FIG. 1 and related discussion herein. To characterize phenotype in a subject, e.g., a human subject having or suspected of having a medical condition, a sample comprising antibodies (Ig) is collected from the subject 212. The sample is contacted with a peptide library as described herein and the library is screened for binder to the antibodies in the sample 213. Peptide sequences that are bound by antibodies in the sample are determined as described herein, e.g., using NGS 214. The enrichment of given peptides is calculated amongst the determined peptide sequences 215. This step may also comprise determining peptide motif(s) present in the sample as described herein. The calculated enrichment(s) of the peptides and/or motifs of interest is compared to established thresholds 216. This comparison is used to characterize the phenotype, e.g., to provide a positive, negative or equivocal diagnosis of a condition.

The thresholds may be referred to herein as cut-offs, control values, reference values, or the like. One of skill will understand that the manner in which a threshold is calculated can depend on the phenotype and desired characteristics. For example, to determine an exposure to given entity, e.g., a pathogen, the threshold may be the expected random occurrence of the enrichment value (i.e., 1) or close to zero observations. In this setting, an enrichment greater than the threshold can indicate exposure to the entity. In other settings, the threshold may be the enrichment observed in one or more control sample. For example, if the phenotype to be characterized is a disease or disorder, the threshold may be the enrichment observed in a sample without the disease or disorder. In this setting, an enrichment greater than the threshold can indicate the presence of the disease or disorder. In some case, the degree of enrichment may provide further information, including without limitation the severity, stage, grade, or progression of the disease or disorder. One of skill will appreciate how to select an appropriate control given the desired phenotype to be characterized. One of skill will also appreciate that enrichment above or below the threshold may be relevant given a particular setting. A threshold value can be chosen to provide the desired balance between sensitivity and specificity, or according to other relevant statistical measures.

The following paragraphs provide an exemplary protocol when performing the methods of the invention using peptide libraries displayed on the surface of a display host. One of skill will appreciate that these methods can use alternate display configurations and/or alternate sample sources. Various useful alternatives are described elsewhere herein.

In an embodiment, a body fluid sample from an individual is collected. Antibodies that bind to the display library scaffold (bacteria, virus, phage, etc) are first depleted from the sample by contacting the specimen with the display host that does not express a member of the peptide library. Antibodies that do not bind to the host are recovered. In some embodiments of the invention, *E. coli* display technology is used. In such cases, the display scaffold eCPX [18] can be expressed on the cell surface without an appended peptide sequence. An aliquot of cells is washed once, and resuspended in a pH buffered salt solution. The body fluid sample after these steps may be referred to herein as a "depleted sample."

The depleted sample is then incubated with the peptide display library under conditions that allow binding of antibodies in the sample with displayed peptides. Peptide library members that are bound to antibodies in the sample are separated. In some embodiments, separation is achieved using by capturing the antibody-peptide complexes to a substrate. The substrate can be coupled to one or more binding agent to the constant region of the antibodies in the sample, thereby facilitating capture. In some embodiments, the substrate comprises microparticles (beads) that are functionalized with a binding agent to antibodies, e.g., Protein A, Protein G, Protein L, or an Ig binding antibody. The microparticles may be magnetized to allow for capture using magnetic force. The process may be repeated as desired, e.g., to increase the purity of antibody binding library members.

From the enriched library, an amplicon library of the DNA encoding the members of the peptide library may be prepared for DNA sequencing. The determined DNA sequences are translated into peptide sequences according to typical genetic code, thereby providing a peptide signature for the sample. The number of instances of each unique peptide in the sample may then be counted. Enrichment of peptides and motifs can be calculated as desired. For example, the number of instances of each peptide, pattern, or motif is tabulated, and divided by the number predicted to occur by random chance according to established probability methods.

In some embodiments, the method is used to provide a diagnosis. A predetermined disease-specific peptide, pattern, or motif indicative of the disease can be determined using the methods herein. To diagnose a subject, the peptide signature for the sample from the subject is compared to a predetermined peptide signature of interest. If the enrichment of the appropriate peptide, pattern, or motif is increased beyond an established threshold, then the individual can be diagnosed with disease. An enrichment threshold can be appropriately determined by determination of the enrichments and their standard deviation within a set of samples from individuals that do not have disease and a separate set with disease (i.e. a reference set). A threshold value can be chosen to provide the desired balance between sensitivity and specificity.

The Examples herein provide a number of examples wherein the methods of the invention were used to determine peptide signatures for various disease settings. For instance, Example 1 provides an application of the methods of the invention to Celiac disease (CD). As further described in the Example, a disease specific motif was identified from a set of 16 CD samples and 13 healthy controls. For the motif QPXXPFX[ED] (SEQ ID NO: 4), a threshold enrichment value that maximizes specificity (100%) and sensitivity (95%) is enrichment >11. Accordingly, if a motif is observed in a test sample with an Enrichment value of 11 or more, the individual may be diagnosed with CD. Diagnostic sensitivity and specificity may be further improved by combining multiple motifs. A set or panel of four motifs (QXXXPF[PS]E (SEQ ID NO: 6), PFSEM (SEQ ID NO: 7), PFSEX[FW] (SEQ ID NO: 8), QPXXPFX[ED] (SEQ ID NO: 4) correctly identifies all disease and control samples in both discovery and validation datasets FIG. 5.

The accuracy of detection of an antibody specificity can be improved be increased by combining the enrichment values of two or more sequences, patterns, or motifs in a linear, non-linear, or weighted average.

Combining Diagnostic Assays into One Test

In an aspect, the present invention enables combination or aggregation of multiple assays into one multiplexed assay. The invention may achieve such multiplex analysis without additional labor or cost. Combining assays can be accomplished by performing searches of the peptide signature with two or more disease specific motif sets. For example, one can use the Celiac Disease specific peptides or motifs selected from QXXXPF[PS]E (SEQ ID NO: 6), PFSEM (SEQ ID NO: 7), PFSEX[FW] (SEQ ID NO: 8), QPXXPFX[ED] (SEQ ID NO: 4) alone or in combination with an arbitrary number of motifs or motif panels associated with other diseases. As a further example, the invention can be used to simultaneously assess a sample for infection with *Borrelia burgdorferi*, *Babesia* sp., *Anaplasma* sp., *Ehrlichia* sp, *Toxoplasma gondii*, *Toxocara canis*, *Taenia solium*, *Trypanosoma cruzi*, HIV, Epstein-Barr virus infection, Zika virus infection and any other condition associated with an antibody response. In such cases, the enrichment of each the disease specific motifs for each disease can be calculated in same manner as for a single disease. An arbitrary number of enrichment calculations can be performed with a given sample. All enrichments that exceed diagnostic thresholds can then be used to make a diagnosis. Accordingly, the compositions and methods of the invention can be used to screen individuals for the presence of various conditions, such as autoimmune diseases and/or infectious agents, in a single assay.

Identification of Peptides, Patterns, and Motifs that Correspond to Known Individual Biomarkers The diagnosis of many individual autoimmune diseases is aided by separate individual tests or panels that detect the presence of common autoantibodies. For example, there are individual tests available for anti-nuclear antibody (ANA), Rheumatoid factor, anti-double stranded DNA antibody (anti-dsDNA), anti-citrulinated peptide (CP), anti-actin antibody, anti-neutrophil cytoplasmic antibody (ANCA) and others. The present invention provides a means to identify peptides, patterns, and motifs that indicate whether one or more of these common autoantibodies is present.

Briefly, one or more samples is analyzed by display-seq as described herein, with and without physical depletion of the target antibody species. For example, to identify motifs that correspond to the known antigen SS-A/Ro, or SS-B/La, a sample demonstrated to containing these antibodies is incubated with cells that display peptides containing putative known antigen motifs (e.g., motif presence is equivalent with SS-A positivity), to affect depletion of antibodies that bind to the known antigen. The original and the depleted samples can be assayed for the presence of antibodies that bind to the known target antigen. Cells displaying motifs that remove, attenuate, or reduce the antigen specific signal (e.g., Absorbance, light emitted, radioactivity, etc) indicate the motif that corresponds to the known antigen.

Identification of Peptides, Patterns, and Motifs that Indicate the Presence of an Autoimmune Disease Autoantibodies have been implicated in a variety of autoimmune diseases and disorders. The type of autoimmune condition and amount of injury to the host organism depend upon the systems and organs targeted by the autoantibodies. In some cases, autoimmune disorders are caused by autoantibodies that primarily affect a single organ and are relatively easier to diagnose and the signs and systems of disease are related to that organ. Examples include targeting of the thyroid in Graves disease or Hashimoto thyroditis. However, other diseases and disorder may be caused by systemic autoantibodies that effect multiple systems and organs, making such conditions much harder to diagnose. Patients may present with non-specific symptoms such as joint pain, fatigue, fever, rash, cold symptoms, weight loss and muscular weakness. In addition, certain diseases, including Crohn's disease, Lupus, Sjogren's syndrome, and mixed connective tissue disease, are diagnosed using biomarkers that indicate a disease is present but do not identify which disease is present. Examples of such non-specific antibody biomarkers include nuclear antibody (ANA), rheumatoid factor, anti-actin antibody, anti-neutrophil cytoplasmic antibody (ANCA), anti-SS-A, and anti-SS-B. Even though diagnostics to detect these biomarkers may not identify specific disease, they are a useful aid to clinicians, suggesting that further testing and diagnostic work-up should be performed. Even so, some of these tests are cumbersome to perform, and lack quantitative precision, or require a pathologist to determine the staining pattern for example for ANA or ANCA tests.

The present invention provides a means to identify peptides motifs and patterns that indicate an autoimmune disease is present, providing quantitative objective rationale for further testing. The invention therefore provides meaningful benefits over the other above mentioned testing because the invention allows multiple tests to be performed quickly, automatically, and quantitatively for a given sample using the disease specific motifs.

Peptide Signatures and Motifs

The present invention provides compositions and methods to determine signatures of antigenic peptides in a sample comprising a plurality of antibodies. The methods of the invention further comprise determining peptide motifs from a peptide signature. Such peptide signatures and motifs can be used to characterize a phenotype in a sample, such as detecting the presence of a medical condition in order to provide a diagnosis. In some cases, the motifs determined by the subject methods may be correlated with various antigens involved in the disease process. For example, a motif determined by the subject methods may be correlated with a peptide from an allergenic protein or a self-antigen in case of autoimmune conditions.

In an aspect, the invention provides peptides and peptide motifs that are indicative of various conditions. Such peptides motifs are disclosed herein. For example, motifs indicative of various conditions are disclosed in the Examples.

In some embodiments, motifs that are indicative of mononucleosis by Epstein Barr Virus (EBV) infection are any one or more of LFGxx[LM]N(SEQ ID NO: 9); GELxGQ, (SEQ ID NO: 852); EWVxx[YF]D (SEQ ID NO: 10), P[LM]ALxL (SEQ ID NO: 11), KxNExWxV (SEQ ID NO: 12), P[AG]xRTxK (SEQ ID NO: 13), AYTxVN(SEQ ID NO: 14), WN[AS]YxxxN(SEQ ID NO: 15), [RKE]xxWxP[LM]Q (SEQ ID NO: 16), [AS]YxSx[SA][YF](SEQ ID NO: 17), ExYxSPS (SEQ ID NO: 18), MNIxDD (SEQ ID NO: 19), EH[ANK]FW (SEQ ID NO: 20), VHNAY(SEQ ID NO: 21), HG[EA]xLN(SEQ ID NO: 22), [GD]xx[LF]xxP[ML]Q (SEQ ID NO: 23), [LVMI]xNAx[TS][FGI](SEQ ID NO: 24), PxNSYT (SEQ ID NO: 25), RxxPLAxxL (SEQ ID NO: 26), CPKxNxT (SEQ ID NO: 27), Q[PA]H[AM]F (SEQ ID NO: 28), PAxENxxx[GSP] (SEQ ID NO: 29), NID[DE]D (SEQ ID NO: 30), RxQx[VS]D[NA] (SEQ ID NO: 31), Wx[DP]PxHL (SEQ ID NO: 32), TWA[FI][FI] (SEQ ID NO: 33), EDxGHP (SEQ ID NO: 34), [ETA]xxx[YF]xxP[SR]Q (SEQ ID NO: 35), GMxP[RK]Q (SEQ ID NO: 36), Wxx[VI]RxxPxQ (SEQ ID NO: 37), [NE][AG]Y[SAT]xxW (SEQ ID NO: 38), KxI[ST]xYW (SEQ ID NO: 39), YYxY-RxxK (SEQ ID NO: 40), KxHExG[FY] (SEQ ID NO: 41), [MLF]xNPQQ (SEQ ID NO: 853); HHFL[VI] (SEQ ID NO: 42), [LV]CNAY (SEQ ID NO: 43) or combinations thereof.

In some embodiments, peptides indicative of mononucleosis by EBV infection are any one or more of LFGanLN (SEQ ID NO: 44), PGpRTcK (SEQ ID NO: 45), PArRTrK (SEQ ID NO: 46), IaNAgSI (SEQ ID NO: 47), WaqIRhiPyQ (SEQ ID NO: 48) or MrNPQQ (SEQ ID NO: 49) or combinations thereof.

In some embodiments, motifs that are indicative of Rhinovirus infection are any one or more of L[EDQ]EV[LIV][IV][DE]K (SEQ ID NO: 50), E[VI][VIL][IV][DEN]K (SEQ ID NO: 51), E[VI][VI][VI]XK (SEQ ID NO: 52), VXPNI (SEQ ID NO: 53), VVPN (SEQ ID NO: 54), LXEVLVVVP (SEQ ID NO: 55), GPXHTXKV (SEQ ID NO: 56), EXY[VI]DX[VT]LN (SEQ ID NO: 57) or combinations thereof.

In some embodiments, peptides indicative of Rhinovirus infection are any one or more of ELEEV[IV]VDK (SEQ ID NO: 58), LNEVLVVVPNI (SEQ ID NO: 59), GPKHTQKV (SEQ ID NO: 60), EEYVDQVLN (SEQ ID NO: 61) or combinations thereof.

In some embodiments, motifs that are indicative of Cytomegalovirus infection are any one or more of KXDPDXXW[ST] (SEQ ID NO: 62) or KPXLGGK (SEQ ID NO: 63) or combinations thereof.

In some embodiments, peptides indicative of Cytomegalovirus infection include the set of peptides specified by KXDPDXXWT (SEQ ID NO: 64); (i.e. some positions vary between different strains of CMV), and KPtLGGK (SEQ ID NO: 65) or combinations thereof.

In some embodiments, motifs that are indicative of *Streptococcus* infection are any one or more of [IV]X[PR]QPEKP (SEQ ID NO: 66), KXDDMLN (SEQ ID NO: 67), KXDX-MLN (SEQ ID NO: 68), LW]XSAEXEEK (SEQ ID NO: 69), SAEXEXK (SEQ ID NO: 70) or combinations thereof.

In some embodiments, peptides that are indicative of *Streptococcus* infection are any one or more of VKPQPEKP (SEQ ID NO: 71), KTDDMLN (SEQ ID NO: 72), LESAE-KEEK (SEQ ID NO: 73) or combinations thereof.

In some embodiments, motifs that are indicative of *Toxoplasma gondii* infection are any one or more of HExE[FY]Q (SEQ ID NO: 74), LD[MLF]WxE (SEQ ID NO: 75), HCSAC (SEQ ID NO: 76), [FY]xGVVN (SEQ ID NO: 77), KxxxGRGxI (SEQ ID NO: 78), GPH[LA]E (SEQ ID NO: 79), PRREP (SEQ ID NO: 80), CNxxxECY (SEQ ID NO: 81), KxCQPxxC (SEQ ID NO: 82), PxPD[FH][TS] (SEQ ID NO: 83), NxxxExY[AG]xD (SEQ ID NO: 84), P[AG]AxxLD (SEQ ID NO: 85), MPSxSxE (SEQ ID NO: 86), [RK]xYxHR[TS] (SEQ ID NO: 87), K[PA]xFxFxK (SEQ ID NO: 88), DD[CST]xGxR (SEQ ID NO: 89), P[ML]

xxHxMY (SEQ ID NO: 90), Kx[ASQ][SAT]xRG (SEQ ID NO: 91), [DG]QPEN (SEQ ID NO: 92), [KHR]N[QN]DG (SEQ ID NO: 93), Nx[EVS]GExY (SEQ ID NO: 94), EP[VI]TG (SEQ ID NO: 95), HGM[PA][KR] (SEQ ID NO: 96), [VIT]PWIF (SEQ ID NO: 97), Kx[STN]VxFQ (SEQ ID NO: 98), [VAI]WSGS (SEQ ID NO: 99), FS[LIAM]xxWG (SEQ ID NO: 100), PTN[PQ]G (SEQ ID NO: 101), [RK]Kxx[YW]xHx[TS] (SEQ ID NO: 102), [HRW]xxHPRF (SEQ ID NO: 103) or combinations thereof.

In some embodiments, motifs that are indicative of *Trypanosoma cruzi* infection (Chagas disease) are any one or more of [RK]MRxID (SEQ ID NO: 104), QHxGHP (SEQ ID NO: 105), KxxLPED (SEQ ID NO: 106), [IV]LxxFGY (SEQ ID NO: 107), PLDxxxxIS (SEQ ID NO: 108), ETXIPXE (SEQ ID NO: 109), [VI]Nx[DE][ML]YxP (SEQ ID NO: 110), FLxxIGA (SEQ ID NO: 111), D[VI]x[MI][ILV]x[KR] (SEQ ID NO: 112), RxSPYx[IL]F (SEQ ID NO: 113), VGPRH (SEQ ID NO: 114), PQxQH[ED] (SEQ ID NO: 115), PxxGGFG (SEQ ID NO: 116), KxEGxxMG (SEQ ID NO: 117), KxxGxTxxLS (SEQ ID NO: 118), EMG[FW]Q (SEQ ID NO: 119), [VI]KxGxxDxP (SEQ ID NO: 120), PE[DN]ExYP (SEQ ID NO: 121), HYEWA (SEQ ID NO: 122), [HR]SNMxF (SEQ ID NO: 123), M[TV]GxxYE (SEQ ID NO: 124), Dxx[KH]ExxLL (SEQ ID NO: 125), RxxWx[EDA]x[IV][AR] (SEQ ID NO: 126), PxDxxAx[GPA][TS] (SEQ ID NO: 127), PDxxSxT[ARG] (SEQ ID NO: 128), GRExDG (SEQ ID NO: 129), GVPGxxxK (SEQ ID NO: 130), [LM]xxx[EDQ]VxxIM (SEQ ID NO: 131), SxxxVSGG (SEQ ID NO: 132), A[KR]AG[DN]K (SEQ ID NO: 133), F[RN]xIN[RQ] (SEQ ID NO: 134), YXPVXPXSY (SEQ ID NO: 135), KxTFPD (SEQ ID NO: 136), PFM[FVM]xxR (SEQ ID NO: 137), EFWEP (SEQ ID NO: 138), [FY]GALS (SEQ ID NO: 139), PxGTEN (SEQ ID NO: 140), Gx[KE]PWE (SEQ ID NO: 141), D[IV]Tx[YF][WN] (SEQ ID NO: 142) or combinations thereof.

In some embodiments, peptides are indicative of *Trypanosoma cruzi* infection (Chagas disease) are any one or more of QHkGHP (SEQ ID NO: 143), QHiGHP (SEQ ID NO: 144), KalLPED (SEQ ID NO: 145), KkhLPED (SEQ ID NO: 146), KitLPED (SEQ ID NO: 147), KtiLPED (SEQ ID NO: 148), KvlLPED (SEQ ID NO: 149), VLkkFGY (SEQ ID NO: 150), VLhlFGY (SEQ ID NO: 151), VLgeFGY (SEQ ID NO: 152), VLepFGY (SEQ ID NO: 153), PLDvekeIS (SEQ ID NO: 154), PLDllkyIS (SEQ ID NO: 155), ETkIPsE (SEQ ID NO: 156), ETeIPsE (SEQ ID NO: 157), ETgIPfE (SEQ ID NO: 158), VNvDLYiP (SEQ ID NO: 159), FLgaIGA (SEQ ID NO: 160), FLlfIGA (SEQ ID NO: 161), FLkaIGA (SEQ ID NO: 162), DIkMIeR (SEQ ID NO: 163), DIiIVsR (SEQ ID NO: 164), DVhMLvR (SEQ ID NO: 165), DVdILeR(SEQ ID NO: 166), RvSPYsIF (SEQ ID NO: 167), VGPRH (SEQ ID NO: 168), PQkQHE (SEQ ID NO: 169), PQgQHD (SEQ ID NO: 170), KsEGefMG (SEQ ID NO: 171), KdEGlaMG (SEQ ID NO: 172), KdnGsTwsLS (SEQ ID NO: 173), KddGsTwaLS (SEQ ID NO: 174), IKqGrlDrP (SEQ ID NO: 175), HYEWA (SEQ ID NO: 176), MVGehYE (SEQ ID NO: 177), MVGkaYE (SEQ ID NO: 178), DqlKEgrLL (SEQ ID NO: 179), DvvKElmLL (SEQ ID NO: 180), DleKEneLL (SEQ ID NO: 181), DldKEvsLL (SEQ ID NO: 182), RhqWyAvVA (SEQ ID NO: 183), RhsWfDdVR (SEQ ID NO: 184), RkeWyDvVA (SEQ ID NO: 185), RdrWtEsIA (SEQ ID NO: 186), RatWlDqVR (SEQ ID NO: 187), RyvWnEwVA (SEQ ID NO: 188), PvDstAhGT (SEQ ID NO: 189), PlDcpAlGS (SEQ ID NO: 190), PaDssAhGT (SEQ ID NO: 191), PkDvkAtGS (SEQ ID NO: 192), PpDvsAsGT (SEQ ID NO: 193), PgDlpAkAT (SEQ ID NO: 194), PaDvsAqAT (SEQ ID NO: 195), PpDvpAsGT (SEQ ID NO: 196), PDpaSiTA (SEQ ID NO: 197), PDasSsTA (SEQ ID NO: 198), PDsrSiTA (SEQ ID NO: 199), PDsrSvTA (SEQ ID NO: 200), PDskSpTA (SEQ ID NO: 201), PDseSpTA (SEQ ID NO: 202), GREsDG (SEQ ID NO: 203), GREaDG (SEQ ID NO: 204), GVPGshaK (SEQ ID NO: 205), GVPGcviK (SEQ ID NO: 206), LsprEVytIM (SEQ ID NO: 207), LtntDVtrIM (SEQ ID NO: 208), LedeDVlqIM (SEQ ID NO: 209), MadpEVaaIM (SEQ ID NO: 210), SqadVSGG (SEQ ID NO: 211), SvgsVSGG (SEQ ID NO: 212), SpsgVSGG (SEQ ID NO: 213), SwfdVSGG (SEQ ID NO: 214), FRiINQ (SEQ ID NO: 215), FRaINR (SEQ ID NO: 216), KqTFPD (SEQ ID NO: 217), KaTFPD (SEQ ID NO: 218), PFMVqmR (SEQ ID NO: 219), FGALS (SEQ ID NO: 220), YGALS (SEQ ID NO: 221), PsGTEN (SEQ ID NO: 222), GfKPWE (SEQ ID NO: 223), DITdYN (SEQ ID NO: 224), DVTgFN (SEQ ID NO: 225) or combinations thereof.

In some embodiments, motifs that are indicative of *Taenia solium* (Cysticercosis) infection are any one or more of AxSPN[QEA] (SEQ ID NO: 226), [RP]xAxSxNx[IFMLV] (SEQ ID NO: 227), PDxGVxP (SEQ ID NO: 869); NxxLGL[VT] (SEQ ID NO: 228), [YF]x[DE]IxxFF (SEQ ID NO: 229), IxHFFxG (SEQ ID NO: 230), [ILM][ILM][RK]H[ED]XQ (SEQ ID NO: 231), [ILM][RK]HExQ (SEQ ID NO: 232), KPxx[IL]xLx[KR] (SEQ ID NO: 233), NxDxxYYxx[WF] (SEQ ID NO: 234), GLDGP (SEQ ID NO: 235), RSxHDxxN (SEQ ID NO: 236), FDxFN[IL] (SEQ ID NO: 237), TIFxGK (SEQ ID NO: 238), R[AV]xS[TQ]H (SEQ ID NO: 239), KWHGxY (SEQ ID NO: 240), MPEDK (SEQ ID NO: 241), Exxx[FY]x[AS]D[NT] (SEQ ID NO: 242), NQSxxKx[VI] (SEQ ID NO: 243), KxY[NAS]PY (SEQ ID NO: 244), [PQ][VL]HPRI (SEQ ID NO: 245), EDGMxxW (SEQ ID NO: 246), YASXQE (SEQ ID NO: 247), KQxQ[QK]E (SEQ ID NO: 248), K[AS]VFD[IVM] (SEQ ID NO: 249), PN[QE]x[DN]P (SEQ ID NO: 250), P[QA]XM[DN]I (SEQ ID NO: 251), [WR]x[RKH][ST]xFD (SEQ ID NO: 252), KxEPGxK (SEQ ID NO: 253), DDCLP (SEQ ID NO: 254), NXXXXGXHLE (SEQ ID NO: 255), DxxHLEG (SEQ ID NO: 256), RPxx[TS]HN (SEQ ID NO: 257), KxHS[IV]Y (SEQ ID NO: 258), KxHSx[IV]S (SEQ ID NO: 259), MSGYE (SEQ ID NO: 260), YXIWGP (SEQ ID NO: 261), RxxWxMN[RK] (SEQ ID NO: 262), QPxxT[FY]E (SEQ ID NO: 263), YGYNQ (SEQ ID NO: 264) or combinations thereof.

In some embodiments, peptides that are indicative of *Taenia solium* (Cysticercosis) infection are any one or more of ArSPN (SEQ ID NO: 265), AgSpNri (SEQ ID NO: 266), PDgGVmP (SEQ ID NO: 267), NpkLGLT (SEQ ID NO: 268) or combinations thereof.

In some embodiments, motifs that are indicative of latent Epstein-Barr virus (EBV) are any one or more of GRRPFF (SEQ ID NO: 269), GGGxGAGGG (SEQ ID NO: 270), EG[PA]ST[GA]R (SEQ ID NO: 271), KXXSC[IVL]GC[RK] (SEQ ID NO: 272), SCIGCK (SEQ ID NO: 273), CIGC (SEQ ID NO: 274), VxLPHW (SEQ ID NO: 275), LPHW (SEQ ID NO: 276), PQDT[GA]PR (SEQ ID NO: 277), GPPWWP (SEQ ID NO: 278), QQPTTXGW (SEQ ID NO: 279), [LMIV]FDXDWYP (SEQ ID NO: 280) or combinations thereof.

In some embodiments, peptides that are indicative of latent Epstein-Barr virus (EBV) are any one or more of GRRPFF (SEQ ID NO: 281), GGGAGAGGG (SEQ ID NO: 282), EGPSTGPR (SEQ ID NO: 283), KRPSCIGCK (SEQ ID NO: 284), KEVKLPHWTPT (SEQ ID NO: 285), PQDTAPR (SEQ ID NO: 286), GPPWWP (SEQ ID NO: 287), QQPTTEGH (SEQ ID NO: 288), LFPDDWYP (SEQ ID NO: 289) or combinations thereof.

In some embodiments, motifs that are indicative of HIV infection are any one or more of CxGxLIC(SEQ ID NO: 290), CxxKx[IV]C[IV] (SEQ ID NO: 291), W[GAS]CxGxxxC (SEQ ID NO: 292), [RK]KL[IV]E (SEQ ID NO: 293), KLIMT (SEQ ID NO: 294), [QE]xxPFRY (SEQ ID NO: 295), CxxKx[IV]C[IV] (SEQ ID NO: 296), [LF]xx[LIV][ND]KW (SEQ ID NO: 297), [AP][GC]GFG (SEQ ID NO: 298), LIx[TS]TY (SEQ ID NO: 299), [RK]KLxx[MV]Y (SEQ ID NO: 300), GF[GA][AQ][AYV] (SEQ ID NO: 301), GFG[RQ]x[FNY] (SEQ ID NO: 302), [KR]KxIH[VIM] (SEQ ID NO: 303), R[IV]PFG (SEQ ID NO: 304), KLIxx[TY]T (SEQ ID NO: 305) or combinations thereof.

In some embodiments, peptides that are indicative of HIV infection are any one or more of CSGKLICT (SEQ ID NO: 306), CSGKLICT (SEQ ID NO: 307), WGCSGKLIC (SEQ ID NO: 308), CSGKLICT (SEQ ID NO: 309), LLALDKW (SEQ ID NO: 310), AVGMG (SEQ ID NO: 311), LICTT (SEQ ID NO: 312), GFGAV (SEQ ID NO: 313), RKgIrI (SEQ ID NO: 314), KKgIaI (SEQ ID NO: 315), RKgIhM (SEQ ID NO: 316), RKsIhM (SEQ ID NO: 317), KLICTT (SEQ ID NO: 318) or combinations thereof.

In some embodiments, IgG motifs that are indicative of a Zika virus infection are any one or more of VRxxYxQH (SEQ ID NO: 319), CEDxxxHxC (SEQ ID NO: 320), DAEQxxR (SEQ ID NO: 321), WPGIF (SEQ ID NO: 322), CCYDXE (SEQ ID NO: 323), LxPDNxT (SEQ ID NO: 324), FxWGQxY (SEQ ID NO: 325), KxEGHxxxxA (SEQ ID NO: 326), CxxGxCQxK (SEQ ID NO: 327), CCxDxx[DE][ED] (SEQ ID NO: 328), RNGxED (SEQ ID NO: 329), [DE]xRxxIYxQ (SEQ ID NO: 330), WxRCGL (SEQ ID NO: 331), D[ED]xRxxYxxH (SEQ ID NO: 332), WCxLx[AV]N (SEQ ID NO: 333), LXTPWI (SEQ ID NO: 334), CWxxxGL[CA] (SEQ ID NO: 335), ID[AV]EP (SEQ ID NO: 336), HF[NK][VT]xK (SEQ ID NO: 337), QxNHQxK (SEQ ID NO: 338) or combinations thereof.

In some embodiments, IgM motifs that are indicative of a Zika virus infection are any one or more of FExKEP (SEQ ID NO: 339), [FYW]DA[VI] (SEQ ID NO: 340), DFDKR (SEQ ID NO: 341), WETC (SEQ ID NO: 342), KLDGP (SEQ ID NO: 343), WIYPxK (SEQ ID NO: 344), V[HS]DSK (SEQ ID NO: 345), EQCGT (SEQ ID NO: 346), [KE][MVIT]PYA (SEQ ID NO: 347), [DE]xxML[RP]W (SEQ ID NO: 348), YExLHx[FY] (SEQ ID NO: 349), WY[TSN]xEK (SEQ ID NO: 350), [YF][H[DNS]AV (SEQ ID NO: 351), DxTG[VI]P (SEQ ID NO: 352), FDxxGEH (SEQ ID NO: 353), QC[AK]xx[HE]C (SEQ ID NO: 354), LW[FY]xPxE (SEQ ID NO: 355), C[MI][PA]GxxC (SEQ ID NO: 356), Cxxxx[AVS]ADC(SEQ ID NO: 357), TTESxV (SEQ ID NO: 854), KDV[GA]E (SEQ ID NO: 855), KPxD[FWM]GxK (SEQ ID NO: 856), VxADGT (SEQ ID NO: 857), M[AP][AT]AD (SEQ ID NO: 858), VPxPK[DG](SEQ ID NO: 859), QxKP[TS]D (SEQ ID NO: 860), F[TS]xDGF (SEQ ID NO: 861), Wx[RK][VY][VA] (SEQ ID NO: 862), [CS][T][TS]Exxx[YF](SEQ ID NO: 863), YxETC[TI](SEQ ID NO: 864) or combinations thereof.

In some embodiments, motifs that are indicative of Borrellia burdorferi infection (Lyme disease) are any one or more of VQQExxxxxP (SEQ ID NO: 358), QQEGxxxx[YC] (SEQ ID NO: 359), QEG[IV]Q (SEQ ID NO: 360), G[IV]QxEG (SEQ ID NO: 361), [LI]xxA[ILV]xxRG (SEQ ID NO: 362), [ATNSD]xxxxAI[LAM]xR (SEQ ID NO: 363), Ix[LM]xGFxK (SEQ ID NO: 364), LxGM[RQ]K (SEQ ID NO: 365), [HR]xDxTNxF (SEQ ID NO: 366), [DA]DPTN (SEQ ID NO: 367), [KR]x[DE]xTNxF (SEQ ID NO: 368), [ET][ML]HKF (SEQ ID NO: 369), [ML]xxEFHK (SEQ ID NO: 370), Q[TI]EQxxxxxK (SEQ ID NO: 371), DxSP[IL]E (SEQ ID NO: 372), PFx[AP]YxK (SEQ ID NO: 373), VxxYFxx[LV]xK (SEQ ID NO: 374), KxVDxDR (SEQ ID NO: 375), [DN][AS]A[AG]F (SEQ ID NO: 376), Cx[NA]xKFC (SEQ ID NO: 377), Kx[GRST]AE[YF] (SEQ ID NO: 378), HQV[PA]xxx[DHE] (SEQ ID NO: 379), IPxxV[IF]xxR (SEQ ID NO: 380), Cx[ALT]xWEx[CA] (SEQ ID NO: 381), CxxxCA[IL]xxR (SEQ ID NO: 382), I[IV]Ixx[MT]xK (SEQ ID NO: 383), QG[ITL]x[KN][FY] (SEQ ID NO: 384), KxxPPxIN (SEQ ID NO: 385), G[YF][FY]FxxK (SEQ ID NO: 386), DKNVx[IV] (SEQ ID NO: 387), [QE][KR][ND]xSG (SEQ ID NO: 388), K[RK]PGD (SEQ ID NO: 389), EGAxQP (SEQ ID NO: 390), GSPEY (SEQ ID NO: 391) or combinations thereof.

In some embodiments, peptides that are indicative of Borellia burdorferi infection (Lyme disease) are any one or more of VQQEgaqqqP (SEQ ID NO: 392), QEGVQ (SEQ ID NO: 393), GVQqEG (SEQ ID NO: 394), IlkAVveRG (SEQ ID NO: 395), IaaAIvlRG (SEQ ID NO: 396), DqiaaAIAlR (SEQ ID NO: 397), AkkmrAlLvR (SEQ ID NO: 398), AenhkAlLfR (SEQ ID NO: 399), IkLpGFkK (SEQ ID NO: 400), IfLeGFlK (SEQ ID NO: 401), LrGMRK (SEQ ID NO: 402), DDPTN (SEQ ID NO: 403), KtDrTNdF (SEQ ID NO: 404), KdDpTNkF (SEQ ID NO: 405), KtDrTNdF (SEQ ID NO: 406), TLHKF (SEQ ID NO: 407), QTEQsststK (SEQ ID NO:408), DISPIE (SEQ ID NO: 409), PFsAYiK (SEQ ID NO: 410), VkdYFdsLaK (SEQ ID NO: 411), DAAAF (SEQ ID NO: 412), KfRAEF (SEQ ID NO: 413), KsSAEF (SEQ ID NO: 414), KgGAEF (SEQ ID NO: 415), IIIidTsK (SEQ ID NO: 416), IIIngMtK (SEQ ID NO: 417), IIItnMeK (SEQ ID NO: 418), QGENY (SEQ ID NO: 419), QGIcNY (SEQ ID NO: 420), KetPPaLN (SEQ ID NO: 421), GFYFifK (SEQ ID NO: 422), DKNVkI (SEQ ID NO: 423), EKNsSG (SEQ ID NO: 424), KKPGD (SEQ ID NO: 425), EGAqQP (SEQ ID NO: 426), GSPEY (SEQ ID NO: 427) or combinations thereof.

In some embodiments, peptides that are indicative of Toxoplasma gondii infection are any one or more of HEhEFQ (SEQ ID NO: 428), LDFWrE (SEQ ID NO: 429), LDFWqE (SEQ ID NO: 430), LDMWeE (SEQ ID NO: 431), HCSAC (SEQ ID NO: 432), FsGVVN (SEQ ID NO: 433), YpGVVN (SEQ ID NO: 434), KgshGRGfI (SEQ ID NO: 435), GPHAE (SEQ ID NO: 436), PRREP (SEQ ID NO: 437), PvPDFS (SEQ ID NO: 438), PvPDFT (SEQ ID NO: 439), PlPDFT (SEQ ID NO: 440), PlPDFS (SEQ ID NO: 441), PaPDFS (SEQ ID NO: 442), NaglEvYAeD (SEQ ID NO: 443), NrrrErYGeD (SEQ ID NO: 444), PGAvlLD (SEQ ID NO: 445), PAAskLD (SEQ ID NO: 446), PAAesLD (SEQ ID NO: 447), PGAarLD (SEQ ID NO: 448), PGAldLD (SEQ ID NO: 449), MPSwSnE (SEQ ID NO: 450), MPStSdE (SEQ ID NO: 451), MPSeStE (SEQ ID NO: 452), MPSaSpE (SEQ ID NO: 453), RlYvHRS (SEQ ID NO: 454), RlYrHRT (SEQ ID NO: 455), KgYfHRT (SEQ ID NO: 456), KPpFeFgK (SEQ ID NO: 457), KPgFvFlK (SEQ ID NO: 458), DDSeGaR (SEQ ID NO: 459), DDScGrR (SEQ ID NO: 460), DDSkGdR (SEQ ID NO: 461), DDSsGyR (SEQ ID NO: 462), KeAAgRG (SEQ ID NO: 463), KdASlRG (SEQ ID NO: 464), KgSSgRG (SEQ ID NO: 465), KtSSrRG (SEQ ID NO: 466), KtQTvRG (SEQ ID NO: 467), KrSTlRG (SEQ ID NO: 468), DQPEN (SEQ ID NO: 469), GQPEN (SEQ ID NO: 470), KNNDG (SEQ ID NO: 471), RNNDG (SEQ ID NO: 472), NIVGEeY (SEQ ID NO: 473), NdSGEiY (SEQ ID NO: 474), EPVTG (SEQ ID NO: 475), HGMPK (SEQ ID NO: 476), HGMAK (SEQ ID NO: 477), VPWIF (SEQ ID NO: 478), KsSVpFQ (SEQ ID NO: 479), KeTVnFQ (SEQ ID NO: 480), VWSGS (SEQ ID NO: 481), IWSGS (SEQ ID NO: 482), FSLenWG (SEQ ID NO: 483), FSMgrWG (SEQ ID NO: 484), FSLvlWG (SEQ ID NO: 485), FSLvlWG (SEQ ID NO: 486), FSLtnWG (SEQ ID NO: 487), PTNQG (SEQ ID NO: 488), PTNPG (SEQ ID NO: 489), RKlhWnHrT (SEQ ID NO: 490), KKyrYrHpT (SEQ ID NO: 491), RKavYqHnT (SEQ ID NO: 492), RtlHPRF (SEQ ID NO: 493), HfrHPRF (SEQ ID NO: 494), RvaHPRF (SEQ ID NO: 495), WqaHPRF (SEQ ID NO: 496) or combinations thereof.

In a related aspect, the invention provides peptide display libraries. The peptide library may comprise random peptide libraries that can be used to identity peptide signatures and motifs. See, e.g., FIG. 1. In other embodiments, the peptide library may be configured to detect previously identified peptide signatures and motifs. See, e.g., FIG. 2A and FIG. 2B. Such peptide libraries may comprise one or more of the motifs described in the paragraph above.

Kits

Various compositions and reagents useful for the invention described herein may be provided in kit format. A kit may include, for instance, some or all of the components necessary to carry out the assays described herein. For instance, the kit may comprise buffers, antibody capture reagents (e.g., microbeads coupled to Protein A, Protein G, Protein L, or other anti-Ig antibody or aptamers), enzymes (e.g., for amplification and/or sequencing of nucleic acids), instructions and any other necessary or useful components. The components of the kit may be provided in any suitable form, including frozen, lyophilized, or in a pharmaceutically acceptable buffer such as TBS or PBS. The kit may also include a solid support containing a peptide display library (e.g., microorganisms such as *E. coli* that express a random peptide library or a peptide library configured for characterizing a phenotype of interest) in any suitable form. The kits may also include other reagents and/or instructions for carrying out assays such as, for example, flow cytometric analysis, ELISA, immunoblotting (e.g., western blot), and sequencing. Kits may also include components such as containers (e.g., tubes) and/or slides pre-formatted to containing control samples and/or reagents with additional space (e.g., tubes, slides and/or space on a slide) for experimental samples. The kit may also comprise one or both of an apparatus for handling and/or storing the sample obtained from the individual and an apparatus for obtaining the sample from the individual (i.e., a needle, lancet, and collection tube or vessel).

EXAMPLES

Below we present examples of the method to identify motifs and peptides useful for the diagnosis of disease. The present method can be applied to any condition wherein an adaptive immune response occurs including infectious, autoimmune, parasitic, allergic, oncological, neurological, cardiovascular, and endocrine diseases and disorders.

Example 1: Celiac Disease—Discovery and Validation of Diagnostic Motifs and Peptides Celiac disease (CD) is characterized by autoimmunity to wheat, barley and rye cereal grain proteins, leading to antibody and T-cell mediated attack of the small intestinal epithelium, and damage to the villi. The resultant damage impairs adsorption of essential nutrients. Two distinct antibody specificities or types are individually diagnostic for the presence of CD. Celiac disease is diagnosed by the presence of IgA autoantibodies towards the human tissue transglutaminase antigen TG2, or alternatively by the presence of IgA and/or IgG antibodies towards deamidated gliadin peptide epitopes of wheat barley and rye proteins. Diagnostic criteria currently require small intestinal biopsy to confirm disease. The only available treatment is a strict gluten-free diet.

Patient Samples

A total of 32 celiac disease and 28 control serum samples (500 μl/sample) were analyzed. Patients were diagnosed with active celiac disease based on symptoms and gluten challenge testing, as well as using a positive result from 1 of the following criteria: 1) small intestinal biopsies with a Marsh 3a-3c histological lesion, and 2) seropositive for tissue transglutaminase 2 (TG2) and/or endomysial antigen (EMA) autoantibodies. Healthy individuals were asymptomatic for celiac disease and tested seronegative for TG2 and EMA autoantibodies. Deamidated gliadin peptide (dGP) ELISA was also performed for the control and disease samples.

Sample CD92 was diagnosed as non-celiac after screening was completed therefore this sample was removed from the CD sample cohort for downstream analysis. After performing discovery, CD88 was also diagnosed as non-celiac, and having been treated with olmesartan.

Serum samples were stored at −80° C. and aliquoted to reduce freeze/thaw cycles. On the day of use, 32 μL were thawed for dilution and remaining serum was marked and re-frozen for future use. Sixteen celiac disease (including CD88) and thirteen control sera were used as an initial discovery set. The validation set consisted of fifteen celiac disease samples and fifteen control samples (i.e., non-CD).

Experimental Protocol for Celiac Disease Biomarker Discovery

A summary of the general processing and sequencing methods used for the celiac and control serum samples are detailed as follows:

1) Serum Depletion Step:

Antibodies targeting *E. coli* cells are removed by incubating serum diluted in PBS with an *E. coli* strain expressing the library scaffold alone. After an overnight incubation, the bacteria along with any bound antibodies are removed using centrifugation and collection of the supernatant (unbound antibodies).

2) Library Clearing Step:

Peptide libraries are first cleared of protein A and protein G binders by incubating the induced library with magnetic beads coated with protein A and protein G. Magnetic separation captures the beads along with any cells that are bound to the protein coating the beads. The unbound fraction is collected for screening for serum antibody binders.

3) Antibody Binding Step:

Collected (*E. coli* depleted) serum diluted in PBS is incubated with Protein A and G cleared cells expressing the peptide library. Antibodies from serum bound to expressed peptides on the cells are harvested using centrifugation followed by washing with PB ST to eliminate non-specific interactions.

4) Library Enrichment Step:

Washed cells are then incubated with magnetic beads coated with protein A and protein G to capture antibodies from the serum along with the cells expressing peptides the antibodies are interacting with. The beads are washed 5 times with PBS while magnetized to remove cells captured non-specifically.

6) Growth Step:

The final enriched library (bound to washed beads) is resuspended in Luria broth (LB) and the captured cells are allowed to grow overnight for replication.

7) Repeat Enrichment Step:

This serum antibody-library peptide enrichment step can be repeated a second time to further enrich for peptide members of the library that interact with antibodies from serum and reduce non-specific binding cells that may have come through the first round of the screen. However, a single enrichment step may be sufficient.

8) Enrichment Analysis Step:

After the second enrichment is completed, the final enriched library is analyzed by FACS to confirm and quantify binding of library members to patient serum antibodies.

9) DNA Isolation from Enriched Library Step:

Plasmid is isolated from the enriched library for each serum sample for preparation for deep sequencing analysis.

10) Amplicon Preparation Step:

The region of interest (random/peptide region from the library) is amplified using the plasmid as template with forward and reverse primers that flank the random region. The primers contain adaptors specific for use on the Illumina NextSeq next-generation sequencing platform (Illumina, Inc, San Diego, Calif.). The PCR product is cleaned using magnetic beads that bind DNA and the resulting product is subjected to a second PCR using primers specific to the adaptors from the first PCR. The primers are provided by the Illumina Nextera XT indexing kit. The second PCR primers contain 8 nucleotide indices to provide a unique index combination specific to the amplicon from each sample for tracking of the sample during the sequencing.

11) Amplicon Quality Control Step:

After cleaning the second PCR product, the purity is confirmed using gel electrophoresis and the quantity of the DNA is determined. Amplicons specific for the enriched libraries from all serum samples screened are normalized and pooled at equal molar concentrations for running on the NextSeq instrument.

12) Sequencing Step:

The amplicon pool is run on the NextSeq instrument through a paid service following instructions from the manufacturer (Illumina). A 75 cycle high-output flow cell is used with single read ("forward" direction) and dual indexing (both 5 prime and 3 prime indices are sequenced). After sequencing is complete, the samples are automatically de-multiplexed using imputed sample identities with Nextera XT indices. These specifications allow for approximately 300 million total indexed sequences per run.

13) Sequence De-Multiplexing Step:

Resulting sequences are de-multiplexed using the index codes to identify which serum samples the sequences originated from. Indexed sequences are sorted for each sample and subjected to bioinformatics analysis.

Sample Analysis Via Display-Seq.

Display-seq was used to identify millions of antibody-binding peptides per specimen as follows. A large high-quality 12-mer peptide library (diversity=$8 \times 10^9$), constructed using triplet-phosphoramidites to remove stop codons and normalize amino acid frequencies was used. The library is self-renewing, and ~100M unique peptides was determined to establish baseline statistics, thereby providing a long-term supply of stable, quantified diversity. Before peptide library selection, clinically characterized sera were depleted of E. coli binding antibodies using cells that display the scaffold without a peptide. Selections were performed as described [19, 20]. In brief, after library growth and induction of expression for display, antibody binding library members were enriched using two cycles of magnetic-activated cell sorting (MACS) to >85% pure binders as measured/confirmed using flow cytometry.

E. coli Specific Serum Antibody Depletion.

To remove E. coli binding antibodies from serum samples prior to library screening, an induced culture of cells expressing the library scaffold alone (eCPX) was incubated with diluted sera. Escherichia coli strain MC1061 [FaraΔ 139 D(ara-leu)7696 GalE15 GalK16 Δ (lac)X74 rpsL (StrR) hsdR2 (rK−mK+) mcrA mcrB1] was used with surface display vector pB33eCPX. eCPX cultures grown overnight at 37° C. with vigorous shaking (250 rpm) in LB (10 g tryptone, 5 g yeast extract, 10 g/L NaCl) supplemented with 34 µg/mL chloramphenicol (CM) and 0.2% glucose were collected by centrifugation, inoculated in fresh LB+CM, grown to an $OD_{600}$=0.6, and induced for 1 hr at 37° C. with 0.02% wt/vol L(+)-arabinose. After induction, the cells were centrifuged at 3,000 relative centrifugal force (rcf) for 5 min., washed once with cold PBST (PBS+0.1% Tween 20), and resuspended in 1 mL PBS containing serum diluted 1:25 ($1 \times 10^6$ cells per µL depletion sample). Samples were incubated overnight at 4° C. with gentle mixing on an orbital shaker (20 rpm). Antibodies that bound to E. coli or the eCPX scaffold were removed by centrifugation of the incubated culture at 5,000 rcf for 5 min. twice, recovering the serum supernatant after each centrifugation. The depleted serum was stored at 4° C. for up to 2 weeks during use.

Bacterial Display Library Screening.

An X12 bacterial display library was used to screen and isolate peptide binders to antibodies in individual serum samples through two rounds of selection.

First Round Selection Using Magnetic Assisted Cell Sorting (MACS):

The first selection round employed MACS to enrich the library for antibody binding peptides. A frozen aliquot of the $X_{12}$ library containing $1 \times 10^{11}$ cells (10× the expected diversity) was thawed and inoculated into 500 mL LB+CM. After growth to an $OD_{600}$=0.6 at 37° C. with 250 rpm shaking, the cells were induced with 0.02% wt/vol L(+)-arabinose for 1 hour using the same growth conditions. Cells ($1 \times 10^{11}$ per sample) were collected by centrifugation (3,000×g for 10 min.) and resuspended in 1 mL cold PBS. Prior to incubation with serum, cells were cleared of peptide clones that bind proteins A/G by incubating cells with washed protein A/G magnetic beads (Pierce) at a ratio of one bead per 50 cells for 45 min. at 4° C. with gentle mixing. Magnetic separation for 5 min. (×2) was used to recover the unbound cells. Recovered cells from the supernatant were centrifuged, resuspended in 500 µL diluted sera (1:25 in PBS), and incubated for 45 min. at 4° C. with gentle mixing. Following serum incubation, cells were washed by centrifugation, and resuspended in 1 mL cold PBST (×3). After the final resuspension, washed protein A/G magnetic beads were added at a ratio of one bead per 50 cells. After a 45 min. incubation with protein A/G beads at 4° C. with gently mixing, a second magnetic separation was performed to isolate cells expressing peptides that bind to serum antibodies. The supernatant (unbound cells) was discarded and the separated cells/beads were washed with 1 mL cold PBST. Five repeat washes were performed while the tube was being magnetized. After the last wash, the beads were resuspended in 1 mL of LB and inoculated into 25 mL LB+CM+glucose to suppress expression. The flask was grown overnight at 37° C. with shaking at 250 rpm. A 10 uL sample was removed prior to inoculation for dilution and plating on LB-agar to estimate the diversity of the enriched library.

Second Round Selection Using Magnetic Assisted Cell Sorting (MACS):

A second round of affinity selection was carried out using MACS to further enrich the library for antibody binding peptides. After overnight growth of the first round MACS enriched library, cells were inoculated (>20× estimated diversity) at 1:50 into 10 mL LB+CM and grown to an OD$_{600}$=0.6. After induction with arabinose for 1 hour, a volume of cells >20× the library diversity was centrifuged and resuspended in 100 μL cold PBST. Prior to incubation with serum, cells were cleared again of peptide clones that bind protein A/G by incubating cells with washed protein A/G magnetic beads (Pierce) at a ratio of one bead per cell for 45 min. at 4° C. with gentle mixing. After clearing the cells of protein A/G binding peptides, the library was incubated with 100 μL diluted sera (1:25 in PBS) for 45 min. at 4° C. Following serum incubation, cells were washed by centrifugation, and resuspended in 100 μL cold PBST (×3). After the final resuspension, washed protein A/G magnetic beads were added at a ratio of one bead per cell. After a 45 min. incubation with protein A/G beads at 4° C. with gently mixing, a second magnetic separation was performed to isolate cells expressing peptides that bind to serum antibodies. The supernatant (unbound cells) was discarded and the separated cells/beads were washed with 500 μL cold PBST. Five repeat washes were performed while the tube was being magnetized. After the last wash, the beads were resuspended in 1 mL of LB and inoculated into 10 mL LB+CM+glucose to suppress expression. The flask was grown overnight at 37° C. with shaking at 250 rpm. A 10 uL sample was removed prior to inoculation for dilution and plating on LB-agar to estimate the diversity of the enriched library.

Analysis of Enriched Library Using Fluorescence Activated Cell Sorting (FACS):

The following day, cells were analyzed for reactivity to the individual serum they were screened against to assess enrichment levels via FACS. After overnight growth of the MACS×2 enriched library (i.e., the library after the two rounds of MACS described above; "MACS×2"), cells were inoculated (>20× estimated diversity) at 1:50 into 5 mL LB+CM and grown to an OD$_{600}$=0.6. After induction with arabinose for 1 hour, a volume of cells >20× the library diversity was centrifuged and resuspended in 50 μL diluted sera (1:25 in PBS) for 45 min. at 4° C. Cells were washed as described in the second round enrichment section (100 uL PBST) and resuspended in □-IgA-PE diluted 1:200 in 100 μL cold PBS. Following a 45 min. incubation at 4° C., the cells were washed again and finally resuspended in 500 μL PBS for FACS sorting. Cells were analyzed for % of the cells with fluorescence signal greater than background (eCPX scaffold) by setting a gate to exclude 99% of the signal from serum incubated with cells containing eCPX scaffold lacking peptide (negative control). Libraries with ~80% or greater enrichment (percent of cells that are above background/percent of peptides that bind serum antibodies) were processed for deep sequencing analysis (next-generation sequencing; NGS).

Enrichment Analysis.

The majority of samples demonstrated >90% enrichment values (percent above background) with the lowest enrichment values at ~78%. In contrast, the background binding (eCPX scaffold percent above background) is minimal. The majority of the samples have background binding at <1% with the highest background at 3.4%. These data demonstrate the MACS X2 enrichment strategy effectively isolated a population of cells that express peptides that bind to serum antibodies and that this procedure collects minimal background (non-specific) binding cells.

Serum dilutions of 1:25 were used in this Example to maximize coverage of the repertoire (including lower titer antibodies), and to simultaneously minimize antibody-mediated cell death (e.g. due to residual complement activation), and non-specific binding. However, serum may be used at any appropriate dilution, including without dilution, as desired. Plasmid DNA was isolated from each enriched specimen-specific library, and used to generate bar-coded amplicon DNA libraries using a two-step PCR with the Illumina Nextera index kit. Amplicon preparations were cleaned using Ampure beads, diluted to a final concentration of 4 nM each for library pooling and sequenced on the Illumina NextSeq 500 1×75 high-output flow cell. To maximize the number of usable reads obtained, we used a i) forward primer in the first PCR step having five degenerate bases, and ii) using 30% spiked PhiX reference DNA. At least one reference specimen from one healthy individual was included in each NGS run to quantify run-to-run variability in read depth and quality, and longitudinal assay stability over 10 months.

Amplicon Preparation and Next Generation Sequencing on the Illumina Platform:

Amplicon Preparation:

Cells grown overnight after the second round of MACS sorting were collected and plasmid was extracted using a plasmid miniprep kit (Qiagen). The random peptide region was amplified using a two-step PCR. For the first PCR step, the primers included adaptors specific to the Illumina platform with annealing regions that flank the random section (peptide library) of the eCPX scaffold (sequences indicated below):

```
Forward primer:
                                    (SEQ ID NO: 870)
TCGTCGGCAGCGTCAGATGTGTATAAGAGACAGnnnnnCCAGTCTGGC

CAGGG.

Bold and underlined region is the annealing
region. nnnnn is 5 random degenerate bases.

Reverse primer:
                                    (SEQ ID NO: 871)
CCAGTACTACGGCATCACTGCTGTCTCTTATACACATCTCCGAGCCCAC

GAGAC.

Bold and underlined region is the annealing
region.
```

Products from the first PCR were purified after 25 rounds of PCR amplification (65° C. annealing temp) using Agencourt Ampure XP (Beckman Coulter) clean up beads. Resulting product was subjected to a second round of PCR using Illumina Nextera XT indexing primers. These primers provide unique 8 base pair indices on the 3 prime and 5 prime ends of the amplicons for tracking the sequences back to the sample used for screening and amplicon preparation. Amplicons were cleaned up as before after 12 rounds of PCR amplification (70° C. annealing temp). The final PCR product (amplicon) was analyzed using a DNA high sensitivity chip on a Bioanalyzer 2100 (Agilent) for purity, and DNA concentration was measured using DNA high sensitivity reagent on a Qbit instrument (Life Technologies). All samples were normalized to 4 nM and pooled together into a sequencing library.

Sequencing on Illumina NextSeq:

After quantification quality control of the pool was performed, the sample was diluted and loaded on to the NextSeq instrument. A 75 cycle high-output flow cell was used with single read (one direction) and dual indexing (both 5 prime and 3 prime indices are sequenced). After sequencing was complete, the samples were automatically de-multiplexed using imputed sample identities with Illumina Nextera XT indices.

NGS Quality Control

After construction, each amplicon was run on an agarose gel to confirm amplification of the correct product (254 bp) and absence of contaminating bands. Amplicons were quantified and pooled at a final concentration of 4 nM. The final amplicon pool was run on the bioanalyzer as a second quality control (QC) step to confirm the pool represented a single amplified band of the appropriate DNA size and concentration.

NGS Results

NGS results are summarized using data provided from Illumina BaseSpace software and from bioinformatics results using a computational algorithm for peptide motif discover in NGS datasets (hereafter referred to as "IMUNE"). The overall run summary indicates the "quality" of the full run in terms of number of sequences, the average number of sequences returned for each patient, and the standard deviation (SD) of the sequences for each patient. Low patient sequences (and total sequences) suggest potential problems with a sequencing run and may trigger repeat sequencing of that pool. A large SD for the sequences indicate poor pooling and may trigger a new quantification measurement and pool creation for a repeat sequencing run. Sequences that are read and assigned to a sample on BaseSpace must meet further quality control criteria for IMUNE. This is noted by comparing the total sequences given by BaseSpace to the total given by IMUNE for each sample. Consistently, ~94% of the indexed sequences for a given sample are recognized by IMUNE. The remaining sequences are often too short (<36 base pairs) to match correctly with an X12 peptide that is displayed. As a result, shorter sequences are filtered and not used for downstream motif analysis. At least 3 million total sequences were obtained from NGS for each CD specimen.

Bioinformatic Analysis

Identification of Celiac-Specific Motifs Using IMUNE Software

Motif discovery algorithms that utilize pairwise sequence comparisons are not amenable to large NGS datasets such as created by the Display-Seq discovery platform. For instance, motif discovery in 10,000 peptides using the MEME algorithm can require one week on a single processor, and computation time scales more than quadratically. To address this limitation, we developed a computational algorithm for Identification of Motifs Using Next-generation sequencing Experiments (IMUNE). IMUNE calculates the enrichments of all possible 4, 5, and 6 amino acid patterns (~8.5 billion) in a window of 10 positions, identifies patterns that are significantly enriched (p<0.001), and clusters these patterns using the PAM30 similarity scoring matrix to build motifs.

IMUNE was used to identify patterns and motifs specific to celiac samples in the discovery set. The discovered motifs were dominated by gliadin motif variants as these sequences were the most abundant in the celiac samples and absent in the control samples. The gliadin motif variants can be mapped to a single gliadin peptide QPEQPFPE (SEQ ID NO: 933). The 8-mer gliadin motif encompasses all the gliadin variant motifs obtained from bioinformatics analysis by sequence alignment and clustering.

Using either IMUNE or MEME 79 redundant motifs were discovered. The 79 redundant motifs associated with gliadin variants clustered into 4 motifs. Diagnostic motifs for Celiac Disease include namely QXXXPF[PS]E (SEQ ID NO: 6), PFSEM (SEQ ID NO: 7), PFSEX[FW] (SEQ ID NO: 8), QPXXPFX[ED] (SEQ ID NO: 4).

Motif Analysis in Validation Sample Set

Figure 5:
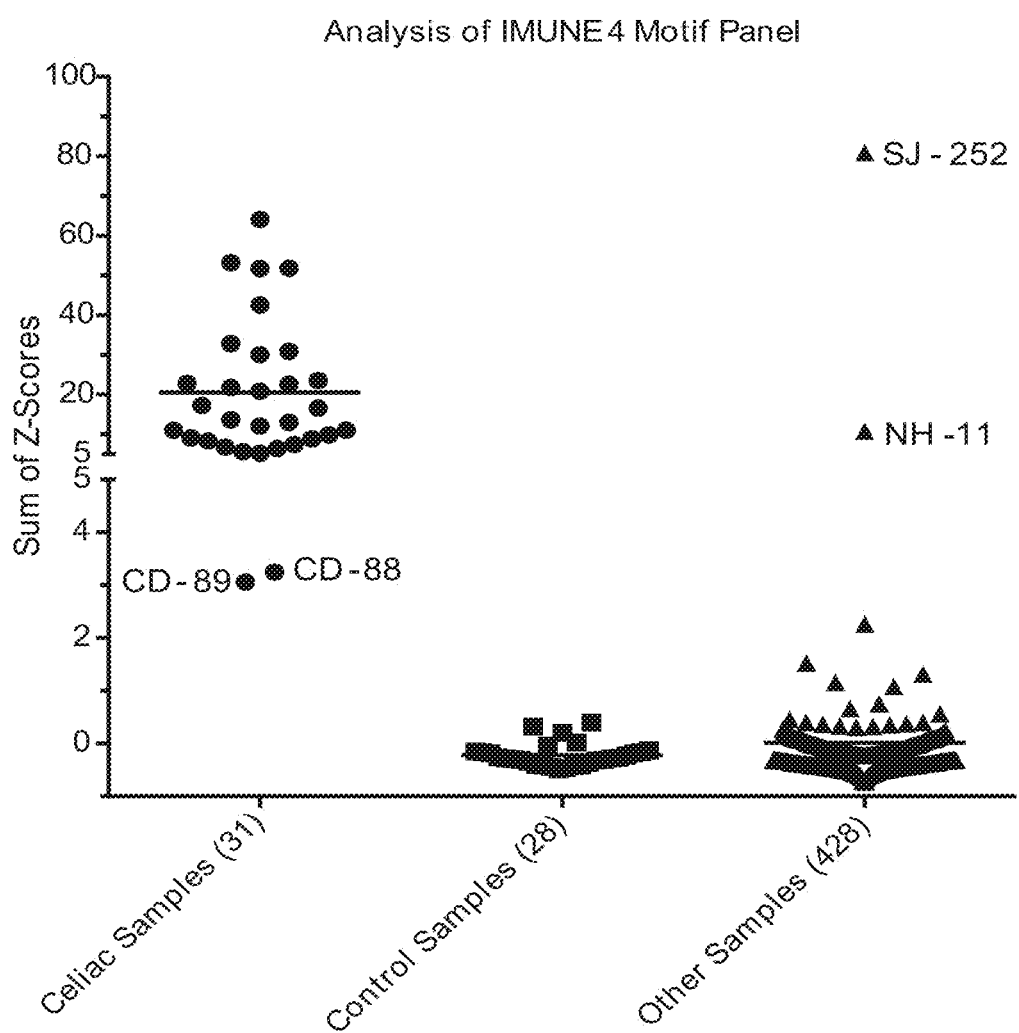
FIG. 5 illustrates the sum of z-scores (Standardized enrichment) for a four motif panel for Celiac disease discovery and validation samples.

The motifs discovered using the discovery set were further analyzed in the validation sample set. Enrichment values in the validation set for the motifs from IMUNE analysis are shown in FIG. 5. Of note, the panel of independent (non-gliadin) motifs performed poorly in the validation sample set while the gliadin variant motifs performed well.

IMUNE and MEME both identified gliadin variant motifs that were sensitive and specific in the validation sample set. The non-gliadin (additional) motifs from both IMUNE and MEME analysis failed to validate and are likely artifacts of common motifs that demonstrated enrichment in the discovery celiac samples.

Both IMUNE and MEME identified multiple motifs that were specific (i.e. occur in <1% of non-celiacs) and sensitive (i.e., in >95% of individuals with celiac disease) to celiac disease and that also correspond to a single gliadin motif.

In FIG. 5. enrichments for all samples were used to calculate z-scores for each motif in the 4-gliadin motif panel (a=IMUNE and b=MEME). Each z-score indicates the enrichment value minus the mean enrichment for all samples divided by the standard deviation of all samples. The summed z-scores are graphed comparing celiac samples to control and additional samples with datasets archived in HASRD. Note the IMUNE panel would correctly diagnose all celiac cases and the two additional samples while the MEME panel would misdiagnose two celiac samples and four additional samples. The celiac diagnostic panel generated by IMUNE was 100% sensitive (31 of 31 celiac samples are positive) with a specificity of at least 99.6% (2 of 456 control samples are positive). These two positive specimens may be from individuals with celiac disease.

Example 2. Discovery of Motifs Diagnostic of Chagas Disease

Chagas disease, also known as American trypanosomiasis, is a tropical parasitic disease caused by the protozoan *Trypanosoma cruzi* (*T. cruzi*). It is mainly spread by insects known as Triatominae, or kissing bugs, but may also be spread through blood transfusion, organ transplantation, contaminated food, and by vertical transmission from mother to fetus. Medication is effective if given early. However, most people infected with the disease do not realize they have the disease and treatment becomes less effective the longer a person has had Chagas disease. Untreated, Chagas can result in death.

Patient Samples

Serum samples (100 µl/sample) from 30 confirmed Chagas patients and 30 confirmed healthy donors were provided by the United States Center for Disease Control (CDC). Chagas diagnosis was made on the basis of two serological tests, the Wiener Chagatest ELISA and the CDC Laboratory Developed Test (LDT) TESA-Immunoblot. If both tests produced discrepancy, a third immunofluorescence assay was used as a tie-breaker test. Serum samples were stored at −80° C. upon receipt and thawed on the day of use.

Experimental Protocol for Chagas Disease Biomarker Discovery

Experiments were performed as described in Example 1.

Serum was diluted 1:25 in PBS at the *E. coli* depletion step and maintained at 4 Deg C. after depletion. For standard ecpx depletion, 1 mL each of *E. coli* cells induced to express ecpx 357 and 428 scaffolds (2 mL total) was used/ul of neat serum for depletion. Both MACS steps were performed at a 1:25 final serum dilution.

FACS Analysis of Enrichment of Chagas and Control Serum after MACS X2 for Discovery and Down Selection The effective removal of E. coli antibodies and the reactivity of each serum sample to its enriched library pool were analyzed by Flow cytometry as a quality control step in the screening process. Samples generally exhibit ≥75% reactivity of above background indicating that the libraries are highly enriched for patient specific peptides.

NGS Quality Control

Each amplicon was run on an agarose gel to confirm amplification of the correct product (254 bp) and absence of other bands representing non-specific PCR products. Amplicons were quantified and pooled at a final concentration of 4 nM each. The final amplicon pool was run on the bioanalyzer as a second QC step to confirm the pool represented a single amplified band of the appropriate amplicon concentration.

NGS Results

NGS raw sequence data from BaseSpace provides a breakdown of the total sequences obtained for each patient based on their unique barcode identifier. In the initial IMUNE processing step, sequences that met the quality criteria including: 1) upstream and downstream annealing regions contain ≤25% insertions, deletions and/or mutations, 2) the random region is of the expected length 3) no base throughout the read is unassigned (i.e. N). Unique reads are the number of sequences per patient after removal of duplicates, combination of similar sequences with few mutations (i.e. 3 or fewer) and removal of sequences that contain stop codons. The percentage of sequences that meet the above criteria relative to the total number of raw sequences is another measure of the quality of the NGS run. After processing, ~95% of the raw sequences from Basespace for each patient contain useable sequence information.

Bioinformatic Analysis

Disease specific motifs were identified using MEME and IMUNE as described in Example 1.

Preliminary IMUNE analysis of the discovery set epitope repertoires from 30 Chagas and 30 control sera discovered 1476 non-redundant motifs. Of those we considered the 200 motifs constructed using the largest number of contributing patterns. All of those motifs were specific and sensitive relative to the Chagas controls. We used HASRD (see Example 1) as a down-selection tool to identify motifs that were highly specific for Chagas based on their lack of enrichment in ~300 additional "control" samples. Additionally, we removed motifs that, while non-redundant were variations on the same epitope. This process revealed at least 39 distinct Chagas-specific motifs with varying sensitivities for Chagas disease in the discovery set Table 1.

TABLE 1

Motifs and peptides comprising panel for the diagnosis of Chagas panel

| ID | Panel motif | Antigen(s); peptide sequence(s) |
|---|---|---|
| 1 | [RK]A4RxID (SEQ ID NO: 104) | |
| 2 | QHxGHP (SEQ ID NO: 105) | Glutathione peroxidase, 60S ribosomal protein L2; QHkGHP(SEQ ID NO: 143), QHiGHP(SEQ ID NO: 144) |
| 3 | KxxLPED (SEQ ID NO: 106) | Gim5A protein, Phosphatidylinositol kinase domain protein, Dynein intermediate chain, Trans-splicing factor, G-actin binding protein; KalLPED(SEQ ID NO: 145), KkhLPED(SEQ ID NO: 146), KitLPED(SEQ ID NO: 147), KtiLPED(SEQ ID NO: 148), KvlLPED(SEQ ID NO: 149) |
| 4 | [IV]LxxFGY (SEQ ID NO: 107) | 60S ribosomal protein L13a, DNA polymerase, Alpha-adaptin, Mucin-associated surface protein (MASP); VLkkFGY(SEQ ID NO: 150), VLhlFGY(SEQ ID NO: 151), VLgeFGY(SEQ ID NO: 152), VLepFGY(SEQ ID NO: 153) |
| 5 | PLDxxxxIS (SEQ ID NO: 108) | Kinesin, Kinetoplast-associated protein Tcp22; PLDvekeIS(SEQ ID NO: 154), PLDllkyIS(SEQ ID NO: 155) |
| 6 | ETXIPXE (SEQ ID NO: 109) | Complement regulatory protein, Trans-sialidase, FL-160-1 epitope, OSM3-like kinesin; ETkIPsE(SEQ ID NO: 156), ETeIPsE(SEQ ID NO: 157), ETgIPfE (SEQ ID NO: 158) |
| 7 | [VI]Nx[DE][ML]YxP (SEQ ID NO: 110) | 40S ribosomal protein S21; VNvDLYiP (SEQ ID NO: 159) |
| 8 | FLxxIGA (SEQ ID NO: 111) | Flagellum-Associated Protein, Membrane protein, Dispersed gene family protein 1 (DGF-1), 60S ribosomal protein L14; FLgaIGA(SEQ ID NO: 160), FLlfIGA(SEQ ID NO: 161), FLkaIGA(SEQ ID NO: 162) |
| 9 | D[VI]x[MI][ILV]x[KR] (SEQ ID NO: 112) | UDP-GlcNAc: polypeptide N-acetylglucosaminyltransferase, Oculocerebrorenal Lowe syndrome protein, Dynein heavy chain, cytosolic, R27-2 protein, Myosin heavy chain; DIkMIeR(SEQ ID NO: 163), DIiIVsR(SEQ ID NO: 164), DVhMLvR(SEQ ID NO: 165), DVdILeR(SEQ ID NO: 166) |

TABLE 1-continued

Motifs and peptides comprising panel for the diagnosis of Chagas panel

| ID | Panel motif | Antigen(s); peptide sequence(s) |
|---|---|---|
| 10 | RxSPYx[IL]F (SEQ ID NO: 113) | Kinetoplast DNA-associated protein 3; RvSPYsIF (SEQ ID NO: 167) |
| 11 | VGPRH (SEQ ID NO: 114) | Microtubule associated protein homolog, Antigen DNA; VGPRH (SEQ ID NO: 168) |
| 12 | PQxQH[ED] (SEQ ID NO: 115) | Helicase, putative, Phosphatidylinositol 3-kinase; PQkQHE(SEQ ID NO: 169), PQgQHD (SEQ ID NO: 170) |
| 13 | PxxGGFG (SEQ ID NO: 116) | |
| 14 | KxEGxxMG (SEQ ID NO: 117) | 60S ribosomal protein L6, Adenosine 5'-monophosphoramidase; KsEGefMG(SEQ ID NO: 171), KdEGlaMG(SEQ ID NO: 172) |
| 15 | KxxGxTxxLS (SEQ ID NO: 118) | 85 kDa surface antigen, Trans-sialidase-like protein, Glycoprotein 82 kDa; KdnGsTwsLS(SEQ ID NO: 173), KddGsTwaLS(SEQ ID NO: 174) |
| 16 | EMG[FW]Q (SEQ ID NO: 119) | |
| 17 | [VI]KxGxxDxP (SEQ ID NO: 120) | ADP, ATP carrier protein 1, mitochondrial; IKqGrlDrP (SEQ ID NO: 175) |
| 18 | PE[DN]ExYP (SEQ ID NO: 121) | |
| 19 | HYEWA (SEQ ID NO: 122) | Lanosterol cyclase, Terpene cyclase/mutase family member; HYEWA (SEQ ID NO: 176) |
| 20 | [HR]SNMxF (SEQ ID NO: 123) | |
| 21 | M[TV]GxxYE (SEQ ID NO: 124) | Lanosterol cyclase, 3-methylcrotonoyl-CoA carboxylase beta subunit; MVGehYE (SEQ ID NO: 177), MVGkaYE (SEQ ID NO: 178) |
| 22 | Dxx[KH]ExxLL (SEQ ID NO: 125) | 40S ribosomal protein S8, Neurobeachin/beige protein, Kinesin, ATP-dependent DNA helicase; DqlKEgrLL(SEQ ID NO: 179), DvvKElmLL(SEQ ID NO: 180), DleKEneLL(SEQ ID NO: 181), DldKEvsLL(SEQ ID NO: 182) |
| 23 | RxxWx[EDA]x[IV][AR] (SEQ ID NO: 126) | 40S ribosomal protein S3a-1, Dynein heavy chain, Protein kinase, Eukaryotic translation initiation factor 4E (EIF4E) interacting protein, AAA ATPase; Mucin-associated surface protein (MASP); RhqWyAvVA(SEQ ID NO: 183), RhsWfDdVR(SEQ ID NO: 184), RkeWyDvVA(SEQ ID NO: 185), RdrWtEsIA(SEQ ID NO: 186), RatWlDqVR(SEQ ID NO: 187), RyvWnEwVA(SEQ ID NO: 188) |
| 24 | PxDxxAx[GPA][TS] (SEQ ID NO: 127) | Shed-acute-phase-antigen, Translation factor GUF1 homolog 1, mitochondrial, Trans-sialidase, Mucin-associated surface protein (MASP), Mucin TcMUCII; PvDstAhGT(SEQ ID NO: 189), PlDcpAlGS(SEQ ID NO: 190), PaDssAhGT(SEQ ID NO: 191), PkDvkAtGS(SEQ ID NO: 192), PpDvsAsGT(SEQ ID NO: 193), PgDlpAkAT(SEQ ID NO: 194), PaDvsAqAT(SEQ ID NO: 195), PpDvpAsGT(SEQ ID NO: 196) |
| 25 | PDxxSxT[ARG] (SEQ ID NO: 128) | UDP-GlcNAc:PI a1-6 GlcNAc-transferase, Small GTP-binding protein RAB6, 90 kDa surface protein, Mucin TcMUCII; PDpaSiTA(SEQ ID NO: 197), PDasSsTA(SEQ ID NO: 198), PDsrSiTA(SEQ ID NO: 199), PDsrSvTA(SEQ ID NO: 200), PDskSpTA(SEQ ID NO: 201), PDseSpTA(SEQ ID NO: 202) |
| 26 | GRExDG (SEQ ID NO: 129) | Mucin-associated surface protein (MASP), Trypanothione synthetase-like protein; GREsDG(SEQ ID NO: 203), GREaDG (SEQ ID NO: 204) |
| 27 | GVPGxxxK (SEQ ID NO: 130) | 60S ribosomal protein L18, Calpain-like cysteine peptidase; GVPGshaK(SEQ ID NO: 205), GVPGcviK(SEQ ID NO: 206) |

TABLE 1-continued

Motifs and peptides comprising panel for the diagnosis of Chagas panel

| ID Panel motif | Antigen(s); peptide sequence(s) |
|---|---|
| 28 [LM]xxx[EDQ]VxxIM (SEQ ID NO: 131) | Sterol 14-alpha demethylase, 60S ribosomal protein L4, GTP-binding protein, Stress-induced protein sti1; LsprEVytIM(SEQ ID NO: 207), LtntDVtrIM(SEQ ID NO: 208), LedeDVlqIM(SEQ ID NO: 209), MadpEVaaIM(SEQ ID NO: 210) |
| 29 SxxxVSGG (SEQ ID NO: 132) | Putative surface protein TASV-B-25, Aquaporin-like protein, Mucin-associated surface protein (MASP), Calcium-transporting ATPase; SqadVSGG(SEQ ID NO: 211), SvgsVSGG(SEQ ID NO: 212), SpsgVSGG(SEQ ID NO: 213), SwfdVSGG(SEQ ID NO: 214) |
| 30 A[KR]AG[DN]K (SEQ ID NO: 133) | |
| 31 F[RN]xIN[RQ] (SEQ ID NO: 134) | Dynein heavy chain, Eukaryotic translation initiation factor 3 subunit 8; FRiINQ(SEQ ID NO: 215), FRaINR(SEQ ID NO: 216) |
| 32 YXPVXPXSY (SEQ ID NO: 135) | |
| 33 KxTFPD (SEQ ID NO: 136) | Trans-sialidase, Neurobeachin/beige protein; KqTFPD(SEQ ID NO: 217), KaTFPD(SEQ ID NO: 218) |
| 34 PFM[FVM]xxR (SEQ ID NO: 137) | Cation-transporting ATPase; PFMVqmR(SEQ ID NO: 219) |
| 35 EFWEP (SEQ ID NO: 138) | |
| 36 [FY]GALS (SEQ ID NO: 139) | Kinetoplast-associated protein Tcp22, Protein kinase, ABC transporter; FGALS(SEQ ID NO: 220), YGALS(SEQ ID NO: 221) |
| 37 PxGTEN (SEQ ID NO: 140) | Trypomastigote small surface antigen; PsGTEN(SEQ ID NO: 222) |
| 38 Gx[KE]PWE (SEQ ID NO: 141) | Metacaspase; GfKPWE(SEQ ID NO: 223) |
| 39 D[IV]Tx[YF][WN] (SEQ ID NO: 142) | Intraflagellar transport protein component, Cyclophilin-like protein; DITdYN(SEQ ID NO: 224), DVTgFN(SEQ ID NO: 225) |

Of the final 39 motifs that comprise the panel, IMUNE identified twenty-six motifs that were highly sensitive and specific to Chagas that were not discovered by MEME. In particular, these included motifs with greater than 40% sensitivity in the Chagas discovery set.

Panel Development

Figure 6:
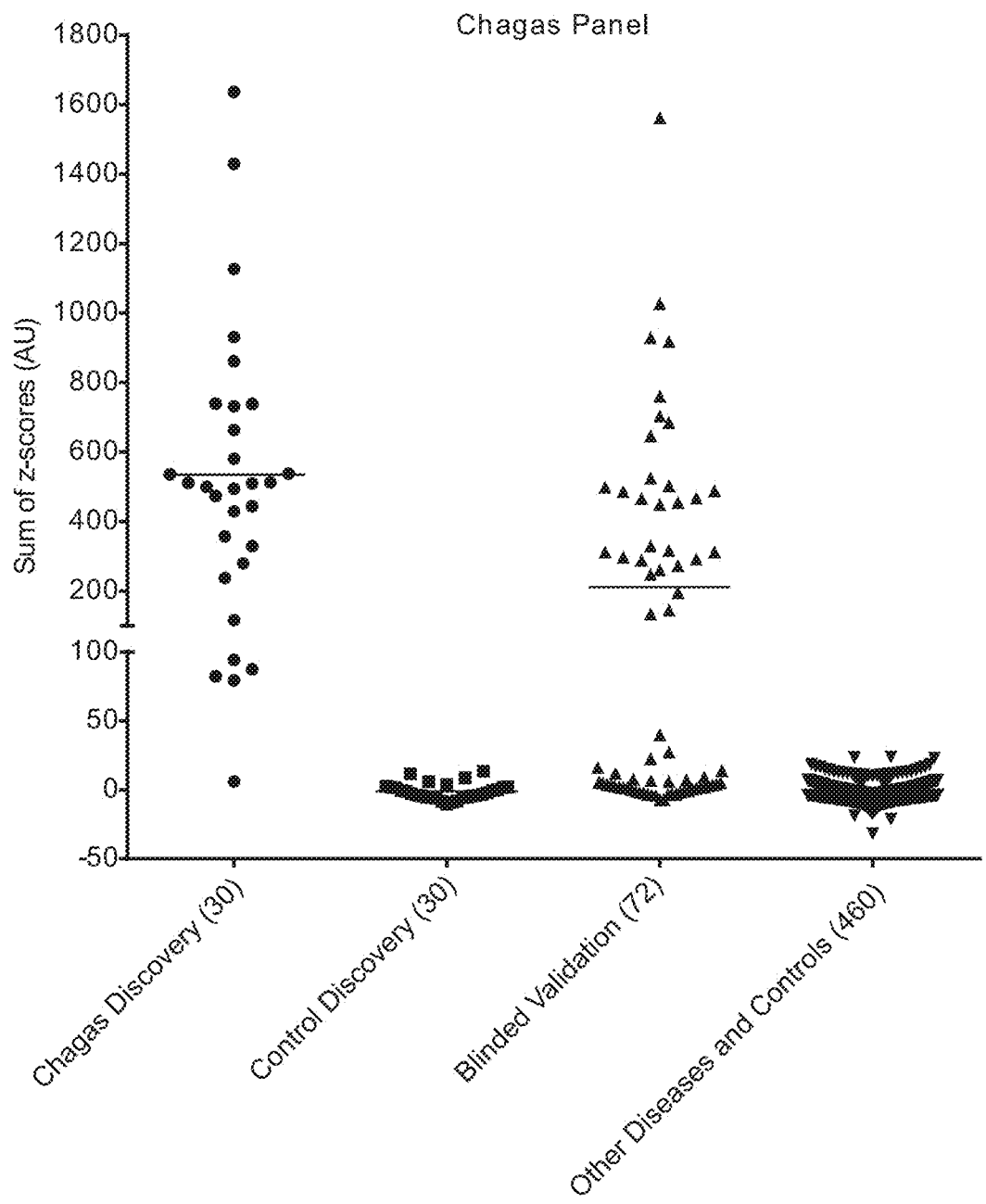
FIG. 6 illustrates the performance of *Trypanosoma cruzi* infection (Chagas disease) motif panel in a discovery and validation sample sets, exhibiting a sensitivity of 100% and specificity of 100% in the validation set.

Two methods were used to generate a panel of motifs that are diagnostic for Chagas disease. In the first method, the average enrichment and standard deviation for the 33 motifs in 416 non-Chagas samples were calculated. A positive signal in a motif is at least 4 standard deviations above the controls. A patient is diagnosed as positive for Chagas if they have a positive signal in at least 3 motifs, indeterminate if they are positive for two motifs and negative if they are positive in one or fewer motifs. Using these criteria, all thirty Chagas disease samples were positive (FIG. 6) and all the Chagas controls were negative. Additionally, all 460 controls in HASRD not used for discovery were also negative. In the second method, the sum of the z scores is calculated for all motifs and a cut off is determined based on the desired sensitivity and specificity. As shown in FIG. 6, using a cut off of 23 yields a sensitivity of 100% and a specificity of 99.5% for all 30 Chagas disease samples and all 460 controls.

Mapping of Chagas Motifs to *Trypanosoma cruzi* Antigens

Motifs identified by IMUNE often carry sufficient information to identify organisms, antigens, and epitopes without prior knowledge of which organism or antigens may be important. About 80% of motifs that IMUNE identified that were sensitive and specific could be associated with a single *T. cruzi* antigen epitope, by performing degenerate motif searches within the entire Swissprot/TrEMBL databases using Scanprosite. See Table 1. Notably, i) three antigens (Surface antigen-2, microtubule associated protein, and small surface antigen/mucin-like protein) have been validated previously, several epitopes were from ribosomal proteins, one ribosomal epitope is identical between *T. cruzi* and *Leishmania* sp, an organism that generates false positives in available Chagas tests. The majority of Chagas antigens are novel and have not been described or characterized previously.

Example 3. Discovery of Motifs for the Diagnosis of Lyme Disease (*Borrelia burgdorferi* Infection)

Lyme disease, also known as Lyme borreliosis, is an infectious disease caused by bacteria of the *Borrelia* genus. Lyme disease is transmitted to humans by the bite of infected ticks. Diagnosis is based upon a combination of symptoms, history of tick exposure, and possibly testing for specific antibodies in the blood. However, blood tests are often negative in the early stages of the disease. If untreated, symptoms may include loss of the ability to move one or both sides of the face, joint pains, severe headaches with neck stiffness, and heart palpitations. Symptoms can persist for months after treatment and may reoccur years later. The disease affects several hundred thousand people a year in the United States.

Patient Samples

Serum samples (100 ul/sample) from 20 confirmed late stage Lyme patients (L1-20) with Lyme Arthritis and 20 controls (L21-40) were provided. Lyme diagnosis was made on the basis of 2-tier testing via ELISA with reflex to Western blot. Serum samples were stored at −80° C. upon receipt and thawed on the day of use.

Experimental Protocol for Lyme Disease Biomarker Discovery

Experiments and analysis were as described in Example 1.

Serum was diluted 1:25 in PBS at the *E. coli* depletion step and maintained at 4° C. after depletion. For standard ecpx depletion, 1 mL each of *E. coli* cells induced to express eCPX 357 and 428 scaffolds (2 mL total) was used per microliter of neat serum for depletion. Both MACS steps were performed at a 1:25 final serum dilution.

FACS Analysis of Enrichment of Lyme and Control Serum after MACS X2 for Discovery and Down Selection The effective removal of *E. coli* antibodies from serum and the effective enrichment of serum antibody binders after two rounds of MACS (M2) was analyzed by Flow cytometry as a quality control step in the screening process. Samples generally exhibit 75% reactivity of above background to M2 library pool, indicating that the libraries are highly enriched for patient-specific peptides.

NGS Quality Control

Each amplicon was run on an agarose gel to confirm amplification of the correct product (254 bp) and absence of other bands representing non-specific PCR products. Amplicons were quantified and pooled at a final concentration of 4 nM each. The final amplicon pool was run on the bioanalyzer as a second QC step to confirm the pool represented a single amplified band of the appropriate amplicon concentration. Half of the disease set and half of the control set sequenced per run (20 samples per chip).

NGS Results

NGS raw sequence data from BaseSpace provides a breakdown of the total sequences obtained for each patient based on their unique barcode identifier. In the initial IMUNE processing step, sequences that met the quality criteria including: 1) upstream and downstream annealing regions contain ≤25% insertions, deletions and/or mutations, 2) the random region is of the expected length 3) no base throughout the read is unassigned (i.e. N). Unique reads are the number of sequences per patient after removal of duplicates, combination of similar sequences with few mutations (i.e. 3 or fewer) and removal of sequences that contain stop codons. The percentage of sequences that meet the above criteria relative to the total number of raw sequences is another measure of the quality of the NGS run. NGS runs for the 60 Lyme and control samples typically resulted in more 5-12 million total sequences, and 2-5 million unique sequences. After processing, ~95% of the raw sequences from Basespace for each patient contain useable sequence information.

Bioinformatic analysis was performed as described in Example 1.

Identification of Lyme-Specific Motifs Using IMUNE Software

Motif discovery algorithms that utilize pairwise sequence comparisons are slow and not amenable to the large NGS datasets created by the methods described herein. For instance, motif discovery in 10,000 peptides using the MEME algorithm can require one week on a single processor, and computation time scales more than quadratically. To address this limitation, a computational algorithm for Identification of Motifs Using Next-generation sequencing Experiments (IMUNE) was developed. IMUNE calculates the enrichments of all possible 4, 5, and (optionally) 6 amino acid patterns (~8.5 billion) in a window of 10 positions, identifies patterns that are significantly enriched (e.g., p<0.001), and clusters these patterns using a similarity scoring matrix (e.g., PAM30) to build motifs.

Identification of Lyme-Specific Motifs Using MEME

MEME is currently the dominant tool in motif finding. We wished to determine whether IMUNE outperforms MEME in terms of the number and specificity of the disease motifs it identifies. For the MEME motif discovery, we compiled a list of all peptides that appeared in at least 11 Lyme disease samples and in zero controls samples. MEME was used to analyze the top 4980 of these peptides that appeared in these Lyme samples, to identify the motifs in Table 30.

Candidate Motifs

Lyme Motifs Discovered by IMUNE

Preliminary IMUNE analysis of the discovery set epitope repertoires from 20 Lyme and 20 control sera discovered 296 non-redundant motifs that were at least 40% sensitive and 100% specific. To identify a subset of these motifs that together are 100% sensitive and specific for Lyme disease following steps were performed:

1) Down-Selection of Motifs Based on Specificity Using HASRD

Figure 7:
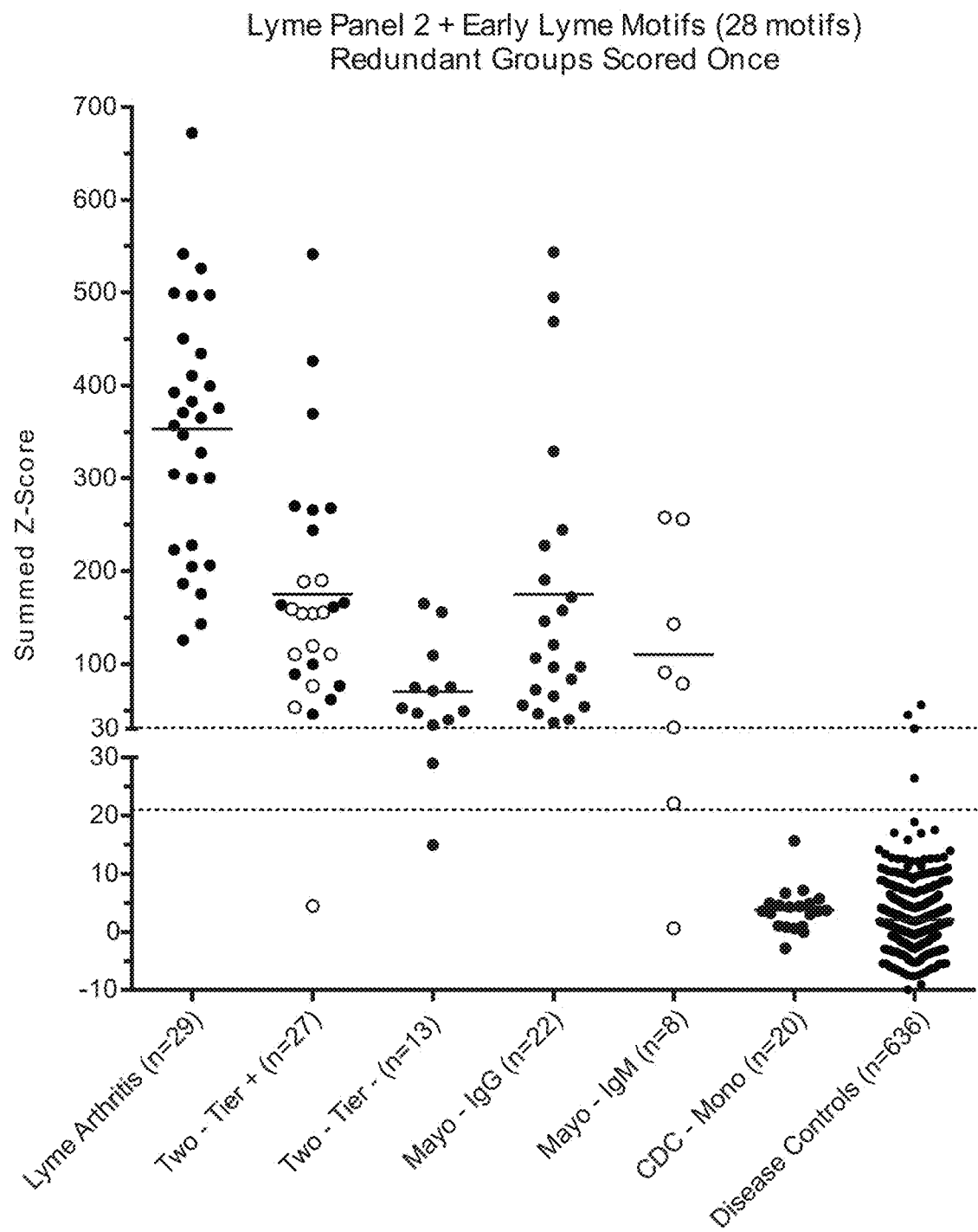
FIG. 7 illustrates the performance of *Borrelia burgdorferi* infection motif panel in a discovery and validation sets of early, early disseminated, and late Lyme disease, exhibiting a sensitivity of 97% and specificity of 99.8%.

We used a database containing hundreds of distinct epitope repertoires (i.e., peptide datasets) as a down-selection tool to identify motifs that were highly specific for Lyme disease based on their lack of enrichment in 636 additional untested, non-Lyme samples. Twenty-eight motifs were highly specific for Lyme disease (significant enrichment in ≤2 of the 20 Lyme controls and 636 additional non-Lyme controls (FIG. 7)) and were considered for further analysis.

2) Grouping of Motifs into Families

Many of the motifs, while non-redundant, were variations on the same epitope and thus were grouped together into families. At least 16 Lyme specific motif families were identified.

3) Down-Selection Based on Motif Sensitivity and Patient Coverage

We further down-selected the motifs based on sensitivity and patient coverage. If two highly specific motifs were present in the same family, the motif that demonstrated the highest sensitivity was selected. Motifs from each family were compared to identify those that captured distinct patient subsets. Of the initial 27 motifs we considered, the final panel includes 14 motifs, each from a distinct motif family, that together exhibit the greatest breadth of patient coverage. A sample was considered positive for any motif if it was >4 standard deviations (SD) above the mean of the controls, indeterminate if it was >3 SD and negative if it was less than 3 SD.

Lyme Motifs Discovered Using MEME

MEME identified a total of twenty-five motifs. To evaluate the performance of the two algorithms, MEME motifs were compared with all IMUNE motifs. Of the twenty-five motifs, eight were redundant within the MEME list. IMUNE identified all of the 17 remaining motifs. See Table 2. Thus, IMUNE identified 15/15 of the motifs identified by MEME.

In contrast, of the final 14 motifs that comprise the panel, IMUNE identified five motifs that were highly sensitive and specific to Lyme that were not discovered by MEME. In particular, these included motifs with ≤60% sensitivity in the Lyme discovery set.

Panel Development

Two methods were used to generate a panel of motifs that are diagnostic for Lyme disease. In the first method, the average enrichment and standard deviation for the 14 motifs in 419 non-Lyme samples were calculated. A positive signal in a motif is at least 4 standard deviations above the controls. A patient is diagnosed as positive for Lyme if they have a positive signal in at least 3 motifs, indeterminate if they are positive for two motifs and negative if they are positive for one or fewer motifs. Using this criteria, all twenty late Lyme disease samples in the discovery set were positive and all the non-Lyme controls were negative. Additionally, 636 Disease controls not used for discovery were also negative.

In the second method, the sum of the z scores is calculated for all motifs and a cut off is determined based on the desired sensitivity and specificity. Using a cut off of 30 yields a sensitivity of 100% and a specificity of 100% for all 20 Lyme disease samples and all 419 controls.

Mapping of Lyme Motifs to Putative *Borrelia burgdorferi* Antigens

Motifs identified by IMUNE often carry sufficient information content to identify organisms, antigens, and epitopes without prior knowledge of which organism or antigens may be important. About 80% of motifs that IMUNE identified that were sensitive and specific could be associated with a *B. burgdorferi* antigen epitope, by performing degenerate motif searches within the entire Swissprot/TrEMBL databases using Scanprosite. See Table 2.

TABLE 2

Motifs and peptides comprising panel for the diagnosis of Lyme Disease.

| ID | Panel motif | Antigen(s); peptide sequence(s) |
|---|---|---|
| 1 | VQQExxxxxP (SEQ ID NO: 358) | Flagellin (Fragment); VQQEgaqqqP (SEQ ID NO: 392) |
| 2 | QQEGxxxx[YC] (SEQ ID NO: 359) | |
| 3 | QEG[IV]Q (SEQ ID NO: 360) | Flagellar filament 41 kDa core protein (Flagellin); QEGVQ (SEQ ID NO: 393) |
| 4 | G[IV]QxEG (SEQ ID NO: 361) | Flagellar filament 41 kDa core protein (Flagellin); GVQqEG (SEQ ID NO: 394) |
| 5 | [LI]xxA[ILV]xxRG (SEQ ID NO: 362) | Flagellar hook-basal body complex protein FliE; IlkAVveRG (SEQ ID NO: 395) Outer surface protein VlsE; IaaAIvlRG (SEQ ID NO: 396) |
| 6 | [ATNSD]xxxxAI[LAM]xR (SEQ ID NO: 363) | Outer surface protein VlsE; DqiaaAIAlR (SEQ ID NO: 397) Flagellar M-ring protein; AkkmrAILvR (SEQ ID NO: 398) Telomere resolvase ResT; AenhkAILfR (SEQ ID NO: 399) |
| 7 | Ix[LM]xGFxK (SEQ ID NO: 364) | Uncharacterized protein; IkLpGFkK (SEQ ID NO: 400) Transglycosylase SLT domain protein IfLeGFlK (SEQ ID NO: 401) |
| 8 | LxGM[RQ]K (SEQ ID NO: 365) | Uncharacterized protein; LrGMRK (SEQ ID NO: 402) |
| 9 | [HR]xDxTNxf (SEQ ID NO: 366) | |
| 10 | [DA]DPTN (SEQ ID NO: 367) | Outer surface protein VlsE1; DDPTN (SEQ ID NO: 403) |
| 11 | [KR]x[DE]xTNxF (SEQ ID NO: 368) | Borrelia ORF-A superfamily protein; KtDrTNdF (SEQ ID NO: 404) Outer surface protein VlsE; KdDpTNkF (SEQ ID NO: 405) CdsJ; KtDrTNdF (SEQ ID NO: 406) BBD14-like protein (Fragment); KtDkTNdF (SEQ ID NO: 936) |
| 12 | [ET][ML]HKF (SEQ ID NO: 369) | PF-32 protein; TLHKF (SEQ ID NO: 407) |
| 13 | [ML]xxEFHK (SEQ ID NO: 370) | |
| 14 | Q[TI]EQxxxxxK (SEQ ID NO: 371) | Integral outer membrane protein P66; QTEQsststK (SEQ ID NO: 408) |
| 15 | DxSP[IL]E (SEQ ID NO: 372) | Uncharacterized protein; D1SPIE (SEQ ID NO: 409) |
| 16 | PFx[AP]YxK (SEQ ID NO: 373) | Integral outer membrane protein P66; PFsAYiK (SEQ ID NO: 410) |
| 17 | VxxYFxx[LV]xK (SEQ ID NO: 374) | VlsE (Fragment); VkdYFdsLaK (SEQ ID NO: 411) |
| 18 | KxVDxDR (SEQ ID NO: 375) | |
| 19 | [DN][AS]A[AG]F (SEQ ID NO: 376) | VlsE (Fragment); DAAAF (SEQ ID NO: 412) |
| 20 | Cx[NA]xKFC (SEQ ID NO: 377) | |

TABLE 2-continued

Motifs and peptides comprising panel for the diagnosis of Lyme Disease.

| ID | Panel motif | Antigen(s); peptide sequence(s) |
|---|---|---|
| 21 | Kx[GRST]AE[YF] (SEQ ID NO: 378) | Flagellar basal-body rod protein FlgG (Distal rod protein); KiRAEF (SEQ ID NO: 934)<br>Putative lipoprotein; KfRAEF (SEQ ID NO: 413)<br>Na+/H+ antiporter family protein; KsSAEF (SEQ ID NO: 414)<br>VlsE (Fragment); KgGAEF (SEQ ID NO: 415) |
| 22 | HQV[PA]xxx[DHE] (SEQ ID NO: 379) | |
| 23 | IPxxV[IF]xxR (SEQ ID NO: 380) | |
| 24 | Cx[ALT]xWEx[CA] (SEQ ID NO: 381) | |
| 25 | CxxxCA[IL]xxR (SEQ ID NO: 382) | |
| 26 | I[IV]Ixx[MT]xK (SEQ ID NO: 383) | Lectin; IIIidTsK (SEQ ID NO: 416)<br>CdsC; IIIngMtK (SEQ ID NO: 417)<br>Mlp; IIItnMeK (SEQ ID NO: 418) |
| 27 | QG[ITL]x[KN][FY] (SEQ ID NO: 384) | Dephospho-CoA kinase; QGENY (SEQ ID NO: 419)<br>Phosphomannomutase; QGIcNY (SEQ ID NO: 420) |
| 28 | KxxPPxIN (SEQ ID NO: 385) | Outer surface protein VlsEl; KetPPaLN (SEQ ID NO: 421) |
| 29 | G[YF][FY]FxxK (SEQ ID NO: 386) | Pts system, iibc component; GFYFifK (SEQ ID NO: 422) |
| 30 | DKNVx[IV] (SEQ ID NO: 387) | Putative lipoprotein; DKNVkI (SEQ ID NO: 423) |
| 31 | [QE][KR][ND]xSG (SEQ ID NO: 388) | Outer surface protein B (OspB); EKNsSG (SEQ ID NO: 424) |
| 32 | K[RK]PGD (SEQ ID NO: 389) | Outer surface protein VlsE; KKPGD (SEQ ID NO: 425) |
| 33 | EGAxQP (SEQ ID NO: 390) | Flagellar filament 41 kDa core protein (Flagellin); EGAqQP (SEQ ID NO: 426) |
| 34 | GSPEY (SEQ ID NO: 391) | Outer membrane protein; GSPEY (SEQ ID NO: 427) |

Example 4. Discovery of Motifs for the Diagnosis of Acute or Active *Toxoplasma gondii* Infection

Figure 8:
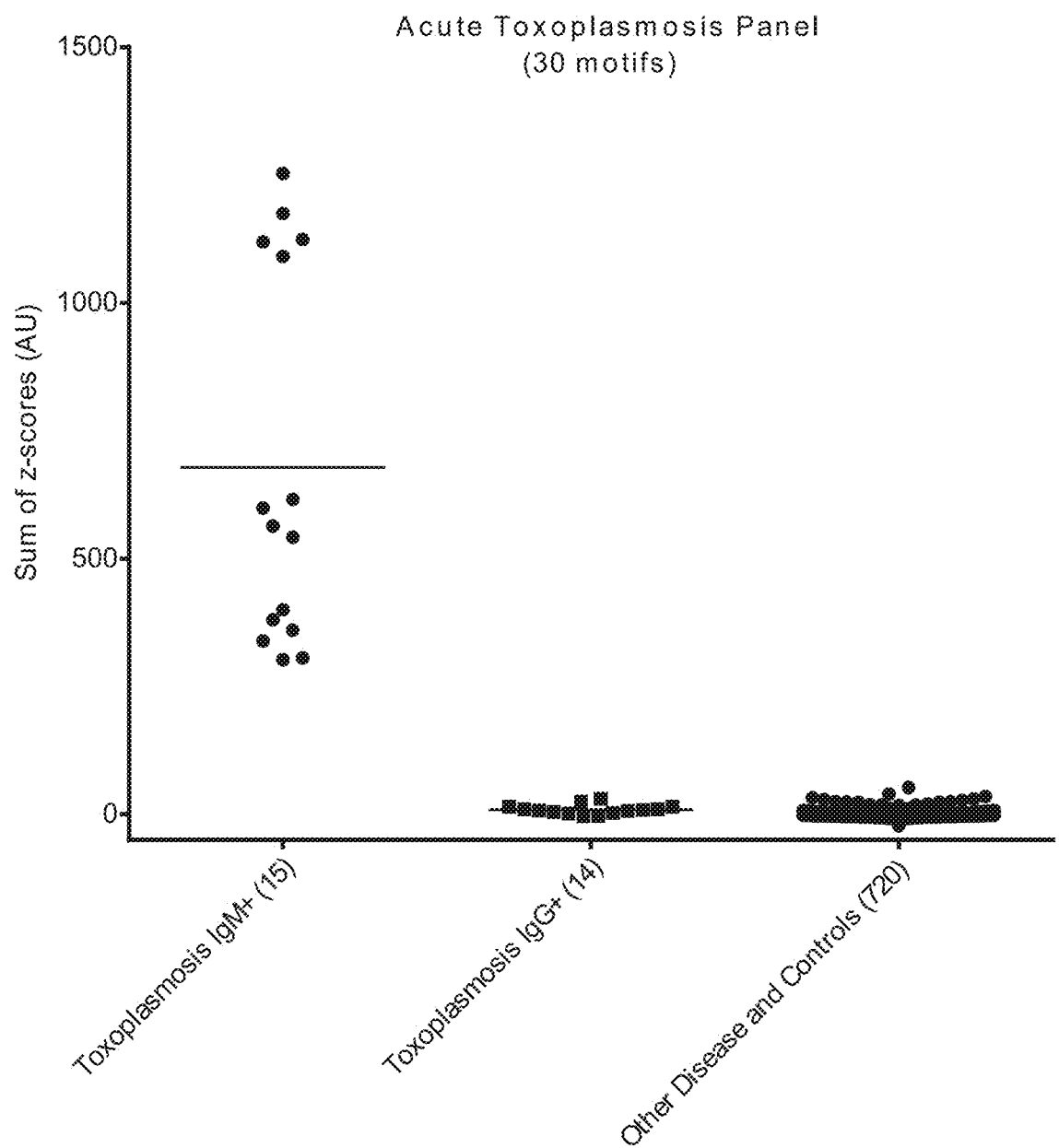
FIG. 8 illustrates the performance of an acute *Toxoplasma gondii* infection motif panel in a discovery sample set, exhibiting a sensitivity of 100% and specificity of 100%.
Figure 9:
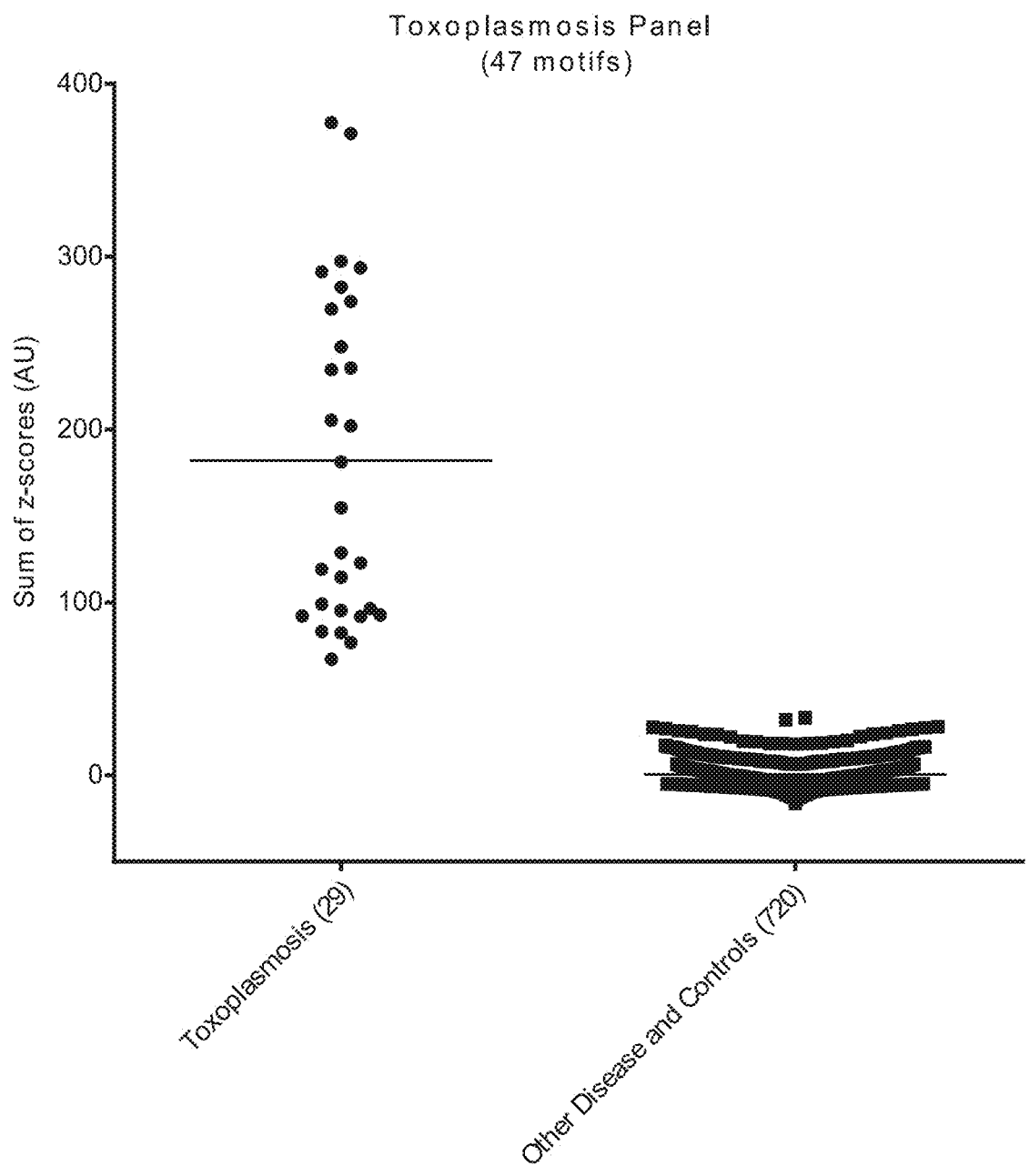
FIG. 9 illustrates the performance of (chronic or acute) *Toxoplasma gondii* infection motif panel in a discovery sample set, exhibiting a sensitivity of 100% and specificity of 100%.

*Toxoplasma gondii* is a common infectious parasite with a seroprevalence of about 20% in the US population. Acute infections can in some cases result in significant morbidities, for example during pregnancy. The method of Example 1 above was applied to a set of 30 sera from individuals that were either positive for IgG or IgM antibodies by enzyme immunoassay or immunoblot. A panel of 30 motifs indicated of Acute *Toxoplasma* infection is shown in Table 3. The panel is capable of correctly detecting 30 specimens in the discovery set (FIG. 8, FIG. 9).

TABLE 3

Motifs and peptides comprising panel for the diagnosis of acute Toxoplasmosis.

| ID | Panel motif | Antigen(s); peptide sequence(s) |
|---|---|---|
| 1 | HExE[FY]Q (SEQ ID NO: 74) | Apical membrane antigen 1 (TgAMA-1); HEhEFQ (SEQ ID NO: 428) |
| 2 | LD[MLF]WxE (SEQ ID NO: 75) | DNA polymerase, TLD protein, Putative transmembrane protein; LDFWrE(SEQ ID NO: 429), LDFWqE(SEQ ID NO: 430), LDMWeE(SEQ ID NO: 431) |
| 3 | HCSAC (SEQ ID NO: 76) | Putative anaphase promoting complex subunit 11, Palmitoyltransferase, Sulfite exporter TauE/SafE protein; HCSAC (SEQ ID NO: 432) |
| 4 | [FY]xGVVN (SEQ ID NO: 77) | Dense granule protein 2 (Protein GRA 2) (28 kDa antigen) (GP28.5), Dynein, axonemal, heavy chain 2 family protein; FsGVVN(SEQ ID NO: 433), YpGVVN(SEQ ID NO: 434) |
| 5 | KxxxGRGxI (SEQ ID NO: 78) | NOL1/NOP2/sun family protein; KgshGRGfI(SEQ ID NO: 435) |
| 6 | GPH[LA]E (SEQ ID NO: 79) | Zinc finger (CCCH type) motif-containing protein, Glycogen synthase, Uncharacterized protein; GPHAE(SEQ ID NO: 436) |
| 7 | PRREP (SEQ ID NO: 80) | Dense granule protein 7 (Protein GRA 7) (29 kDa excretory dense granule protein), Putative transmembrane protein, Dense granule protein GRA9; 1,3-beta-glucan synthase component protein; PRREP(SEQ ID NO: 437) |

TABLE 3-continued

Motifs and peptides comprising panel for the diagnosis of acute Toxoplasmosis.

| ID | Panel motif | Antigen(s); peptide sequence(s) |
|---|---|---|
| 8 | CNxxxECY (SEQ ID NO: 81) | |
| 9 | KxCQPxxC (SEQ ID NO: 82) | |
| 10 | PxPD[FH][TS] (SEQ ID NO: 83) | Dense granule protein 2 (Protein GRA 2) (28 kDa antigen) and SAG-related sequence protein SRS15A; Uncharacterized protein; Tetratricopeptide repeat-containing protein; Flagellar/basal body protein, PGAP1 family protein; PvPDFS(SEQ ID NO: 438), PvPDFT(SEQ ID NO: 439), PlPDFT(SEQ ID NO: 440), PlPDFS(SEQ ID NO: 441), PaPDFS(SEQ ID NO: 442 |
| 11 | NxxxExY[AG]xD (SEQ ID NO: 84) | O-linked N-acetylglucosamine transferase, Zinc knuckle protein; NaglEvYAeD(SEQ ID NO: 443, NrrrErYGeD(SEQ ID NO: 444 |
| 12 | P[AG]AxxLD (SEQ ID NO: 85) | Dense granule protein 3 (P30), Uncharacterized protein, GRAM domain-containing protein, Concanavalin A-like lectin/glucanase family protein; PGAvlLD(SEQ ID NO: 445, PAAskLD(SEQ ID NO: 446), PAAesLD(SEQ ID NO: 447), PGAarLD(SEQ ID NO: 448), PGAldLD(SEQ ID NO: 449) |
| 13 | MPSxSxE (SEQ ID NO: 86) | Uncharacterized protein, Toxoplasma gondii family A protein, Putative Tbc domain related protein; MPSwSnE(SEQ ID NO: 450), MPStSdE(SEQ ID NO: 451, MPSeStE(SEQ ID NO: 452), MPSaSpE(SEQ ID NO: 453) |
| 14 | [RK]xYxHR[TS] (SEQ ID NO: 87) | Putative 5'-3' exoribonuclease, Glycosyltransferase, Ribosomal protein RPL3; RlYvHRS(SEQ ID NO: 454), RlYrHRT(SEQ ID NO: 455), KgYfHRT(SEQ ID NO: 456) |
| 15 | K[PA]xFxFxK (SEQ ID NO: 88) | Micronemal protein 6, GCC2 and GCC3 domain-containing protein; KPpFeFgK(SEQ ID NO: 457), KPgFvFlK(SEQ ID NO: 458) |
| 16 | DD[CST]xGxR (SEQ ID NO: 89) | Dense granule protein 5 (Protein GRA 5) (p21), Uncharacterized protein, RNA pseudouridine synthase superfamily protein, AP2 domain transcription factor AP2XI-5; DDSeGaR(SEQ ID NO: 459), DDScGrR(SEQ ID NO: 460), DDSkGdR(SEQ ID NO: 461), DDSsGyR(SEQ ID NO: 462) |
| 17 | P[ML]xxHxMY (SEQ ID NO: 90) | |
| 18 | Kx[ASQ][SAT]xRG (SEQ ID NO: 91) | Dense granule protein 2 (Protein GRA 2) (28 kDa antigen), Alpha/beta hydrolase family protein, Putative transmembrane protein, Radical SAM domain-containing protein, Rhoptry neck protein RON8; KeAAgRG(SEQ ID NO: 463), KdASlRG(SEQ ID NO: 464), KgSSgRG(SEQ ID NO: 465), KtSSrRG(SEQ ID NO: 466), KtQTvRG(SEQ ID NO: 467), KrSTlRG(SEQ ID NO: 468) |
| 19 | [DG]QPEN (SEQ ID NO: 92) | Dense granule protein 3 (P30), FHA domain-containing protein, Uncharacterized protein; DQPEN(SEQ ID NO: 469), GQPEN(SEQ ID NO: 470) |
| 20 | [KHR]N[QN]DG (SEQ ID NO: 93) | Calcium-dependent protein kinase CDPK1, La domain protein, DNA polymerase, SAG-related sequence SRS34A, Surface antigen 2 (p22); KNNDG(SEQ ID NO: 471), RNNDG(SEQ ID NO: 472) |
| 21 | Nx[EVS]GExY (SEQ ID NO: 94) | EGF family domain-containing protein, Kringle domain-containing protein; NlVGEeY(SEQ ID NO: 473), NdSGEiY(SEQ ID NO: 474) |
| 22 | EP[VI]TG (SEQ ID NO: 95) | Dense granule protein 3 (P30), Corepressor complex CRC230, Cpw-wpc domain-containing protein; EPVTG(SEQ ID NO: 475) |
| 23 | HGM[PA][KR](SEQ ID NO: 96) | Dense granule protein GRA8, Tetratricopeptide repeat-containing protein; HGMPK(SEQ ID NO: 476), HGMAK(SEQ ID NO: 477) |

TABLE 3-continued

Motifs and peptides comprising panel for the diagnosis of acute Toxoplasmosis.

| ID | Panel motif | Antigen(s); peptide sequence(s) |
|---|---|---|
| 24 | [VIT]PWIF (SEQ ID NO: 97) | SAG-related sequence SRS57, Putative zinc finger protein; VPWIF(SEQ ID NO: 478) |
| 25 | Kx[STN]VxFQ (SEQ ID NO: 98) | Putative cell-cycle-control protein (Translation regulation), MaoC family domain-containing protein, Hydrolase, NUDIX family protein; KsSVpFQ(SEQ ID NO: 479), KeTVnFQ(SEQ ID NO: 480) |
| 26 | [VAI]WSGS (SEQ ID NO: 99) | Sma protein, Ribosomal protein L9, N-terminal domain-containing protein; VWSGS(SEQ ID NO: 481), IWSGS(SEQ ID NO: 482) |
| 27 | FS[LIAM]xxWG (SEQ ID NO: 100) | Pyruvate carboxylase, AP2 domain transcription factor AP2IX-5, Putative transmembrane protein, Putative major facilitator family transporter, Tub family protein; FSLenWG(SEQ ID NO: 483), FSMgrWG(SEQ ID NO: 484), FSLvlWG(SEQ ID NO: 485), FSLvlWG(SEQ ID NO: 486), FSLtnWG(SEQ ID NO: 487) |
| 28 | PTN[PQ]G (SEQ ID NO: 101) | Uncharacterized protein; PTNQG(SEQ ID NO: 488), PTNPG(SEQ ID NO: 489) |
| 29 | [RK]Kxx[YW]xHx[TS] (SEQ ID NO: 102) | Putative type I fatty acid synthase, O-phosphoseryl-tRNA(Sec) selenium transferase, NAD(+)/NADH kinase domain-containing protein; RKlhWnHrT(SEQ ID NO: 490), KKyrYrHpT(SEQ ID NO: 491), RKavYqHnT(SEQ ID NO: 492) |
| 30 | [HRW]xxHPRF (SEQ ID NO: 103) | Uncharacterized protein, Putative calcium signaling protein kinase RAD53, Glutamate 5-kinase domain-containing protein; RtlHPRF(SEQ ID NO: 493), HfrHPRF(SEQ ID NO: 494), RvaHPRF(SEQ ID NO: 495), WqaHPRF(SEQ ID NO: 496) |

Example 5. Discovery of Motifs for the Diagnosis of *Taenia solium* Infection (Cysticercosis)

Figure 10:
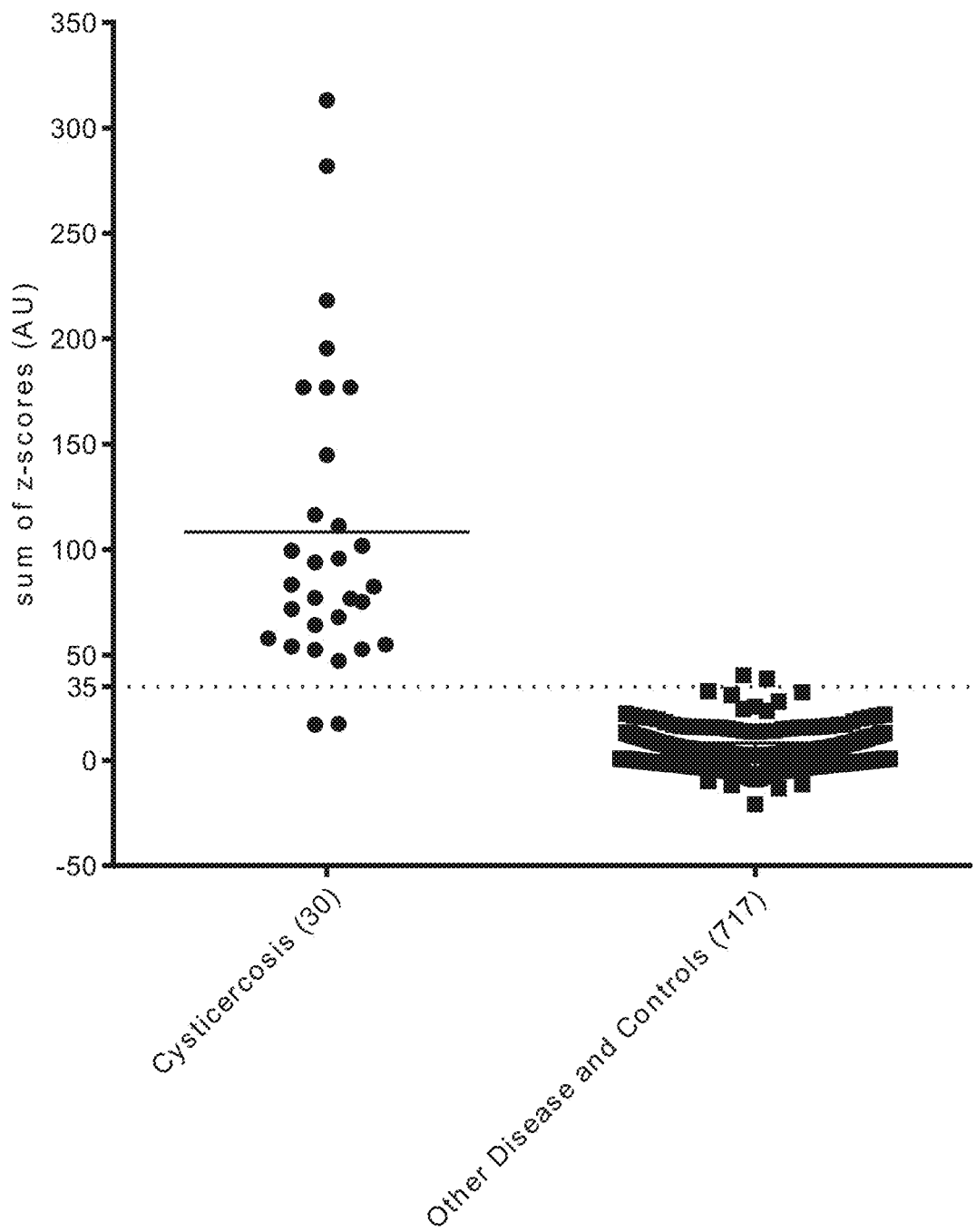
FIG. 10 illustrates the performance of *Taenia solium* (Cysticercosis) infection motif panel in a discovery sample set, exhibiting a sensitivity of >95%% and specificity of 99.5%.

Cysticercosis cause by the tapeworm *Taenia solium*, is considered a US neglected parasitic infection is a cause of cerebral parasitosis, and the single most common cause of epilepsy of unknown etiology. Diagnosis currently requires costly imaging studies to determine the presence, and number, of cysts present in the brain. A total of 30 samples from individuals diagnosed with Cysticercosis, with 1 or more cysts, were analyzed to determine their epitope repertoires. The method of Example 4 was applied to identify infection specific motifs (Table 4). A panel of motifs was capable of identifying Cysticercosis specimens (FIG. 10) with high specificity.

TABLE 4

Motifs and peptides comprising panel for the diagnosis of Cysticercosis.

| ID | Panel motif or Peptides |
|---|---|
| 1 | AxSPN[QEA]; (SEQ ID NO: 226) Huntingtin interacting protein 1; Trypsin-like protein, ArSPN (SEQ ID NO: 265), AgSpNri (SEQ ID NO: 266) |
| 2 | [RP]xAxSxNx[IFMLV] (SEQ ID NO: 227) |
| 3 | PDxGVxP (SEQ ID NO: 869); Putative DSCR5 protein, PDgGVmP (SEQ ID NO: 267) |
| 4 | NxxLGL[VT] (SEQ ID NO: 228); Protein Wnt, NpkLGLT (SEQ ID NO: 268) |
| 5 | [YF]x[DE]IxxFF (SEQ ID NO: 229) |
| 6 | IxHFFxG (SEQ ID NO: 230) |
| 7 | [ILM][ILM][RK]H[ED]XQ (SEQ ID NO: 231) |
| 8 | [ILM][RK]HExQ (SEQ ID NO: 232) |
| 9 | KPxx[IL]xLx[KR] (SEQ ID NO: 233) |
| 10 | NxDxxYYxx[WF] (SEQ ID NO: 234) |
| 11 | GLDGP (SEQ ID NO: 235) |
| 12 | RSxHDxxN (SEQ ID NO: 236) |
| 13 | FDxFN[IL] (SEQ ID NO: 237) |
| 14 | TIFxGK (SEQ ID NO: 238) |
| 15 | R[AV]xS[TQ]H (SEQ ID NO: 239) |
| 16 | KWHGxY (SEQ ID NO: 240) |
| 17 | MPEDK (SEQ ID NO: 241) |
| 18 | Exxx[FY]x[AS]D[NT] (SEQ ID NO: 242) |
| 19 | NQSxxKx[VI] (SEQ ID NO: 243) |
| 20 | KxY[NAS]PY (SEQ ID NO: 244) |
| 21 | [PQ][VL]HPRI (SEQ ID NO: 245) |

TABLE 4-continued

Motifs and peptides comprising panel for the diagnosis of Cysticercosis.

| ID | Panel motif or Peptides |
|---|---|
| 22 | EDGMxxW (SEQ ID NO: 246) |
| 23 | YASXQE (SEQ ID NO: 247) |
| 24 | KQxQ[QK]E (SEQ ID NO: 248) |
| 25 | K[AS]VFD[IVM] (SEQ ID NO: 249) |
| 26 | PN[QE]x[DN]P (SEQ ID NO: 250) |
| 27 | P[QA]XM[DN]I (SEQ ID NO: 251) |
| 28 | [WR]x[RKH][ST]xFD (SEQ ID NO: 252) |
| 29 | KxEPGxK (SEQ ID NO: 253) |
| 30 | DDCLP (SEQ ID NO: 254) |
| 31 | NXXXXGXHLE (SEQ ID NO: 255) |
| 32 | DxxHLEG (SEQ ID NO: 256) |
| 33 | RPxx[TS]HN (SEQ ID NO: 257) |
| 34 | KxHS[IV]Y (SEQ ID NO: 258) |
| 35 | KxHSx[IV]S (SEQ ID NO: 259) |
| 36 | MSGYE (SEQ ID NO: 260) |
| 37 | YXIWGP (SEQ ID NO: 261) |
| 38 | RxxWxMN[RK] (SEQ ID NO: 262) |
| 39 | QPxxT[FY]E (SEQ ID NO: 263) |
| 40 | YGYNQ (SEQ ID NO: 264) |

Figure 11A:
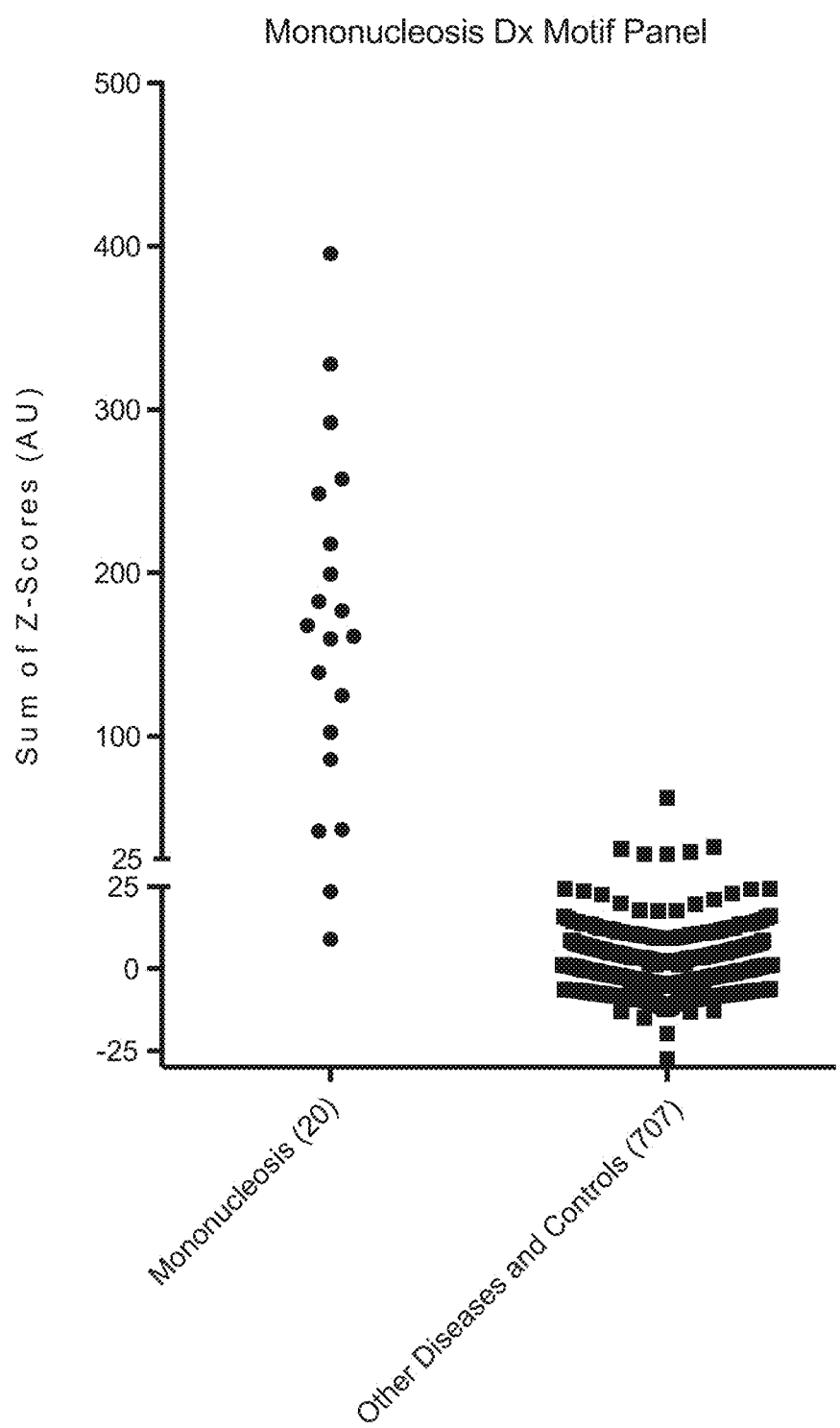
FIG. 11A illustrates the performance of an Esptein Barr Virus Mononucleosis infection motif panel in a discovery and validation sample sets, exhibiting a sensitivity of 90% and specificity of 99%.

Example 6. Discovery of Motifs for the Diagnosis of Mononucleosis by EBV Infection Mononucleosis caused by EBV can be difficult to diagnosis and discriminate from prior EBV exposure and/or viral reactivation. Twenty samples from individuals with confirmed EBV mononucleosis were characterized according to the Method of Example 1. Motifs discovered (Table 5) were capable of identifying all specimens from EBV infection Mono cases, with high specificity (FIG. 11). The absence of a particular motif (for example the RRPFF (SEQ ID NO: 937) epitope of EBNA-1) was helpful as an aid to identify individuals with prior infections, or with prolonged course of primary infection.

TABLE 5

Motifs and peptides comprising panel for the diagnosis of Mononucleosis.

| ID | Panel motif and Antigen(s); peptide sequence(s) |
|---|---|
| 1 | LFGxx[LM]N (SEQ ID NO: 9);<br>BKRF2 (Envelope glycoprotein L); LFGanLN (SEQ ID NO: 44) |
| 2 | GELxGQ (SEQ ID NO: 852) |
| 3 | EWVxx[YF]D (SEQ ID NO: 10) |
| 4 | P[LM]ALxL (SEQ ID NO: 11) |
| 5 | KxNExWxV (SEQ ID NO: 12) |
| 6 | P[AG]xRTxK (SEQ ID NO: 13);<br>BFLF1 (Packaging protein UL32 homolog); PGpRTcK (SEQ ID NO: 45)<br>BZLF1 (Viral immediate early antigen); PArRTrK (SEQ ID NO: 46) |
| 7 | AYTxVN (SEQ ID NO: 14) |
| 8 | WN[AS]YxxxN (SEQ ID NO: 15) |
| 9 | [RKE]xxWxP[LM]Q (SEQ ID NO: 16) |
| 10 | [AS]YxSx[SA][YF] (SEQ ID NO: 17) |
| 11 | ExYxSPS (SEQ ID NO: 18) |
| 12 | MNIxDD (SEQ ID NO: 19) |
| 13 | EH[ANK]FW (SEQ ID NO: 20) |
| 14 | VHNAY (SEQ ID NO: 21) |
| 15 | HG[EA]xLN (SEQ ID NO: 22) |
| 16 | [GD]xx[LF]xxP[ML]Q (SEQ ID NO: 23) |
| 17 | [LVMI]xNAx[TS][FGI] (SEQ ID NO: 24);<br>BPLF2 (Large tegument protein); IaNAgSI (SEQ ID NO: 47) |
| 18 | PxNSYT (SEQ ID NO: 25) |
| 19 | RxxPLAxxL (SEQ ID NO: 26) |
| 20 | CPKxNxT (SEQ ID NO: 27) |
| 21 | Q[PA]H[AM]F (SEQ ID NO: 28) |
| 22 | PAxENxxx[GSP] (SEQ ID NO: 29) |
| 23 | NID[DE]D (SEQ ID NO: 30) |
| 24 | RxQx[VS]D[NA] (SEQ ID NO: 31) |
| 25 | Wx[DP]PxHL (SEQ ID NO: 32) |
| 26 | TWA[FI][FI] (SEQ ID NO: 33) |
| 27 | EDxGHP (SEQ ID NO: 34) |
| 28 | [ETA]xxx[YF]xxP[SR]Q (SEQ ID NO: 35) |
| 29 | GMxP[RK]Q (SEQ ID NO: 36) |
| 30 | Wxx[VI]RxxPxQ (SEQ ID NO: 37); EBNA-3B nuclear protein;<br>WaqIRhiPyQ (SEQ ID NO: 48) |
| 31 | [NE][AG]Y[SAT]xxW (SEQ ID NO: 38) |
| 32 | KxI[ST]xYW (SEQ ID NO: 39) |
| 33 | YYxYltxxK (SEQ ID NO: 40) |
| 34 | KxHExG[FY] (SEQ ID NO: 41) |
| 35 | [MLF]xNPQQ (SEQ ID NO: 853); Major capsid protein (MCP);<br>MrNPQQ (SEQ ID NO: 49) |

TABLE 5-continued

Motifs and peptides comprising panel for the diagnosis of Mononucleosis.

| ID | Panel motif and Antigen(s); peptide sequence(s) |
|---|---|
| 36 | HHFL[VI] (SEQ ID NO: 42) |
| 37 | [LV]CNAY (SEQ ID NO: 43) |

Example 7. Discovery of Motifs for the Diagnosis of Zika Virus Infection

Figure 12A:
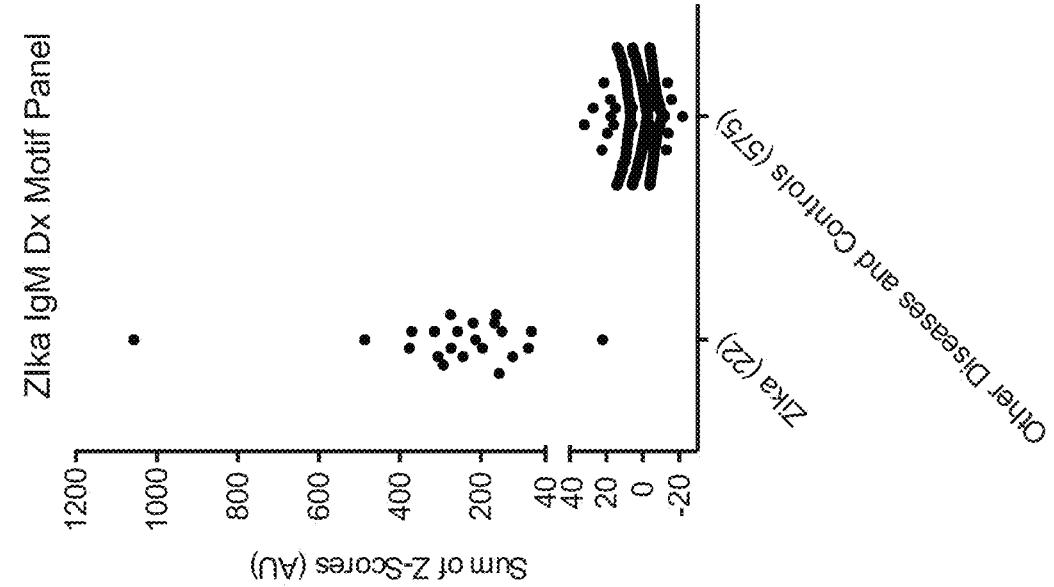
FIG. 12A illustrates the performance of IgG ZIKA virus infection motif panel in a discovery sample set.
Figure 12B:
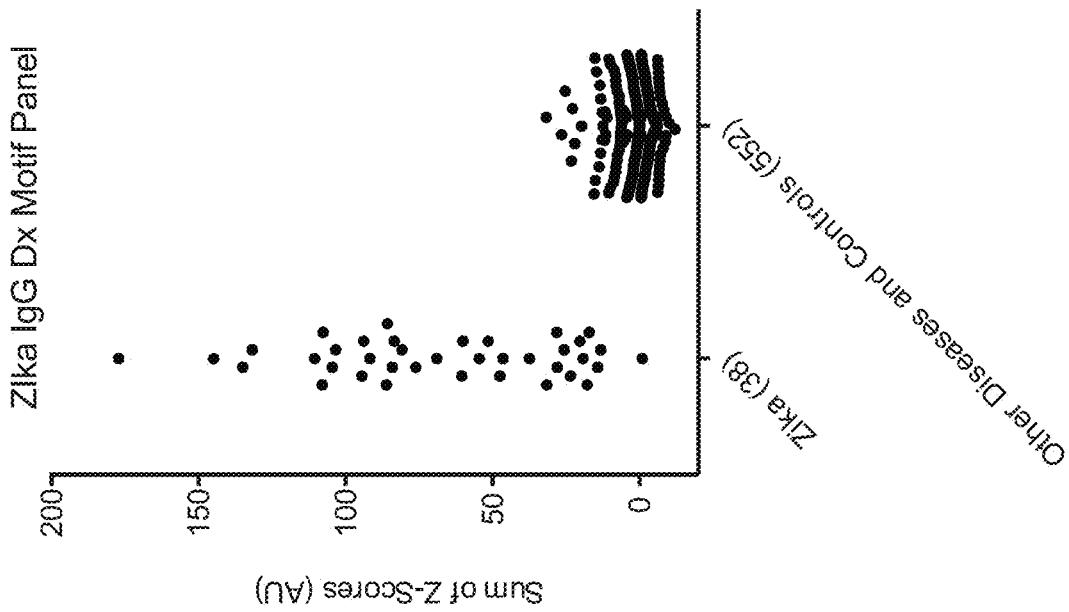
FIG. 12B illustrates the performance of an IgM motif panel for diagnosis of Zika virus infection, exhibiting a sensitivity of 95% and specificity of 100%.

A total of 38 specimens from individuals positive for Zika virus infection by IgG and/or IgM serology and clinical criteria (e.g. red eyes, fatigue, joint pain, etc) using an enzyme immunoassay were analyzed. The method of Example 1 was to identify IgG and IgM motifs specific to Zika virus infection (Table 6, Table 7) Motif panels were capable of identifying individuals with Zika virus infections (FIG. 12). Similarly, the method of example 1, with the following modifications was used to identify IgM motifs indicative of Zika infection. Rather than using protein A/G beads, peptide displaying cells complexed with IgM were separated and enriched from non-binders using a biotinylated monoclonal antibody specific for human IgM, followed by cell capture on streptavidin-conjugated magnetic beads.

TABLE 6

IgG motifs comprising IgG panel for the diagnosis of Zika

| ID | Panel motif |
|---|---|
| 1 | VRxxYxQH (SEQ ID NO: 319) |
| 2 | CEDxxxHxC (SEQ ID NO: 320) |
| 3 | DAEQxxR (SEQ ID NO: 321) |
| 4 | WPGIF (SEQ ID NO: 322) |
| 5 | CCYDXE (SEQ ID NO: 323) |
| 6 | LxPDNxT (SEQ ID NO: 324) |
| 7 | FxWGQxY (SEQ ID NO: 325) |
| 8 | KxEGHxxxxA (SEQ ID NO: 326) |
| 9 | CxxGxCQxK (SEQ ID NO: 327) |
| 10 | CCxDxx[DE][ED] (SEQ ID NO: 328) |
| 11 | RNGxED (SEQ ID NO: 329) |
| 12 | [DE]xRxIYxQ (SEQ ID NO: 330) |
| 13 | WxRCGL (SEQ ID NO: 331) |
| 14 | D[ED]xRxxYxxH (SEQ ID NO: 332) |
| 15 | WCxLx[AV]N (SEQ ID NO: 333) |
| 16 | LXTPWI (SEQ ID NO: 334) |
| 17 | CWxxxGL[CA] (SEQ ID NO: 335) |
| 18 | ID[AV]EP (SEQ ID NO: 336) |
| 19 | HF[NK][VT]xK (SEQ ID NO: 337) |
| 20 | QxNHQxK (SEQ ID NO: 338) |

TABLE 7

IgM motifs comprising IgM panel for the diagnosis of Zika.

| ID | Panel motif |
|---|---|
| 1 | FExKEP (SEQ ID NO: 339) |
| 2 | [FYW]DA[VI] (SEQ ID NO: 340) |
| 3 | DFDKR (SEQ ID NO: 341) |
| 4 | WETC (SEQ ID NO: 342) |
| 5 | KLDGP (SEQ ID NO: 343) |
| 6 | WIYPxK (SEQ ID NO: 344) |
| 7 | V[HS]DSK (SEQ ID NO: 345) |
| 8 | EQCGT (SEQ ID NO: 346) |
| 9 | [KE][MVIT]PYA (SEQ ID NO: 347) |
| 10 | [DE]xxML[RP]W (SEQ ID NO: 348) |
| 11 | YExLHx[FY] (SEQ ID NO: 349) |
| 12 | WY[TSN]xEK (SEQ ID NO: 350) |
| 13 | [YF]H[DNS]AV (SEQ ID NO: 351) |
| 14 | DxTG[VI]P (SEQ ID NO: 352) |
| 15 | FDxxGEH (SEQ ID NO: 353) |
| 16 | QC[AK]xx[HE]C (SEQ ID NO: 354) |
| 17 | LW[FY]xPxE (SEQ ID NO: 355) |
| 18 | C[MI][PA]GxxC (SEQ ID NO: 356) |
| 19 | Cxxxx[AVS]ADC (SEQ ID NO: 357) |
| 20 | TTESxV (SEQ ID NO: 854) |
| 21 | KDV[GA]E (SEQ ID NO: 855) |
| 22 | KPxD[FWM]GxK (SEQ ID NO: 856) |
| 23 | VxADGT (SEQ ID NO: 857) |
| 24 | M[AP][AT]AD (SEQ ID NO: 858) |
| 25 | VPxPK[DG] (SEQ ID NO: 859) |
| 26 | QxKP[TS]D (SEQ ID NO: 860) |
| 27 | F[TS]xDGF (SEQ ID NO: 861) |
| 28 | Wx[RK]VY[VA] (SEQ ID NO: 862) |
| 29 | [CS]T[TS]Exxx[YF] (SEQ ID NO: 863) |
| 30 | YxETC[TI] (SEQ ID NO: 864) |

Example 8. Discovery of Motifs for the Diagnosis for HIV Infection

Figure 13:
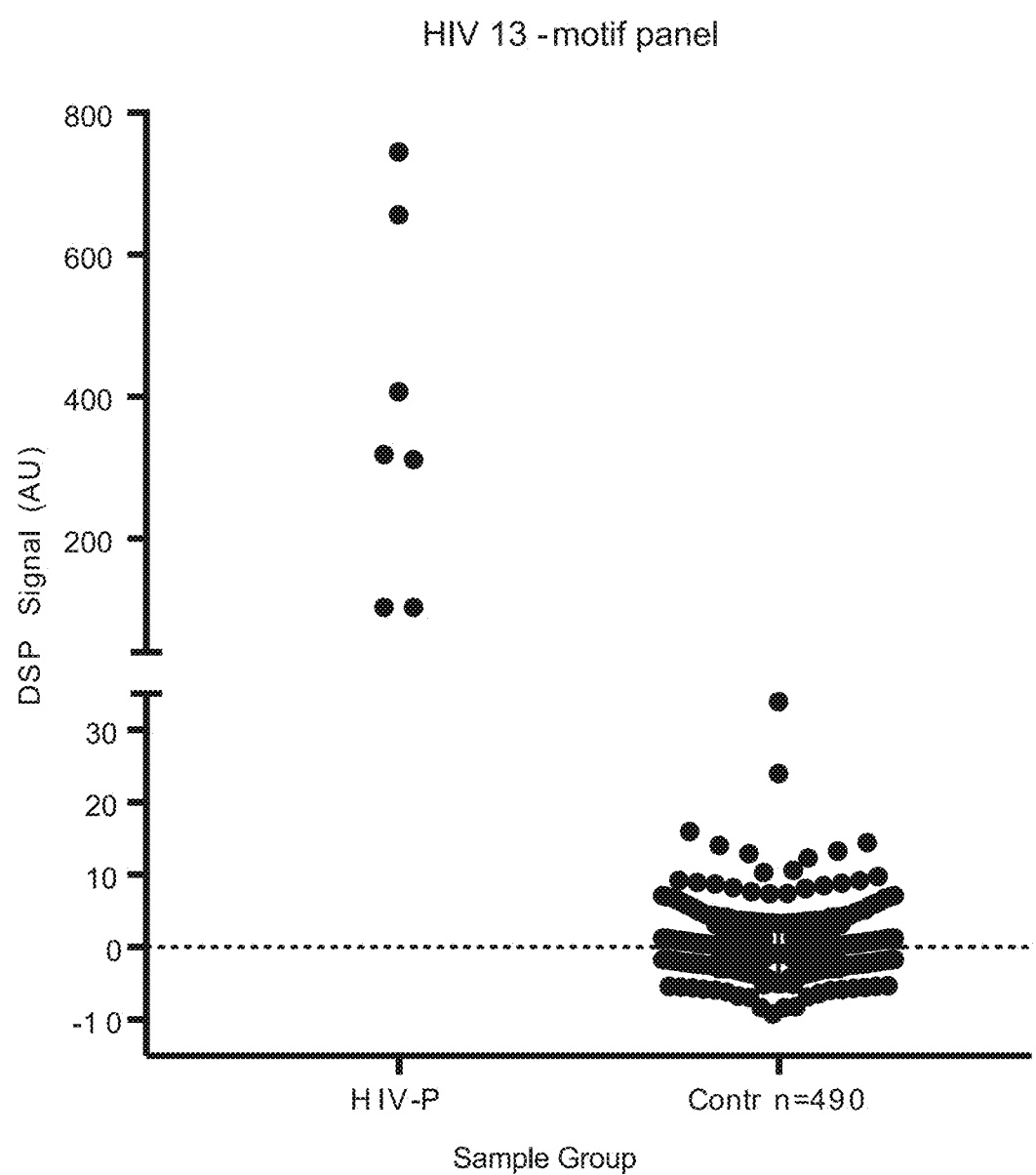
FIG. 13 illustrates the performance of HIV infection motif panel in a discovery and validation sample sets, exhibiting a sensitivity of 100% and specificity of 100%.

Sera from seven individuals with HIV infection were analyzed as described for Example 1. Motifs specific to HIV infection are as shown in Table 8. A panel of motifs was capable of identifying individuals with HIV (FIG. 13), and discriminating those with infections from those without infections.

TABLE 8

| Motifs and peptides comprising panel for the diagnosis of HIV infection. | | |
|---|---|---|
| ID | Panel motif | Antigen(s); peptide sequence(s) |
| 1 | CxGxLIC (SEQ ID NO: 290 | Envelope glycoprotein gp160; CSGKLIC (SEQ ID NO: 306) |
| 2 | CxxKX[IV]C[IV] (SEQ ID NO: 291 | Envelope glycoprotein gp160; CSGKLICT (SEQ ID NO: 306) |
| 3 | W[GAS]CxGxxxC (SEQ ID NO: 292) | Envelope glycoprotein gp160; WGCSGKLIC (SEQ ID NO: 308) |
| 4 | [RK]KL[IV]E (SEQ ID NO: 293 | |
| 5 | KLIMT (SEQ ID NO: 294) | |
| 6 | [QE]xxPFRY (SEQ ID NO: 295) | |
| 7 | CxxKx[IV]C[IV] (SEQ ID NO: 296) | Envelope glycoprotein gp160; CSGKLICT (SEQ ID NO: 309) |
| 8 | [LF]xX[LIV][ND]KW (SEQ ID NO: 297) | Envelope glycoprotein gp160; LLALDKW (SEQ ID NO: 310) |
| 9 | [AP][GC]GFG (SEQ ID NO: 298 | Envelope glycoprotein gp160; AVGMG (SEQ ID NO: 311) |
| 10 | LIx[TS]TY (SEQ ID NO: 299 | Envelope glycoprotein gp160; LICTT (SEQ ID NO: 312) |
| 11 | [RK]KLxx[MV]Y (SEQ ID NO: 300) | |
| 12 | GF[GA][AQ][AYV] (SEQ ID NO: 301) | Envelope glycoprotein gp160; GFGAV (SEQ ID NO: 313) |
| 13 | GFG[RQ]x[FNY] (SEQ ID NO: 302) | |
| 14 | [KR]KxIH[VIM] (SEQ ID NO: 303) | Envelope glycoprotein gp160; RKgIrI (SEQ ID NO: 314) KKgIaI (SEQ ID NO: 315), RKgIhM (SEQ ID NO: 316), RKsIhM (SEQ ID NO: 317) |
| 15 | R[IV]PFG (SEQ ID NO: 304) | |
| 16 | KLIxx[TY]T (SEQ ID NO: 305) | Envelope glycoprotein gp160; KLICTT (SEQ ID NO: 318) |

Example 9: Sjogren's Syndrome—Discovery of Diagnostic Motifs and Peptides

Primary Sjogren's Syndrome (SS) is a chronic, highly prevalent autoimmune disease affecting about 0.3-0.5% of people in the western world. The hallmark symptoms are dry eyes and mouth, which are a result of T cell and autoantibody infiltration of the exocrine glands leading to loss of secretory function and, over time, eventual gland destruction. The gradual destruction of the exocrine glands underscores the importance of early diagnosis and treatment to patient quality of life. The heterogeneity of symptoms, their association with aging and lack of specific diagnostic tests all contribute to delayed diagnosis with an average time of 4.7 years. Serological testing for autoantibodies including La/SS-B, Ro/SS-A, Anti-nuclear antibodies (ANAs) and rheumatoid factor (RF) are used to aid in SS diagnosis, however, they do not provide sufficient specificity to be used as a stand-alone diagnostic test, Identification of novel SS specific biomarkers is thus an important unmet diagnostic need. The heterogeneity of SS may reflect different subcategories of SS with unique sets of autoantibodies, posing an additional diagnostic challenge. In this Example, we identified biomarkers that are specific to SS and defined their association with specific disease subpopulations. The tests can be combined into a single multiplex assay having greater overall specificity and sensitivity than current tests.

Until recently, no SS classification criteria have been universally accepted because of the subjective and non-specific nature of SS diagnostics. The new criteria, endorsed by the American College of Rheumatology, requires a positive result in 2 out of 3 of the following objective tests:

1. Positive serum anti-SSA/Ro and/or anti-SSB/La or (positive rheumatoid factor (RF) and ANA titer 1:320), requiring 3 separate ELISAs and an indirect immunofluorescence assay (IFA).

2. Labial salivary gland biopsy exhibiting focal lymphocytic sialadenitis (focus score 1 focus/4 mm2)

3. Dry eye as measured by staining on the surface of the eye with ocular staining score 3.

The need for multiple testing modalities is redundant, costly and labor intensive. Identification of a panel of biomarkers that could identify SS with high sensitivity and specificity as a single serological test could streamline and expedite SS diagnosis and improve patient outcomes.

In this Example, we identified motifs, patterns and peptides specific for primary Sjogren's Syndrome (pSS). The experiment procedure is as described in Example 1.

Figure 14:
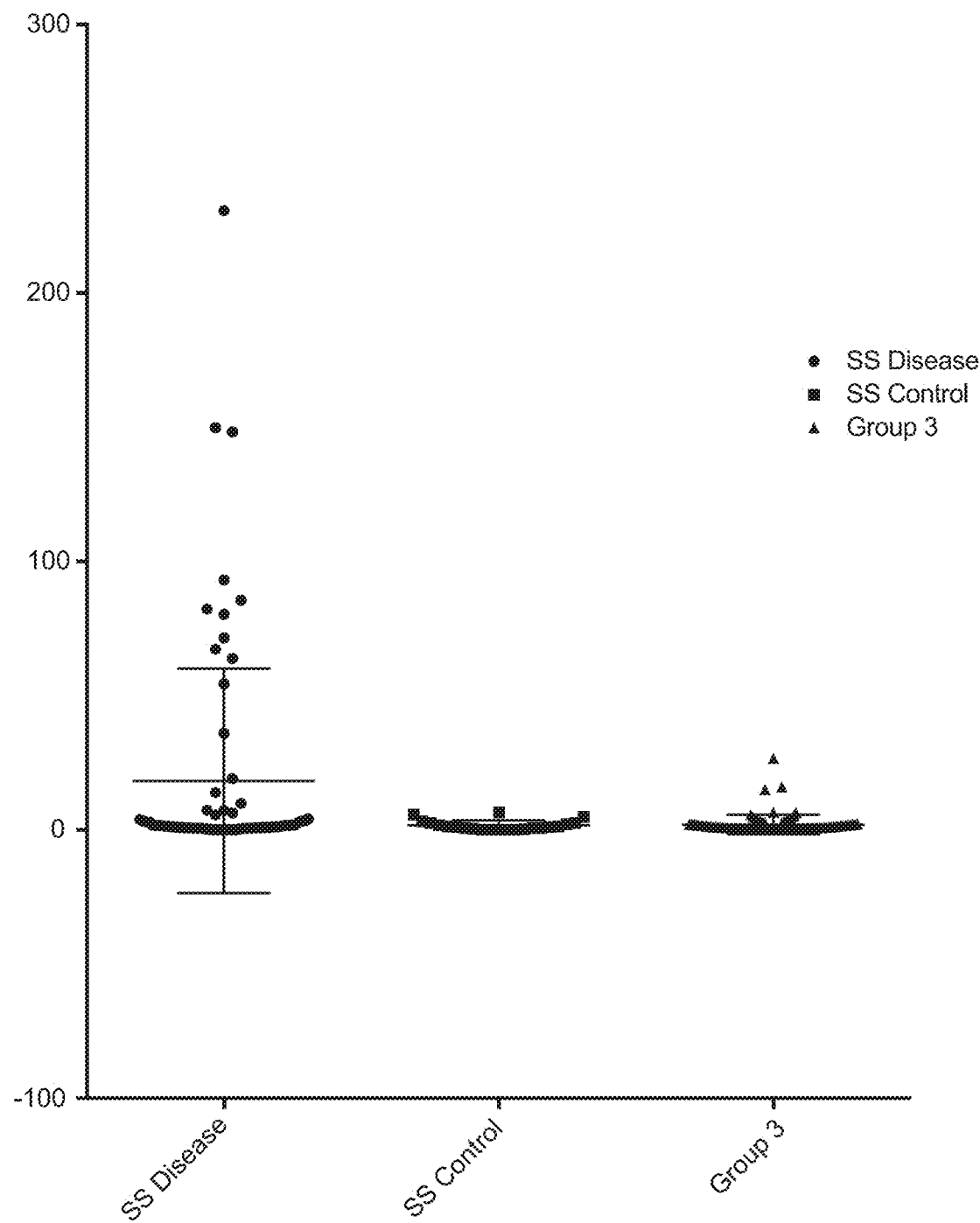
FIG. 14 illustrates the performance of an individual Sjogren's syndrome diagnostic motif (SEQ ID NO: 929) in a discovery and validation sample sets.

Examples of motifs specific to pSS include KPXFXGXK (SEQ ID NO: 929). Specificity of individual motifs (e.g., KPXFXGXK (SEQ ID NO: 929)) is also evident in dot plots (FIG. 14).

To use the pSS motifs for diagnosis of pSS, one obtains a serum or blood sample, screens a peptide display library using that sample, determines the resulting enriched sequences, and then queries for the enrichment of disease specific motifs. If one or more disease specific motif is present, then enrichment values for the pSS specific motifs are determined, and compared to a reference cutoff value.

Example 10. Discovery of Motifs Indicating Latent Epstein-Barr Virus Infection

Epstein-Barr virus (EBV) is a ubiquitous latent infection in the human population, with B-cells being the primary host for the virus. Despite being ubiquitous active EBV is associated with mononucleosis, and reactivation of latent EBV has been associated with various autoimmune diseases. Furthermore, EBV serology has shown to a risk factor for autoimmune diseases, since negative serology for EBV dramatically lowers the risk of multiple sclerosis. For these reasons, EBV serology is clinically useful.

To identify diagnostic motifs and epitopes useful for EBV serology, 20 samples from samples obtained from individuals with EBV mononucleosis were analyzed for peptide motifs using the methods described above. Peptide motifs were discovered by pattern clustering (e.g. using IMUNE algorithm).

Among the top 40 most abundant motifs, motifs corresponding to EBV epitopes were identified by searching the motif against the non-redundant protein database for all exact matches. Nine EBV motifs were identified that exactly matched a corresponding epitope in an EBV protein. See Table 9. Multiple motifs were experimentally validated to correspond to the indicated epitope within EBV.

To diagnose active infection, one or more of the motifs in Table 9 are searched within an epitope repertoire from any individual to determine serological status for EBV infection. For each motif, an enrichment of 3-fold or greater is indicative of infection See FIG. 25. Active infection can be ascertained by measuring the enrichment for motifs corresponding to BFRF2, GP42, and BVRF2, which correspond to epitopes in viral capsid antigens (VCA).

TABLE 9

Exemplary motifs and peptides for serological detection of latent EBV infection.

| EBV Motif ID | Motif | Peptide epitope in EBV protein |
|---|---|---|
| EBV.EBNA-1.1 | GRRPFF (SEQ ID NO: 269) | GRRPFF (SEQ ID NO: 281) |
| EBV.EBNA-1.2 | GGGxGAGGG (SEQ ID NO: 270) | GGGAGAGGG (SEQ ID NO: 282) |
| EBV.EBNA-1.3 | EG[PA]ST[GA]R (SEQ ID NO: 271) | EGPSTGPR (SEQ ID NO: 283) |
| EBV.EBNA-1.4 | KXXSC[IVL]GC[RK] (SEQ ID NO: 272), SCIGCK (SEQ ID NO: 273), CIGC (SEQ ID NO: 274) | KRPSCIGCK (SEQ ID NO: 284) |
| EBV.GP42.1 | VxLPHW (SEQ ID NO: 275), LPHW (SEQ ID NO: 276) | KEVKLPHWTPT (SEQ ID NO: 285) |
| EBV.BFRF2 | PQDT[GA]PR (SEQ ID NO: 277) | PQDTAPR (SEQ ID NO: 286) |
| EBV.EBNA-2.1 | GPPWWP (SEQ ID NO: 278) | GPPWWP (SEQ ID NO: 287) |
| EBV.BVRF2/BdRF1 | QQPTTXGW (SEQ ID NO: 279) | QQPTTEGH (SEQ ID NO: 288) |
| EBV.EBNA-2.2 | [LMIV]FDXDWYP (SEQ ID NO: 280) | LFPDDWYP (SEQ ID NO: 289) |

Example 11. Discovery of Motifs Related to Rhinovirus Virus Infection, and Determination of Prior Rhinovirus Infection Human rhinovirus is a common upper respiratory infection in humans, and is associated with a robust immune response. Recent infections typically increase the titer of Rhinovirus specific antibodies. Thus, by measuring the titer of antibodies towards Rhinovirus motifs or patterns, one can identify prior or recent infection with Rhinovirus.

Motifs indicative of Rhinovirus are shown in Table 10, searching epitope repertoires for rhinovirus patterns, peptides, and motifs identifies individuals with a humoral immune response against these epitopes, which can provide a measure of whom has been infected, and whether their infection was recent (by the magnitude of the enrichment signal).

TABLE 10

Exemplary motifs and peptides for serological detection of Rhinovirus infection or exposure

| Motif ID | Motif | Peptide epitope in protein |
|---|---|---|
| Rhinovirus.VP1.1 | L[EDQ]EV[LIV][IV][DE]K (SEQ ID NO: 50), E[VI][VIL][IV][DEN]K (SEQ ID NO: 51), E[VI][VI][VI]XK (SEQ ID NO: 52) | ELEEV[IV]VDK (SEQ ID NO: 58) |
| Rhinovirus.VP1.2 | VXPNI (SEQ ID NO: 53), VVPN (SEQ ID NO: 54), LXEVLVVVP (SEQ ID NO: 55) | LNEVLVVVPNI (SEQ ID NO: 59) |
| Rhinovirus.VP1.3 | GPXHTXKV (SEQ ID NO: 56) | GPKHTQKV (SEQ ID NO: 60) |
| Rhinovirus A.VP1 | EXY[VI]DX[VT]LN (SEQ ID NO: 57) | EEYVDQVLN (SEQ ID NO: 61) |

Example 12. Discovery of Motifs Related to Cytomegalovirus Infection

Human cytomegalovirus (CMV) is a common infectious herpes virus (HHV-5), often infecting salivary glands. CMV can remain dormant or latent in tissues for long periods of time, but can be reactivated by various stimuli. Infections can be life threatening in immunocompromised individuals, for instance when infected with human immunodeficiency virus (HIV) or after organ transplantation. CMV has been associated with cancers, diabetes, arterial hypertension, and other diseases. See [41, 42]. Given this, there is need to identify those infected with CMV and determine whether infected individuals are at higher risk of developing specific diseases.

Diagnosis of CMV infection can be made by looking for the presence of anti-CMV antibodies although not all of the protein and peptide antigen epitopes are known. Epitope specific detection of prior CMV infection can also be useful, for example, to associate clinical phenotypes and risks to specific antibody species.

To identify motifs indicative of latent CMV infection, epitope repertoires were determined using laboratory analysis as described above for 40 individuals with Sjogren's syndrome and 40 healthy controls, wherein a subset of each group are positive for CMV infection. Peptides present in five or more pSS and five or more healthy control epitope repertoires were then extracted from the sequence files in order to perform motif discovery via clustering with MEME. Among the resulting motifs were KXDPDXXW[ST] (SEQ ID NO: 62) and KPXLGGK (SEQ ID NO: 63), both of which occur in CMV proteins. See Table 11. These CMV associated motifs can be detected in individual epitope repertoires to assess CMV serology and exposure.

TABLE 11

Exemplary motifs and peptides for serological detection of Cytomegalovirus infection or exposure.

| Motif ID | Motif | Peptide epitope in protein |
|---|---|---|
| CMV.RL13.1 | KXDPDXXW[ST] (SEQ ID NO: 62) | KXDPDXXWT (X = variable positions in viral protein) (SEQ ID NO: 64) |

TABLE 11-continued

Exemplary motifs and peptides for serological detection of Cytomegalovirus infection or exposure.

| Motif ID | Motif | Peptide epitope in protein |
|---|---|---|
| CMV.Teg.1 | KPXLGGK (SEQ ID NO: 63) | KPtLGGK (SEQ ID NO: 65) |

Example 13. Discovery of Motifs Related to *Streptococcus* Infection

*Streptococcus pyogenes* and other *Streptococcus* species are common pathogens in humans, and accurate diagnosis can help to identify proper treatments. Antibody titer can increase in response to ongoing or recent infection. Several motifs were identified by using the methodology described herein in a set of individuals with and without autoimmune disease, grouping peptides present in >30% of samples, and then performing motif discovery. See Table 12. Motifs identified were used to search for proteins containing these motifs in the non-redundant protein database using Scanprosite. Three motifs identified primarily *Streptococcus* associated antigens, including PspC, Streptolysin O, the later of which is a known target of the human immune response. Here, however, we have identified the protein site targeted by antibodies, and specific motifs and peptides useful for the detection of these antibodies in an epitope repertoire, or serum sample, respectively.

TABLE 12

Exemplary motifs and peptides for serological detection of *Streptococcus* infection

| Motif ID | Motif | Peptide epitope in protein |
|---|---|---|
| Streptococcus.PspC.1 | [IV]X[PR]QPEKP (SEQ ID NO: 66) | VKPQPEKP (SEQ ID NO: 71) |
| Streptococcus.Streptolysin O.1 | KXDDMLN (SEQ ID NO: 67), KXDXMLN (SEQ ID NO: 68) | KTDDMLN (SEQ ID NO: 72) |

TABLE 12-continued

Exemplary motifs and peptides for serological detection of *Streptococcus* infection

| Motif ID | Motif | Peptide epitope in protein |
|---|---|---|
| *Streptococcus.* Streptolysin 0.2 | LW]XSAEXEEK (SEQ ID NO: 69), SAEXEXK (SEQ ID NO: 70) | LESAEKEEK (SEQ ID NO: 73) |

Example 14. Discovery of Motifs Diagnostic of *Haemophilus influenza* Infection

*Haemophilus influenza* is a gram positive bacteria that infects humans, and is associated with pneumonia, meningitis, sinusitis, and other conditions. Determination of infection or of specific serotypes or species can help to determine proper antibiotic therapy.

To identify motifs indicative of *Haemophilus influenza* infection or exposure, the methods provided herein were used to determine epitope repertoires in 40 individuals with Sjogren's syndrome, and 40 healthy controls. Peptides present in five or more pSS and five or more healthy control epitope repertoires were then extracted from the sequence files in order to perform motif discovery via clustering with MEME. Clustering identified the motif MKEAX[SA]EK (SEQ ID NO: 497) which as an epitope MKEAASEK (SEQ ID NO: 498) in an poorly characterized protein antigen of *Haemophilus influenza*.

Example 15. Discovery of Motifs Diagnostic of *Leishmania* Infection

Figure 15:
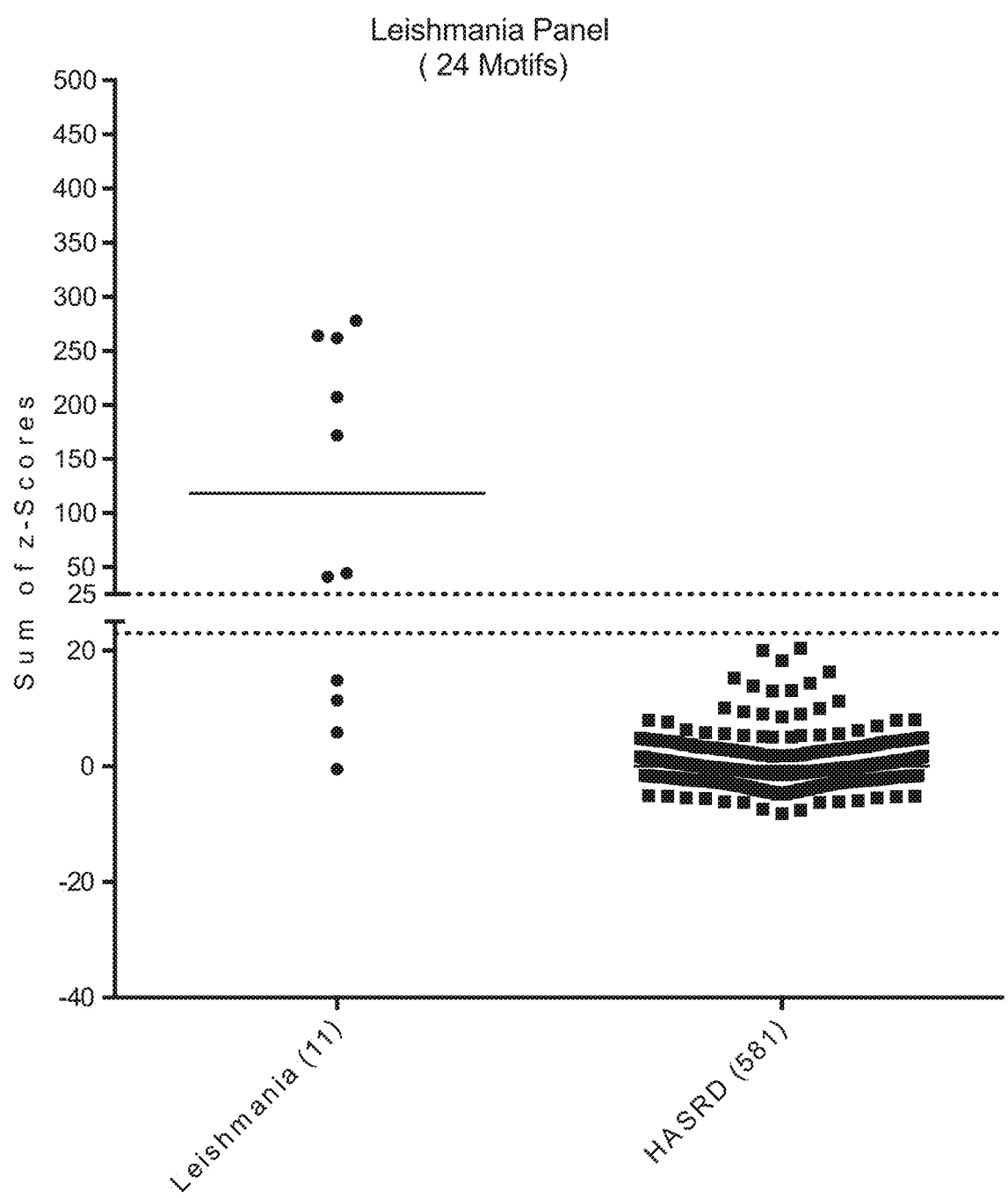
FIG. 15 illustrates the performance of *Leishmania* infection motif panel in a discovery and validation sample sets, exhibiting a sensitivity of 65% and specificity of 100%.

Samples from individuals (n=11) with *Leishmania* infections were analyzed by the methods described herein resulting in the motif panel in Table 13. A panel of motifs from Table 13 was capable of identifying individuals with *Leishmania* infections (FIG. 15).

TABLE 13

Motifs indicative of *Leishmania* infection.

| *Leishmania* motif | Peptide Hit(s) | Putative Antigen |
|---|---|---|
| R[IV]PFG (SEQ ID NO: 499) | RVPFG (SEQ ID NO: 519) | Uncharacterized protein. *Leishmania panamensis* and other sp |
|  | RIPFG (SEQ ID NO: 520) | DNA-directed RNA polymerase subunit *Leishmania panamensis* |
|  | RIPFG (SEQ ID NO: 521) | DNA-directed RNA polymerase subunit (EC 2.7.7.6). *Leishmania braziliensis* |
|  | GGlfRVPFG (SEQ ID NO: 522) | 1-acyl-sn-glycerol-3-phosphateacyltransferase-like protein, putative *Leishmania panamensis* |
| KGXATP (SEQ ID NO: 500) | KGKATPS (SEQ ID NO: 523) | Histone H2A.1. *Leishmania infantum* |
|  | KGKATPS (SEQ ID NO: 524) | Histone H2A. *Leishmania donovani* |
| P[ML]xVGP (SEQ ID NO: 501) | PL[VSPLR]VGP (SEQ ID NO: 525) | Uncharacterized protein. *Leishmania panamensis* and other sp |
| PKxDG[RY] (SEQ ID NO: 502) | PKvDGR (SEQ ID NO: 526) | Protein kinase, putative (EC 2.7.11.1). *Leishmania panamensis* |
|  | PKaDGR (SEQ ID NO: 527) | Uncharacterized protein. *Leishmania panamensis* |
|  | PKaDGY (SEQ ID NO: 528) | Uncharacterized protein. *Leishmania panamensis* |
|  | PKeDGR (SEQ ID NO: 529) | Hydrophilic acylated surface protein b. *Leishmania infantum* peptide has multiple repeats |
|  | PKeDGR (SEQ ID NO: 530) | K26 protein (Fragment). *Leishmania infantum* peptide has multiple repeats |
| KxDGH[ES] (SEQ ID NO: 503) | KyDGHS (SEQ ID NO: 531) | Uncharacterized protein. *Leishmania panamensis* |
|  | KcDGHE (SEQ ID NO: 532) | Uncharacterized protein. *Leishmania panamensis* |
| VQx[FY]Mx[RK] (SEQ ID NO: 504) | VQhYMhR (SEQ ID NO: 865) | Uncharacterized protein. *Leishmania panamensis* and other sp |
|  | VQtFMlR (SEQ ID NO: 533) | Uncharacterized protein. *Leishmania panamensis* and other sp |
|  | VQiYMaK (SEQ ID NO: 534) | Uncharacterized protein. *Leishmania panamensis* and other sp |
|  | VQlFMrR (SEQ ID NO: 535) | Uncharacterized protein. *Leishmania panamensis* and other sp |
| DRxPx[GA]x[VA] (SEQ ID NO: 505) | VQsYMlR (SEQ ID NO: 536) | Uncharacterized protein. *Leishmania panamensis* and other sp |
|  | VQlYMdK (SEQ ID NO: 537) | Uncharacterized protein. *Leishmania panamensis* and other sp |
|  | VQlYMdK (SEQ ID NO: 538) | Aquaglyceroporin. *Leishmania donovani* |

TABLE 13-continued

Motifs indicative of *Leishmania* infection.

| *Leishmania* motif | Peptide Hit(s) | Putative Antigen |
| --- | --- | --- |
| DXIDX[VL]W (SEQ ID NO: 506) | DdIDlLW (SEQ ID NO: 539) | ATPase domain protein, putative. *Leishmania panamensis* and other sp |
| RQPxG[RQ] (SEQ ID NO: 507) | RQPcGQ (SEQ ID NO: 540) | Mitochondrial chaperone BCS1, putative. *Leishmania panamensis* |
|  | RQPqGR (SEQ ID NO: 866) | Protein kinase, putative (EC 2.7.11.1). *Leishmania panamensis* |
|  | RQPiGR (SEQ ID NO: 541) | ENOL protein (EC 4.2.1.11) (Fragment). *Leishmania braziliensis* |
| PxHGTH (SEQ ID NO: 508) |  |  |
| DGDGP (SEQ ID NO: 509) | DGDGP (SEQ ID NO: 509) | Inositol polyphosphate phosphatase, putative (EC 3.1.3.36). *Leishmania panamensis* |
|  | DGDGP (SEQ ID NO: 509) | Putative inositol polyphosphate phosphatase (EC 3.1.3.36). *Leishmania braziliensis* |
|  | DGDGP (SEQ ID NO: 509) | Hydrophilic acylated surface protein b. *Leishmania infantum* |
| Hxx[NQ]TP4KR] (SEQ ID NO: 510) | HptNTPeK (SEQ ID NO: 542) | Uncharacterized protein. *Leishmania panamensis* and other sp |
|  | HpvNTPdK (SEQ ID NO: 543) | Uncharacterized protein. *Leishmania panamensis* and other sp |
|  | HavQTPsK (SEQ ID NO: 544) | Uncharacterized protein. *Leishmania panamensis* and other sp |
|  | HtfQTPqR (SEQ ID NO: 545) | Uncharacterized protein. *Leishmania panamensis* and other sp |
|  | HvnQTPyR (SEQ ID NO: 546) | Uncharacterized protein. *Leishmania panamensis* and other sp |
|  | HdgNTPaK (SEQ ID NO: 547) | Putative kinesin (EC 3.6.4.4). *Leishmania infantum* |
| K[SA]xNP[HE] (SEQ ID NO: 511) | KSaNPE (SEQ ID NO: 548) | Uncharacterized protein. *Leishmania panamensis* |
|  | KSiNPE (SEQ ID NO: 549) | RNase III domain-containing protein. *Leishmania panamensis* |
|  | KAsNPH (SEQ ID NO: 550) | Histone H2B. *Leishmania donovani* |
| [EQDN]xLPHE (SEQ ID NO: 512) | NaLPHE (SEQ ID NO: 551) | Uncharacterized protein. *Leishmania panamensis* |
|  | DaLPHE (SEQ ID NO: 552) | Uncharacterized protein. *Leishmania panamensis* |
|  | EpLPHE (SEQ ID NO: 553) | Uncharacterized protein. *Leishmania panamensis* |
|  | EmLPHE (SEQ ID NO: 554) | 2-oxoglutarate dehydrogenase subunit, putative (EC 1.2.4.2). *Leishmania panamensis* |
|  | QpLPHE (SEQ ID NO: 555) |  |
| GQYG[VIM] (SEQ ID NO: 513) | GQYGV (SEQ ID NO: 556) | Uncharacterized protein. *Leishmania panamensis* |
| PR[ML]x[DN]K (SEQ ID NO: 514) |  |  |
| FGQ[GQ]xxxD (SEQ ID NO: 515) |  |  |
| DD[GRS]xTxK (SEQ ID NO: 516) |  |  |
| IxT[FP]DR (SEQ ID NO: 517) |  |  |
| KxxNIGxx[FY] (SEQ ID NO: 518) | KipNIGdkF (SEQ ID NO: 557) | DNA-directed RNA polymerase subunit beta (EC 2.7.7.6). *Leishmania panamensis* |

Example 16. Discovery of Motifs Diagnostic of *Babesia microti* Infection

Figure 16:
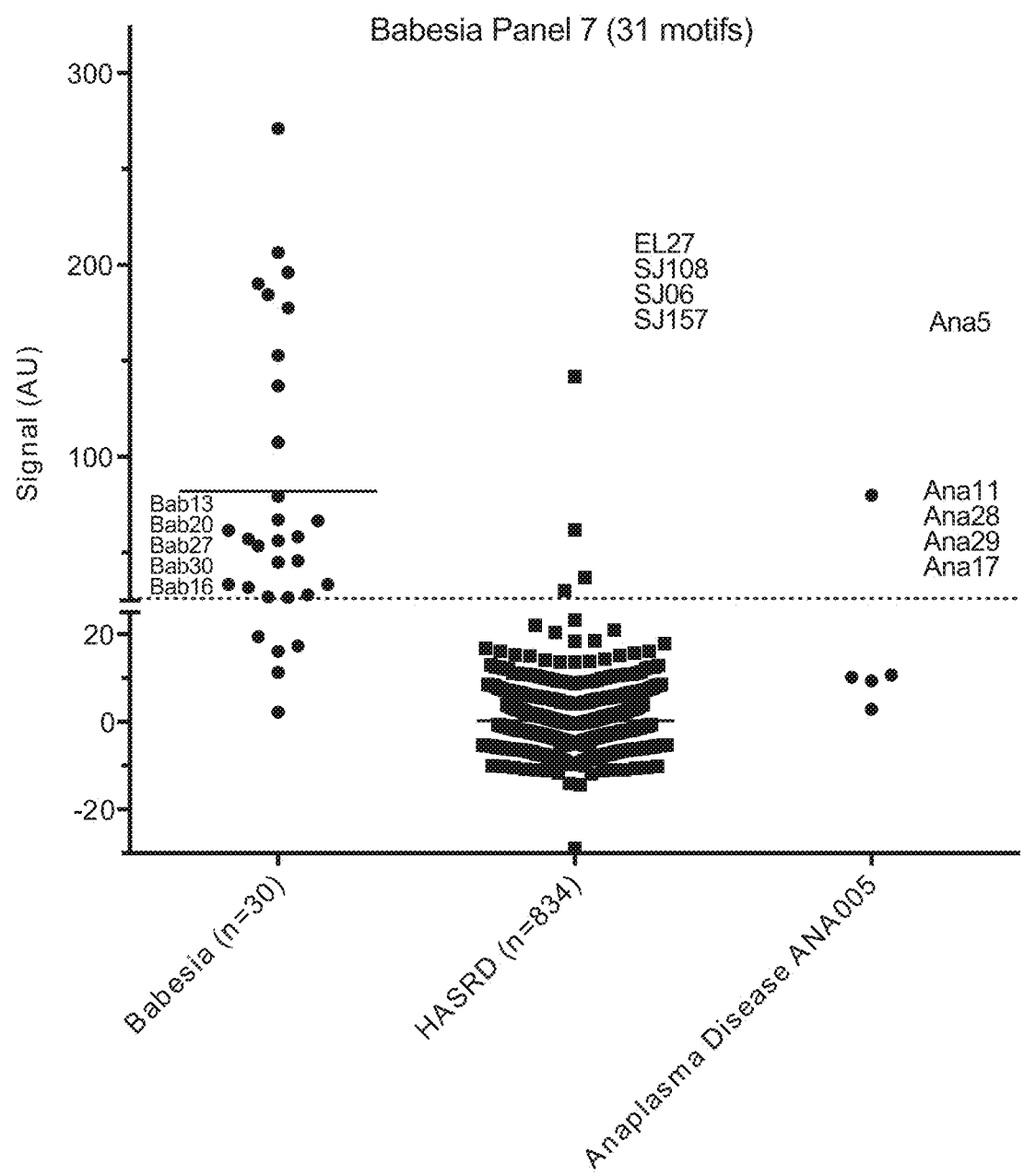
FIG. 16 illustrates the performance of *Babesia* infection motif panel in a discovery and validation sample sets, exhibiting a specificity of >99.5%.

*Babesia* infections are one of the most common infections transmitted by blood transfusions. *Babesia* can be spread by ticks and is commonly a co-infection in individuals infected with Lyme disease. A total of 30 samples with confirmed serology for *Babesia* infections, were analyzed according to the methods of Example 1. Motifs specific to individuals with probable or confirmed *Babesia* infections are shown in Table 14. A panel of motifs was capable of identifying individuals with Babesiosis (FIG. 16), and discriminating those with infections from those without infections.

TABLE 14

Exemplary motifs and peptides for serological detection of *Babesia* infection

| ID | Panel motif |
|---|---|
| 1 | [ML]L[AS][TA]xK (SEQ ID NO: 558) |
| 2 | [VL]x[AS]xDPxxP (SEQ ID NO: 559) |
| 3 | [KR]x[IL]x[ST][MLF]N (SEQ ID NO: 560) |
| 4 | TG[KR[MxxxxQ (SEQ ID NO: 561) |
| 5 | GxPY[STA]xxxx[ML] (SEQ ID NO: 562) |
| 6 | WE[EDA]x[PA]I (SEQ ID NO: 563) |
| 7 | E[IV]xHxxFxR (SEQ ID NO: 564) |
| 8 | Kxx[TS]HRxK (SEQ ID NO: 565) |
| 9 | TFExGxK (SEQ ID NO: 566) |
| 10 | WENx[RA]xxx[FI] (SEQ ID NO: 567) |
| 11 | [NT][MF]FxxxxWxD (SEQ ID NO: 568) |
| 12 | [PA][GA][IV][MITV]xxP (SEQ ID NO: 569) |
| 13 | KxxRxS[YWh]D (SEQ ID NO: 570) |
| 14 | EKxxRxx[YF][DN] (SEQ ID NO: 571) |
| 15 | DTxTPxE (SEQ ID NO: 572) |
| 16 | WL[DA]QW (SEQ ID NO: 573) |
| 17 | K[EN]xxDxWN (SEQ ID NO: 574) |
| 18 | [GT]GNGG (SEQ ID NO: 575) |
| 19 | G[YFW]DxxQT]P (SEQ ID NO: 576) |
| 20 | [IV[GxS[RK]x[CR] (SEQ ID NO: 577) |
| 21 | [SAT]TPx[ML]E (SEQ ID NO: 578) |
| 22 | S[DQ]WxWE (SEQ ID NO: 579) |
| 23 | DxxY[IT]xx[HF]K (SEQ ID NO: 580) |
| 24 | K[YF]xxxL[IVT]K (SEQ ID NO: 581) |
| 25 | P[VI]xYMQ (SEQ ID NO: 582) |
| 26 | WPTGxxx[SN] (SEQ ID NO: 583) |
| 27 | Kx[IM][VN]xWA (SEQ ID NO: 584) |
| 28 | W[AP]TG[KR] (SEQ ID NO: 585) |

Example 17. Discovery of Motifs Diagnostic of *Ehrlichia* Infection

Figure 17:
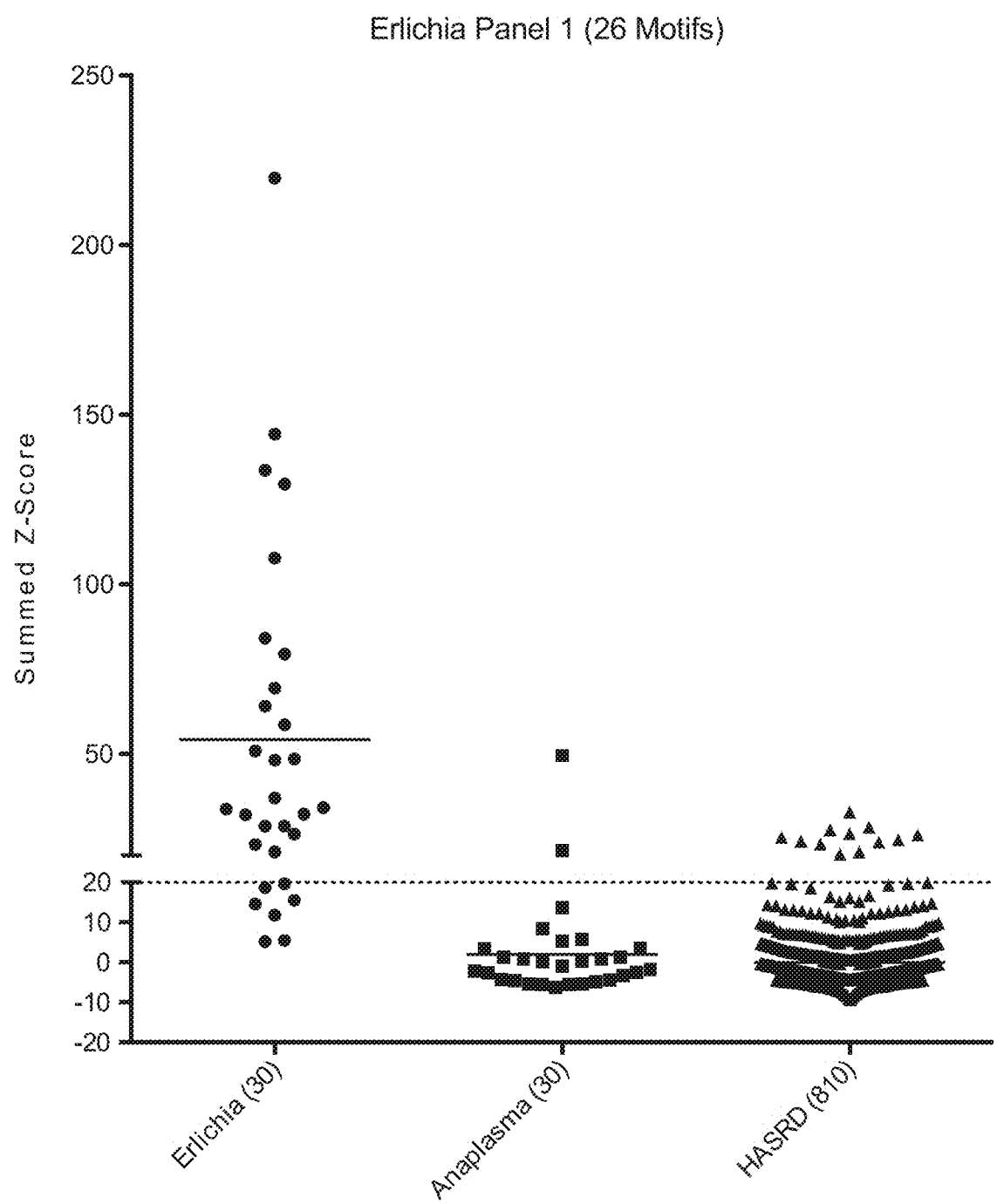
FIG. 17 illustrates the performance of *Ehrlichia* infection motif panel in a discovery and sample set.

A total of 30 specimens with positive IgG or IgM serology for *Ehrlichia* infection were analyzed according to the method of Example 1. Motifs specific to *Ehrlichia* infection are shown in Table 15. A panel of motifs was capable of identifying individuals with Ehrlichiosis (FIG. 17), and discrimiting those with infections from those without infections.

TABLE 15

Exemplary motifs and peptides for serological detection of *Erhlichia* infection

| ID | Panel motif |
|---|---|
| 1 | YxxL[IV]xP[KR] (SEQ ID NO: 586) |
| 2 | [SA]Nx[ML]FY (SEQ ID NO: 587) |
| 3 | WDGSx[IV] (SEQ ID NO: 588) |
| 4 | PxxL[IV]KP (SEQ ID NO: 589) |
| 5 | KxDWDG (SEQ ID NO: 590) |
| 6 | RxxxxKxD[HY]D (SEQ ID NO: 591) |
| 7 | VDVMGN (SEQ ID NO: 592) |
| 8 | Ex[NQ][QN]xFY (SEQ ID NO: 593) |
| 9 | Vx[TS][TS]N (SEQ ID NO: 594) |
| 10 | KLHDP (SEQ ID NO: 595) |
| 11 | KxDxDT[GN] (SEQ ID NO: 596) |
| 12 | Y[HA]GWx[SAE] (SEQ ID NO: 597) |
| 13 | NPEH[DTE] (SEQ ID NO: 598) |
| 14 | NPAxQ[HR] (SEQ ID NO: 599) |
| 15 | [KR]MNKxx[TP] (SEQ ID NO: 600) |
| 16 | DWxxx[FY][VK]K (SEQ ID NO: 601) |
| 17 | GVN[APTS]xK (SEQ ID NO: 602) |
| 18 | [IV]x[PR]EGxK (SEQ ID NO: 603) |
| 19 | RVF[ST][MA] (SEQ ID NO: 604) |
| 20 | NxRxx[VI]W[YF] (SEQ ID NO: 605) |
| 21 | Yxx[MTL]xYNA (SEQ ID NO: 606) |
| 22 | Kx[VI]x[ND][IV]W (SEQ ID NO: 607) |
| 23 | [ED][YF]Q[LQ]H (SEQ ID NO: 608) |
| 24 | FGxPSI (SEQ ID NO: 609) |
| 25 | QLVGxxK (SEQ ID NO: 610) |
| 26 | YxxL[IV]xP[KR] (SEQ ID NO: 611) |

Example 18. Discovery of Motifs Diagnostic of *Anaplasma* Infection

Figure 18:
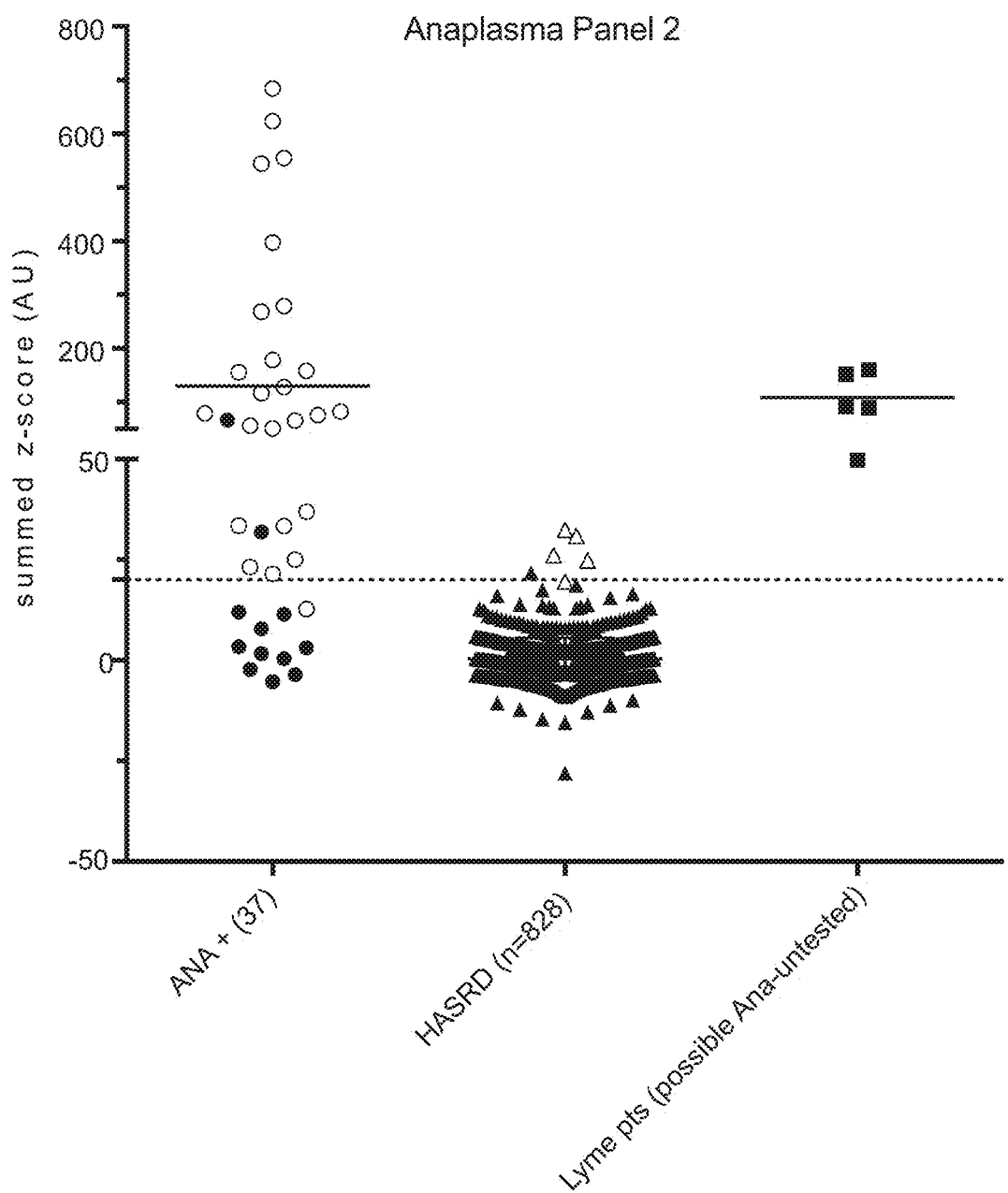
FIG. 18 illustrates the performance of *Anaplasma phagocytophilium* infection motif panel in a discovery sets, exhibiting a specificity of >99.5%.

A total of 30 specimens with positive IgG serology for *Anaplasma phagocytophilium* were analyzed according to the method of Example 1. Motifs specific to *Anaplasma* infection are shown in Table 16. A panel of motifs was capable of identifying individuals with Anaplasmosis (FIG. 18), and discriminating those with infections from those without infections.

TABLE 16

Exemplary motifs and peptides for serological detection of *Anaplasma* infection.

| ID | Panel motif |
|---|---|
| 1 | W[YK]Wx[PA]K (SEQ ID NO: 612) |
| 2 | KxExH[NK]F (SEQ ID NO: 613) |
| 3 | QxxxWPYxK (SEQ ID NO: 614) |
| 4 | YxFDxNxR (SEQ ID NO: 615) |
| 5 | FxWN[VI]P (SEQ ID NO: 616) |
| 6 | [FW][LM]EXAH (SEQ ID NO: 617) |
| 7 | DF[LI]xAT (SEQ ID NO: 618) |
| 8 | KxMSxFV (SEQ ID NO: 619) |
| 9 | W[YK]Wx[PA]K (SEQ ID NO: 620) |
| 10 | KxExH[NK]F (SEQ ID NO: 621) |
| 11 | QxxxWPYxK (SEQ ID NO: 622) |
| 12 | WPT[SF]T (SEQ ID NO: 623) |
| 13 | WP[TA]GR (SEQ ID NO: 624) |
| 14 | KNWPx[GF] (SEQ ID NO: 625) |
| 15 | KxxP[LI]FA (SEQ ID NO: 626) |
| 16 | WPxGQV (SEQ ID NO: 627) |
| 17 | [VI][LR]KDF (SEQ ID NO: 628) |

TABLE 16-continued

Exemplary motifs and peptides for serological detection of *Anaplasma* infection.

| ID | Panel motif |
|---|---|
| 18 | WPT[SF]T (SEQ ID NO: 629) |
| 19 | Kx[IM][VN]xWA (SEQ ID NO: 630) |
| 20 | [YW]TxEPF (SEQ ID NO: 631) |
| 21 | [AM][PTS]WExF (SEQ ID NO: 632) |
| 22 | R[PT][RTK]F[NS] (SEQ ID NO: 633) |
| 23 | VY[SA]HW (SEQ ID NO: 634) |
| 24 | [WF]xxKPxWxxM (SEQ ID NO: 635) |
| 25 | KGx[SA]HxF (SEQ ID NO: 636) |
| 26 | KGxVxF[AS] (SEQ ID NO: 637) |
| 27 | [IV]xHxTID (SEQ ID NO: 638) |
| 28 | MLSXXVN (SEQ ID NO: 639) |
| 29 | KxYSxxVR (SEQ ID NO: 640) |
| 30 | Kx[VK]VNP (SEQ ID NO: 641) |

Example 19. Discovery of Motifs for the Diagnosis of *Toxocara canis* Infection

Figure 19:
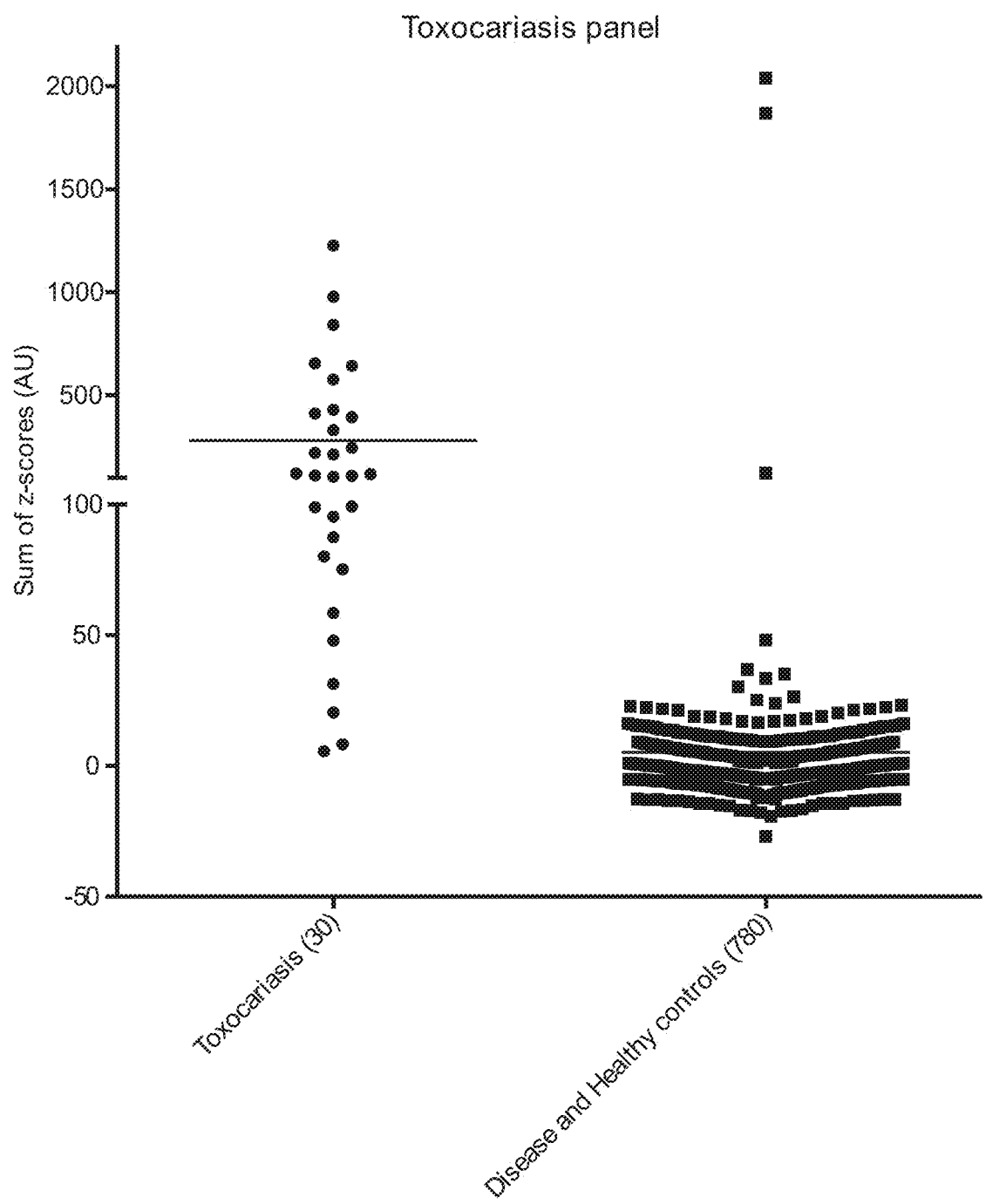
FIG. 19 illustrates the performance of a *Toxocara canis* infection motif panel in a discovery sample set, exhibiting a specificity of >99.5%.

*Toxocara canis* is a common parasitic infection, present in 5-20% of individuals in the United states. Diagnosis is dependent upon the use of serology to detect antibodies present in blood or other body fluids. The methods of Example 1 were used to develop a panel of motifs (Table 17), which correctly identified individuals with *Toxocara canis* infections (FIG. 19).

TABLE 17

Exemplary motifs and peptides for serological detection of Toxocara canis infection.

| ID | Panel motif | Antigen(s); peptide sequence(s) |
|---|---|---|
| 1 | [RKH]EPGD (SEQ ID NO: 642) | Putative ubiquitin-conjugating enzyme E2 7, Alpha/beta hydrolase domain-containing protein 14A, Multidrug resistance protein pgp-1, Filamin-A; HEPGD (SEQ ID NO: 680), REPGD (SEQ ID NO: 681), KEPGD (SEQ ID NO: 682), REPGD (SEQ ID NO: 683) |
| 2 | CxxIxNExC (SEQ ID NO: 643) | Uncharacterized protein; CkkIvNEtC (SEQ ID NO: 684) |
| 3 | ESR[SN]I (SEQ ID NO: 644) | Disintegrin and metalloproteinase domain-containing protein 12, 5-formyltetrahydrofolate cyclo-ligase, Putative neurobeachin-like protein, Putative glycogen [starch] synthase; ESRSI (SEQ ID NO: 685), ESRNI (SEQ ID NO: 686) |
| 4 | HPDx[QN]L (SEQ ID NO: 645) | Acetylcholinesterase 1, Sex comb on midleg-like protein 2, Cysteine string protein, Transport and Golgi organization 2-like protein, Secreted frizzled-related protein 5; HPDvNL (SEQ ID NO: 687), HPDgNL (SEQ ID NO: 688), HPDkNL (SEQ ID NO: 689), HPDeQL (SEQ ID NO: 690), HPDtQL (SEQ ID NO: 691) |
| 5 | RYxH[FY][ED] (SEQ ID NO: 646) | Uncharacterized protein, G2/M phase-specific E3 ubiquitin-protein ligase, Sorting nexin-33; RYcHFD (SEQ ID NO: 692), RYyHYD (SEQ ID NO: 693), RYkEIFD (SEQ ID NO: 694) |

TABLE 17-continued

Exemplary motifs and peptides for serological detection of Toxocara canis infection.

| ID | Panel motif | Antigen(s); peptide sequence(s) |
|---|---|---|
| 6 | F[AS]xRQxP (SEQ ID NO: 647) | Uncharacterized protein; Methyltransferase-like protein 13, Choline transporter-like protein 1, WD repeat-containing protein 46; FSfRQqP (SEQ ID NO: 695), FAhRQqP (SEQ ID NO: 696), FAhRQrP (SEQ ID NO: 697), FAtRQgP (SEQ ID NO: 698) |
| 7 | QD[AP]RN (SEQ ID NO: 648) | Voltage-dependent T-type calcium channel subunit alpha-1H; QDPRN (SEQ ID NO: 699) |
| 8 | Lxx[ILM]NQQ (SEQ ID NO: 649) | Uncharacterized protein, Putative U5 small nuclear ribonucleoprotein helicase, Cullin-5, Signal recognition particle 54 kDa protein, Soluble guanylate cyclase gcy-36; LlqLNQQ (SEQ ID NO: 700), LslMNQQ (SEQ ID NO: 701), LfwINQQ (SEQ ID NO: 702), LqkLNQQ (SEQ ID NO: 703), LilLNQQ (SEQ ID NO: 704) |
| 9 | [VA]xDGA[WF] (SEQ ID NO: 650) | Disintegrin and metalloproteinase domain-containing protein 12, Chondroadherin-like protein, Eukaryotic translation initiation factor 4E transporter, Zinc finger A20 and AN1 domain-containing stress-associated protein 9, Ras-related protein Rab-21; ApDGAF (SEQ ID NO: 705), VqDGAF (SEQ ID NO: 706), AgDGAF (SEQ ID NO: 707), AcDGAF (SEQ ID NO: 708), AiDGAF (SEQ ID NO: 709) |
| 10 | CxLPE[MTS] (SEQ ID NO: 651) | Leucine-rich repeat-containing protein 57, Odorant response abnormal protein 4, Transforming protein v-Fos/v-Fox, Choline kinase alpha, Neprilysin-2, Kynurenine formamidase; CsLPES (SEQ ID NO: 710), CpLPET (SEQ ID NO: 711), CvLPES (SEQ ID NO: 712), CrLPET (SEQ ID NO: 713), CpLPET (SEQ ID NO: 714), CdLPET (SEQ ID NO: 715) |
| 11 | FxxMQ[THS]K (SEQ ID NO: 652) | 2-acylglycerol O-acyltransferase 1, Melanoma-associated antigen G1; FkkMQSK (SEQ ID NO: 716), FlfMQHK (SEQ ID NO: 717) |
| 12 | GH[GAS]xLR (SEQ ID NO: 653) | Hemicentin-2, PX domain-containing protein kinase-like protein, Putative UDP-glucuronosyltransferase ugt-47, Zinc finger and BTB domain-containing protein 16; GHStLR (SEQ ID NO: 718), GHSaLR (SEQ ID NO: 719), GHGtLR (SEQ ID NO: 720), GHGrLR (SEQ ID NO: 721), GHGfLR (SEQ ID NO: 722) |
| 13 | Wxx[DE]YxxL (SEQ ID NO: 654) | Guanylate cyclase receptor-type gcy-1; WqiDYtsLV (SEQ ID NO: 723) |
| 14 | F[HDN][YF]PR (SEQ ID NO: 655) | Nuclear hormone receptor family member nhr-6, Laminin-like protein epi-1, Striatin-interacting protein 2, ATP-dependent RNA helicase cgh-1, Metal tolerance protein 4, IST1-like protein, FERM domain-containing protein 4A; FDFPR (SEQ ID NO: 724), FDYPR (SEQ ID NO: 725), FNYPR (SEQ ID NO: 726) |
| 15 | PE[FY]TS (SEQ ID NO: 656) | Lysine-tRNA ligase, Sodium bicarbonate transporter-like protein 11; PEFTS (SEQ ID NO: 727) |
| 16 | CDxPSxxxC (SEQ ID NO: 657) | Tripartite motif-containing protein 2; CDaPStrsC (SEQ ID NO: 935) |
| 17 | [FY]xxNGHxF (SEQ ID NO: 658) | Protein kinase C-binding protein NELL1, Protein kinase C; YyqNGHeF (SEQ ID NO: 728), YhvNGHrF (SEQ ID NO: 729) |
| 18 | YxICxExxC (SEQ ID NO: 659) | |
| 19 | DCMGxxC (SEQ ID NO: 660) | Dynein heavy chain-like protein; DCMGtfC (SEQ ID NO: 867) |
| 20 | [ML]xTGLx[DE] (SEQ ID NO: 661) | TBC1 domain family member 9B, Synaptobrevin-like protein YKT6, Acyl-CoA dehydrogenase family member 10, Cohesin subunit SA-1, Geranylgeranyl transferase type-1 subunit beta, Methyltransferase-like protein 13; LiTGLpD (SEQ ID NO: 730), MyTGLpE (SEQ ID NO: 731), LwTGLeE (SEQ ID NO: 732), LlTGLaD (SEQ ID NO: 733), LlTGL1D (SEQ ID NO: 734), MdTGLvD (SEQ ID NO: 735) |
| 21 | MxLGYY (SEQ ID NO: 662) | Latrophilin-3; MrLGYY (SEQ ID NO: 736) |
| 22 | MP[LT]Gx[YH] (SEQ ID NO: 663) | Epoxide hydrolase 1; MPTGgH (SEQ ID NO: 737) |

TABLE 17-continued

Exemplary motifs and peptides for serological detection of Toxocara canis infection.

| ID | Panel motif | Antigen(s); peptide sequence(s) |
|---|---|---|
| 23 | [FL]QTGx[IL] (SEQ ID NO: 664) | Protein FAM43A, Protein NDNF, 4-coumarate--CoA ligase 1; LQTGtL (SEQ ID NO: 738), LQTGkL (SEQ ID NO: 739), FQTGdI (SEQ ID NO: 740) |
| 24 | Kx[TS]CPC (SEQ ID NO: 665) | |
| 25 | CKD[TSD]C (SEQ ID NO: 666) | |
| 26 | CG[VA]F[EQ] (SEQ ID NO: 667) | C-type lectin Tc-ctl-4, Collectin-12, Thyroid adenoma-associated-like protein; CGAFE (SEQ ID NO: 741), CGVFQ (SEQ ID NO: 742) |
| 27 | SNx[IVAE]Axx[IML] (SEQ ID NO: 668) | E3 ubiquitin-protein ligase UBR5, Hyaluronidase-1, DNA repair protein RAD2, Seipin, Ectopic P granules protein 5, Serpentine receptor class alpha/beta-14; SNrVAsfL (SEQ ID NO: 743), SNkAArqM (SEQ ID NO: 744), SNsAAvdL (SEQ ID NO: 745), SNdVAkiI (SEQ ID NO: 746), SNaVAqvL (SEQ ID NO: 747), SNnVAfeI (SEQ ID NO: 748) |
| 28 | PTxLxHx[KR] (SEQ ID NO: 669) | Putative thiosulfate sulfurtransferase, Sodium/hydrogen exchanger, F-box/WD repeat-containing protein 5; PTgLdHhR (SEQ ID NO: 749), PTyLiHeR (SEQ ID NO: 750) |
| 29 | WPVNN (SEQ ID NO: 670) | |
| 30 | [VIA]CN[GD]xxxxC (SEQ ID NO: 671) | Anoctamin-5, Laminin subunit alpha-2, Laminin-like protein epi-1, Vacuolar protein sorting-associated protein 45; ICNDssrrC (SEQ ID NO: 751), ACNGhsitC (SEQ ID NO: 752), VCNGhadtC (SEQ ID NO: 753), ACNGehsqC (SEQ ID NO: 754) |
| 31 | [KR]NP[YS]L (SEQ ID NO: 672) | ATP synthase lipid-binding protein, mitochondrial, Transmembrane cell adhesion receptor mua-3, Putative 39S ribosomal protein L49, mitochondrial, Nuclear distribution protein nudE-like 1, Putative serine protease, Cytosolic non-specific dipeptidase; RNPSL (SEQ ID NO: 755), KNPSL (SEQ ID NO: 756) |
| 32 | CXXXPMXVXC (SEQ ID NO: 673) | |
| 33 | G[LM][KQT]FxxD (SEQ ID NO: 674) | Meiotic recombination protein DMC1/LIM15-like protein, Serine/threonine-protein kinase WNK1, 40S ribosomal protein 53a, Epidermal growth factor receptor kinase substrate 8, WD repeat-containing protein 82, Dipeptidyl peptidase family member 6; GLTFqaD (SEQ ID NO: 757), GLQFafD (SEQ ID NO: 758), GMKFtrD (SEQ ID NO: 759), GLQFpsD (SEQ ID NO: 760), GLKFspD (SEQ ID NO: 761), GLTFtpD (SEQ ID NO: 762) |
| 34 | [IA]PMx[PAK]N (SEQ ID NO: 675) | Phosphopantothenoylcysteine decarboxylase, Protein kinase C, Achaete-scute-like protein 5, Small nuclear ribonucleoprotein Sm D3; APMdAN (SEQ ID NO: 763), IPMdPN (SEQ ID NO: 764), APMpKN (SEQ ID NO: 765), APMfKN (SEQ ID NO: 766) |
| 35 | WxWCx[HT]xxxC (SEQ ID NO: 676) | |
| 36 | FxxM[QMHE][TH]K (SEQ ID NO: 677) | Melanoma-associated antigen G1, Uncharacterized protein; FlfMQHK (SEQ ID NO: 767), FfdMETK (SEQ ID NO: 768), FeeMQTK (SEQ ID NO: 769) |
| 37 | KxEx[VI]xWR (SEQ ID NO: 678) | Uncharacterized protein; KrEiVfWR (SEQ ID NO: 868) |
| 38 | CH[NT]GxC (SEQ ID NO: 679) | Transcriptional repressor NF-X1-like protein; CHTGpC (SEQ ID NO: 770) |

Example 20. Agents for the Removal or Depletion of Commonly Occurring Antibodies from a Sample Circulating antibody biomarkers have multiple applications in medicine, including without limitation the diagnosis and monitoring of infections, autoimmunity and cancer, as well as therapeutic and vaccine development and validation. One of the greatest challenges in the unbiased discovery of disease-specific antibody biomarkers is the sorting and filtering of the vast number ($10^5$-$10^8$) of unique antibody specificities in any individual repertoire to identify those shared antibody specificities associated with disease. Although each person's antibody repertoire is unique, a large proportion of antibodies react with common environmental antigens to which people are routinely exposed. Many of these antibodies map to one or a few common epitopes on a given antigen. Removal of these common antibodies from serum prior to biomarker discovery could, in principle, substantially narrow the individual antibody repertoire "noise" allowing for more sensitive and streamlined discovery of disease specific antibodies.

The purpose of this Example is to create a library of peptides that bind to common shared antibody specificities that can be used to remove these antibodies from serum to facilitate improved biomarker discovery. For Display-seq analysis, this "Depletion reagent" could be used in addition to or in lieu of standard *E. coli* cell depletion as described in the Examples above. The resulting depleted serum would contain a smaller, more patient specific subset of each person's antibody repertoire and would eliminate noise from high titer, non-disease specific antibodies.

Experimental Design Summary

Serum was pooled (3 samples/pool) and used to iteratively sort the X12 peptide library for 14 rounds of affinity selection by a combination of Magnetic activated cell sorting (MACS) and Fluorescence activated cell sorting (FACS). To establish whether this process would converge on a similar set of peptides, two tracks were performed in parallel, each containing a unique set of sera (no overlap). Sorting was stopped when the libraries demonstrated a similar reactivity to serum pools used for screening and naïve pools not used for screening.

Serum Sample Preparation

Each pool was comprised of serum samples from a combination of healthy, Sjogren's syndrome, Myasthenia Gravis and Systemic Lupus Erythematosa sera. Each pool was diluted to a final pooled serum concentration of 1:100 (1:300 individual serum concentration). The pooling strategy and serum dilution were chosen to favor common specificities that would be at a higher titer and/or present in more than one patient in a given pool. Serum pools were depleted of *E. coli* binding antibodies by incubation with *E. coli* expressing scaffold only (standard *E. coli* depletion protocol, see Example 1).

X12 Library Screen

*E. coli* depleted serum pools were used to screen a naïve bacterial display peptide library with twelve random positions (X12 naïve library) to enrich for peptide mimitopes representing common, abundant antibody specificities. A total of fourteen rounds of screening were performed using a combination of MACS and FACS. The final four rounds of sorting were performed using pools composed exclusively of serum from healthy donors to reduce the likelihood of selecting for a disease-specific antibody specificity that may have been enriched in an earlier sort with a disease-containing serum pool.

The X12 library (diversity $7 \times 10^9$) was grown, induced to express peptides and sorted by MACS and FACS using standard protocols. A summary of the steps is given below:

Library Propagation Step:

The X12 library was grown to OD 0.4-0.6 in LB medium with chloramphenicol, and peptide expression was induce with 0.02% arabinose for 1 hour.

Library Clearing Step:

Peptide libraries were first cleared of protein A and protein G binders by incubating the induced library with magnetic beads coated with protein A and protein G. Magnetic separation captures the beads along with any cells that are bound to the protein coating the beads. The unbound fraction is collected for screening for serum antibody binders.

MACS Enrichment

Antibody Binding Step:

A pool of (*E. coli* depleted) serum diluted in PBS was incubated with Protein A and G cleared cells expressing the peptide library. Antibodies from serum that bound to expressed peptides on the cells were harvested using centrifugation followed by washing with PBST to eliminate non-specific interactions.

Library Enrichment Step:

Washed cells were then incubated with magnetic beads coated with protein A and protein G to capture antibodies from the serum along with the cells expressing peptides the antibodies are interacting with. The beads were washed 5 times with PBST while magnetized to remove cells captured non-specifically.

Growth Step:

The enriched library (bound to washed beads) was resuspended in LB medium and grown overnight to amplify the library.

Repeat MACS Enrichment:

MACS enrichment was repeated (×3) with a new serum pool until the estimated library diversity was in the ~$10^5$ range and could be sorted using FACS.

FACS Enrichment and Analysis

Antibody Binding Step:

A different serum pool was used for each subsequent round of enrichment. A pellet of induced cells from the previous enrichment round representing 10× the predicted library diversity was incubated with serum, the sample was centrifuged, unbound antibodies in the supernatant were removed and the pellet was washed to remove non-specific antibody binders.

Library Enrichment Step:

The cell pellet was resuspended in PBS containing a secondary anti-human IgG antibody labeled with Phycoerythrin and incubated to allow for binding to serum antibody-peptide complexes. Cells were centrifuged, the supernatant was removed and the pellet was resuspended in PBS. Cells with bound secondary antibody above background fluorescence were sorted. A minimum of 10 fold over the predicted library diversity was sorted for each round for enrichment steps.

Growth Step:

The enriched library was resuspended in LB medium and the captured cells were grown overnight to amplify the library.

Next Generation Sequencing to Identify Peptide Sequences

To identify the peptides that were enriched in each of the libraries, the plasmids were purified from the final round of sorting of each library and the amplicons prepared for next-generation sequencing using established Illumina protocols. Briefly, the peptide-encoding region of the plasmid DNA was amplified and barcoded using two rounds of PCR. Samples were pooled and run on the Illumina NextSeq Platform. Parallel tracks were run with separate bar codes to enable a comparison of total sequence diversity in each library and evaluate the motif overlap and determine whether both tracks converged on a set of similar motifs.

Depletion Library Analysis

The Depletion Screen Enriched for Common Antibody Specificities

To evaluate whether the screening process was effective and establish an endpoint for the screen, enriched library pools were analyzed for reactivity to naïve serum pools at various points throughout the screening process. Results are the combined data from both tracks. The final libraries showed >75% binding to ten naïve serum pools indicating that the libraries are highly enriched for cross-reactive antibody mimitopes.

NGS Results and Motif Analysis

The Screening Process Identified a Highly Overlapping Set of Motifs from Two Independent Screens Each library track contained a similar number of unique sequences (Track 1—49,413 Track 2—51,956). To identify enriched motifs and determine whether the screening process selected for a similar set antibody specificities, peptide sequences were compared between the two libraries using IMUNE software, and separated into those that were present in both tracks versus those that were unique to one or the other track. The two tracks shared a total of 1605 full peptides, representing ~3% of the individual library diversities. Next, the peptide sequences that were present in both libraries versus those unique to Track 1 or Track 2 were ranked according to the number of times they appeared in the NGS data. Motifs were generated from the top 5000 peptides from Track 1 only, Track 2 only or both Tracks using MEME. The MEME motifs discovered from each of these analyses are in data room/Depletion Reagent/MEME. A total of 81 unique motifs were identified from the three MEME analyses. See Table 18.

The degree of motif overlap between the two libraries was quantified using the Human Antibody Specificity Repertoire Database (HASRD). The NGS sequence data for the libraries was uploaded and samples were queried with all identified MEME motifs. Of the 81 motifs identified, 91% were present in both libraries indicating a high degree of motif overlap between the two Tracks. Thus, even though the libraries primarily contained unique peptides, the two separate screens both selected for a common set of highly cross-reactive antibody specificities. The peptide and motif overlap is summarized in Table 19.

TABLE 18

Top Depletion Reagent Motifs Identified by MEME

| | | |
|---|---|---|
| [VI]PEFXG[SA] (SEQ ID NO: 771) | Y[IVM]DXX[LM]N (SEQ ID NO: 772) | DDKGK (SEQ ID NO: 773) |
| KXPEEP (SEQ ID NO: 774) | [LM]XLPDK (SEQ ID NO: 775) | [IVY]DXXGN (SEQ ID NO: 776) |
| E[VI][VI][VI]DK (SEQ ID NO: 777) | [ML][WY]WMDK (SEQ ID NO: 778) | NPVE (SEQ ID NO: 779) |
| CMNXXC (SEQ ID NO: 780) | [RK]DX[ML]GR (SEQ ID NO: 781) | [IV]XXPXY[DE]K (SEQ ID NO: 782) |
| PXG[TV]LXK (SEQ ID NO: 783) | [VI]XXQPXKP (SEQ ID NO: 784) | DTXP[RK] (SEQ ID NO: 785) |
| CXXPWXXEXC (SEQ ID NO: 786) | W[WF]X[QIV]PDK (SEQ ID NO: 787) | PPWW (SEQ ID NO: 788) |
| [LI]N[KR]P (SEQ ID NO: 789) | P[IL]XNX[HP]XW (SEQ ID NO: 790) | [FY]XHXX[LIM]N (SEQ ID NO: 791) |
| [PW]FXXM[DN]KP (SEQ ID NO: 792) | K[FYW]THP (SEQ ID NO: 793) | YXPTXX[WY] (SEQ ID NO: 794) |
| PXAIXD[LMI][LVI] (SEQ ID NO: 795) | YXDXX[LM]N (SEQ ID NO: 796) | C[WN]X[WR]XC (SEQ ID NO: 797) |
| KXDPDXXW (SEQ ID NO: 798) | [RK]C[YF][LIVM]C[ED] (SEQ ID NO: 799) | WCWK[DE] (SEQ ID NO: 800) |
| [VI]X[LFM]PHW (SEQ ID NO: 801) | PXL[ST]XXE (SEQ ID NO: 802) | PX[IV]XEXXM[FW] (SEQ ID NO: 803) |
| DPYQXX[WF] (SEQ ID NO: 804) | [VI]PXLXXXE (SEQ ID NO: 805) | YNPF (SEQ ID NO: 806) |
| PVXF[ND]K (SEQ ID NO: 807) | PXXFYN (SEQ ID NO: 808) | PYXXYQ (SEQ ID NO: 809) |
| [RH][RK][PW]FF (SEQ ID NO: 810) | KXRPXW (SEQ ID NO: 811) | CXNWXXXC (SEQ ID NO: 812) |
| C[IWML]NXXDC (SEQ ID NO: 813) | KXDXMXN (SEQ ID NO: 814) | WXKXXGXW (SEQ ID NO: 815) |
| PXDT[SA]PR (SEQ ID NO: 816) | PPT[YFW][LM]G (SEQ ID NO: 817) | [YF]X[YF]XXFN (SEQ ID NO: 818) |
| [LM]XXGWNXKP (SEQ ID NO: 819) | KX[IVF]PXYL (SEQ ID NO: 820) | YXX[IV]PW[ML] (SEQ ID NO: 821) |
| GAGGG (SEQ ID NO: 822) | CX[ND]XPXXC (SEQ ID NO: 823) | HXP[ML][FMY]Y (SEQ ID NO: 824) |
| PDDI[SG]K (SEQ ID NO: 825) | FPXXWYP (SEQ ID NO: 826) | DMNXH (SEQ ID NO: 827) |
| [KR][LMI]VXQS[SN] (SEQ ID NO: 828) | WDXXDG (SEQ ID NO: 829) | PXXNXX[LI][TS] (SEQ ID NO: 830) |
| [VMI]VPEXK (SEQ ID NO: 831) | PX[VI][FYW]XNXP (SEQ ID NO: 832) | SGP[KR][HY] (SEQ ID NO: 833) |
| KXXFPQ (SEQ ID NO: 834) | PDXXWXK (SEQ ID NO: 835) | QP[LM][FM]Y (SEQ ID NO: 836) |
| [YF]XCT[FYM]MC (SEQ ID NO: 837) | [FW]XPXX[LMI][QN][RK] (SEQ ID NO: 838) | [IV]CWSX[PC] (SEQ ID NO: 839) |
| PDXP[VI]S (SEQ ID NO: 840) | P[LI]XGXPW (SEQ ID NO: 841) | ELPRX[YML] (SEQ ID NO: 842) |
| PESHN[DW] (SEQ ID NO: 843) | YXXTLX[YW] (SEQ ID NO: 844) | [VI]XWNXP (SEQ ID NO: 845) |
| G[WYF]DXXD[GP] (SEQ ID NO: 846) | KX[TSN]HPG[ED] (SEQ ID NO: 847) | MMXHI (SEQ ID NO: 848) |
| KPXLGX[KR] (SEQ ID NO: 849) | N[SD]SMN (SEQ ID NO: 850) | WXXWF (SEQ ID NO: 851) |

TABLE 19

Full peptides versus motif overlap in Depletion reagent tracks

|  | Track I | Track II |
| --- | --- | --- |
| NGS Unique sequences | 49413 | 51956 |
| # unique peptides common to both libraries | 1605 (~3%) | |
| # of motifs common to both libraries | 74/81 (91%) | |

Figure 20:
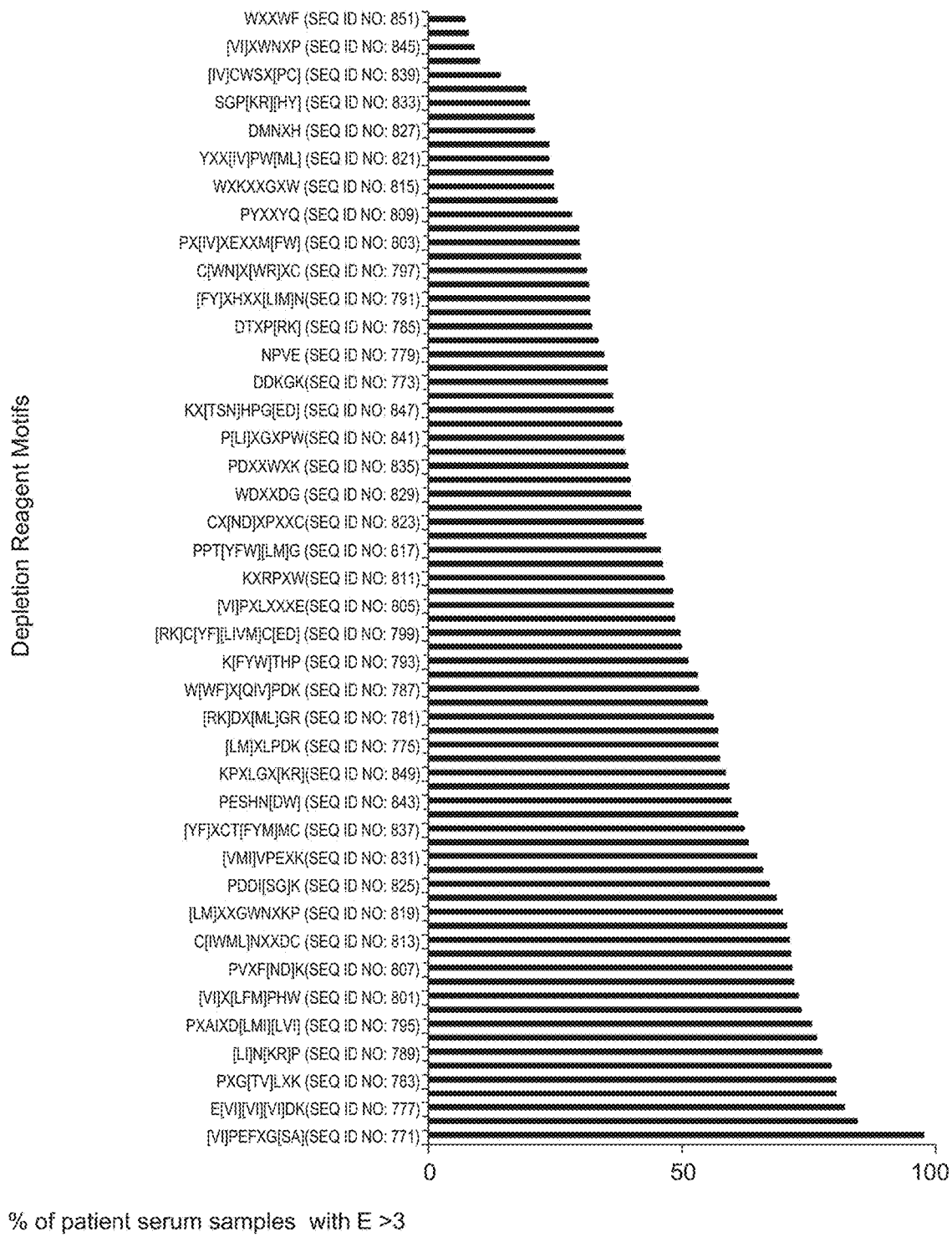
FIG. 20: Percentage of subjects with >3 fold enrichment of depletion reagent motifs in HASRD (n=358 subjects) (SEQ ID NOS 851, 845, 839, 833, 827, 821, 815, 809, 803, 797, 791, 785, 779, 773, 847, 841, 835, 829, 823, 817, 811, 805, 799, 793, 787, 781, 775, 849, 843, 837, 831, 825, 819, 813, 807, 801, 795, 789, 783, 777, and 771, respectively, in order of appearance).

The Depletion Library Enriched for Motifs that are Well Represented in the General Population To establish the cross-reactivity of the Depletion reagent motifs in the general population, 358 serum samples (including healthy, Sjogren's syndrome, Systemic Lupus Erythmatosus, Myasthenia Gravis, Celiac and Chagas disease sera) that had been screened using Display Seq were queried for motif enrichment in HASRD. Display seq recovers between ~0.5-3×10$^6$ unique antibody binding peptides per serum sample representing the diversity of each subject's antibody repertoire. These sequences were uploaded to HASRD and the percentage of subjects that showed enrichment for each motif was tabulated. "Enrichment" was defined as an E value of ≥3 where an E=1 is background (the number of unique peptides observed for a given motifs is equal to what would be expected by random chance). The percentage of patient serum samples that showed ≥3-fold enrichment for each of the 81 motifs queried is shown in FIG. 20. Serum cross-reactivity ranged from 8-98% with an average of 48% of subjects showing motif enrichment. Ninety four percent of the motifs were enriched in at least 20% of the samples queried and enrichment was evenly distributed between healthy and disease sera.

Depletion Reagent Validation

Figure 21:
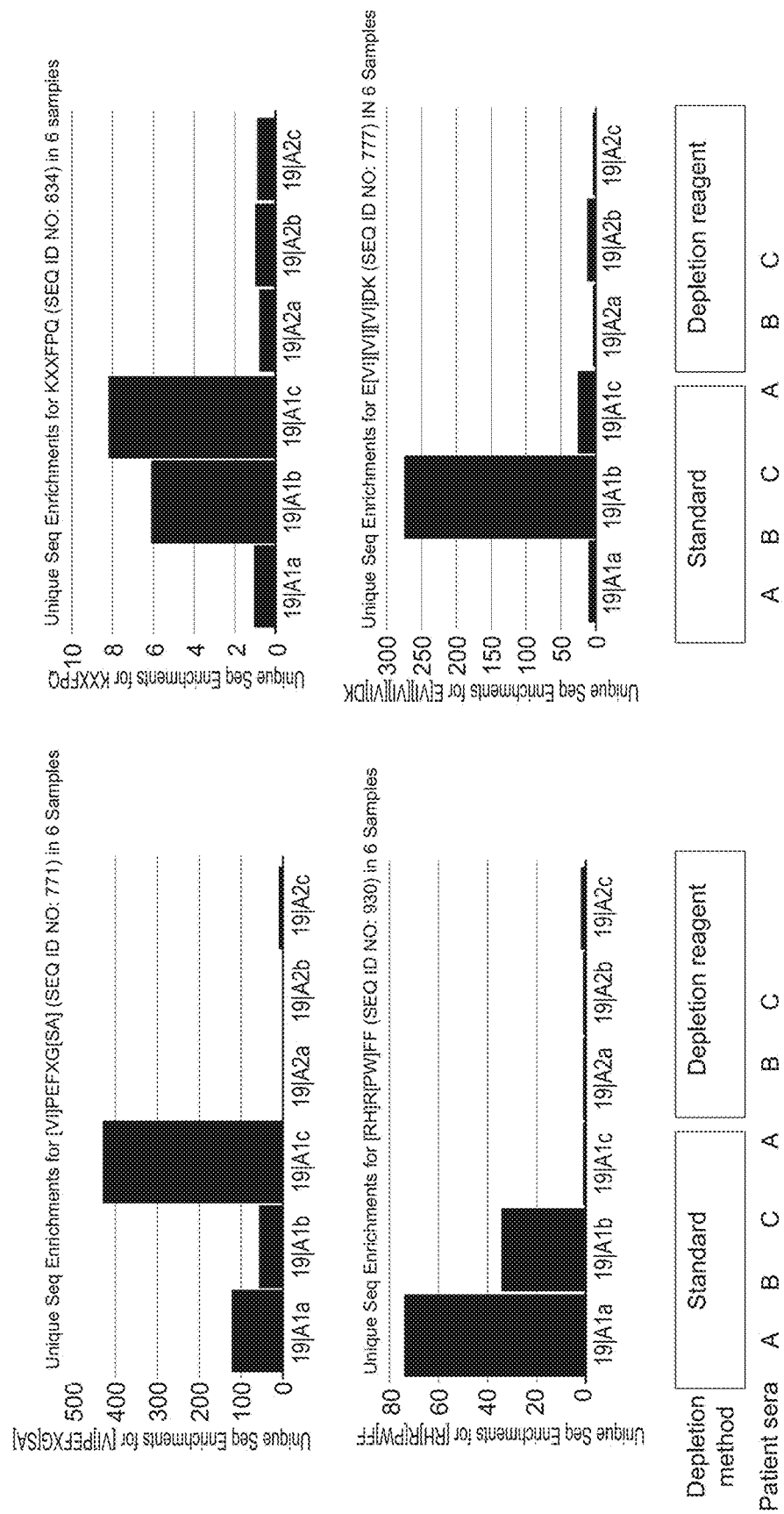
FIG. 21 illustrates that the depletion reagent and method effectively removes antibodies from serum prior to screening. Three separate motifs are shown. On each graph, first 3 bars represent the enrichment value for the given motif in 3 separate patients after standard depletion. The second three bars are the enrichment values for the same 3 patients after depletion with the depletion reagent. "[VI]PEFXG[SA]" is disclosed as SEQ ID NO: 771, "[RH]R[PW]FF" is disclosed as SEQ ID NO: 930, "KXXFPQ" is disclosed as SEQ ID NO: 834, and "E[VI][VI][VI]DK" is disclosed as SEQ ID NO: 777.

The Depletion Reagent Effectively Removes Common Antibody Specificities from Serum In order to be a useful tool in biomarker discovery, the Depletion Reagent should effectively remove common antibodies from serum, thereby enhancing biomarker discovery. To test the ability of the library to effectively deplete sera of common antibody specificities, three healthy serum samples were depleted using either standard conditions with E. coli expressing eCPX scaffold alone, or with the Depletion reagent consisting of both Track 1 and Track 2 pooled libraries, according to established protocols. Depleted serum was then used to screen the X12 bacterial display library at a final serum dilution of 1:25 by the Display Seq method. Samples were processed for NGS as described previously and the unique peptide sequences returned for each sample were uploaded to HASRD and queried with motifs known to be present in the Depletion Reagent. The enrichment values for several common motifs from serum depleted using standard conditions or with the Depletion reagent are shown in FIG. 21. Motifs spanned a large range of enrichment values (~6 to 400 fold enrichment). Regardless of the level of enrichment, the Depletion reagent effectively removed antibodies from the serum, resulting in reduction in enrichment to or near background levels.

Figure 22:
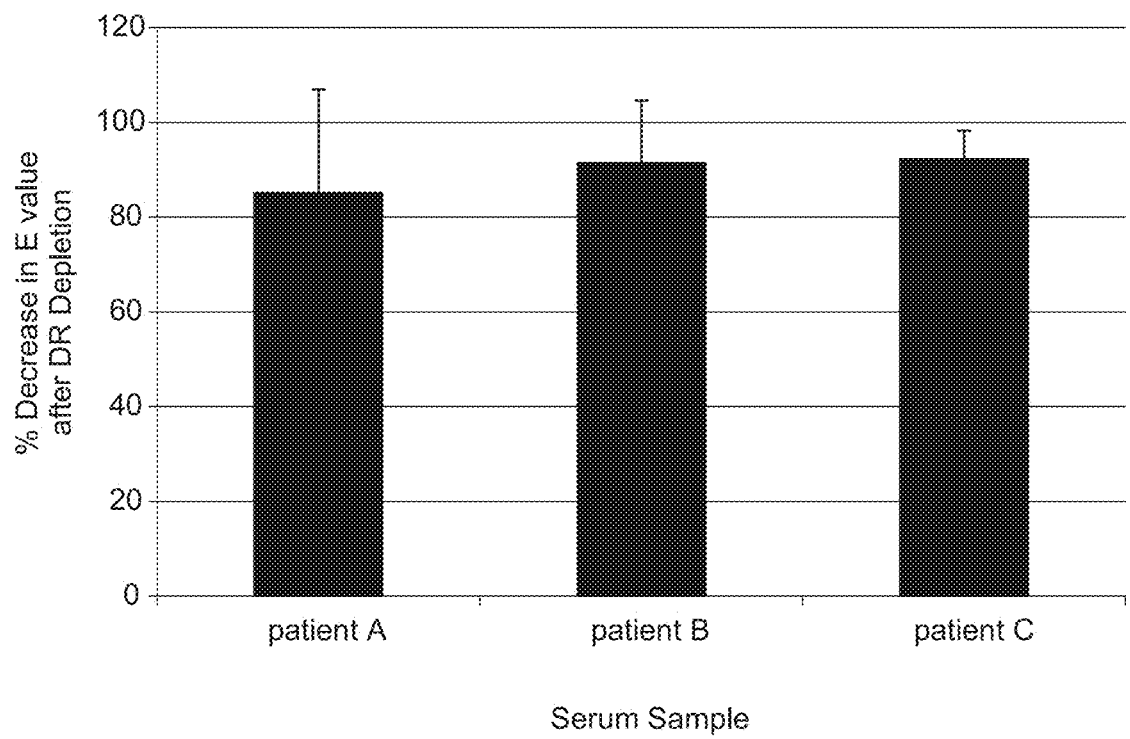
FIG. 22: The depletion reagent removed 80-90% of antibodies associated with 11 motifs for each patient. The enrichment for each motif was determined on sera that had been processed for display seq using both depletion methods. The percent decrease for each motif after treatment with the depletion reagent was calculated. All motifs included in the analysis were known to be present in the depletion reagent.

The ability of the Depletion Reagent to remove common antibodies was further quantified by calculating the percent decrease in motif enrichment after treatment with the Depletion reagent. See FIG. 22. In three separate patients, the average enrichment decreased by ~80-90%.

Figure 23:
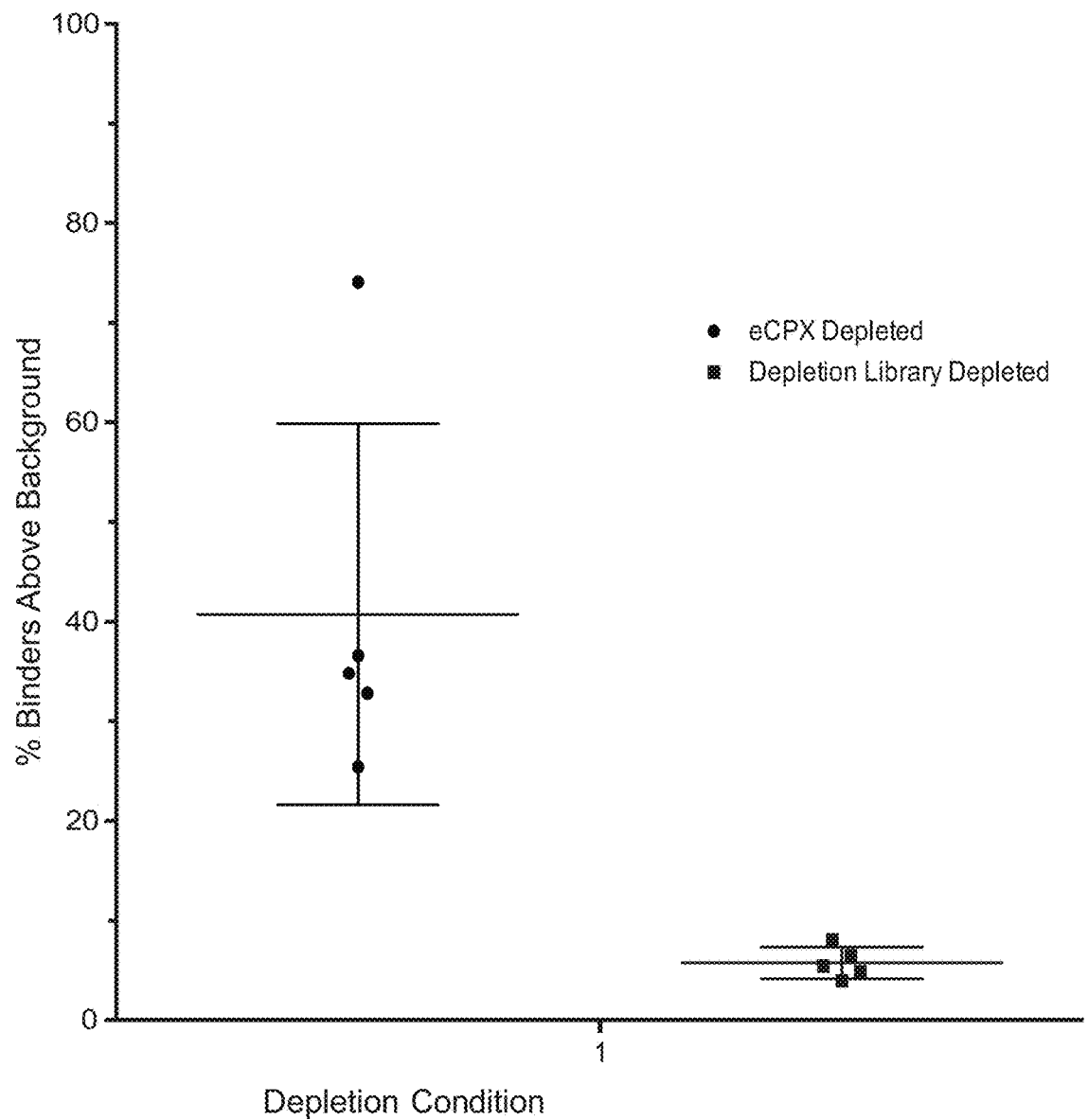
FIG. 23: The depletion reagent reduces reactivity of serum to the X12 library by 5-10 fold. The results are the average and standard deviation of 5 serum samples. The reactivity of the serum samples to the eCPX scaffold only represents background binding of serum in the absence of peptides.

To understand the effect of the Depletion reagent on reducing the diversity of the antibody repertoire in depleted serum, we compared the reactivity of five serum samples that had been depleted using standard conditions or with the Depletion reagent to the naïve X12 library. The depletion reagent reduced the reactivity by ~5-10-fold, indicating that a significant fraction of antibodies are removed. See FIG. 23.

Figure 24:
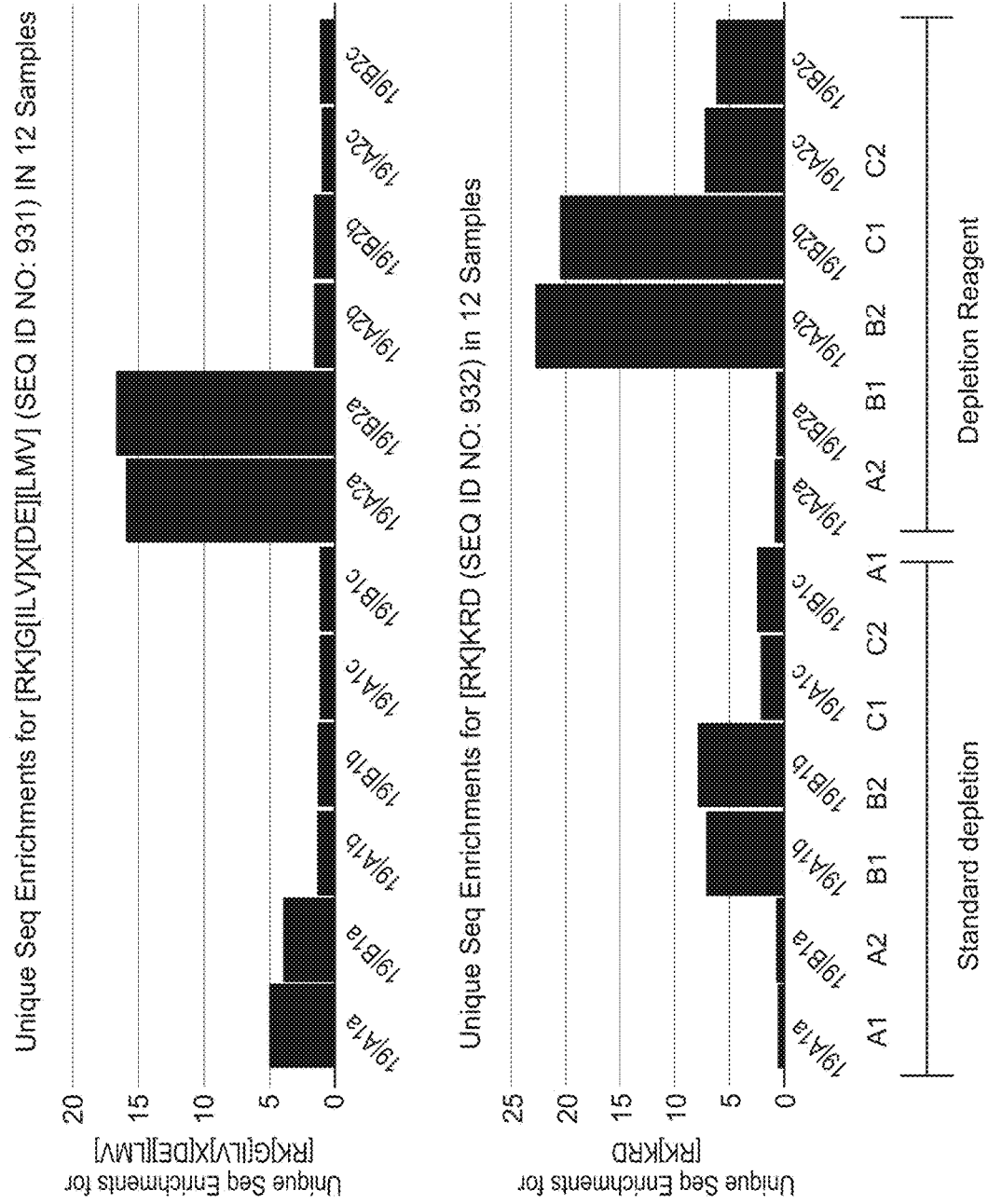
FIG. 24: Two motifs that were not present in the depletion reagent demonstrate increased enrichment in serum treated with the depletion reagent as compared with eCPX depleted sera. Three serum samples are shown and each was run in duplicate. The depletion reagent enhances enrichment by ~3 fold as compared with standard depletion. "[RK]G[ILV]X[DE][LMV]" is disclosed as SEQ ID NO: 931 and "[RK]KRD" is disclosed as SEQ ID NO: 932.

Removal of Common Antibody Specificities by the Depletion Reagent Improves Detection of Other Antibody Specificities We wanted to determine whether the Depletion reagent also enhances the ability to detect the remaining antibody specificities and/or allows for capture of a wider diversity of an individuals' antibody repertoire. To ask this question, we queried the serum samples that had been depleted under both conditions with motifs not present in the Depletion reagent. An example of this analysis, shown in FIG. 24, indicates that removal of common antibody specificities by the Depletion reagent can enhance detection of remaining antibody specificities. Motif enrichment increased an average of 3-fold after DR depletion.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

References referred to throughout this disclosure by bracketed numbers (e.g., [1], [2], etc.) are listed below. Each reference is incorporated herein by reference in its entirety.

1. Carmona, S. J., et al., *Towards high-throughput immunomics for infectious diseases: use of next-generation peptide microarrays for rapid discovery and mapping of antigenic determinants*. Mol Cell Proteomics, 2015.
2. Plebani, M., et al., *Recent advances in diagnostic technologies for autoimmune diseases*. Autoimmun Rev, 2009. 8(3): p. 238-43.
3. Maynard, J. and G. Georgiou, *Antibody engineering*. Annu Rev Biomed Eng, 2000. 2: p. 339-76.
4. Anderson, K. S., et al., *Protein microarray signature of autoantibody biomarkers for the early detection of breast cancer*. J Proteome Res, 2011. 10(1): p. 85-96.
5. Wang, X., et al., *Autoantibody signatures in prostate cancer*. N Engl J Med, 2005. 353(12): p. 1224-35.
6. Spatola, B. N., et al., *Antibody Repertoire Profiling Using Bacterial Display Identifies Reactivity Signatures of Celiac Disease*. Analytical Chemistry, 2012. 85(2): p. 1215-1222.
7. Johansen Taber, K. A., B. D. Dickinson, and M. Wilson, *The promise and challenges of next-generation genome sequencing for clinical care*. JAMA Intern Med, 2014. 174(2): p. 275-80.
8. Georgiou, G., et al., *The promise and challenge of high-throughput sequencing of the antibody repertoire*. Nat Biotechnol, 2014. 32(2): p. 158-68.
9. Larman, H. B., et al., *PhIP-Seq characterization of autoantibodies from patients with multiple sclerosis, type 1 diabetes and rheumatoid arthritis*. J Autoimmun, 2013. 43: p. 1-9.
10. Xu, G. J., et al., *Viral immunology. Comprehensive serological profiling of human populations using a synthetic human virome*. Science, 2015. 348(6239): p. aaa0698.

11. Borrebaeck, C. A. K., *Antibody engineering*. 2nd ed. Breakthroughs in molecular biology. 1995, New York: Oxford University Press. xv, 390 p.
12. Daugherty, P. S., *Protein engineering with bacterial display*. Curr Opin Struct Biol, 2007. 17(4): p. 474-80.
13. Andreatta, M., O. Lund, and M. Nielsen, *Simultaneous alignment and clustering of peptide data using a Gibbs sampling approach*. Bioinformatics, 2013. 29(1): p. 8-14.
14. Bailey, T. L. and C. Elkan, *The value of prior knowledge in discovering motifs with MEME*. Proc Int Conf Intell Syst Mol Biol, 1995. 3: p. 21-9.
15. Bailey, T. L. and C. Elkan, *Fitting a mixture model by expectation maximization to discover motifs in biopolymers*. Proc Int Conf Intell Syst Mol Biol, 1994. 2: p. 28-36.
16. Amstutz, P., et al., *In vitro display technologies: novel developments and applications*. Curr Opin Biotechnol, 2001. 12(4): p. 400-5.
17. Gould Rothberg, B. E. and J. M. Rothberg, *Massively parallel ("next-generation") DNA sequencing*. Clin Chem, 2015. 61(7): p. 997-8.
18. Rice, J. J. and P. S. Daugherty, *Directed evolution of a biterminal bacterial display scaffold enhances the display of diverse peptides*. Protein Eng Des Sel, 2008. 21(7): p. 435-42.
19. Getz, J. A., T. D. Schoep, and P. S. Daugherty, *Peptide discovery using bacterial display and flow cytometry*. Methods Enzymol. 503: p. 75-97.
20. Ballew, J. T., et al., *Antibody biomarker discovery through in vitro directed evolution of consensus recognition epitopes*. Proc Natl Acad Sci USA, 2013. 110(48): p. 19330-5.
21. Wallis, A. B., et al., *Secular trends in the rates of preeclampsia, eclampsia, and gestational hypertension, United States, 1987-2004*. Am J Hypertens, 2008. 21(5): p. 521-6.
22. Samadi, A. R., et al., *Maternal hypertension and associated pregnancy complications among African-American and other women in the United States*. Obstet Gynecol, 1996. 87(4): p. 557-63.
23. Wagner, L. K., *Diagnosis and management of preeclampsia*. Am Fam Physician, 2004. 70(12): p. 2317-24.
24. Hadker, N., et al., *Financial impact of a novel pre-eclampsia diagnostic test versus standard practice: a decision-analytic modeling analysis from a UK healthcare payer perspective*. J Med Econ. 13(4): p. 728-37.
25. MacKay, A. P., C. J. Berg, and H. K. Atrash, *Pregnancy-related mortality from preeclampsia and eclampsia*. Obstet Gynecol, 2001. 97(4): p. 533-8.
26. Masoura, S., et al., *Biomarkers in pre-eclampsia: a novel approach to early detection of the disease*. J Obstet Gynaecol, 2012. 32(7): p. 609-16.
27. Kleinrouweler, C. E., et al., *Accuracy of circulating placental growth factor, vascular endothelial growth factor, soluble fms-like tyrosine kinase 1 and soluble endoglin in the prediction of pre-eclampsia: a systematic review and meta-analysis*. BJOG, 2012. 119(7): p. 778-87.
28. Levine, R. J., et al., *Circulating angiogenic factors and the risk of preeclampsia*. N Engl J Med, 2004. 350(7): p. 672-83.
29. Schiettecatte, J., et al., *Multicenter evaluation of the first automated Elecsys sFlt-1 and PlGF assays in normal pregnancies and preeclampsia*. Clin Biochem. 43(9): p. 768-70.
30. Ohkuchi, A., et al., *Evaluation of a new and automated electrochemiluminescence immunoassay for plasma sFlt-1 and PlGF levels in women with preeclampsia*. Hypertens Res. 33(5): p. 422-7.
31. Lain, K. Y. and J. M. Roberts, *Contemporary concepts of the pathogenesis and management of preeclampsia*. JAMA, 2002. 287(24): p. 3183-6.
32. Walther, T., et al., *Angiotensin II type 1 receptor agonistic antibodies reflect fundamental alterations in the uteroplacental vasculature*. Hypertension, 2005. 46(6): p. 1275-9.
33. Roberts, J. M., *Angiotensin-1 receptor autoantibodies: A role in the pathogenesis of preeclampsia?* Circulation, 2000. 101(20): p. 2335-7.
34. Wallukat, G., et al., *Patients with preeclampsia develop agonistic autoantibodies against the angiotensin AT1 receptor*. J Clin Invest, 1999. 103(7): p. 945-52.
35. Rossitto, G., et al., *Elevation of Angiotensin II Type-1-Receptor Autoantibodies Titer in Primary Aldosteronism as a Result of Aldosterone-Producing Adenoma*. Hypertension, 2013. 61(2): p. 526-33.
36. Zhou, C. C., et al., *Autoantibody from women with preeclampsia induces soluble Fms-like tyrosine kinase-1 production via angiotensin type 1 receptor and calcineurin/nuclear factor of activated T-cells signaling*. Hypertension, 2008. 51(4): p. 1010-9.
37. Parrish, M. R., et al., *The effect of immune factors, tumor necrosis factor-alpha, and agonistic autoantibodies to the angiotensin II type I receptor on soluble fms-like tyrosine-1 and soluble endoglin production in response to hypertension during pregnancy*. Am J Hypertens. 23(8): p. 911-6.
38. Zhou, C. C., et al., *Angiotensin receptor agonistic autoantibodies induce pre-eclampsia in pregnant mice*. Nat Med, 2008. 14(8): p. 855-62.
39. Herse, F., et al., *Prevalence of agonistic autoantibodies against the angiotensin II type 1 receptor and soluble fms-like tyrosine kinase 1 in a gestational age-matched case study*. Hypertension, 2009. 53(2): p. 393-8.
40. Wallukat, G., et al., *Spontaneously beating neonatal rat heart myocyte culture-a model to characterize angiotensin II at(1) receptor autoantibodies in patients with preeclampsia*. In Vitro Cell Dev Biol Anim, 2002. 38(7): p. 376-7.
41. Griffiths, P. and S. Lumley, *Cytomegalovirus*. Curr Opin Infect Dis, 2014. 27(6): p. 554-9.
42. Halenius, A. and H. Hengel, *Human cytomegalovirus and autoimmune disease*. Biomed Res Int, 2014. 2014: p. 472978.

The present application and invention further includes the subject matter of the following numbered clauses:

1. A method of identifying a plurality of peptides, comprising: providing a biological sample comprising a plurality of antibodies; contacting the biological sample with a plurality of peptides; and identifying members of the plurality of peptides that form a complex with members of the plurality of antibodies.

2. The method of clause 1, wherein the biological sample comprises a bodily fluid.

3. The method of clause 2, wherein the bodily fluid comprises peripheral blood, lymphatic fluid, sweat, saliva, mucus, or a derivative of any thereof.

4. The method of any preceding clauses, wherein identifying members of the plurality of peptides that form a complex members of the plurality of antibodies comprises sequencing a nucleic acid that encodes the peptide.

5. The method of clause 4, wherein the sequencing comprises next generation sequencing (NGS), Sanger sequencing, real-time PCR, or pyrosequencing.

6. The method of any of clauses 4-5, wherein each member of the plurality of peptides is coupled to a nucleic acid molecule encoding that peptide.

7. The method of any of clauses 4-5, wherein the nucleic acid molecule comprises deoxyribonucleic acid (DNA), ribonucleic acid (RNA), or a derivative of any thereof.

8. The method of clause 6, wherein each peptide is directly coupled to its corresponding nucleic acid molecule.

9. The method of clause 6, wherein each peptide is indirectly coupled to its corresponding nucleic acid molecule.

10. The method of clause 9, wherein the corresponding nucleic acid molecule is within a vector that encodes the peptide.

11. The method of clause 10, wherein the vector is configured to express the peptide.

12. The method of clause 10, wherein the vector is comprised in a host cell.

13. The method of clause 12, wherein the host cell expresses the peptide.

14. The method of clause 13, wherein the peptide is expressed on the surface of the host cell.

15. The method of any of clauses 12-14, wherein the host cell comprises a microbial cell, a bacterial cell, an *E. coli* cell, a eukaryotic cell, a yeast cell, or a mammalian cell.

16. The method of any one of clauses 1-15, further comprising capturing members of the plurality of peptides that form a complex with members of the plurality of antibodies prior to identifying members of the plurality of peptides that form a complex with members of the plurality of antibodies.

17. The method of clause 16, wherein the capturing comprises capturing the peptide-bound members of the plurality of antibodies.

18. The method of clause 17, wherein the peptide-bound members of the plurality of antibodies are captured to a substrate.

19. The method of clause 18, wherein the substrate comprises a planar surface or a plurality of microbeads.

20. The method of clause 19, wherein the plurality of microbeads are magnetic or fluorescent.

21. The method of any one of clauses 17-20, wherein the bound members of the plurality of antibodies are captured using Protein A, Protein G, Protein L and/or an anti-immunoglobulin antibody or aptamer.

22. The method of any one of clauses 1-21, further comprising filtering the plurality of antibodies prior to contacting the biological sample with a plurality of peptides.

23. The method of clause 22, wherein the filtering comprises contacting the plurality of antibodies with at least one reagent configured to deplete antibodies that bind to assay components other than the plurality of peptides.

24. The method of clause 23, wherein the at least one reagent comprises the host cell.

25. The method of any one of clauses 1-24, further comprising filtering the plurality of peptides prior to contacting the biological sample with a plurality of peptides.

26. The method of clause 25, wherein the filtering the plurality of peptides comprises contacting the plurality of peptides with at least one reagent configured to deplete peptides that form a complex with assay components other than the plurality of antibodies.

27. The method of clause 26, wherein the at least one reagent configured to deplete peptides comprises Protein A, Protein G, Protein L, and/or an anti-immunoglobulin antibody or aptamer.

28. The method of any of clauses 1-27, further comprising determining at least one peptide motif from the members of the plurality of peptides identified in c).

29. The method of clause 28, wherein determining the at least one peptide motif comprises aligning the sequences of the members of the plurality of peptides identified in c).

30. The method of clause 29, wherein the aligning comprises using a computational alignment algorithm.

31. A method of identifying at least one peptide indicative of a phenotype in a biological sample comprising: (a) identifying a plurality of peptides in the biological sample according to any one of clauses 1-30; (b) comparing the presence or level of each member of the plurality of peptides identified in a) to a reference value; and (c) identifying a peptide with a presence or level that differs from the reference based on the comparison in b), thereby identifying the at least peptide indicative of the phenotype.

32. The method of clause 31, wherein the reference value for each member of the plurality of peptides comprises a presence or level of that member of the plurality of peptides in a control sample.

33. A method of identifying at least one peptide motif indicative of a phenotype in a biological sample comprising: (a) identifying at least one peptide motif in the biological sample according to any one of clauses 28-30; (b) comparing the presence or level of the at least one peptide motif identified in step a) to a reference value; and (c) identifying at least one peptide motif with a presence or level that differs from the reference based on the comparison in b), thereby identifying the at least one peptide motif indicative of the phenotype.

34. The method of clause 33, wherein the reference value comprises a presence or level of the same peptide motif in a control sample.

35. A method of characterizing a phenotype in a biological sample comprising: (a) identifying a plurality of peptides in the biological sample according to any one of clauses 1-30; (b) comparing the presence or level of each member of the plurality of peptides identified in a) to a reference value; and (c) identifying a peptide with a presence or level that differs from the reference based on the comparison in b), thereby characterizing the phenotype.

36. The method of clause 35, wherein the reference value for each member of the plurality of peptides comprises a presence or level of that member of the plurality of peptides in a control sample.

37. A method of characterizing a phenotype in a biological sample comprising: (a) identifying at least one peptide motif in the biological sample according to any one of clauses 28-30; (b) comparing the presence or level of the at least one peptide motif identified in step a) to a reference value; and (c) identifying at least one peptide motif with a presence or level that differs from the reference based on the comparison in b), thereby identifying the at least one peptide motif indicative of the phenotype.

38. The method of clause 37, wherein the reference value comprises a presence or level of the same peptide motif in a control sample.

39. The method of any one of clause 32, 34, 36 or 38, wherein the control sample has a different phenotype than the biological sample.

40. A method comprising detecting at least one peptide in a biological sample, wherein optionally the detecting is used to characterize a phenotype.

41. The method of clause 39 or clause 40, wherein the phenotype comprises a disease or disorder.

42. The method of any one of clauses 35, 37 or 40, wherein the characterizing comprises a diagnosis, prognosis or theranosis of the disease or disorder.

43. The method of any of clauses 35, 37 or 40, wherein the characterizing comprises determining a stage, grade, progression, treatment regimen and/or treatment response of the disease or disorder.

44. The method of any one of clauses 41-43, wherein the disease or disorder comprises an infectious, autoimmune, parasitic, allergic, oncological, neurological, cardiovascular, pregnancy-related or endocrine disease or disorder.

45. The method of any one of clauses 41-43, wherein the disease or disorder comprises an infectious disease or an autoimmune disease.

46. The method of any one of clauses 41-43, wherein the disease or disorder comprises Celiac disease (CD), Sjogren's Syndrome (SS), Myasthenia Gravis (MG), preeclampsia (PE), systemic lupus erythematosis (SLE), Epstein-Barr virus (EBV), rhinovirus, cytomegalovirus (CMV), *Streptococcus*, human immunodeficiency virus (HIV), *Haemophilus influenza*, Chagas disease or Lyme disease.

47. The method of any one of clauses 41-43, wherein the disease or disorder comprises a microbial infection, viral infection, bacterial infection or fungal infection.

48. A peptide comprising a sequence in any of SEQ ID NOs.1-868.

49. A composition comprising at least one peptide of clause 48.

50. Use of at least one reagent to carry out the method of any of clauses 1-47.

51. The use of clause 50, wherein the at least one reagent comprises at least one of: at least one peptide from any of SEQ ID NOs.1-868; a peptide library display system; an antibody binding agent; a primer set; and a depletion reagent.

52. The use clause 51, wherein the peptide library display system comprises an *E. coli* display system.

53. The use of clause 51, wherein the peptide library display system comprises a naïve peptide library.

54. The use of clause 51, wherein the peptide library display system is configured to characterize a phenotype 55. A kit comprising at least one reagent to carry out the method of any of clauses 1-47.

56. The kit of clause 55, wherein the at least one reagent comprises at least one of: at least one peptide from any of SEQ ID NOs.1-868; a peptide library display system; an antibody binding agent; a primer set; and a depletion reagent.

57. The kit of clause 56, wherein the peptide library display system comprises an *E. coli* display system.

58. The kit of clause 69, wherein the peptide library display system comprises a naïve peptide library.

59. The kit of clause 69, wherein the peptide library display system is configured to characterize a phenotype.

60. A composition comprising at least 1, 2, 3, 4, 5, 6, 7, 8, 9, 10, 11, 12, 13, 14, 15, 16, 17, 18, 19, 20, 25, 30, 35, 40, 45, 50, 65, 70, 75, 80, 90, 100, 200, 300, 400, 500, 600, 700, 800, 900, 1000, 10000, or at least 100000 peptides matching a peptide sequence in SEQ ID NOs. 1-868.

61. A composition comprising a library of nucleic acids having sequences encoding at least 1, 2, 3, 4, 5, 6, 7, 8, 9, 10, 11, 12, 13, 14, 15, 16, 17, 18, 19, 20, 25, 30, 35, 40, 45, 50, 65, 70, 75, 80, 90, 100, 200, 300, 400, 500, 600, 700, 800, 900, 1000, 10000, or at least 100000 peptides matching a peptide sequence in SEQ ID NOs.1-868.

62. A composition comprising host cells comprising a library of nucleic acids having sequences encoding at least 1, 2, 3, 4, 5, 6, 7, 8, 9, 10, 11, 12, 13, 14, 15, 16, 17, 18, 19, 20, 25, 30, 35, 40, 45, 50, 65, 70, 75, 80, 90, 100, 200, 300, 400, 500, 600, 700, 800, 900, 1000, 10000, or at least 100000 peptides matching a peptide sequence in SEQ ID NOs.1-868.

63. The composition of clause 62, wherein the host cells comprise microbial cells, bacterial cells, *E. coli* cells, eukaryotic cells, yeast cells, or mammalian cells.

64. The composition of clause 62, wherein the host cells express the peptides on their surface.

65. A method of depleting a biological sample of an antibody repertoire, comprising: (a) contacting the biological sample with a composition of clauses 60 or 61; (b) separating the host cells from the biological sample, thereby depleting the biological sample of the antibody repertoire.

A method comprising using the depleted biological sample of clause 65 as the biological sample in step a) of clause 65.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. An array comprising an array surface and at least five peptide probes, wherein each of the at least five peptide probes comprises a binding motif selected from the group consisting of: SEQ ID NO: 362, SEQ ID NO: 364, SEQ ID NO: 365, SEQ ID NO: 368, SEQ ID NO: 369, SEQ ID NO: 374, SEQ ID NO: 375, SEQ ID NO: 376, SEQ ID NO: 378, and SEQ ID NO: 383, and wherein the at least five peptide probes extend from the array surface.

2. The array of claim 1, wherein the at least five peptide probes are capable of binding to an antibody associated with *Borrelia burgdorferi* infection.

3. The array of claim 1, wherein the array surface is a solid surface.

4. The array of claim 3, wherein the solid surface is a microparticle.

5. The array of claim 1, wherein the array surface is a biological particle.

6. The array of claim 5, wherein the biological particle is a cell, a virus, or a bacteriophage.

7. The array of claim 6, wherein the biological particle is an *Escherichia coli* cell.

8. The array of claim 7, wherein the *Escherichia coli* cell expresses the peptide probe on its surface.

9. The array of claim 1, wherein the at least five peptide probes comprises at least a portion of an *Escherichia coli* eCPX scaffold.

10. The array of claim 1, wherein the at least five peptide probe further comprises a label.

11. A method of diagnosing *Borrelia burgdorferi* infection in a subject comprising:
    contacting a biological sample from the subject with the array of claim 1, wherein the biological sample comprises a plurality of antibodies;
    incubating the biological sample and the array under conditions allowing binding of the at least five peptide probes to its target antibody;
    measuring the binding of the at least five peptide probes to its target antibody in the biological sample.

12. The method of claim 11, wherein the method further comprises the prior step of contacting the biological sample with at least one reagent configured to remove antibodies that bind to array components other than the at least five peptide probes.

13. The method of claim 12, wherein the at least one reagent comprises the array surface.

14. The method of claim 11, wherein the measuring comprises an ELISA assay.

15. The method of claim 11, wherein the measuring comprises detecting binding of at least three peptide probes to their target antibodies.

16. The method of claim 15, wherein the binding of at least three peptide probes to their target antibodies indicates the subject is positive for *Borrelia burgdorferi* infection.

17. The method of claim 11, wherein the measuring comprises detecting binding of two peptide probes to their target antibodies.

18. The method of claim 17, wherein the binding of two peptide probes to their target antibodies indicates the subject is indeterminate for *Borrelia burgdorferi* infection.

19. The method of claim 11, wherein the measuring comprises detecting binding of one peptide probe to its target antibody or no binding of peptide probe to its target antibody.

20. The method of claim 19, wherein the binding of one peptide probe to its target antibody or no binding of peptide probe to its target antibody indicates the subject is negative for *Borrelia burgdorferi* infection.

21. The method of claim 11, wherein the measuring comprises calculating the sum of z-scores for the at least five peptide probes.

22. The method of claim 11, wherein the biological sample comprises a bodily fluid.

23. The method of claim 22, wherein the bodily fluid is peripheral blood, lymphatic fluid, sweat, saliva, or mucus.

24. The method of claim 11, wherein the method has a sensitivity of 100%.

25. The method of claim 11, wherein the method has a specificity of 100%.

26. The method of claim 11, wherein the method has a sensitivity of 100% and a specificity of 100%.

27. The array of claim 1, wherein the at least five peptide probes comprises at least a portion of an *Escherichia coli* eCPX scaffold, wherein the array surface is a biological particle, and wherein the biological particle is an *Escherichia coli* cell.

28. The array of claim 1, wherein the at least five peptide probes are capable of binding to an antibody associated with *Borrelia burgdorferi* infection, wherein the at least five peptide probes comprises at least a portion of an *Escherichia coli* eCPX scaffold, wherein the array surface is a biological particle, and wherein the biological particle is an *Escherichia coli* cell.

* * * * *

SEQUENCE LISTING

```
<160> NUMBER OF SEQ ID NOS: 937

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be D or E
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be F, Y or L

<400> SEQUENCE: 1

Xaa Thr Xaa Xaa Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Asp Thr Xaa Phe Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
```

```
<400> SEQUENCE: 3

Asp Xaa Thr Xaa Phe Xaa Xaa Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be E or D

<400> SEQUENCE: 4

Gln Pro Xaa Xaa Pro Phe Xaa Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 5

Gln Pro Xaa Xaa Pro Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be P or S

<400> SEQUENCE: 6

Gln Xaa Xaa Xaa Pro Phe Xaa Glu
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 7

Pro Phe Ser Glu Met
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be F or W

<400> SEQUENCE: 8

Pro Phe Ser Glu Xaa Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be L or M

<400> SEQUENCE: 9

Leu Phe Gly Xaa Xaa Xaa Asn
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be Y or F

<400> SEQUENCE: 10

Glu Trp Val Xaa Xaa Xaa Asp
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be L or M
```

```
<220> FEATURE:
<221> NAME/KEY: misc_feature
<222> LOCATION: (5)..(5)
<223> OTHER INFORMATION: Xaa can be any naturally occurring amino acid

<400> SEQUENCE: 11

Pro Xaa Ala Leu Xaa Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 12

Lys Xaa Asn Glu Xaa Trp Xaa Val
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be A or G
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 13

Pro Xaa Xaa Arg Thr Xaa Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Ala Tyr Thr Xaa Val Asn
1               5

<210> SEQ ID NO 15
```

```
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be A or S
<220> FEATURE:
<221> NAME/KEY: misc_feature
<222> LOCATION: (5)..(7)
<223> OTHER INFORMATION: Xaa can be any naturally occurring amino acid

<400> SEQUENCE: 15

Trp Asn Xaa Tyr Xaa Xaa Xaa Asn
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R, K or E
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be L or M

<400> SEQUENCE: 16

Xaa Xaa Xaa Trp Xaa Pro Xaa Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be A or S
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be S or A
<220> FEATURE:
<221> NAME/KEY: MISC_FEATURE
<222> LOCATION: (7)..(7)
<223> OTHER INFORMATION: Xaa can be Y or F

<400> SEQUENCE: 17

Xaa Tyr Xaa Ser Xaa Xaa Xaa
```

```
<210> SEQ ID NO 18
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 18

Glu Xaa Tyr Xaa Ser Pro Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 19

Met Asn Ile Xaa Asp Asp
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be A, N or K

<400> SEQUENCE: 20

Glu His Xaa Phe Trp
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Val His Asn Ala Tyr
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (3)..(3)
<223> OTHER INFORMATION: Xaa can be E or A
<220> FEATURE:
<221> NAME/KEY: misc_feature
<222> LOCATION: (4)..(4)
<223> OTHER INFORMATION: Xaa can be any naturally occurring amino acid

<400> SEQUENCE: 22

His Gly Xaa Xaa Leu Asn
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be G or D
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be L or F
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be M or L

<400> SEQUENCE: 23

Xaa Xaa Xaa Xaa Xaa Xaa Pro Xaa Gln
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L, V, M or I
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be T or S
<220> FEATURE:
<221> NAME/KEY: MISC_FEATURE
<222> LOCATION: (7)..(7)
<223> OTHER INFORMATION: Xaa can be F, G or I

<400> SEQUENCE: 24

Xaa Xaa Asn Ala Xaa Xaa Xaa
1               5
```

```
<210> SEQ ID NO 25
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 25

Pro Xaa Asn Ser Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 26

Arg Xaa Xaa Pro Leu Ala Xaa Xaa Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 27

Cys Pro Lys Xaa Asn Xaa Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be P or A
<220> FEATURE:
<221> NAME/KEY: MISC_FEATURE
<222> LOCATION: (4)..(4)
<223> OTHER INFORMATION: Xaa can be A or M

<400> SEQUENCE: 28

Gln Xaa His Xaa Phe
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be G, S or P

<400> SEQUENCE: 29

Pro Ala Xaa Glu Asn Xaa Xaa Xaa Xaa
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can  be D or E

<400> SEQUENCE: 30

Asn Ile Asp Xaa Asp
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can ne V or S
<220> FEATURE:
<221> NAME/KEY: MISC_FEATURE
<222> LOCATION: (5)..(5)
<223> OTHER INFORMATION: Xaa can be V or S
<220> FEATURE:
<221> NAME/KEY: MISC_FEATURE
<222> LOCATION: (7)..(7)
<223> OTHER INFORMATION: Xaa can be N or A

<400> SEQUENCE: 31

Arg Xaa Gln Xaa Xaa Asp Xaa
1               5

<210> SEQ ID NO 32
<211> LENGTH: 7
<212> TYPE: PRT
```

<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be D or P
<220> FEATURE:
<221> NAME/KEY: misc_feature
<222> LOCATION: (5)..(5)
<223> OTHER INFORMATION: Xaa can be any naturally occurring amino acid

<400> SEQUENCE: 32

Trp Xaa Xaa Pro Xaa His Leu
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be F or I
<220> FEATURE:
<221> NAME/KEY: MISC_FEATURE
<222> LOCATION: (5)..(5)
<223> OTHER INFORMATION: Xaa can be F or I

<400> SEQUENCE: 33

Thr Trp Ala Xaa Xaa
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 34

Glu Asp Xaa Gly His Pro
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be E, T or A
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Y or F
<220> FEATURE:

```
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be S or R

<400> SEQUENCE: 35

Xaa Xaa Xaa Xaa Xaa Xaa Xaa Pro Xaa Gln
1               5                   10

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be R or K

<400> SEQUENCE: 36

Gly Met Xaa Pro Xaa Gln
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be V or I
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 37

Trp Xaa Xaa Xaa Arg Xaa Xaa Pro Xaa Gln
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be N or E
<220> FEATURE:
<221> NAME/KEY: MISC_FEATURE
<222> LOCATION: (2)..(2)
<223> OTHER INFORMATION: Xaa can be A or G
<220> FEATURE:
```

```
<221> NAME/KEY: MISC_FEATURE
<222> LOCATION: (4)..(4)
<223> OTHER INFORMATION: Xaa can be S, A or T
<220> FEATURE:
<221> NAME/KEY: misc_feature
<222> LOCATION: (5)..(6)
<223> OTHER INFORMATION: Xaa can be any naturally occurring amino acid

<400> SEQUENCE: 38

Xaa Xaa Tyr Xaa Xaa Xaa Trp
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be S or T
<220> FEATURE:
<221> NAME/KEY: misc_feature
<222> LOCATION: (5)..(5)
<223> OTHER INFORMATION: Xaa can be any naturally occurring amino acid

<400> SEQUENCE: 39

Lys Xaa Ile Xaa Xaa Tyr Trp
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 40

Tyr Tyr Xaa Tyr Arg Xaa Xaa Lys
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can  be F or Y
```

```
<400> SEQUENCE: 41

Lys Xaa His Glu Xaa Gly Xaa
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa can be V or I

<400> SEQUENCE: 42

His His Phe Leu Xaa
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L or V

<400> SEQUENCE: 43

Xaa Cys Asn Ala Tyr
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Leu Phe Gly Ala Asn Leu Asn
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic peptide

<400> SEQUENCE: 45

Pro Gly Pro Arg Thr Cys Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide

<400> SEQUENCE: 46

Pro Ala Arg Arg Thr Arg Lys
1               5
```

-continued

```
<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Ile Ala Asn Ala Gly Ser Ile
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48

Trp Ala Gln Ile Arg His Ile Pro Tyr Gln
1               5                   10

<210> SEQ ID NO 49
<211> LENGTH: 6
<212> TYPE: PRT
<213> ORGANISM: Artificial Sequence
<220> FEATURE:
<223> OTHER INFORMATION: Synthetic peptide

<400> SEQUENCE: 49

Met Arg Asn Pro Gln Gln
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be E, D or Q
<220> FEATURE:
<221> NAME/KEY: MISC_FEATURE
<222> LOCATION: (5)..(5)
<223> OTHER INFORMATION: Xaa can be L, I or V
<220> FEATURE:
<221> NAME/KEY: MISC_FEATURE
<222> LOCATION: (6)..(6)
<223> OTHER INFORMATION: Xaa can be I or V
<220> FEATURE:
<221> NAME/KEY: MISC_FEATURE
<222> LOCATION: (7)..(7)
<223> OTHER INFORMATION: Xaa can be D or E

<400> SEQUENCE: 50

Leu Xaa Glu Val Xaa Xaa Xaa Lys
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be V or I
<220> FEATURE:
```

```
<221> NAME/KEY: MISC_FEATURE
<222> LOCATION: (3)..(3)
<223> OTHER INFORMATION: Xaa can be V, I, or L
<220> FEATURE:
<221> NAME/KEY: MISC_FEATURE
<222> LOCATION: (4)..(4)
<223> OTHER INFORMATION: Xaa can be I or V
<220> FEATURE:
<221> NAME/KEY: MISC_FEATURE
<222> LOCATION: (5)..(5)
<223> OTHER INFORMATION: Xaa can be D, E or N

<400> SEQUENCE: 51

Glu Xaa Xaa Xaa Xaa Lys
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be V or I
<220> FEATURE:
<221> NAME/KEY: MISC_FEATURE
<222> LOCATION: (3)..(3)
<223> OTHER INFORMATION: Xaa can be V or I
<220> FEATURE:
<221> NAME/KEY: MISC_FEATURE
<222> LOCATION: (4)..(4)
<223> OTHER INFORMATION: Xaa can be V or I
<220> FEATURE:
<221> NAME/KEY: misc_feature
<222> LOCATION: (5)..(5)
<223> OTHER INFORMATION: Xaa can be any naturally occurring amino acid

<400> SEQUENCE: 52

Glu Xaa Xaa Xaa Xaa Lys
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 53

Val Xaa Pro Asn Ile
1               5

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide

<400> SEQUENCE: 54

Val Val Pro Asn
1

<210> SEQ ID NO 55
<211> LENGTH: 9
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 55

Leu Xaa Glu Val Leu Val Val Val Pro
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 56

Gly Pro Xaa His Thr Xaa Lys Val
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be V or I
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be V or T

<400> SEQUENCE: 57

Glu Xaa Tyr Xaa Asp Xaa Xaa Leu Asn
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa can be I or V

<400> SEQUENCE: 58

Glu Leu Glu Glu Val Xaa Val Asp Lys
```

```
<210> SEQ ID NO 59
<211> LENGTH: 11
<212> TYPE: PRT
<213> ORGANISM: Artificial Sequence
<220> FEATURE:
<223> OTHER INFORMATION: Synthetic peptide

<400> SEQUENCE: 59

Leu Asn Glu Val Leu Val Val Val Pro Asn Ile
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Synthetic peptide

<400> SEQUENCE: 60

Gly Pro Lys His Thr Gln Lys Val
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide

<400> SEQUENCE: 61

Glu Glu Tyr Val Asp Gln Val Leu Asn
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be S or T

<400> SEQUENCE: 62

Lys Xaa Asp Pro Asp Xaa Xaa Trp Xaa
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 63
```

```
Lys Pro Xaa Leu Gly Gly Lys
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 64

Lys Xaa Asp Pro Asp Xaa Xaa Trp Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic peptide

<400> SEQUENCE: 65

Lys Pro Thr Leu Gly Gly Lys
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I or V
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be P or R

<400> SEQUENCE: 66

Xaa Xaa Xaa Gln Pro Glu Lys Pro
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 67

Lys Xaa Asp Asp Met Leu Asn
1               5
```

```
<210> SEQ ID NO 68
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 68

Lys Xaa Asp Xaa Met Leu Asn
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L or W
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 69

Xaa Xaa Ser Ala Glu Xaa Glu Glu Lys
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 70

Ser Ala Glu Xaa Glu Xaa Lys
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic peptide

<400> SEQUENCE: 71

Val Lys Pro Gln Pro Glu Lys Pro
```

```
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic peptide

<400> SEQUENCE: 72

Lys Thr Asp Asp Met Leu Asn
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Leu Glu Ser Ala Glu Lys Glu Glu Lys
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be F or Y

<400> SEQUENCE: 74

His Glu Xaa Glu Xaa Gln
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be M, L or F
<220> FEATURE:
<221> NAME/KEY: misc_feature
<222> LOCATION: (5)..(5)
<223> OTHER INFORMATION: Xaa can be any naturally occurring amino acid

<400> SEQUENCE: 75

Leu Asp Xaa Trp Xaa Glu
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic peptide

<400> SEQUENCE: 76
```

```
His Cys Ser Ala Cys
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be F or Y
<220> FEATURE:
<221> NAME/KEY: misc_feature
<222> LOCATION: (2)..(2)
<223> OTHER INFORMATION: Xaa can be any naturally occurring amino acid

<400> SEQUENCE: 77

Xaa Xaa Gly Val Val Asn
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 78

Lys Xaa Xaa Xaa Gly Arg Gly Xaa Ile
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be L or A

<400> SEQUENCE: 79

Gly Pro His Xaa Glu
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic peptide

<400> SEQUENCE: 80

Pro Arg Arg Glu Pro
1               5

<210> SEQ ID NO 81
<211> LENGTH: 8
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(5)
<223> OTHER INFORMATION: Xaa can be any naturally occurring amino acid

<400> SEQUENCE: 81

Cys Asn Xaa Xaa Xaa Glu Cys Tyr
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 82

Lys Xaa Cys Gln Pro Xaa Xaa Cys
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be F or H
<220> FEATURE:
<221> NAME/KEY: MISC_FEATURE
<222> LOCATION: (6)..(6)
<223> OTHER INFORMATION: Xaa can be T or S

<400> SEQUENCE: 83

Pro Xaa Pro Asp Xaa Xaa
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be A or G
```

```
<220> FEATURE:
<221> NAME/KEY: misc_feature
<222> LOCATION: (9)..(9)
<223> OTHER INFORMATION: Xaa can be any naturally occurring amino acid

<400> SEQUENCE: 84

Asn Xaa Xaa Xaa Glu Xaa Tyr Xaa Xaa Asp
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be A or G
<220> FEATURE:
<221> NAME/KEY: misc_feature
<222> LOCATION: (4)..(5)
<223> OTHER INFORMATION: Xaa can be any naturally occurring amino acid

<400> SEQUENCE: 85

Pro Xaa Ala Xaa Xaa Leu Asp
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 86

Met Pro Ser Xaa Ser Xaa Glu
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or K
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be T or S

<400> SEQUENCE: 87

Xaa Xaa Tyr Xaa His Arg Xaa
```

<210> SEQ ID NO 88
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be P or A
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 88

Lys Xaa Xaa Phe Xaa Phe Xaa Lys
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be C, S or T
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 89

Asp Asp Xaa Xaa Gly Xaa Arg
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be M or L
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 90

Pro Xaa Xaa Xaa His Xaa Met Tyr

```
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be A, S or Q
<220> FEATURE:
<221> NAME/KEY: MISC_FEATURE
<222> LOCATION: (4)..(4)
<223> OTHER INFORMATION: Xaa can be S, A or T
<220> FEATURE:
<221> NAME/KEY: misc_feature
<222> LOCATION: (5)..(5)
<223> OTHER INFORMATION: Xaa can be any naturally occurring amino acid

<400> SEQUENCE: 91

Lys Xaa Xaa Xaa Xaa Arg Gly
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be D or G

<400> SEQUENCE: 92

Xaa Gln Pro Glu Asn
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be K, H or R
<220> FEATURE:
<221> NAME/KEY: MISC_FEATURE
<222> LOCATION: (3)..(3)
<223> OTHER INFORMATION: Xaa can be Q or N

<400> SEQUENCE: 93

Xaa Asn Xaa Asp Gly
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
```

```
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be E, V or S
<220> FEATURE:
<221> NAME/KEY: misc_feature
<222> LOCATION: (6)..(6)
<223> OTHER INFORMATION: Xaa can be any naturally occurring amino acid

<400> SEQUENCE: 94

Asn Xaa Xaa Gly Glu Xaa Tyr
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be V or I

<400> SEQUENCE: 95

Glu Pro Xaa Thr Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be P or A
<220> FEATURE:
<221> NAME/KEY: MISC_FEATURE
<222> LOCATION: (5)..(5)
<223> OTHER INFORMATION: Xaa can be K or R

<400> SEQUENCE: 96

His Gly Met Xaa Xaa
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V, I or T

<400> SEQUENCE: 97

Xaa Pro Trp Ile Phe
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be S, T or N
<220> FEATURE:
<221> NAME/KEY: misc_feature
<222> LOCATION: (5)..(5)
<223> OTHER INFORMATION: Xaa can be any naturally occurring amino acid

<400> SEQUENCE: 98

Lys Xaa Xaa Val Xaa Phe Gln
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Xaa can be V, A or I
<220> FEATURE:
<221> NAME/KEY: MISC_FEATURE
<222> LOCATION: (1)..(1)
<223> OTHER INFORMATION: Xaa can be V, A or I

<400> SEQUENCE: 99

Xaa Trp Ser Gly Ser
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be L, I, A or M
<220> FEATURE:
<221> NAME/KEY: misc_feature
<222> LOCATION: (4)..(5)
<223> OTHER INFORMATION: Xaa can be any naturally occurring amino acid

<400> SEQUENCE: 100

Phe Ser Xaa Xaa Xaa Trp Gly
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be P or Q

<400> SEQUENCE: 101

Pro Thr Asn Xaa Gly
1               5

<210> SEQ ID NO 102
<211> LENGTH: 9
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or K
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Y or W
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be T or S

<400> SEQUENCE: 102

Xaa Lys Xaa Xaa Xaa Xaa His Xaa Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be H, R or W
<220> FEATURE:
<221> NAME/KEY: misc_feature
<222> LOCATION: (2)..(3)
<223> OTHER INFORMATION: Xaa can be any naturally occurring amino acid

<400> SEQUENCE: 103

Xaa Xaa Xaa His Pro Arg Phe
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or K
<220> FEATURE:
<221> NAME/KEY: misc_feature
<222> LOCATION: (4)..(4)
<223> OTHER INFORMATION: Xaa can be any naturally occurring amino acid

<400> SEQUENCE: 104

Xaa Met Arg Xaa Ile Asp
1               5

<210> SEQ ID NO 105
<211> LENGTH: 6
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 105

Gln His Xaa Gly His Pro
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 106

Lys Xaa Xaa Leu Pro Glu Asp
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I or V
<220> FEATURE:
<221> NAME/KEY: misc_feature
<222> LOCATION: (3)..(4)
<223> OTHER INFORMATION: Xaa can be any naturally occurring amino acid

<400> SEQUENCE: 107

Xaa Leu Xaa Xaa Phe Gly Tyr
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(7)
<223> OTHER INFORMATION: Xaa can be any naturally occurring amino acid

<400> SEQUENCE: 108

Pro Leu Asp Xaa Xaa Xaa Xaa Ile Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
```

```
<221> NAME/KEY: misc_feature
<222> LOCATION: (6)..(6)
<223> OTHER INFORMATION: Xaa can be any naturally occurring amino acid

<400> SEQUENCE: 109

Glu Thr Xaa Ile Pro Xaa Glu
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or I
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be D or E
<220> FEATURE:
<221> NAME/KEY: MISC_FEATURE
<222> LOCATION: (5)..(5)
<223> OTHER INFORMATION: Xaa can be M or L
<220> FEATURE:
<221> NAME/KEY: misc_feature
<222> LOCATION: (7)..(7)
<223> OTHER INFORMATION: Xaa can be any naturally occurring amino acid

<400> SEQUENCE: 110

Xaa Asn Xaa Xaa Xaa Tyr Xaa Pro
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 111

Phe Leu Xaa Xaa Ile Gly Ala
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be V or I
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be M or I
<220> FEATURE:
```

```
<221> NAME/KEY: MISC_FEATURE
<222> LOCATION: (5)..(5)
<223> OTHER INFORMATION: Xaa can be I, L or V
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be K or R
<220> FEATURE:
<221> NAME/KEY: MISC_FEATURE
<222> LOCATION: (7)..(7)

<400> SEQUENCE: 112

Asp Xaa Xaa Xaa Xaa Xaa Xaa
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be I or L

<400> SEQUENCE: 113

Arg Xaa Ser Pro Tyr Xaa Xaa Phe
1               5

<210> SEQ ID NO 114
<211> LENGTH: 5
<212> TYPE: PRT
<213> ORGANISM: Artificial Sequence
<220> FEATURE:
<223> OTHER INFORMATION: Synthetic peptide

<400> SEQUENCE: 114

Val Gly Pro Arg His
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be E or D

<400> SEQUENCE: 115

Pro Gln Xaa Gln His Xaa
1               5
```

```
<210> SEQ ID NO 116
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 116

Pro Xaa Xaa Gly Gly Phe Gly
1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 117

Lys Xaa Glu Gly Xaa Xaa Met Gly
1               5

<210> SEQ ID NO 118
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 118

Lys Xaa Xaa Gly Xaa Thr Xaa Xaa Leu Ser
1               5                   10

<210> SEQ ID NO 119
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be F or W

<400> SEQUENCE: 119

Glu Met Gly Xaa Gln
1               5
```

```
<210> SEQ ID NO 120
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or I
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 120

Xaa Lys Xaa Gly Xaa Xaa Asp Xaa Pro
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be D or N
<220> FEATURE:
<221> NAME/KEY: misc_feature
<222> LOCATION: (5)..(5)
<223> OTHER INFORMATION: Xaa can be any naturally occurring amino acid

<400> SEQUENCE: 121

Pro Glu Xaa Glu Xaa Tyr Pro
1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic peptide

<400> SEQUENCE: 122

His Tyr Glu Trp Ala
1               5

<210> SEQ ID NO 123
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be H or R
<220> FEATURE:
<221> NAME/KEY: misc_feature
<222> LOCATION: (5)..(5)
<223> OTHER INFORMATION: Xaa can be any naturally occurring amino acid
```

```
<400> SEQUENCE: 123

Xaa Ser Asn Met Xaa Phe
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be T or V
<220> FEATURE:
<221> NAME/KEY: misc_feature
<222> LOCATION: (4)..(5)
<223> OTHER INFORMATION: Xaa can be any naturally occurring amino acid

<400> SEQUENCE: 124

Met Xaa Gly Xaa Xaa Tyr Glu
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be K or H
<220> FEATURE:
<221> NAME/KEY: misc_feature
<222> LOCATION: (6)..(7)
<223> OTHER INFORMATION: Xaa can be any naturally occurring amino acid

<400> SEQUENCE: 125

Asp Xaa Xaa Xaa Glu Xaa Xaa Leu Leu
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be E, D or A
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be I or V
```

```
<220> FEATURE:
<221> NAME/KEY: MISC_FEATURE
<222> LOCATION: (9)..(9)
<223> OTHER INFORMATION: Xaa can be A or R

<400> SEQUENCE: 126

Arg Xaa Xaa Trp Xaa Xaa Xaa Xaa Xaa
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be G, P or A
<220> FEATURE:
<221> NAME/KEY: MISC_FEATURE
<222> LOCATION: (9)..(9)
<223> OTHER INFORMATION: Xaa can be T or S

<400> SEQUENCE: 127

Pro Xaa Asp Xaa Xaa Ala Xaa Xaa Xaa
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be A, R or G

<400> SEQUENCE: 128

Pro Asp Xaa Xaa Ser Xaa Thr Xaa
1               5

<210> SEQ ID NO 129
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
```

```
<400> SEQUENCE: 129

Gly Arg Glu Xaa Asp Gly
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(7)
<223> OTHER INFORMATION: Xaa can be any naturally occurring amino acid

<400> SEQUENCE: 130

Gly Val Pro Gly Xaa Xaa Xaa Lys
1               5

<210> SEQ ID NO 131
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L or M
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be E, D or Q
<220> FEATURE:
<221> NAME/KEY: misc_feature
<222> LOCATION: (7)..(8)
<223> OTHER INFORMATION: Xaa can be any naturally occurring amino acid

<400> SEQUENCE: 131

Xaa Xaa Xaa Xaa Xaa Val Xaa Xaa Ile Met
1               5                   10

<210> SEQ ID NO 132
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 132

Ser Xaa Xaa Xaa Val Ser Gly Gly
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
```

```
<223> OTHER INFORMATION: Xaa can be K or R
<220> FEATURE:
<221> NAME/KEY: MISC_FEATURE
<222> LOCATION: (5)..(5)
<223> OTHER INFORMATION: Xaa can be D or N

<400> SEQUENCE: 133

Ala Xaa Ala Gly Xaa Lys
1               5

<210> SEQ ID NO 134
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be R or N
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be R or Q

<400> SEQUENCE: 134

Phe Xaa Xaa Ile Asn Xaa
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 135

Tyr Xaa Pro Val Xaa Pro Xaa Ser Tyr
1               5

<210> SEQ ID NO 136
<211> LENGTH: 6
<212> TYPE: PRT
<213> ORGANISM: Artificial Sequence
<220> FEATURE:
<223> OTHER INFORMATION: Synethetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 136

Lys Xaa Thr Phe Pro Asp
1               5
```

```
<210> SEQ ID NO 137
<211> LENGTH: 7
<212> TYPE: PRT
<213> ORGANISM: Artificial Sequence
<220> FEATURE:
<223> OTHER INFORMATION: Synethetic peptide
<220> FEATURE:
<221> NAME/KEY: MISC_FEATURE
<222> LOCATION: (4)..(4)
<223> OTHER INFORMATION: Xaa can be F, V or M
<220> FEATURE:
<221> NAME/KEY: misc_feature
<222> LOCATION: (5)..(6)
<223> OTHER INFORMATION: Xaa can be any naturally occurring amino acid

<400> SEQUENCE: 137

Pro Phe Met Xaa Xaa Xaa Arg
1               5

<210> SEQ ID NO 138
<211> LENGTH: 5
<212> TYPE: PRT
<213> ORGANISM: Artificial Sequence
<220> FEATURE:
<223> OTHER INFORMATION: Synethetic peptide

<400> SEQUENCE: 138

Glu Phe Trp Glu Pro
1               5

<210> SEQ ID NO 139
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be F or Y

<400> SEQUENCE: 139

Xaa Gly Ala Leu Ser
1               5

<210> SEQ ID NO 140
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 140

Pro Xaa Gly Thr Glu Asn
1               5

<210> SEQ ID NO 141
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
```

```
<221> NAME/KEY: MISC_FEATURE
<222> LOCATION: (3)..(3)
<223> OTHER INFORMATION: Xaa can be K or E

<400> SEQUENCE: 141

Gly Xaa Xaa Pro Trp Glu
1               5

<210> SEQ ID NO 142
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I or V
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Y or F
<220> FEATURE:
<221> NAME/KEY: MISC_FEATURE
<222> LOCATION: (6)..(6)
<223> OTHER INFORMATION: Xaa can be W or N

<400> SEQUENCE: 142

Asp Xaa Thr Xaa Xaa Xaa
1               5

<210> SEQ ID NO 143
<211> LENGTH: 6
<212> TYPE: PRT
<213> ORGANISM: Artificial Sequence
<220> FEATURE:
<223> OTHER INFORMATION: Synthetic peptide

<400> SEQUENCE: 143

Gln His Lys Gly His Pro
1               5

<210> SEQ ID NO 144
<211> LENGTH: 6
<212> TYPE: PRT
<213> ORGANISM: Artificial Sequence
<220> FEATURE:
<223> OTHER INFORMATION: Synthetic peptide

<400> SEQUENCE: 144

Gln His Ile Gly His Pro
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic peptide

<400> SEQUENCE: 145

Lys Ala Leu Leu Pro Glu Asp
1               5

<210> SEQ ID NO 146
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 146

Lys Lys His Leu Pro Glu Asp
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide

<400> SEQUENCE: 147

Lys Ile Thr Leu Pro Glu Asp
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic peptide

<400> SEQUENCE: 148

Lys Thr Ile Leu Pro Glu Asp
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic peptide

<400> SEQUENCE: 149

Lys Val Leu Leu Pro Glu Asp
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic peptide

<400> SEQUENCE: 150

Val Leu Lys Lys Phe Gly Tyr
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic peptide

<400> SEQUENCE: 151

Val Leu His Leu Phe Gly Tyr
1               5

<210> SEQ ID NO 152
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 152

Val Leu Gly Glu Phe Gly Tyr
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic peptide

<400> SEQUENCE: 153

Val Leu Glu Pro Phe Gly Tyr
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic peptide

<400> SEQUENCE: 154

Pro Leu Asp Val Glu Lys Glu Ile Ser
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic peptide

<400> SEQUENCE: 155

Pro Leu Asp Leu Leu Lys Tyr Ile Ser
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic peptide

<400> SEQUENCE: 156

Glu Thr Lys Ile Pro Ser Glu
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic peptide

<400> SEQUENCE: 157

Glu Thr Glu Ile Pro Ser Glu
1               5

<210> SEQ ID NO 158
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 158

Glu Thr Gly Ile Pro Phe Glu
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic peptide

<400> SEQUENCE: 159

Val Asn Val Asp Leu Tyr Ile Pro
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic peptide

<400> SEQUENCE: 160

Phe Leu Gly Ala Ile Gly Ala
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic peptide

<400> SEQUENCE: 161

Phe Leu Leu Phe Ile Gly Ala
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic peptide

<400> SEQUENCE: 162

Phe Leu Lys Ala Ile Gly Ala
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic peptide

<400> SEQUENCE: 163

Asp Ile Lys Met Ile Glu Arg
1               5

<210> SEQ ID NO 164
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 164

Asp Ile Ile Ile Val Ser Arg
1               5

<210> SEQ ID NO 165
<211> LENGTH: 7
<212> TYPE: PRT
<213> ORGANISM: Artificial Sequence
<220> FEATURE:
<223> OTHER INFORMATION: Synthetic peptide

<400> SEQUENCE: 165

Asp Val His Met Leu Val Arg
1               5

<210> SEQ ID NO 166
<211> LENGTH: 7
<212> TYPE: PRT
<213> ORGANISM: Artificial Sequence
<220> FEATURE:
<223> OTHER INFORMATION: Synthetic peptide

<400> SEQUENCE: 166

Asp Val Asp Ile Leu Glu Arg
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic peptide

<400> SEQUENCE: 167

Arg Val Ser Pro Tyr Ser Ile Phe
1               5

<210> SEQ ID NO 168
<211> LENGTH: 5
<212> TYPE: PRT
<213> ORGANISM: Artificial Sequence
<220> FEATURE:
<223> OTHER INFORMATION: Synthetic peptide

<400> SEQUENCE: 168

Val Gly Pro Arg His
1               5

<210> SEQ ID NO 169
<211> LENGTH: 6
<212> TYPE: PRT
<213> ORGANISM: Artificial Sequence
<220> FEATURE:
<223> OTHER INFORMATION: Synthetic peptide

<400> SEQUENCE: 169

Pro Gln Lys Gln His Glu
1               5

<210> SEQ ID NO 170
<211> LENGTH: 6
<212> TYPE: PRT
<213> ORGANISM: Artificial Sequence
<220> FEATURE:
```

```
<223> OTHER INFORMATION: Synthetic peptide

<400> SEQUENCE: 170

Pro Gln Gly Gln His Asp
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic peptide

<400> SEQUENCE: 171

Lys Ser Glu Gly Glu Phe Met Gly
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic peptide

<400> SEQUENCE: 172

Lys Asp Glu Gly Leu Ala Met Gly
1               5

<210> SEQ ID NO 173
<211> LENGTH: 10
<212> TYPE: PRT
<213> ORGANISM: Artificial Sequence
<220> FEATURE:
<223> OTHER INFORMATION: Synthetic peptide

<400> SEQUENCE: 173

Lys Asp Asn Gly Ser Thr Trp Ser Leu Ser
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic peptide

<400> SEQUENCE: 174

Lys Asp Asp Gly Ser Thr Trp Ala Leu Ser
1               5                   10

<210> SEQ ID NO 175
<211> LENGTH: 9
<212> TYPE: PRT
<213> ORGANISM: Artificial Sequence
<220> FEATURE:
<223> OTHER INFORMATION: Synthetic peptide

<400> SEQUENCE: 175

Ile Lys Gln Gly Arg Leu Asp Arg Pro
1               5

<210> SEQ ID NO 176
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 176

His Tyr Glu Trp Ala
1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic peptide

<400> SEQUENCE: 177

Met Val Gly Glu His Tyr Glu
1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic peptide

<400> SEQUENCE: 178

Met Val Gly Lys Ala Tyr Glu
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic peptide

<400> SEQUENCE: 179

Asp Gln Leu Lys Glu Gly Arg Leu Leu
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic peptide

<400> SEQUENCE: 180

Asp Val Val Lys Glu Leu Met Leu Leu
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic peptide

<400> SEQUENCE: 181

Asp Leu Glu Lys Glu Asn Glu Leu Leu
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 182

Asp Leu Asp Lys Glu Val Ser Leu Leu
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic peptide

<400> SEQUENCE: 183

Arg His Gln Trp Tyr Ala Val Val Ala
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic peptide

<400> SEQUENCE: 184

Arg His Ser Trp Phe Asp Asp Val Arg
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic peptide

<400> SEQUENCE: 185

Arg Lys Glu Trp Tyr Asp Val Val Ala
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic peptide

<400> SEQUENCE: 186

Arg Asp Arg Trp Thr Glu Ser Ile Ala
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic peptide

<400> SEQUENCE: 187

Arg Ala Thr Trp Leu Asp Gln Val Arg
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic peptide

<400> SEQUENCE: 188
```

```
Arg Tyr Val Trp Asn Glu Trp Val Ala
1               5
```

<210> SEQ ID NO 189
<211> LENGTH: 9
<212> TYPE: PRT
<213> ORGANISM: Artificial Sequence
<220> FEATURE:
<223> OTHER INFORMATION: Synthetic peptide

<400> SEQUENCE: 189

```
Pro Val Asp Ser Thr Ala His Gly Thr
1               5
```

<210> SEQ ID NO 190
<211> LENGTH: 9
<212> TYPE: PRT
<213> ORGANISM: Artificial Sequence
<220> FEATURE:
<223> OTHER INFORMATION: Synthetic peptide

<400> SEQUENCE: 190

```
Pro Leu Asp Cys Pro Ala Leu Gly Ser
1               5
```

<210> SEQ ID NO 191
<211> LENGTH: 9
<212> TYPE: PRT
<213> ORGANISM: Artificial Sequence
<220> FEATURE:
<223> OTHER INFORMATION: Synthetic peptide

<400> SEQUENCE: 191

```
Pro Ala Asp Ser Ser Ala His Gly Thr
1               5
```

<210> SEQ ID NO 192
<211> LENGTH: 9
<212> TYPE: PRT
<213> ORGANISM: Artificial Sequence
<220> FEATURE:
<223> OTHER INFORMATION: Synthetic peptide

<400> SEQUENCE: 192

```
Pro Lys Asp Val Lys Ala Thr Gly Ser
1               5
```

<210> SEQ ID NO 193
<211> LENGTH: 9
<212> TYPE: PRT
<213> ORGANISM: Artificial Sequence
<220> FEATURE:
<223> OTHER INFORMATION: Synthetic peptide

<400> SEQUENCE: 193

```
Pro Pro Asp Val Ser Ala Ser Gly Thr
1               5
```

<210> SEQ ID NO 194
<211> LENGTH: 9
<212> TYPE: PRT
<213> ORGANISM: Artificial Sequence
<220> FEATURE:
<223> OTHER INFORMATION: Synthetic peptide

<400> SEQUENCE: 194

```
Pro Gly Asp Leu Pro Ala Lys Ala Thr
1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic peptide

<400> SEQUENCE: 195

Pro Ala Asp Val Ser Ala Gln Ala Thr
1               5

<210> SEQ ID NO 196
<211> LENGTH: 9
<212> TYPE: PRT
<213> ORGANISM: Artificial Sequence
<220> FEATURE:
<223> OTHER INFORMATION: Synthetic peptide

<400> SEQUENCE: 196

Pro Pro Asp Val Pro Ala Ser Gly Thr
1               5

<210> SEQ ID NO 197
<211> LENGTH: 8
<212> TYPE: PRT
<213> ORGANISM: Artificial Sequence
<220> FEATURE:
<223> OTHER INFORMATION: Synthetic peptide

<400> SEQUENCE: 197

Pro Asp Pro Ala Ser Ile Thr Ala
1               5

<210> SEQ ID NO 198
<211> LENGTH: 8
<212> TYPE: PRT
<213> ORGANISM: Artificial Sequence
<220> FEATURE:
<223> OTHER INFORMATION: Synthetic peptide

<400> SEQUENCE: 198

Pro Asp Ala Ser Ser Ser Thr Ala
1               5

<210> SEQ ID NO 199
<211> LENGTH: 8
<212> TYPE: PRT
<213> ORGANISM: Artificial Sequence
<220> FEATURE:
<223> OTHER INFORMATION: Synthetic peptide

<400> SEQUENCE: 199

Pro Asp Ser Arg Ser Ile Thr Ala
1               5

<210> SEQ ID NO 200
<211> LENGTH: 8
<212> TYPE: PRT
<213> ORGANISM: Artificial Sequence
<220> FEATURE:
<223> OTHER INFORMATION: Synthetic peptide

<400> SEQUENCE: 200

Pro Asp Ser Arg Ser Val Thr Ala
```

```
1               5

<210> SEQ ID NO 201
<211> LENGTH: 8
<212> TYPE: PRT
<213> ORGANISM: Artificial Sequence
<220> FEATURE:
<223> OTHER INFORMATION: Synthetic peptide

<400> SEQUENCE: 201

Pro Asp Ser Lys Ser Pro Thr Ala
1               5

<210> SEQ ID NO 202
<211> LENGTH: 8
<212> TYPE: PRT
<213> ORGANISM: Artificial Sequence
<220> FEATURE:
<223> OTHER INFORMATION: Synthetic peptide

<400> SEQUENCE: 202

Pro Asp Ser Glu Ser Pro Thr Ala
1               5

<210> SEQ ID NO 203
<211> LENGTH: 6
<212> TYPE: PRT
<213> ORGANISM: Artificial Sequence
<220> FEATURE:
<223> OTHER INFORMATION: Synthetic peptide

<400> SEQUENCE: 203

Gly Arg Glu Ser Asp Gly
1               5

<210> SEQ ID NO 204
<211> LENGTH: 6
<212> TYPE: PRT
<213> ORGANISM: Artificial Sequence
<220> FEATURE:
<223> OTHER INFORMATION: Synthetic peptide

<400> SEQUENCE: 204

Gly Arg Glu Ala Asp Gly
1               5

<210> SEQ ID NO 205
<211> LENGTH: 8
<212> TYPE: PRT
<213> ORGANISM: Artificial Sequence
<220> FEATURE:
<223> OTHER INFORMATION: Synthetic peptide

<400> SEQUENCE: 205

Gly Val Pro Gly Ser His Ala Lys
1               5

<210> SEQ ID NO 206
<211> LENGTH: 8
<212> TYPE: PRT
<213> ORGANISM: Artificial Sequence
<220> FEATURE:
<223> OTHER INFORMATION: Synthetic peptide

<400> SEQUENCE: 206

Gly Val Pro Gly Cys Val Ile Lys
1               5
```

-continued

```
<210> SEQ ID NO 207
<211> LENGTH: 10
<212> TYPE: PRT
<213> ORGANISM: Artificial Sequence
<220> FEATURE:
<223> OTHER INFORMATION: Synthetic peptide

<400> SEQUENCE: 207

Leu Ser Pro Arg Glu Val Tyr Thr Ile Met
1               5                   10

<210> SEQ ID NO 208
<211> LENGTH: 10
<212> TYPE: PRT
<213> ORGANISM: Artificial Sequence
<220> FEATURE:
<223> OTHER INFORMATION: Synthetic peptide

<400> SEQUENCE: 208

Leu Thr Asn Thr Asp Val Thr Arg Ile Met
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Synthetic peptide

<400> SEQUENCE: 209

Leu Glu Asp Glu Asp Val Leu Gln Ile Met
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Synthetic peptide

<400> SEQUENCE: 210

Met Ala Asp Pro Glu Val Ala Ala Ile Met
1               5                   10

<210> SEQ ID NO 211
<211> LENGTH: 8
<212> TYPE: PRT
<213> ORGANISM: Artificial Sequence
<220> FEATURE:
<223> OTHER INFORMATION: Synthetic peptide

<400> SEQUENCE: 211

Ser Gln Ala Asp Val Ser Gly Gly
1               5

<210> SEQ ID NO 212
<211> LENGTH: 8
<212> TYPE: PRT
<213> ORGANISM: Artificial Sequence
<220> FEATURE:
<223> OTHER INFORMATION: Synthetic peptide

<400> SEQUENCE: 212

Ser Val Gly Ser Val Ser Gly Gly
1               5
```

```
<210> SEQ ID NO 213
<211> LENGTH: 8
<212> TYPE: PRT
<213> ORGANISM: Artificial Sequence
<220> FEATURE:
<223> OTHER INFORMATION: Synthetic peptide

<400> SEQUENCE: 213

Ser Pro Ser Gly Val Ser Gly Gly
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic peptide

<400> SEQUENCE: 214

Ser Trp Phe Asp Val Ser Gly Gly
1               5

<210> SEQ ID NO 215
<211> LENGTH: 6
<212> TYPE: PRT
<213> ORGANISM: Artificial Sequence
<220> FEATURE:
<223> OTHER INFORMATION: Synthetic peptide

<400> SEQUENCE: 215

Phe Arg Ile Ile Asn Gln
1               5

<210> SEQ ID NO 216
<211> LENGTH: 6
<212> TYPE: PRT
<213> ORGANISM: Artificial Sequence
<220> FEATURE:
<223> OTHER INFORMATION: Synthetic peptide

<400> SEQUENCE: 216

Phe Arg Ala Ile Asn Arg
1               5

<210> SEQ ID NO 217
<211> LENGTH: 6
<212> TYPE: PRT
<213> ORGANISM: Artificial Sequence
<220> FEATURE:
<223> OTHER INFORMATION: Synthetic peptide

<400> SEQUENCE: 217

Lys Gln Thr Phe Pro Asp
1               5

<210> SEQ ID NO 218
<211> LENGTH: 6
<212> TYPE: PRT
<213> ORGANISM: Artificial Sequence
<220> FEATURE:
<223> OTHER INFORMATION: Synthetic peptide

<400> SEQUENCE: 218

Lys Ala Thr Phe Pro Asp
1               5
```

```
<210> SEQ ID NO 219
<211> LENGTH: 7
<212> TYPE: PRT
<213> ORGANISM: Artificial Sequence
<220> FEATURE:
<223> OTHER INFORMATION: Synthetic peptide

<400> SEQUENCE: 219

Pro Phe Met Val Gln Met Arg
1               5

<210> SEQ ID NO 220
<211> LENGTH: 5
<212> TYPE: PRT
<213> ORGANISM: Artificial Sequence
<220> FEATURE:
<223> OTHER INFORMATION: Synthetic peptide

<400> SEQUENCE: 220

Phe Gly Ala Leu Ser
1               5

<210> SEQ ID NO 221
<211> LENGTH: 5
<212> TYPE: PRT
<213> ORGANISM: Artificial Sequence
<220> FEATURE:
<223> OTHER INFORMATION: Synthetic peptide

<400> SEQUENCE: 221

Tyr Gly Ala Leu Ser
1               5

<210> SEQ ID NO 222
<211> LENGTH: 6
<212> TYPE: PRT
<213> ORGANISM: Artificial Sequence
<220> FEATURE:
<223> OTHER INFORMATION: Synthetic peptide

<400> SEQUENCE: 222

Pro Ser Gly Thr Glu Asn
1               5

<210> SEQ ID NO 223
<211> LENGTH: 6
<212> TYPE: PRT
<213> ORGANISM: Artificial Sequence
<220> FEATURE:
<223> OTHER INFORMATION: Synthetic peptide

<400> SEQUENCE: 223

Gly Phe Lys Pro Trp Glu
1               5

<210> SEQ ID NO 224
<211> LENGTH: 6
<212> TYPE: PRT
<213> ORGANISM: Artificial Sequence
<220> FEATURE:
<223> OTHER INFORMATION: Synthetic peptide

<400> SEQUENCE: 224

Asp Ile Thr Asp Tyr Asn
1               5

<210> SEQ ID NO 225
```

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 225

Asp Val Thr Gly Phe Asn
1               5

<210> SEQ ID NO 226
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be Q, E or A

<400> SEQUENCE: 226

Ala Xaa Ser Pro Asn Xaa
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or P
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be I, F, M, L or V

<400> SEQUENCE: 227

Xaa Xaa Ala Xaa Ser Xaa Asn Xaa Xaa
1               5

<210> SEQ ID NO 228
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
```

```
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be V or T

<400> SEQUENCE: 228

Asn Xaa Xaa Leu Gly Leu Xaa
1               5

<210> SEQ ID NO 229
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be Y or F
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be D or E
<220> FEATURE:
<221> NAME/KEY: misc_feature
<222> LOCATION: (5)..(6)
<223> OTHER INFORMATION: Xaa can be any naturally occurring amino acid

<400> SEQUENCE: 229

Xaa Xaa Xaa Ile Xaa Xaa Phe Phe
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 230

Ile Xaa His Phe Phe Xaa Gly
1               5

<210> SEQ ID NO 231
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I, L or M
<220> FEATURE:
<221> NAME/KEY: MISC_FEATURE
<222> LOCATION: (2)..(2)
<223> OTHER INFORMATION: Xaa can be I, L or M
<220> FEATURE:
<221> NAME/KEY: MISC_FEATURE
<222> LOCATION: (3)..(3)
```

```
<223> OTHER INFORMATION: Xaa can be R or K
<220> FEATURE:
<221> NAME/KEY: MISC_FEATURE
<222> LOCATION: (5)..(5)
<223> OTHER INFORMATION: Xaa can be E or D
<220> FEATURE:
<221> NAME/KEY: misc_feature
<222> LOCATION: (6)..(6)
<223> OTHER INFORMATION: Xaa can be any naturally occurring amino acid

<400> SEQUENCE: 231

Xaa Xaa Xaa His Xaa Xaa Gln
1               5

<210> SEQ ID NO 232
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I, L or M
<220> FEATURE:
<221> NAME/KEY: MISC_FEATURE
<222> LOCATION: (2)..(2)
<223> OTHER INFORMATION: Xaa can be R or K
<220> FEATURE:
<221> NAME/KEY: misc_feature
<222> LOCATION: (5)..(5)
<223> OTHER INFORMATION: Xaa can be any naturally occurring amino acid

<400> SEQUENCE: 232

Xaa Xaa His Glu Xaa Gln
1               5

<210> SEQ ID NO 233
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be I or L
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be K or R

<400> SEQUENCE: 233

Lys Pro Xaa Xaa Xaa Xaa Leu Xaa Xaa
1               5

<210> SEQ ID NO 234
<211> LENGTH: 10
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be W or F

<400> SEQUENCE: 234

Asn Xaa Asp Xaa Xaa Tyr Tyr Xaa Xaa Xaa
1               5                   10

<210> SEQ ID NO 235
<211> LENGTH: 5
<212> TYPE: PRT
<213> ORGANISM: Artificial Sequence
<220> FEATURE:
<223> OTHER INFORMATION: Synthetic peptide

<400> SEQUENCE: 235

Gly Leu Asp Gly Pro
1               5

<210> SEQ ID NO 236
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 236

Arg Ser Xaa His Asp Xaa Xaa Asn
1               5

<210> SEQ ID NO 237
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be I or L

<400> SEQUENCE: 237

Phe Asp Xaa Phe Asn Xaa
1               5
```

```
<210> SEQ ID NO 238
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 238

Thr Ile Phe Xaa Gly Lys
1               5

<210> SEQ ID NO 239
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be A or V
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be T or Q

<400> SEQUENCE: 239

Arg Xaa Xaa Ser Xaa His
1               5

<210> SEQ ID NO 240
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 240

Lys Trp His Gly Xaa Tyr
1               5

<210> SEQ ID NO 241
<211> LENGTH: 5
<212> TYPE: PRT
<213> ORGANISM: Artificial Sequence
<220> FEATURE:
<223> OTHER INFORMATION: Synthetic peptide

<400> SEQUENCE: 241

Met Pro Glu Asp Lys
1               5

<210> SEQ ID NO 242
<211> LENGTH: 9
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be F or Y
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be A or S
<220> FEATURE:
<221> NAME/KEY: MISC_FEATURE
<222> LOCATION: (9)..(9)
<223> OTHER INFORMATION: Xaa can be N or T

<400> SEQUENCE: 242

Glu Xaa Xaa Xaa Xaa Xaa Xaa Asp Xaa
1               5

<210> SEQ ID NO 243
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be V or I

<400> SEQUENCE: 243

Asn Gln Ser Xaa Xaa Lys Xaa Xaa
1               5

<210> SEQ ID NO 244
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be N, A or S

<400> SEQUENCE: 244

Lys Xaa Tyr Xaa Pro Tyr
1               5

<210> SEQ ID NO 245
<211> LENGTH: 6
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Xaa can be P or Q
<220> FEATURE:
<221> NAME/KEY: MISC_FEATURE
<222> LOCATION: (2)..(2)
<223> OTHER INFORMATION: Xaa can be V or L

<400> SEQUENCE: 245

Xaa Xaa His Pro Arg Ile
1               5

<210> SEQ ID NO 246
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 246

Glu Asp Gly Met Xaa Xaa Trp
1               5

<210> SEQ ID NO 247
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 247

Tyr Ala Ser Xaa Gln Glu
1               5

<210> SEQ ID NO 248
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Q or K

<400> SEQUENCE: 248

Lys Gln Xaa Gln Xaa Glu
1               5

<210> SEQ ID NO 249
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be A or S
```

```
<220> FEATURE:
<221> NAME/KEY: MISC_FEATURE
<222> LOCATION: (6)..(6)
<223> OTHER INFORMATION: Xaa can be I, V or M

<400> SEQUENCE: 249

Lys Xaa Val Phe Asp Xaa
1               5

<210> SEQ ID NO 250
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be Q or E
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be D or N

<400> SEQUENCE: 250

Pro Asn Xaa Xaa Xaa Pro
1               5

<210> SEQ ID NO 251
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be Q or A
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be D or N

<400> SEQUENCE: 251

Pro Xaa Xaa Met Xaa Ile
1               5

<210> SEQ ID NO 252
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be W or R
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be R, K or H
```

```
<220> FEATURE:
<221> NAME/KEY: MISC_FEATURE
<222> LOCATION: (4)..(4)
<223> OTHER INFORMATION: Xaa can be S or T
<220> FEATURE:
<221> NAME/KEY: misc_feature
<222> LOCATION: (5)..(5)
<223> OTHER INFORMATION: Xaa can be any naturally occurring amino acid

<400> SEQUENCE: 252

Xaa Xaa Xaa Xaa Xaa Phe Asp
1               5

<210> SEQ ID NO 253
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 253

Lys Xaa Glu Pro Gly Xaa Lys
1               5

<210> SEQ ID NO 254
<211> LENGTH: 5
<212> TYPE: PRT
<213> ORGANISM: Artificial Sequence
<220> FEATURE:
<223> OTHER INFORMATION: Synthetic peptide

<400> SEQUENCE: 254

Asp Asp Cys Leu Pro
1               5

<210> SEQ ID NO 255
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 255

Asn Xaa Xaa Xaa Xaa Gly Xaa His Leu Glu
1               5                   10

<210> SEQ ID NO 256
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
```

<223> OTHER INFORMATION: Xaa can be any naturally occurring amino acid

<400> SEQUENCE: 256

Asp Xaa Xaa His Leu Glu Gly
1               5

<210> SEQ ID NO 257
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be T or S

<400> SEQUENCE: 257

Arg Pro Xaa Xaa Xaa His Asn
1               5

<210> SEQ ID NO 258
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be I or V

<400> SEQUENCE: 258

Lys Xaa His Ser Xaa Tyr
1               5

<210> SEQ ID NO 259
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be I or V

<400> SEQUENCE: 259

Lys Xaa His Ser Xaa Xaa Ser
1               5

<210> SEQ ID NO 260
<211> LENGTH: 5
<212> TYPE: PRT
<213> ORGANISM: Artificial Sequence

```
<220> FEATURE:
<223> OTHER INFORMATION: Synthetic peptide

<400> SEQUENCE: 260

Met Ser Gly Tyr Glu
1               5

<210> SEQ ID NO 261
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 261

Tyr Xaa Ile Trp Gly Pro
1               5

<210> SEQ ID NO 262
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be R or K

<400> SEQUENCE: 262

Arg Xaa Xaa Trp Xaa Met Asn Xaa
1               5

<210> SEQ ID NO 263
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be F or Y

<400> SEQUENCE: 263

Gln Pro Xaa Xaa Thr Xaa Glu
1               5

<210> SEQ ID NO 264
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 264

Tyr Gly Tyr Asn Gln
1               5

<210> SEQ ID NO 265
<211> LENGTH: 5
<212> TYPE: PRT
<213> ORGANISM: Artificial Sequence
<220> FEATURE:
<223> OTHER INFORMATION: Synthetic peptide

<400> SEQUENCE: 265

Ala Arg Ser Pro Asn
1               5

<210> SEQ ID NO 266
<211> LENGTH: 7
<212> TYPE: PRT
<213> ORGANISM: Artificial Sequence
<220> FEATURE:
<223> OTHER INFORMATION: Synthetic peptide

<400> SEQUENCE: 266

Ala Gly Ser Pro Asn Arg Ile
1               5

<210> SEQ ID NO 267
<211> LENGTH: 7
<212> TYPE: PRT
<213> ORGANISM: Artificial Sequence
<220> FEATURE:
<223> OTHER INFORMATION: Synthetic peptide

<400> SEQUENCE: 267

Pro Asp Gly Gly Val Met Pro
1               5

<210> SEQ ID NO 268
<211> LENGTH: 7
<212> TYPE: PRT
<213> ORGANISM: Artificial Sequence
<220> FEATURE:
<223> OTHER INFORMATION: Synthetic peptide

<400> SEQUENCE: 268

Asn Pro Lys Leu Gly Leu Thr
1               5

<210> SEQ ID NO 269
<211> LENGTH: 6
<212> TYPE: PRT
<213> ORGANISM: Artificial Sequence
<220> FEATURE:
<223> OTHER INFORMATION: Synthetic peptide

<400> SEQUENCE: 269

Gly Arg Arg Pro Phe Phe
1               5

<210> SEQ ID NO 270
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (4)..(4)
<223> OTHER INFORMATION: Xaa can be any naturally occurring amino acid

<400> SEQUENCE: 270

Gly Gly Gly Xaa Gly Ala Gly Gly Gly
1               5

<210> SEQ ID NO 271
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be P or A
<220> FEATURE:
<221> NAME/KEY: MISC_FEATURE
<222> LOCATION: (6)..(6)
<223> OTHER INFORMATION: Xaa can be G or A

<400> SEQUENCE: 271

Glu Gly Xaa Ser Thr Xaa Arg
1               5

<210> SEQ ID NO 272
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be I, V or L
<220> FEATURE:
<221> NAME/KEY: MISC_FEATURE
<222> LOCATION: (9)..(9)
<223> OTHER INFORMATION: Xaa can be R or K

<400> SEQUENCE: 272

Lys Xaa Xaa Ser Cys Xaa Gly Cys Xaa
1               5

<210> SEQ ID NO 273
<211> LENGTH: 6
<212> TYPE: PRT
<213> ORGANISM: Artificial Sequence
<220> FEATURE:
<223> OTHER INFORMATION: Synthetic peptide

<400> SEQUENCE: 273

Ser Cys Ile Gly Cys Lys
1               5

<210> SEQ ID NO 274
<211> LENGTH: 4
<212> TYPE: PRT
<213> ORGANISM: Artificial Sequence
<220> FEATURE:
<223> OTHER INFORMATION: Synthetic peptide

<400> SEQUENCE: 274

Cys Ile Gly Cys
1
```

```
<210> SEQ ID NO 275
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 275

Val Xaa Leu Pro His Trp
1               5

<210> SEQ ID NO 276
<211> LENGTH: 4
<212> TYPE: PRT
<213> ORGANISM: Artificial Sequence
<220> FEATURE:
<223> OTHER INFORMATION: Synthetic peptide

<400> SEQUENCE: 276

Leu Pro His Trp
1

<210> SEQ ID NO 277
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa can be G or A
<220> FEATURE:
<221> NAME/KEY: MISC_FEATURE
<222> LOCATION: (5)..(5)
<223> OTHER INFORMATION: Xaa can be G or A

<400> SEQUENCE: 277

Pro Gln Asp Thr Xaa Pro Arg
1               5

<210> SEQ ID NO 278
<211> LENGTH: 6
<212> TYPE: PRT
<213> ORGANISM: Artificial Sequence
<220> FEATURE:
<223> OTHER INFORMATION: Synthetic peptide

<400> SEQUENCE: 278

Gly Pro Pro Trp Trp Pro
1               5

<210> SEQ ID NO 279
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 279
```

```
Gln Gln Pro Thr Thr Xaa Gly Trp
1               5
```

<210> SEQ ID NO 280
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L, M, I or V
<220> FEATURE:
<221> NAME/KEY: misc_feature
<222> LOCATION: (4)..(4)
<223> OTHER INFORMATION: Xaa can be any naturally occurring amino acid

<400> SEQUENCE: 280

```
Xaa Phe Asp Xaa Asp Trp Tyr Pro
1               5
```

<210> SEQ ID NO 281
<211> LENGTH: 6
<212> TYPE: PRT
<213> ORGANISM: Artificial Sequence
<220> FEATURE:
<223> OTHER INFORMATION: Synthetic peptide

<400> SEQUENCE: 281

```
Gly Arg Arg Pro Phe Phe
1               5
```

<210> SEQ ID NO 282
<211> LENGTH: 9
<212> TYPE: PRT
<213> ORGANISM: Artificial Sequence
<220> FEATURE:
<223> OTHER INFORMATION: Synthetic peptide

<400> SEQUENCE: 282

```
Gly Gly Gly Ala Gly Ala Gly Gly Gly
1               5
```

<210> SEQ ID NO 283
<211> LENGTH: 8
<212> TYPE: PRT
<213> ORGANISM: Artificial Sequence
<220> FEATURE:
<223> OTHER INFORMATION: Synthetic peptide

<400> SEQUENCE: 283

```
Glu Gly Pro Ser Thr Gly Pro Arg
1               5
```

<210> SEQ ID NO 284
<211> LENGTH: 9
<212> TYPE: PRT
<213> ORGANISM: Artificial Sequence
<220> FEATURE:
<223> OTHER INFORMATION: Synthetic peptide

<400> SEQUENCE: 284

```
Lys Arg Pro Ser Cys Ile Gly Cys Lys
1               5
```

<210> SEQ ID NO 285
<211> LENGTH: 11

```
<212> TYPE: PRT
<213> ORGANISM: Artificial Sequence
<220> FEATURE:
<223> OTHER INFORMATION: Synthetic peptide

<400> SEQUENCE: 285

Lys Glu Val Lys Leu Pro His Trp Thr Pro Thr
1               5                   10

<210> SEQ ID NO 286
<211> LENGTH: 7
<212> TYPE: PRT
<213> ORGANISM: Artificial Sequence
<220> FEATURE:
<223> OTHER INFORMATION: Synthetic peptide

<400> SEQUENCE: 286

Pro Gln Asp Thr Ala Pro Arg
1               5

<210> SEQ ID NO 287
<211> LENGTH: 6
<212> TYPE: PRT
<213> ORGANISM: Artificial Sequence
<220> FEATURE:
<223> OTHER INFORMATION: Synthetic peptide

<400> SEQUENCE: 287

Gly Pro Pro Trp Trp Pro
1               5

<210> SEQ ID NO 288
<211> LENGTH: 8
<212> TYPE: PRT
<213> ORGANISM: Artificial Sequence
<220> FEATURE:
<223> OTHER INFORMATION: Synthetic peptide

<400> SEQUENCE: 288

Gln Gln Pro Thr Thr Glu Gly His
1               5

<210> SEQ ID NO 289
<211> LENGTH: 8
<212> TYPE: PRT
<213> ORGANISM: Artificial Sequence
<220> FEATURE:
<223> OTHER INFORMATION: Synthetic peptide

<400> SEQUENCE: 289

Leu Phe Pro Asp Asp Trp Tyr Pro
1               5

<210> SEQ ID NO 290
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 290
```

```
Cys Xaa Gly Xaa Leu Ile Cys
1               5
```

<210> SEQ ID NO 291
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be I or V
<220> FEATURE:
<221> NAME/KEY: MISC_FEATURE
<222> LOCATION: (8)..(8)
<223> OTHER INFORMATION: Xaa can be I or V

<400> SEQUENCE: 291

```
Cys Xaa Xaa Lys Xaa Xaa Cys Xaa
1               5
```

<210> SEQ ID NO 292
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be G, A or S
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 292

```
Trp Xaa Cys Xaa Gly Xaa Xaa Xaa Cys
1               5
```

<210> SEQ ID NO 293
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or K
<220> FEATURE:
<221> NAME/KEY: MISC_FEATURE
<222> LOCATION: (4)..(4)
<223> OTHER INFORMATION: Xaa can be I or V

<400> SEQUENCE: 293

```
Xaa Lys Leu Xaa Glu
1               5
```

```
<210> SEQ ID NO 294
<211> LENGTH: 5
<212> TYPE: PRT
<213> ORGANISM: Artificial Sequence
<220> FEATURE:
<223> OTHER INFORMATION: Synthetic peptide

<400> SEQUENCE: 294

Lys Leu Ile Met Thr
1               5

<210> SEQ ID NO 295
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be Q or E
<220> FEATURE:
<221> NAME/KEY: misc_feature
<222> LOCATION: (2)..(3)
<223> OTHER INFORMATION: Xaa can be any naturally occurring amino acid

<400> SEQUENCE: 295

Xaa Xaa Xaa Pro Phe Arg Tyr
1               5

<210> SEQ ID NO 296
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be I or V
<220> FEATURE:
<221> NAME/KEY: MISC_FEATURE
<222> LOCATION: (8)..(8)
<223> OTHER INFORMATION: Xaa can be I or V

<400> SEQUENCE: 296

Cys Xaa Xaa Lys Xaa Xaa Cys Xaa
1               5

<210> SEQ ID NO 297
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L or F
<220> FEATURE:
<221> NAME/KEY: misc_feature
<222> LOCATION: (2)..(3)
<223> OTHER INFORMATION: Xaa can be any naturally occurring amino acid
<220> FEATURE:
```

```
<221> NAME/KEY: MISC_FEATURE
<222> LOCATION: (4)..(4)
<223> OTHER INFORMATION: Xaa can be L, I or V
<220> FEATURE:
<221> NAME/KEY: MISC_FEATURE
<222> LOCATION: (5)..(5)
<223> OTHER INFORMATION: Xaa can be N or D

<400> SEQUENCE: 297

Xaa Xaa Xaa Xaa Xaa Lys Trp
1               5

<210> SEQ ID NO 298
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be A or P
<220> FEATURE:
<221> NAME/KEY: MISC_FEATURE
<222> LOCATION: (2)..(2)
<223> OTHER INFORMATION: Xaa can be G or C

<400> SEQUENCE: 298

Xaa Xaa Gly Phe Gly
1               5

<210> SEQ ID NO 299
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be T or S

<400> SEQUENCE: 299

Leu Ile Xaa Xaa Thr Tyr
1               5

<210> SEQ ID NO 300
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or K
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be M or V

<400> SEQUENCE: 300

Xaa Lys Leu Xaa Xaa Xaa Tyr
1               5
```

```
<210> SEQ ID NO 301
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be G or A
<220> FEATURE:
<221> NAME/KEY: MISC_FEATURE
<222> LOCATION: (4)..(4)
<223> OTHER INFORMATION: Xaa can be A or Q
<220> FEATURE:
<221> NAME/KEY: MISC_FEATURE
<222> LOCATION: (5)..(5)
<223> OTHER INFORMATION: Xaa can be A, Y or V

<400> SEQUENCE: 301

Gly Phe Xaa Xaa Xaa
1               5

<210> SEQ ID NO 302
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be R or Q
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be F, N or Y

<400> SEQUENCE: 302

Gly Phe Gly Xaa Xaa Xaa
1               5

<210> SEQ ID NO 303
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be K or R
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be V, I or M

<400> SEQUENCE: 303

Xaa Lys Xaa Ile His Xaa
1               5

<210> SEQ ID NO 304
<211> LENGTH: 5
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I or V

<400> SEQUENCE: 304

Arg Xaa Pro Phe Gly
1               5

<210> SEQ ID NO 305
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be T or Y

<400> SEQUENCE: 305

Lys Leu Ile Xaa Xaa Xaa Thr
1               5

<210> SEQ ID NO 306
<211> LENGTH: 8
<212> TYPE: PRT
<213> ORGANISM: Artificial Sequence
<220> FEATURE:
<223> OTHER INFORMATION: Synthetic peptide

<400> SEQUENCE: 306

Cys Ser Gly Lys Leu Ile Cys Thr
1               5

<210> SEQ ID NO 307
<211> LENGTH: 8
<212> TYPE: PRT
<213> ORGANISM: Artificial Sequence
<220> FEATURE:
<223> OTHER INFORMATION: Synthetic peptide

<400> SEQUENCE: 307

Cys Ser Gly Lys Leu Ile Cys Thr
1               5

<210> SEQ ID NO 308
<211> LENGTH: 9
<212> TYPE: PRT
<213> ORGANISM: Artificial Sequence
<220> FEATURE:
<223> OTHER INFORMATION: Synthetic peptide

<400> SEQUENCE: 308

Trp Gly Cys Ser Gly Lys Leu Ile Cys
1               5

<210> SEQ ID NO 309
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 309

Cys Ser Gly Lys Leu Ile Cys Thr
1               5

<210> SEQ ID NO 310
<211> LENGTH: 7
<212> TYPE: PRT
<213> ORGANISM: Artificial Sequence
<220> FEATURE:
<223> OTHER INFORMATION: Synthetic peptide

<400> SEQUENCE: 310

Leu Leu Ala Leu Asp Lys Trp
1               5

<210> SEQ ID NO 311
<211> LENGTH: 5
<212> TYPE: PRT
<213> ORGANISM: Artificial Sequence
<220> FEATURE:
<223> OTHER INFORMATION: Synthetic peptide

<400> SEQUENCE: 311

Ala Val Gly Met Gly
1               5

<210> SEQ ID NO 312
<211> LENGTH: 5
<212> TYPE: PRT
<213> ORGANISM: Artificial Sequence
<220> FEATURE:
<223> OTHER INFORMATION: Synthetic peptide

<400> SEQUENCE: 312

Leu Ile Cys Thr Thr
1               5

<210> SEQ ID NO 313
<211> LENGTH: 5
<212> TYPE: PRT
<213> ORGANISM: Artificial Sequence
<220> FEATURE:
<223> OTHER INFORMATION: Synthetic peptide

<400> SEQUENCE: 313

Gly Phe Gly Ala Val
1               5

<210> SEQ ID NO 314
<211> LENGTH: 6
<212> TYPE: PRT
<213> ORGANISM: Artificial Sequence
<220> FEATURE:
<223> OTHER INFORMATION: Synthetic peptide

<400> SEQUENCE: 314

Arg Lys Gly Ile Arg Ile
1               5

<210> SEQ ID NO 315
<211> LENGTH: 6
<212> TYPE: PRT
<213> ORGANISM: Artificial Sequence
<220> FEATURE:
```

```
<223> OTHER INFORMATION: Synthetic peptide

<400> SEQUENCE: 315

Lys Lys Gly Ile Ala Ile
1               5

<210> SEQ ID NO 316
<211> LENGTH: 6
<212> TYPE: PRT
<213> ORGANISM: Artificial Sequence
<220> FEATURE:
<223> OTHER INFORMATION: Synthetic peptide

<400> SEQUENCE: 316

Arg Lys Gly Ile His Met
1               5

<210> SEQ ID NO 317
<211> LENGTH: 6
<212> TYPE: PRT
<213> ORGANISM: Artificial Sequence
<220> FEATURE:
<223> OTHER INFORMATION: Synthetic peptide

<400> SEQUENCE: 317

Arg Lys Ser Ile His Met
1               5

<210> SEQ ID NO 318
<211> LENGTH: 6
<212> TYPE: PRT
<213> ORGANISM: Artificial Sequence
<220> FEATURE:
<223> OTHER INFORMATION: Synthetic peptide

<400> SEQUENCE: 318

Lys Leu Ile Cys Thr Thr
1               5

<210> SEQ ID NO 319
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 319

Val Arg Xaa Xaa Tyr Xaa Gln His
1               5

<210> SEQ ID NO 320
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid
<220> FEATURE:
```

```
<221> NAME/KEY: misc_feature
<222> LOCATION: (8)..(8)
<223> OTHER INFORMATION: Xaa can be any naturally occurring amino acid

<400> SEQUENCE: 320

Cys Glu Asp Xaa Xaa Xaa His Xaa Cys
1               5

<210> SEQ ID NO 321
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 321

Asp Ala Glu Gln Xaa Xaa Arg
1               5

<210> SEQ ID NO 322
<211> LENGTH: 5
<212> TYPE: PRT
<213> ORGANISM: Artificial Sequence
<220> FEATURE:
<223> OTHER INFORMATION: Synthetic peptide

<400> SEQUENCE: 322

Trp Pro Gly Ile Phe
1               5

<210> SEQ ID NO 323
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 323

Cys Cys Tyr Asp Xaa Glu
1               5

<210> SEQ ID NO 324
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 324

Leu Xaa Pro Asp Asn Xaa Thr
1               5

<210> SEQ ID NO 325
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 325

Phe Xaa Trp Gly Gln Xaa Tyr
1               5

<210> SEQ ID NO 326
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid

<400> SEQUENCE: 326

Lys Xaa Glu Gly His Xaa Xaa Xaa Xaa Ala
1               5                   10

<210> SEQ ID NO 327
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 327

Cys Xaa Xaa Gly Xaa Cys Gln Xaa Lys
1               5

<210> SEQ ID NO 328
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
```

```
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be D or E
<220> FEATURE:
<221> NAME/KEY: MISC_FEATURE
<222> LOCATION: (8)..(8)
<223> OTHER INFORMATION: Xaa can be E or D

<400> SEQUENCE: 328

Cys Cys Xaa Asp Xaa Xaa Xaa Xaa
1               5

<210> SEQ ID NO 329
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 329

Arg Asn Gly Xaa Glu Asp
1               5

<210> SEQ ID NO 330
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be D or E
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 330

Xaa Xaa Arg Xaa Ile Tyr Xaa Gln
1               5

<210> SEQ ID NO 331
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 331

Trp Xaa Arg Cys Gly Leu
1               5
```

```
<210> SEQ ID NO 332
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be E or D
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 332

Asp Xaa Xaa Arg Xaa Xaa Tyr Xaa Xaa His
1               5                   10

<210> SEQ ID NO 333
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be A or V

<400> SEQUENCE: 333

Trp Cys Xaa Leu Xaa Xaa Asn
1               5

<210> SEQ ID NO 334
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 334

Leu Xaa Thr Pro Trp Ile
1               5

<210> SEQ ID NO 335
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (3)..(5)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be C or A

<400> SEQUENCE: 335

Cys Trp Xaa Xaa Xaa Gly Leu Xaa
1               5

<210> SEQ ID NO 336
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be A or V

<400> SEQUENCE: 336

Ile Asp Xaa Glu Pro
1               5

<210> SEQ ID NO 337
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be N or K
<220> FEATURE:
<221> NAME/KEY: MISC_FEATURE
<222> LOCATION: (4)..(4)
<223> OTHER INFORMATION: Xaa can be V or T
<220> FEATURE:
<221> NAME/KEY: misc_feature
<222> LOCATION: (5)..(5)
<223> OTHER INFORMATION: Xaa can be any naturally occurring amino acid

<400> SEQUENCE: 337

His Phe Xaa Xaa Xaa Lys
1               5

<210> SEQ ID NO 338
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 338

Gln Xaa Asn His Gln Xaa Lys
1               5

<210> SEQ ID NO 339
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 339

Phe Glu Xaa Lys Glu Pro
1               5

<210> SEQ ID NO 340
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be F, Y or W
<220> FEATURE:
<221> NAME/KEY: MISC_FEATURE
<222> LOCATION: (4)..(4)
<223> OTHER INFORMATION: Xaa can be V or I

<400> SEQUENCE: 340

Xaa Asp Ala Xaa
1

<210> SEQ ID NO 341
<211> LENGTH: 5
<212> TYPE: PRT
<213> ORGANISM: Artificial Sequence
<220> FEATURE:
<223> OTHER INFORMATION: Synthetic peptide

<400> SEQUENCE: 341

Asp Phe Asp Lys Arg
1               5

<210> SEQ ID NO 342
<211> LENGTH: 4
<212> TYPE: PRT
<213> ORGANISM: Artificial Sequence
<220> FEATURE:
<223> OTHER INFORMATION: Synthetic peptide

<400> SEQUENCE: 342

Trp Glu Thr Cys
1

<210> SEQ ID NO 343
<211> LENGTH: 5
<212> TYPE: PRT
<213> ORGANISM: Artificial Sequence
<220> FEATURE:
<223> OTHER INFORMATION: Synthetic peptide

<400> SEQUENCE: 343

Lys Leu Asp Gly Pro
1               5

<210> SEQ ID NO 344
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 344

Trp Ile Tyr Pro Xaa Lys
1               5

<210> SEQ ID NO 345
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be H or S

<400> SEQUENCE: 345

Val Xaa Asp Ser Lys
1               5

<210> SEQ ID NO 346
<211> LENGTH: 5
<212> TYPE: PRT
<213> ORGANISM: Artificial Sequence
<220> FEATURE:
<223> OTHER INFORMATION: Synthetic peptide

<400> SEQUENCE: 346

Glu Gln Cys Gly Thr
1               5

<210> SEQ ID NO 347
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be K or E
<220> FEATURE:
<221> NAME/KEY: MISC_FEATURE
<222> LOCATION: (2)..(2)
<223> OTHER INFORMATION: Xaa can be M, V, I or T

<400> SEQUENCE: 347

Xaa Xaa Pro Tyr Ala
1               5

<210> SEQ ID NO 348
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be D or E
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
```

```
<222> LOCATION: (6)..(6)
<223> OTHER INFORMATION: Xaa can be R or P

<400> SEQUENCE: 348

Xaa Xaa Xaa Met Leu Xaa Trp
1               5

<210> SEQ ID NO 349
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be F or Y

<400> SEQUENCE: 349

Tyr Glu Xaa Leu His Xaa Xaa
1               5

<210> SEQ ID NO 350
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be T, S or N
<220> FEATURE:
<221> NAME/KEY: misc_feature
<222> LOCATION: (4)..(4)
<223> OTHER INFORMATION: Xaa can be any naturally occurring amino acid

<400> SEQUENCE: 350

Trp Tyr Xaa Xaa Glu Lys
1               5

<210> SEQ ID NO 351
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Xaa can be Y or F
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be D, N or S

<400> SEQUENCE: 351

Xaa His Xaa Ala Val
1               5
```

```
<210> SEQ ID NO 352
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be V or I

<400> SEQUENCE: 352

Asp Xaa Thr Gly Xaa Pro
1               5

<210> SEQ ID NO 353
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be A or V

<400> SEQUENCE: 353

Phe Asp Xaa Xaa Gly Glu His
1               5

<210> SEQ ID NO 354
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be A or K
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be H or E

<400> SEQUENCE: 354

Gln Cys Xaa Xaa Xaa Xaa Cys
1               5

<210> SEQ ID NO 355
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be F or Y
<220> FEATURE:
<221> NAME/KEY: misc_feature
```

```
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 355

Leu Trp Xaa Xaa Pro Xaa Glu
1               5

<210> SEQ ID NO 356
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be M or I
<220> FEATURE:
<221> NAME/KEY: MISC_FEATURE
<222> LOCATION: (3)..(3)
<223> OTHER INFORMATION: Xaa can be P or A
<220> FEATURE:
<221> NAME/KEY: misc_feature
<222> LOCATION: (5)..(6)
<223> OTHER INFORMATION: Xaa can be any naturally occurring amino acid

<400> SEQUENCE: 356

Cys Xaa Xaa Gly Xaa Xaa Cys
1               5

<210> SEQ ID NO 357
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be A, V or S

<400> SEQUENCE: 357

Cys Xaa Xaa Xaa Xaa Xaa Ala Asp Cys
1               5

<210> SEQ ID NO 358
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(9)
<223> OTHER INFORMATION: Xaa can be any naturally occurring amino acid

<400> SEQUENCE: 358

Val Gln Gln Glu Xaa Xaa Xaa Xaa Xaa Pro
1               5                   10

<210> SEQ ID NO 359
<211> LENGTH: 9
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be Y or C

<400> SEQUENCE: 359

Gln Gln Glu Gly Xaa Xaa Xaa Xaa Xaa
1               5

<210> SEQ ID NO 360
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be I or V

<400> SEQUENCE: 360

Gln Glu Gly Xaa Gln
1               5

<210> SEQ ID NO 361
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I or V
<220> FEATURE:
<221> NAME/KEY: misc_feature
<222> LOCATION: (4)..(4)
<223> OTHER INFORMATION: Xaa can be any naturally occurring amino acid

<400> SEQUENCE: 361

Gly Xaa Gln Xaa Glu Gly
1               5

<210> SEQ ID NO 362
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L or I
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be I, L or V
<220> FEATURE:
<221> NAME/KEY: misc_feature
<222> LOCATION: (6)..(7)
<223> OTHER INFORMATION: Xaa can be any naturally occurring amino acid
```

```
<400> SEQUENCE: 362

Xaa Xaa Xaa Ala Xaa Xaa Xaa Arg Gly
1               5

<210> SEQ ID NO 363
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be A, T, N, S or  D
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be L, A or M
<220> FEATURE:
<221> NAME/KEY: misc_feature
<222> LOCATION: (9)..(9)
<223> OTHER INFORMATION: Xaa can be any naturally occurring amino acid

<400> SEQUENCE: 363

Xaa Xaa Xaa Xaa Xaa Ala Ile Xaa Xaa Arg
1               5                   10

<210> SEQ ID NO 364
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be L or M
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 364

Ile Xaa Xaa Xaa Gly Phe Xaa Lys
1               5

<210> SEQ ID NO 365
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be R or Q
```

```
<400> SEQUENCE: 365

Leu Xaa Gly Met Xaa Lys
1               5

<210> SEQ ID NO 366
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be H or R
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 366

Xaa Xaa Asp Xaa Thr Asn Xaa Phe
1               5

<210> SEQ ID NO 367
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be D or A

<400> SEQUENCE: 367

Xaa Asp Pro Thr Asn
1               5

<210> SEQ ID NO 368
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be K or R
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be D or E
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
```

```
<400> SEQUENCE: 368

Xaa Xaa Xaa Xaa Thr Asn Xaa Phe
1               5

<210> SEQ ID NO 369
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be E or T
<220> FEATURE:
<221> NAME/KEY: MISC_FEATURE
<222> LOCATION: (2)..(2)
<223> OTHER INFORMATION: Xaa can be M or L

<400> SEQUENCE: 369

Xaa Xaa His Lys Phe
1               5

<210> SEQ ID NO 370
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be M or L
<220> FEATURE:
<221> NAME/KEY: misc_feature
<222> LOCATION: (2)..(3)
<223> OTHER INFORMATION: Xaa can be any naturally occurring amino acid

<400> SEQUENCE: 370

Xaa Xaa Xaa Glu Phe His Lys
1               5

<210> SEQ ID NO 371
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be T or I
<220> FEATURE:
<221> NAME/KEY: misc_feature
<222> LOCATION: (5)..(9)
<223> OTHER INFORMATION: Xaa can be any naturally occurring amino acid

<400> SEQUENCE: 371

Gln Xaa Glu Gln Xaa Xaa Xaa Xaa Xaa Lys
1               5                   10

<210> SEQ ID NO 372
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
```

```
<220> FEATURE:
<221> NAME/KEY: MISC_FEATURE
<222> LOCATION: (5)..(5)
<223> OTHER INFORMATION: Xaa can be I or L

<400> SEQUENCE: 372

Asp Xaa Ser Pro Xaa Glu
1               5

<210> SEQ ID NO 373
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be A or P
<220> FEATURE:
<221> NAME/KEY: misc_feature
<222> LOCATION: (6)..(6)
<223> OTHER INFORMATION: Xaa can be any naturally occurring amino acid

<400> SEQUENCE: 373

Pro Phe Xaa Xaa Tyr Xaa Lys
1               5

<210> SEQ ID NO 374
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be L or V
<220> FEATURE:
<221> NAME/KEY: misc_feature
<222> LOCATION: (9)..(9)
<223> OTHER INFORMATION: Xaa can be any naturally occurring amino acid

<400> SEQUENCE: 374

Val Xaa Xaa Tyr Phe Xaa Xaa Xaa Xaa Lys
1               5                   10

<210> SEQ ID NO 375
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
```

<400> SEQUENCE: 375

Lys Xaa Val Asp Xaa Asp Arg
1               5

<210> SEQ ID NO 376
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be D or N
<220> FEATURE:
<221> NAME/KEY: MISC_FEATURE
<222> LOCATION: (2)..(2)
<223> OTHER INFORMATION: Xaa can be A or S
<220> FEATURE:
<221> NAME/KEY: MISC_FEATURE
<222> LOCATION: (4)..(4)
<223> OTHER INFORMATION: Xaa can be A or G

<400> SEQUENCE: 376

Xaa Xaa Ala Xaa Phe
1               5

<210> SEQ ID NO 377
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be N or A
<220> FEATURE:
<221> NAME/KEY: misc_feature
<222> LOCATION: (4)..(4)
<223> OTHER INFORMATION: Xaa can be any naturally occurring amino acid

<400> SEQUENCE: 377

Cys Xaa Xaa Xaa Lys Phe Cys
1               5

<210> SEQ ID NO 378
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be G, R, S or T
<220> FEATURE:
<221> NAME/KEY: MISC_FEATURE
<222> LOCATION: (6)..(6)
<223> OTHER INFORMATION: Xaa can be Y or F

<400> SEQUENCE: 378

Lys Xaa Xaa Ala Glu Xaa
1               5

```
<210> SEQ ID NO 379
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be P or A
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be D, H or E

<400> SEQUENCE: 379

His Gln Val Xaa Xaa Xaa Xaa Xaa
1               5

<210> SEQ ID NO 380
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be I or F
<220> FEATURE:
<221> NAME/KEY: MISC_FEATURE
<222> LOCATION: (6)..(6)
<220> FEATURE:
<221> NAME/KEY: misc_feature
<222> LOCATION: (7)..(8)
<223> OTHER INFORMATION: Xaa can be any naturally occurring amino acid

<400> SEQUENCE: 380

Ile Pro Xaa Xaa Val Xaa Xaa Xaa Arg
1               5

<210> SEQ ID NO 381
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be A, L or T
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
```

```
<221> NAME/KEY: MISC_FEATURE
<222> LOCATION: (8)..(8)
<223> OTHER INFORMATION: Xaa can be C or A

<400> SEQUENCE: 381

Cys Xaa Xaa Xaa Trp Glu Xaa Xaa
1               5

<210> SEQ ID NO 382
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be I or L
<220> FEATURE:
<221> NAME/KEY: misc_feature
<222> LOCATION: (8)..(9)
<223> OTHER INFORMATION: Xaa can be any naturally occurring amino acid

<400> SEQUENCE: 382

Cys Xaa Xaa Xaa Cys Ala Xaa Xaa Xaa Arg
1               5                   10

<210> SEQ ID NO 383
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I or V
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be M or T
<220> FEATURE:
<221> NAME/KEY: misc_feature
<222> LOCATION: (7)..(7)
<223> OTHER INFORMATION: Xaa can be any naturally occurring amino acid

<400> SEQUENCE: 383

Ile Xaa Ile Xaa Xaa Xaa Xaa Lys
1               5

<210> SEQ ID NO 384
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be I, T or L
<220> FEATURE:
<221> NAME/KEY: misc_feature
<222> LOCATION: (4)..(4)
<223> OTHER INFORMATION: Xaa can be any naturally occurring amino acid
<220> FEATURE:
```

```
<221> NAME/KEY: MISC_FEATURE
<222> LOCATION: (5)..(5)
<223> OTHER INFORMATION: Xaa can be K or N
<220> FEATURE:
<221> NAME/KEY: MISC_FEATURE
<222> LOCATION: (6)..(6)
<223> OTHER INFORMATION: Xaa can be F or Y

<400> SEQUENCE: 384

Gln Gly Xaa Xaa Xaa Xaa
1               5

<210> SEQ ID NO 385
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 385

Lys Xaa Xaa Pro Pro Xaa Ile Asn
1               5

<210> SEQ ID NO 386
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be Y or F
<220> FEATURE:
<221> NAME/KEY: MISC_FEATURE
<222> LOCATION: (3)..(3)
<223> OTHER INFORMATION: Xaa can be F or Y
<220> FEATURE:
<221> NAME/KEY: misc_feature
<222> LOCATION: (5)..(6)
<223> OTHER INFORMATION: Xaa can be any naturally occurring amino acid

<400> SEQUENCE: 386

Gly Xaa Xaa Phe Xaa Xaa Lys
1               5

<210> SEQ ID NO 387
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa  can be I or V

<400> SEQUENCE: 387

Asp Lys Asn Val Xaa Xaa
1               5
```

```
<210> SEQ ID NO 388
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be Q or E
<220> FEATURE:
<221> NAME/KEY: MISC_FEATURE
<222> LOCATION: (2)..(2)
<223> OTHER INFORMATION: Xaa can be K or R
<220> FEATURE:
<221> NAME/KEY: MISC_FEATURE
<222> LOCATION: (3)..(3)
<223> OTHER INFORMATION: Xaa can be N or D
<220> FEATURE:
<221> NAME/KEY: misc_feature
<222> LOCATION: (4)..(4)
<223> OTHER INFORMATION: Xaa can be any naturally occurring amino acid

<400> SEQUENCE: 388

Xaa Xaa Xaa Xaa Ser Gly
1               5

<210> SEQ ID NO 389
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be R or K

<400> SEQUENCE: 389

Lys Xaa Pro Gly Asp
1               5

<210> SEQ ID NO 390
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 390

Glu Gly Ala Xaa Gln Pro
1               5

<210> SEQ ID NO 391
<211> LENGTH: 5
<212> TYPE: PRT
<213> ORGANISM: Artificial Sequence
<220> FEATURE:
<223> OTHER INFORMATION: Synthetic peptide

<400> SEQUENCE: 391

Gly Ser Pro Glu Tyr
1               5

<210> SEQ ID NO 392
```

<211> LENGTH: 10
<212> TYPE: PRT
<213> ORGANISM: Artificial Sequence
<220> FEATURE:
<223> OTHER INFORMATION: Synthetic peptide

<400> SEQUENCE: 392

Val Gln Gln Glu Gly Ala Gln Gln Gln Pro
1               5                   10

<210> SEQ ID NO 393
<211> LENGTH: 5
<212> TYPE: PRT
<213> ORGANISM: Artificial Sequence
<220> FEATURE:
<223> OTHER INFORMATION: Synthetic peptide

<400> SEQUENCE: 393

Gln Glu Gly Val Gln
1               5

<210> SEQ ID NO 394
<211> LENGTH: 6
<212> TYPE: PRT
<213> ORGANISM: Artificial Sequence
<220> FEATURE:
<223> OTHER INFORMATION: Synthetic peptide

<400> SEQUENCE: 394

Gly Val Gln Gln Glu Gly
1               5

<210> SEQ ID NO 395
<211> LENGTH: 9
<212> TYPE: PRT
<213> ORGANISM: Artificial Sequence
<220> FEATURE:
<223> OTHER INFORMATION: Synthetic peptide

<400> SEQUENCE: 395

Ile Leu Lys Ala Val Val Glu Arg Gly
1               5

<210> SEQ ID NO 396
<211> LENGTH: 9
<212> TYPE: PRT
<213> ORGANISM: Artificial Sequence
<220> FEATURE:
<223> OTHER INFORMATION: Synthetic peptide

<400> SEQUENCE: 396

Ile Ala Ala Ala Ile Val Leu Arg Gly
1               5

<210> SEQ ID NO 397
<211> LENGTH: 10
<212> TYPE: PRT
<213> ORGANISM: Artificial Sequence
<220> FEATURE:
<223> OTHER INFORMATION: Synthetic peptide

<400> SEQUENCE: 397

Asp Gln Ile Ala Ala Ala Ile Ala Leu Arg
1               5                   10

<210> SEQ ID NO 398
<211> LENGTH: 10

```
<212> TYPE: PRT
<213> ORGANISM: Artificial Sequence
<220> FEATURE:
<223> OTHER INFORMATION: Synthetic peptide

<400> SEQUENCE: 398

Ala Lys Lys Met Arg Ala Ile Leu Val Arg
1               5                   10

<210> SEQ ID NO 399
<211> LENGTH: 10
<212> TYPE: PRT
<213> ORGANISM: Artificial Sequence
<220> FEATURE:
<223> OTHER INFORMATION: Synthetic peptide

<400> SEQUENCE: 399

Ala Glu Asn His Lys Ala Ile Leu Phe Arg
1               5                   10

<210> SEQ ID NO 400
<211> LENGTH: 8
<212> TYPE: PRT
<213> ORGANISM: Artificial Sequence
<220> FEATURE:
<223> OTHER INFORMATION: Synthetic peptide

<400> SEQUENCE: 400

Ile Lys Leu Pro Gly Phe Lys Lys
1               5

<210> SEQ ID NO 401
<211> LENGTH: 8
<212> TYPE: PRT
<213> ORGANISM: Artificial Sequence
<220> FEATURE:
<223> OTHER INFORMATION: Synthetic peptide

<400> SEQUENCE: 401

Ile Phe Leu Glu Gly Phe Leu Lys
1               5

<210> SEQ ID NO 402
<211> LENGTH: 6
<212> TYPE: PRT
<213> ORGANISM: Artificial Sequence
<220> FEATURE:
<223> OTHER INFORMATION: Synthetic peptide

<400> SEQUENCE: 402

Leu Arg Gly Met Arg Lys
1               5

<210> SEQ ID NO 403
<211> LENGTH: 5
<212> TYPE: PRT
<213> ORGANISM: Artificial Sequence
<220> FEATURE:
<223> OTHER INFORMATION: Synthetic peptide

<400> SEQUENCE: 403

Asp Asp Pro Thr Asn
1               5

<210> SEQ ID NO 404
<211> LENGTH: 8
<212> TYPE: PRT
```

```
<213> ORGANISM: Artificial Sequence
<220> FEATURE:
<223> OTHER INFORMATION: Synthetic peptide

<400> SEQUENCE: 404

Lys Thr Asp Arg Thr Asn Asp Phe
1               5

<210> SEQ ID NO 405
<211> LENGTH: 8
<212> TYPE: PRT
<213> ORGANISM: Artificial Sequence
<220> FEATURE:
<223> OTHER INFORMATION: Synthetic peptide

<400> SEQUENCE: 405

Lys Asp Asp Pro Thr Asn Lys Phe
1               5

<210> SEQ ID NO 406
<211> LENGTH: 8
<212> TYPE: PRT
<213> ORGANISM: Artificial Sequence
<220> FEATURE:
<223> OTHER INFORMATION: Synthetic peptide

<400> SEQUENCE: 406

Lys Thr Asp Arg Thr Asn Asp Phe
1               5

<210> SEQ ID NO 407
<211> LENGTH: 5
<212> TYPE: PRT
<213> ORGANISM: Artificial Sequence
<220> FEATURE:
<223> OTHER INFORMATION: Synthetic peptide

<400> SEQUENCE: 407

Thr Leu His Lys Phe
1               5

<210> SEQ ID NO 408
<211> LENGTH: 10
<212> TYPE: PRT
<213> ORGANISM: Artificial Sequence
<220> FEATURE:
<223> OTHER INFORMATION: Synthetic peptide

<400> SEQUENCE: 408

Gln Thr Glu Gln Ser Ser Thr Ser Thr Lys
1               5                   10

<210> SEQ ID NO 409
<211> LENGTH: 6
<212> TYPE: PRT
<213> ORGANISM: Artificial Sequence
<220> FEATURE:
<223> OTHER INFORMATION: Synthetic peptide

<400> SEQUENCE: 409

Asp Leu Ser Pro Ile Glu
1               5

<210> SEQ ID NO 410
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 410

Pro Phe Ser Ala Tyr Ile Lys
1               5

<210> SEQ ID NO 411
<211> LENGTH: 10
<212> TYPE: PRT
<213> ORGANISM: Artificial Sequence
<220> FEATURE:
<223> OTHER INFORMATION: Synthetic peptide

<400> SEQUENCE: 411

Val Lys Asp Tyr Phe Asp Ser Leu Ala Lys
1               5                   10

<210> SEQ ID NO 412
<211> LENGTH: 5
<212> TYPE: PRT
<213> ORGANISM: Artificial Sequence
<220> FEATURE:
<223> OTHER INFORMATION: Synthetic peptide

<400> SEQUENCE: 412

Asp Ala Ala Ala Phe
1               5

<210> SEQ ID NO 413
<211> LENGTH: 6
<212> TYPE: PRT
<213> ORGANISM: Artificial Sequence
<220> FEATURE:
<223> OTHER INFORMATION: Synthetic peptide

<400> SEQUENCE: 413

Lys Phe Arg Ala Glu Phe
1               5

<210> SEQ ID NO 414
<211> LENGTH: 6
<212> TYPE: PRT
<213> ORGANISM: Artificial Sequence
<220> FEATURE:
<223> OTHER INFORMATION: Synthetic peptide

<400> SEQUENCE: 414

Lys Ser Ser Ala Glu Phe
1               5

<210> SEQ ID NO 415
<211> LENGTH: 6
<212> TYPE: PRT
<213> ORGANISM: Artificial Sequence
<220> FEATURE:
<223> OTHER INFORMATION: Synthetic peptide

<400> SEQUENCE: 415

Lys Gly Gly Ala Glu Phe
1               5

<210> SEQ ID NO 416
<211> LENGTH: 8
<212> TYPE: PRT
<213> ORGANISM: Artificial Sequence
<220> FEATURE:
```

```
<223> OTHER INFORMATION: Synthetic peptide

<400> SEQUENCE: 416

Ile Ile Ile Ile Asp Thr Ser Lys
1               5

<210> SEQ ID NO 417
<211> LENGTH: 8
<212> TYPE: PRT
<213> ORGANISM: Artificial Sequence
<220> FEATURE:
<223> OTHER INFORMATION: Synthetic peptide

<400> SEQUENCE: 417

Ile Ile Ile Asn Gly Met Thr Lys
1               5

<210> SEQ ID NO 418
<211> LENGTH: 8
<212> TYPE: PRT
<213> ORGANISM: Artificial Sequence
<220> FEATURE:
<223> OTHER INFORMATION: Synthetic peptide

<400> SEQUENCE: 418

Ile Ile Ile Thr Asn Met Glu Lys
1               5

<210> SEQ ID NO 419
<211> LENGTH: 6
<212> TYPE: PRT
<213> ORGANISM: Artificial Sequence
<220> FEATURE:
<223> OTHER INFORMATION: Synthetic peptide

<400> SEQUENCE: 419

Gln Gly Ile Ile Asn Tyr
1               5

<210> SEQ ID NO 420
<211> LENGTH: 6
<212> TYPE: PRT
<213> ORGANISM: Artificial Sequence
<220> FEATURE:
<223> OTHER INFORMATION: Synthetic peptide

<400> SEQUENCE: 420

Gln Gly Ile Cys Asn Tyr
1               5

<210> SEQ ID NO 421
<211> LENGTH: 8
<212> TYPE: PRT
<213> ORGANISM: Artificial Sequence
<220> FEATURE:
<223> OTHER INFORMATION: Synthetic peptide

<400> SEQUENCE: 421

Lys Glu Thr Pro Pro Ala Leu Asn
1               5

<210> SEQ ID NO 422
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 422

Gly Phe Tyr Phe Ile Phe Lys
1               5

<210> SEQ ID NO 423
<211> LENGTH: 6
<212> TYPE: PRT
<213> ORGANISM: Artificial Sequence
<220> FEATURE:
<223> OTHER INFORMATION: Synthetic peptide

<400> SEQUENCE: 423

Asp Lys Asn Val Lys Ile
1               5

<210> SEQ ID NO 424
<211> LENGTH: 6
<212> TYPE: PRT
<213> ORGANISM: Artificial Sequence
<220> FEATURE:
<223> OTHER INFORMATION: Synthetic peptide

<400> SEQUENCE: 424

Glu Lys Asn Ser Ser Gly
1               5

<210> SEQ ID NO 425
<211> LENGTH: 5
<212> TYPE: PRT
<213> ORGANISM: Artificial Sequence
<220> FEATURE:
<223> OTHER INFORMATION: Synthetic peptide

<400> SEQUENCE: 425

Lys Lys Pro Gly Asp
1               5

<210> SEQ ID NO 426
<211> LENGTH: 6
<212> TYPE: PRT
<213> ORGANISM: Artificial Sequence
<220> FEATURE:
<223> OTHER INFORMATION: Synthetic peptide

<400> SEQUENCE: 426

Glu Gly Ala Gln Gln Pro
1               5

<210> SEQ ID NO 427
<211> LENGTH: 5
<212> TYPE: PRT
<213> ORGANISM: Artificial Sequence
<220> FEATURE:
<223> OTHER INFORMATION: Synthetic peptide

<400> SEQUENCE: 427

Gly Ser Pro Glu Tyr
1               5

<210> SEQ ID NO 428
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 428

His Glu His Glu Phe Gln
1               5

<210> SEQ ID NO 429
<211> LENGTH: 6
<212> TYPE: PRT
<213> ORGANISM: Artificial Sequence
<220> FEATURE:
<223> OTHER INFORMATION: Synthetic peptide

<400> SEQUENCE: 429

Leu Asp Phe Trp Arg Glu
1               5

<210> SEQ ID NO 430
<211> LENGTH: 6
<212> TYPE: PRT
<213> ORGANISM: Artificial Sequence
<220> FEATURE:
<223> OTHER INFORMATION: Synthetic peptide

<400> SEQUENCE: 430

Leu Asp Phe Trp Gln Glu
1               5

<210> SEQ ID NO 431
<211> LENGTH: 6
<212> TYPE: PRT
<213> ORGANISM: Artificial Sequence
<220> FEATURE:
<223> OTHER INFORMATION: Synthetic peptide

<400> SEQUENCE: 431

Leu Asp Met Trp Glu Glu
1               5

<210> SEQ ID NO 432
<211> LENGTH: 5
<212> TYPE: PRT
<213> ORGANISM: Artificial Sequence
<220> FEATURE:
<223> OTHER INFORMATION: Synthetic peptide

<400> SEQUENCE: 432

His Cys Ser Ala Cys
1               5

<210> SEQ ID NO 433
<211> LENGTH: 6
<212> TYPE: PRT
<213> ORGANISM: Artificial Sequence
<220> FEATURE:
<223> OTHER INFORMATION: Synthetic peptide

<400> SEQUENCE: 433

Phe Ser Gly Val Val Asn
1               5

<210> SEQ ID NO 434
<211> LENGTH: 6
<212> TYPE: PRT
<213> ORGANISM: Artificial Sequence
<220> FEATURE:
<223> OTHER INFORMATION: Synthetic peptide

<400> SEQUENCE: 434
```

```
Tyr Pro Gly Val Val Asn
1               5

<210> SEQ ID NO 435
<211> LENGTH: 9
<212> TYPE: PRT
<213> ORGANISM: Artificial Sequence
<220> FEATURE:
<223> OTHER INFORMATION: Synthetic peptide

<400> SEQUENCE: 435

Lys Gly Ser His Gly Arg Gly Phe Ile
1               5

<210> SEQ ID NO 436
<211> LENGTH: 5
<212> TYPE: PRT
<213> ORGANISM: Artificial Sequence
<220> FEATURE:
<223> OTHER INFORMATION: Synthetic peptide

<400> SEQUENCE: 436

Gly Pro His Ala Glu
1               5

<210> SEQ ID NO 437
<211> LENGTH: 5
<212> TYPE: PRT
<213> ORGANISM: Artificial Sequence
<220> FEATURE:
<223> OTHER INFORMATION: Synthetic peptide

<400> SEQUENCE: 437

Pro Arg Arg Glu Pro
1               5

<210> SEQ ID NO 438
<211> LENGTH: 6
<212> TYPE: PRT
<213> ORGANISM: Artificial Sequence
<220> FEATURE:
<223> OTHER INFORMATION: Synthetic peptide

<400> SEQUENCE: 438

Pro Val Pro Asp Phe Ser
1               5

<210> SEQ ID NO 439
<211> LENGTH: 6
<212> TYPE: PRT
<213> ORGANISM: Artificial Sequence
<220> FEATURE:
<223> OTHER INFORMATION: Synthetic peptide

<400> SEQUENCE: 439

Pro Val Pro Asp Phe Thr
1               5

<210> SEQ ID NO 440
<211> LENGTH: 6
<212> TYPE: PRT
<213> ORGANISM: Artificial Sequence
<220> FEATURE:
<223> OTHER INFORMATION: Synthetic peptide

<400> SEQUENCE: 440
```

```
Pro Leu Pro Asp Phe Thr
1               5

<210> SEQ ID NO 441
<211> LENGTH: 6
<212> TYPE: PRT
<213> ORGANISM: Artificial Sequence
<220> FEATURE:
<223> OTHER INFORMATION: Synthetic peptide

<400> SEQUENCE: 441

Pro Leu Pro Asp Phe Ser
1               5

<210> SEQ ID NO 442
<211> LENGTH: 6
<212> TYPE: PRT
<213> ORGANISM: Artificial Sequence
<220> FEATURE:
<223> OTHER INFORMATION: Synthetic peptide

<400> SEQUENCE: 442

Pro Ala Pro Asp Phe Ser
1               5

<210> SEQ ID NO 443
<211> LENGTH: 10
<212> TYPE: PRT
<213> ORGANISM: Artificial Sequence
<220> FEATURE:
<223> OTHER INFORMATION: Synthetic peptide

<400> SEQUENCE: 443

Asn Ala Gly Leu Glu Val Tyr Ala Glu Asp
1               5                   10

<210> SEQ ID NO 444
<211> LENGTH: 10
<212> TYPE: PRT
<213> ORGANISM: Artificial Sequence
<220> FEATURE:
<223> OTHER INFORMATION: Synthetic peptide

<400> SEQUENCE: 444

Asn Arg Arg Arg Glu Arg Tyr Gly Glu Asp
1               5                   10

<210> SEQ ID NO 445
<211> LENGTH: 7
<212> TYPE: PRT
<213> ORGANISM: Artificial Sequence
<220> FEATURE:
<223> OTHER INFORMATION: Synthetic peptide

<400> SEQUENCE: 445

Pro Gly Ala Val Leu Leu Asp
1               5

<210> SEQ ID NO 446
<211> LENGTH: 7
<212> TYPE: PRT
<213> ORGANISM: Artificial Sequence
<220> FEATURE:
<223> OTHER INFORMATION: Synthetic peptide

<400> SEQUENCE: 446

Pro Ala Ala Ser Lys Leu Asp
```

```
<210> SEQ ID NO 447
<211> LENGTH: 7
<212> TYPE: PRT
<213> ORGANISM: Artificial Sequence
<220> FEATURE:
<223> OTHER INFORMATION: Synthetic peptide

<400> SEQUENCE: 447

Pro Ala Ala Glu Ser Leu Asp
1               5

<210> SEQ ID NO 448
<211> LENGTH: 7
<212> TYPE: PRT
<213> ORGANISM: Artificial Sequence
<220> FEATURE:
<223> OTHER INFORMATION: Synthetic peptide

<400> SEQUENCE: 448

Pro Gly Ala Ala Arg Leu Asp
1               5

<210> SEQ ID NO 449
<211> LENGTH: 7
<212> TYPE: PRT
<213> ORGANISM: Artificial Sequence
<220> FEATURE:
<223> OTHER INFORMATION: Synthetic peptide

<400> SEQUENCE: 449

Pro Gly Ala Leu Asp Leu Asp
1               5

<210> SEQ ID NO 450
<211> LENGTH: 7
<212> TYPE: PRT
<213> ORGANISM: Artificial Sequence
<220> FEATURE:
<223> OTHER INFORMATION: Synthetic peptide

<400> SEQUENCE: 450

Met Pro Ser Trp Ser Asn Glu
1               5

<210> SEQ ID NO 451
<211> LENGTH: 7
<212> TYPE: PRT
<213> ORGANISM: Artificial Sequence
<220> FEATURE:
<223> OTHER INFORMATION: Synthetic peptide

<400> SEQUENCE: 451

Met Pro Ser Thr Ser Asp Glu
1               5

<210> SEQ ID NO 452
<211> LENGTH: 7
<212> TYPE: PRT
<213> ORGANISM: Artificial Sequence
<220> FEATURE:
<223> OTHER INFORMATION: Synthetic peptide

<400> SEQUENCE: 452

Met Pro Ser Glu Ser Thr Glu
1               5
```

```
<210> SEQ ID NO 453
<211> LENGTH: 7
<212> TYPE: PRT
<213> ORGANISM: Artificial Sequence
<220> FEATURE:
<223> OTHER INFORMATION: Synthetic peptide

<400> SEQUENCE: 453

Met Pro Ser Ala Ser Pro Glu
1               5

<210> SEQ ID NO 454
<211> LENGTH: 7
<212> TYPE: PRT
<213> ORGANISM: Artificial Sequence
<220> FEATURE:
<223> OTHER INFORMATION: Synthetic peptide

<400> SEQUENCE: 454

Arg Leu Tyr Val His Arg Ser
1               5

<210> SEQ ID NO 455
<211> LENGTH: 7
<212> TYPE: PRT
<213> ORGANISM: Artificial Sequence
<220> FEATURE:
<223> OTHER INFORMATION: Synthetic peptide

<400> SEQUENCE: 455

Arg Leu Tyr Arg His Arg Thr
1               5

<210> SEQ ID NO 456
<211> LENGTH: 7
<212> TYPE: PRT
<213> ORGANISM: Artificial Sequence
<220> FEATURE:
<223> OTHER INFORMATION: Synthetic peptide

<400> SEQUENCE: 456

Lys Gly Tyr Phe His Arg Thr
1               5

<210> SEQ ID NO 457
<211> LENGTH: 8
<212> TYPE: PRT
<213> ORGANISM: Artificial Sequence
<220> FEATURE:
<223> OTHER INFORMATION: Synthetic peptide

<400> SEQUENCE: 457

Lys Pro Pro Phe Glu Phe Gly Lys
1               5

<210> SEQ ID NO 458
<211> LENGTH: 8
<212> TYPE: PRT
<213> ORGANISM: Artificial Sequence
<220> FEATURE:
<223> OTHER INFORMATION: Synthetic peptide

<400> SEQUENCE: 458

Lys Pro Gly Phe Val Phe Leu Lys
1               5
```

```
<210> SEQ ID NO 459
<211> LENGTH: 7
<212> TYPE: PRT
<213> ORGANISM: Artificial Sequence
<220> FEATURE:
<223> OTHER INFORMATION: Synthetic peptide

<400> SEQUENCE: 459

Asp Asp Ser Glu Gly Ala Arg
1               5

<210> SEQ ID NO 460
<211> LENGTH: 7
<212> TYPE: PRT
<213> ORGANISM: Artificial Sequence
<220> FEATURE:
<223> OTHER INFORMATION: Synthetic peptide

<400> SEQUENCE: 460

Asp Asp Ser Cys Gly Arg Arg
1               5

<210> SEQ ID NO 461
<211> LENGTH: 7
<212> TYPE: PRT
<213> ORGANISM: Artificial Sequence
<220> FEATURE:
<223> OTHER INFORMATION: Synthetic peptide

<400> SEQUENCE: 461

Asp Asp Ser Lys Gly Asp Arg
1               5

<210> SEQ ID NO 462
<211> LENGTH: 7
<212> TYPE: PRT
<213> ORGANISM: Artificial Sequence
<220> FEATURE:
<223> OTHER INFORMATION: Synthetic peptide

<400> SEQUENCE: 462

Asp Asp Ser Ser Gly Tyr Arg
1               5

<210> SEQ ID NO 463
<211> LENGTH: 7
<212> TYPE: PRT
<213> ORGANISM: Artificial Sequence
<220> FEATURE:
<223> OTHER INFORMATION: Synthetic peptide

<400> SEQUENCE: 463

Lys Glu Ala Ala Gly Arg Gly
1               5

<210> SEQ ID NO 464
<211> LENGTH: 7
<212> TYPE: PRT
<213> ORGANISM: Artificial Sequence
<220> FEATURE:
<223> OTHER INFORMATION: Synthetic peptide

<400> SEQUENCE: 464

Lys Asp Ala Ser Leu Arg Gly
1               5
```

```
<210> SEQ ID NO 465
<211> LENGTH: 7
<212> TYPE: PRT
<213> ORGANISM: Artificial Sequence
<220> FEATURE:
<223> OTHER INFORMATION: Synthetic peptide

<400> SEQUENCE: 465

Lys Gly Ser Ser Gly Arg Gly
1               5

<210> SEQ ID NO 466
<211> LENGTH: 7
<212> TYPE: PRT
<213> ORGANISM: Artificial Sequence
<220> FEATURE:
<223> OTHER INFORMATION: Synthetic peptide

<400> SEQUENCE: 466

Lys Thr Ser Ser Arg Arg Gly
1               5

<210> SEQ ID NO 467
<211> LENGTH: 7
<212> TYPE: PRT
<213> ORGANISM: Artificial Sequence
<220> FEATURE:
<223> OTHER INFORMATION: Synthetic peptide

<400> SEQUENCE: 467

Lys Thr Gln Thr Val Arg Gly
1               5

<210> SEQ ID NO 468
<211> LENGTH: 7
<212> TYPE: PRT
<213> ORGANISM: Artificial Sequence
<220> FEATURE:
<223> OTHER INFORMATION: Synthetic peptide

<400> SEQUENCE: 468

Lys Arg Ser Thr Leu Arg Gly
1               5

<210> SEQ ID NO 469
<211> LENGTH: 5
<212> TYPE: PRT
<213> ORGANISM: Artificial Sequence
<220> FEATURE:
<223> OTHER INFORMATION: Synthetic peptide

<400> SEQUENCE: 469

Asp Gln Pro Glu Asn
1               5

<210> SEQ ID NO 470
<211> LENGTH: 5
<212> TYPE: PRT
<213> ORGANISM: Artificial Sequence
<220> FEATURE:
<223> OTHER INFORMATION: Synthetic peptide

<400> SEQUENCE: 470

Gly Gln Pro Glu Asn
1               5

<210> SEQ ID NO 471
```

<211> LENGTH: 5
<212> TYPE: PRT
<213> ORGANISM: Artificial Sequence
<220> FEATURE:
<223> OTHER INFORMATION: Synthetic peptide

<400> SEQUENCE: 471

Lys Asn Asn Asp Gly
1               5

<210> SEQ ID NO 472
<211> LENGTH: 5
<212> TYPE: PRT
<213> ORGANISM: Artificial Sequence
<220> FEATURE:
<223> OTHER INFORMATION: Synthetic peptide

<400> SEQUENCE: 472

Arg Asn Asn Asp Gly
1               5

<210> SEQ ID NO 473
<211> LENGTH: 7
<212> TYPE: PRT
<213> ORGANISM: Artificial Sequence
<220> FEATURE:
<223> OTHER INFORMATION: Synthetic peptide

<400> SEQUENCE: 473

Asn Leu Val Gly Glu Glu Tyr
1               5

<210> SEQ ID NO 474
<211> LENGTH: 7
<212> TYPE: PRT
<213> ORGANISM: Artificial Sequence
<220> FEATURE:
<223> OTHER INFORMATION: Synthetic peptide

<400> SEQUENCE: 474

Asn Asp Ser Gly Glu Ile Tyr
1               5

<210> SEQ ID NO 475
<211> LENGTH: 5
<212> TYPE: PRT
<213> ORGANISM: Artificial Sequence
<220> FEATURE:
<223> OTHER INFORMATION: Synthetic peptide

<400> SEQUENCE: 475

Glu Pro Val Thr Gly
1               5

<210> SEQ ID NO 476
<211> LENGTH: 5
<212> TYPE: PRT
<213> ORGANISM: Artificial Sequence
<220> FEATURE:
<223> OTHER INFORMATION: Synthetic peptide

<400> SEQUENCE: 476

His Gly Met Pro Lys
1               5

<210> SEQ ID NO 477
<211> LENGTH: 5

```
<212> TYPE: PRT
<213> ORGANISM: Artificial Sequence
<220> FEATURE:
<223> OTHER INFORMATION: Synthetic peptide

<400> SEQUENCE: 477

His Gly Met Ala Lys
1               5

<210> SEQ ID NO 478
<211> LENGTH: 5
<212> TYPE: PRT
<213> ORGANISM: Artificial Sequence
<220> FEATURE:
<223> OTHER INFORMATION: Synthetic peptide

<400> SEQUENCE: 478

Val Pro Trp Ile Phe
1               5

<210> SEQ ID NO 479
<211> LENGTH: 7
<212> TYPE: PRT
<213> ORGANISM: Artificial Sequence
<220> FEATURE:
<223> OTHER INFORMATION: Synthetic peptide

<400> SEQUENCE: 479

Lys Ser Ser Val Pro Phe Gln
1               5

<210> SEQ ID NO 480
<211> LENGTH: 7
<212> TYPE: PRT
<213> ORGANISM: Artificial Sequence
<220> FEATURE:
<223> OTHER INFORMATION: Synthetic peptide

<400> SEQUENCE: 480

Lys Glu Thr Val Asn Phe Gln
1               5

<210> SEQ ID NO 481
<211> LENGTH: 5
<212> TYPE: PRT
<213> ORGANISM: Artificial Sequence
<220> FEATURE:
<223> OTHER INFORMATION: Synthetic peptide

<400> SEQUENCE: 481

Val Trp Ser Gly Ser
1               5

<210> SEQ ID NO 482
<211> LENGTH: 5
<212> TYPE: PRT
<213> ORGANISM: Artificial Sequence
<220> FEATURE:
<223> OTHER INFORMATION: Synthetic peptide

<400> SEQUENCE: 482

Ile Trp Ser Gly Ser
1               5

<210> SEQ ID NO 483
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 483

Phe Ser Leu Glu Asn Trp Gly
1               5

<210> SEQ ID NO 484
<211> LENGTH: 7
<212> TYPE: PRT
<213> ORGANISM: Artificial Sequence
<220> FEATURE:
<223> OTHER INFORMATION: Synthetic peptide

<400> SEQUENCE: 484

Phe Ser Met Gly Arg Trp Gly
1               5

<210> SEQ ID NO 485
<211> LENGTH: 7
<212> TYPE: PRT
<213> ORGANISM: Artificial Sequence
<220> FEATURE:
<223> OTHER INFORMATION: Synthetic peptide

<400> SEQUENCE: 485

Phe Ser Leu Val Leu Trp Gly
1               5

<210> SEQ ID NO 486
<211> LENGTH: 7
<212> TYPE: PRT
<213> ORGANISM: Artificial Sequence
<220> FEATURE:
<223> OTHER INFORMATION: Synthetic peptide

<400> SEQUENCE: 486

Phe Ser Leu Val Leu Trp Gly
1               5

<210> SEQ ID NO 487
<211> LENGTH: 7
<212> TYPE: PRT
<213> ORGANISM: Artificial Sequence
<220> FEATURE:
<223> OTHER INFORMATION: Synthetic peptide

<400> SEQUENCE: 487

Phe Ser Leu Thr Asn Trp Gly
1               5

<210> SEQ ID NO 488
<211> LENGTH: 5
<212> TYPE: PRT
<213> ORGANISM: Artificial Sequence
<220> FEATURE:
<223> OTHER INFORMATION: Synthetic peptide

<400> SEQUENCE: 488

Pro Thr Asn Gln Gly
1               5

<210> SEQ ID NO 489
<211> LENGTH: 5
<212> TYPE: PRT
<213> ORGANISM: Artificial Sequence
```

<220> FEATURE:
<223> OTHER INFORMATION: Synthetic peptide

<400> SEQUENCE: 489

Pro Thr Asn Pro Gly
1               5

<210> SEQ ID NO 490
<211> LENGTH: 9
<212> TYPE: PRT
<213> ORGANISM: Artificial Sequence
<220> FEATURE:
<223> OTHER INFORMATION: Synthetic peptide

<400> SEQUENCE: 490

Arg Lys Leu His Trp Asn His Arg Thr
1               5

<210> SEQ ID NO 491
<211> LENGTH: 9
<212> TYPE: PRT
<213> ORGANISM: Artificial Sequence
<220> FEATURE:
<223> OTHER INFORMATION: Synthetic peptide

<400> SEQUENCE: 491

Lys Lys Tyr Arg Tyr Arg His Pro Thr
1               5

<210> SEQ ID NO 492
<211> LENGTH: 9
<212> TYPE: PRT
<213> ORGANISM: Artificial Sequence
<220> FEATURE:
<223> OTHER INFORMATION: Synthetic peptide

<400> SEQUENCE: 492

Arg Lys Ala Val Tyr Gln His Asn Thr
1               5

<210> SEQ ID NO 493
<211> LENGTH: 7
<212> TYPE: PRT
<213> ORGANISM: Artificial Sequence
<220> FEATURE:
<223> OTHER INFORMATION: Synthetic peptide

<400> SEQUENCE: 493

Arg Thr Leu His Pro Arg Phe
1               5

<210> SEQ ID NO 494
<211> LENGTH: 7
<212> TYPE: PRT
<213> ORGANISM: Artificial Sequence
<220> FEATURE:
<223> OTHER INFORMATION: Synthetic peptide

<400> SEQUENCE: 494

His Phe Arg His Pro Arg Phe
1               5

<210> SEQ ID NO 495
<211> LENGTH: 7
<212> TYPE: PRT
<213> ORGANISM: Artificial Sequence
<220> FEATURE:

```
<223> OTHER INFORMATION: Synthetic peptide

<400> SEQUENCE: 495

Arg Val Ala His Pro Arg Phe
1               5

<210> SEQ ID NO 496
<211> LENGTH: 7
<212> TYPE: PRT
<213> ORGANISM: Artificial Sequence
<220> FEATURE:
<223> OTHER INFORMATION: Synthetic peptide

<400> SEQUENCE: 496

Trp Gln Ala His Pro Arg Phe
1               5

<210> SEQ ID NO 497
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be S or A

<400> SEQUENCE: 497

Met Lys Glu Ala Xaa Xaa Glu Lys
1               5

<210> SEQ ID NO 498
<211> LENGTH: 8
<212> TYPE: PRT
<213> ORGANISM: Artificial Sequence
<220> FEATURE:
<223> OTHER INFORMATION: Synthetic peptide

<400> SEQUENCE: 498

Met Lys Glu Ala Ala Ser Glu Lys
1               5

<210> SEQ ID NO 499
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I or V

<400> SEQUENCE: 499

Arg Xaa Pro Phe Gly
1               5

<210> SEQ ID NO 500
<211> LENGTH: 6
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (3)..(3)
<223> OTHER INFORMATION: Xaa can be any naturally occurring amino acid

<400> SEQUENCE: 500

Lys Gly Xaa Ala Thr Pro
1               5

<210> SEQ ID NO 501
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be M or L
<220> FEATURE:
<221> NAME/KEY: misc_feature
<222> LOCATION: (3)..(3)
<223> OTHER INFORMATION: Xaa can be any naturally occurring amino acid

<400> SEQUENCE: 501

Pro Xaa Xaa Val Gly Pro
1               5

<210> SEQ ID NO 502
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be R or Y

<400> SEQUENCE: 502

Pro Lys Xaa Asp Gly Xaa
1               5

<210> SEQ ID NO 503
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be E or S

<400> SEQUENCE: 503

Lys Xaa Asp Gly His Xaa
1               5

<210> SEQ ID NO 504
<211> LENGTH: 7
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be F or Y
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be R or K

<400> SEQUENCE: 504

Val Gln Xaa Xaa Met Xaa Xaa
1               5

<210> SEQ ID NO 505
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be G or A
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be V or A

<400> SEQUENCE: 505

Asp Arg Xaa Pro Xaa Xaa Xaa Xaa
1               5

<210> SEQ ID NO 506
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be V or L

<400> SEQUENCE: 506

Asp Xaa Ile Asp Xaa Xaa Trp
1               5
```

```
<210> SEQ ID NO 507
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be R or Q

<400> SEQUENCE: 507

Arg Gln Pro Xaa Gly Xaa
1               5

<210> SEQ ID NO 508
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 508

Pro Xaa His Gly Ile His
1               5

<210> SEQ ID NO 509
<211> LENGTH: 5
<212> TYPE: PRT
<213> ORGANISM: Artificial Sequence
<220> FEATURE:
<223> OTHER INFORMATION: Synthetic peptide

<400> SEQUENCE: 509

Asp Gly Asp Gly Pro
1               5

<210> SEQ ID NO 510
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be N or Q
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be K or R

<400> SEQUENCE: 510

His Xaa Xaa Xaa Thr Pro Xaa Xaa
```

```
<210> SEQ ID NO 511
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be S or A
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be H or E

<400> SEQUENCE: 511

Lys Xaa Xaa Asn Pro Xaa
1               5

<210> SEQ ID NO 512
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be E, Q, D or N
<220> FEATURE:
<221> NAME/KEY: misc_feature
<222> LOCATION: (2)..(2)
<223> OTHER INFORMATION: Xaa can be any naturally occurring amino acid

<400> SEQUENCE: 512

Xaa Xaa Leu Pro His Glu
1               5

<210> SEQ ID NO 513
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be V, I or M

<400> SEQUENCE: 513

Gly Gln Tyr Gly Xaa
1               5

<210> SEQ ID NO 514
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be M or L
<220> FEATURE:
<221> NAME/KEY: misc_feature
<222> LOCATION: (4)..(4)
```

```
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be D or N

<400> SEQUENCE: 514

Pro Arg Xaa Xaa Xaa Lys
1               5

<210> SEQ ID NO 515
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be G or Q
<220> FEATURE:
<221> NAME/KEY: misc_feature
<222> LOCATION: (5)..(7)
<223> OTHER INFORMATION: Xaa can be any naturally occurring amino acid

<400> SEQUENCE: 515

Phe Gly Gln Xaa Xaa Xaa Xaa Asp
1               5

<210> SEQ ID NO 516
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be G, R or S
<220> FEATURE:
<221> NAME/KEY: MISC_FEATURE
<222> LOCATION: (3)..(3)
<223> OTHER INFORMATION: Xaa can be G, R or S
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 516

Asp Asp Xaa Xaa Thr Xaa Lys
1               5

<210> SEQ ID NO 517
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be F or P

<400> SEQUENCE: 517
```

```
Ile Xaa Thr Xaa Asp Arg
1               5

<210> SEQ ID NO 518
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be F or Y

<400> SEQUENCE: 518

Lys Xaa Xaa Asn Ile Gly Xaa Xaa Xaa
1               5

<210> SEQ ID NO 519
<211> LENGTH: 5
<212> TYPE: PRT
<213> ORGANISM: Artificial Sequence
<220> FEATURE:
<223> OTHER INFORMATION: Synthetic peptide

<400> SEQUENCE: 519

Arg Val Pro Phe Gly
1               5

<210> SEQ ID NO 520
<211> LENGTH: 5
<212> TYPE: PRT
<213> ORGANISM: Artificial Sequence
<220> FEATURE:
<223> OTHER INFORMATION: Synthetic peptide

<400> SEQUENCE: 520

Arg Ile Pro Phe Gly
1               5

<210> SEQ ID NO 521
<211> LENGTH: 5
<212> TYPE: PRT
<213> ORGANISM: Artificial Sequence
<220> FEATURE:
<223> OTHER INFORMATION: Synthetic peptide

<400> SEQUENCE: 521

Arg Ile Pro Phe Gly
1               5

<210> SEQ ID NO 522
<211> LENGTH: 9
<212> TYPE: PRT
<213> ORGANISM: Artificial Sequence
<220> FEATURE:
<223> OTHER INFORMATION: Synthetic peptide

<400> SEQUENCE: 522

Gly Gly Leu Phe Arg Val Pro Phe Gly
1               5
```

<210> SEQ ID NO 523
<211> LENGTH: 7
<212> TYPE: PRT
<213> ORGANISM: Artificial Sequence
<220> FEATURE:
<223> OTHER INFORMATION: Synthetic peptide

<400> SEQUENCE: 523

Lys Gly Lys Ala Thr Pro Ser
1               5

<210> SEQ ID NO 524
<211> LENGTH: 7
<212> TYPE: PRT
<213> ORGANISM: Artificial Sequence
<220> FEATURE:
<223> OTHER INFORMATION: Synthetic peptide

<400> SEQUENCE: 524

Lys Gly Lys Ala Thr Pro Ser
1               5

<210> SEQ ID NO 525
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be V, S, P, L or R

<400> SEQUENCE: 525

Pro Leu Xaa Val Gly Pro
1               5

<210> SEQ ID NO 526
<211> LENGTH: 6
<212> TYPE: PRT
<213> ORGANISM: Artificial Sequence
<220> FEATURE:
<223> OTHER INFORMATION: Synthetic peptide

<400> SEQUENCE: 526

Pro Lys Val Asp Gly Arg
1               5

<210> SEQ ID NO 527
<211> LENGTH: 6
<212> TYPE: PRT
<213> ORGANISM: Artificial Sequence
<220> FEATURE:
<223> OTHER INFORMATION: Synthetic peptide

<400> SEQUENCE: 527

Pro Lys Ala Asp Gly Arg
1               5

<210> SEQ ID NO 528
<211> LENGTH: 6
<212> TYPE: PRT
<213> ORGANISM: Artificial Sequence
<220> FEATURE:
<223> OTHER INFORMATION: Synthetic peptide

<400> SEQUENCE: 528

```
Pro Lys Ala Asp Gly Tyr
1               5

<210> SEQ ID NO 529
<211> LENGTH: 6
<212> TYPE: PRT
<213> ORGANISM: Artificial Sequence
<220> FEATURE:
<223> OTHER INFORMATION: Synthetic peptide

<400> SEQUENCE: 529

Pro Lys Glu Asp Gly Arg
1               5

<210> SEQ ID NO 530
<211> LENGTH: 6
<212> TYPE: PRT
<213> ORGANISM: Artificial Sequence
<220> FEATURE:
<223> OTHER INFORMATION: Synthetic peptide

<400> SEQUENCE: 530

Pro Lys Glu Asp Gly Arg
1               5

<210> SEQ ID NO 531
<211> LENGTH: 6
<212> TYPE: PRT
<213> ORGANISM: Artificial Sequence
<220> FEATURE:
<223> OTHER INFORMATION: Synthetic peptide

<400> SEQUENCE: 531

Lys Tyr Asp Gly His Ser
1               5

<210> SEQ ID NO 532
<211> LENGTH: 6
<212> TYPE: PRT
<213> ORGANISM: Artificial Sequence
<220> FEATURE:
<223> OTHER INFORMATION: Synthetic peptide

<400> SEQUENCE: 532

Lys Cys Asp Gly His Glu
1               5

<210> SEQ ID NO 533
<211> LENGTH: 7
<212> TYPE: PRT
<213> ORGANISM: Artificial Sequence
<220> FEATURE:
<223> OTHER INFORMATION: Synthetic peptide

<400> SEQUENCE: 533

Val Gln Thr Phe Met Leu Arg
1               5

<210> SEQ ID NO 534
<211> LENGTH: 7
<212> TYPE: PRT
<213> ORGANISM: Artificial Sequence
<220> FEATURE:
<223> OTHER INFORMATION: Synthetic peptide

<400> SEQUENCE: 534
```

```
Val Gln Ile Tyr Met Ala Lys
1               5

<210> SEQ ID NO 535
<211> LENGTH: 7
<212> TYPE: PRT
<213> ORGANISM: Artificial Sequence
<220> FEATURE:
<223> OTHER INFORMATION: Synthetic peptide

<400> SEQUENCE: 535

Val Gln Leu Phe Met Arg Arg
1               5

<210> SEQ ID NO 536
<211> LENGTH: 7
<212> TYPE: PRT
<213> ORGANISM: Artificial Sequence
<220> FEATURE:
<223> OTHER INFORMATION: Synthetic peptide

<400> SEQUENCE: 536

Val Gln Ser Tyr Met Leu Arg
1               5

<210> SEQ ID NO 537
<211> LENGTH: 7
<212> TYPE: PRT
<213> ORGANISM: Artificial Sequence
<220> FEATURE:
<223> OTHER INFORMATION: Synthetic peptide

<400> SEQUENCE: 537

Val Gln Leu Tyr Met Asp Lys
1               5

<210> SEQ ID NO 538
<211> LENGTH: 7
<212> TYPE: PRT
<213> ORGANISM: Artificial Sequence
<220> FEATURE:
<223> OTHER INFORMATION: Synthetic peptide

<400> SEQUENCE: 538

Val Gln Leu Tyr Met Asp Lys
1               5

<210> SEQ ID NO 539
<211> LENGTH: 7
<212> TYPE: PRT
<213> ORGANISM: Artificial Sequence
<220> FEATURE:
<223> OTHER INFORMATION: Synthetic peptide

<400> SEQUENCE: 539

Asp Asp Ile Asp Leu Leu Trp
1               5

<210> SEQ ID NO 540
<211> LENGTH: 6
<212> TYPE: PRT
<213> ORGANISM: Artificial Sequence
<220> FEATURE:
<223> OTHER INFORMATION: Synthetic peptide

<400> SEQUENCE: 540

Arg Gln Pro Cys Gly Gln
```

```
1               5

<210> SEQ ID NO 541
<211> LENGTH: 6
<212> TYPE: PRT
<213> ORGANISM: Artificial Sequence
<220> FEATURE:
<223> OTHER INFORMATION: Synthetic peptide

<400> SEQUENCE: 541

Arg Gln Pro Ile Gly Arg
1               5

<210> SEQ ID NO 542
<211> LENGTH: 8
<212> TYPE: PRT
<213> ORGANISM: Artificial Sequence
<220> FEATURE:
<223> OTHER INFORMATION: Synthetic peptide

<400> SEQUENCE: 542

His Pro Thr Asn Thr Pro Glu Lys
1               5

<210> SEQ ID NO 543
<211> LENGTH: 8
<212> TYPE: PRT
<213> ORGANISM: Artificial Sequence
<220> FEATURE:
<223> OTHER INFORMATION: Synthetic peptide

<400> SEQUENCE: 543

His Pro Val Asn Thr Pro Asp Lys
1               5

<210> SEQ ID NO 544
<211> LENGTH: 8
<212> TYPE: PRT
<213> ORGANISM: Artificial Sequence
<220> FEATURE:
<223> OTHER INFORMATION: Synthetic peptide

<400> SEQUENCE: 544

His Ala Val Gln Thr Pro Ser Lys
1               5

<210> SEQ ID NO 545
<211> LENGTH: 8
<212> TYPE: PRT
<213> ORGANISM: Artificial Sequence
<220> FEATURE:
<223> OTHER INFORMATION: Synthetic peptide

<400> SEQUENCE: 545

His Thr Phe Gln Thr Pro Gln Arg
1               5

<210> SEQ ID NO 546
<211> LENGTH: 8
<212> TYPE: PRT
<213> ORGANISM: Artificial Sequence
<220> FEATURE:
<223> OTHER INFORMATION: Synthetic peptide

<400> SEQUENCE: 546

His Val Asn Gln Thr Pro Tyr Arg
1               5
```

```
<210> SEQ ID NO 547
<211> LENGTH: 8
<212> TYPE: PRT
<213> ORGANISM: Artificial Sequence
<220> FEATURE:
<223> OTHER INFORMATION: Synthetic peptide

<400> SEQUENCE: 547

His Asp Gly Asn Thr Pro Ala Lys
1               5

<210> SEQ ID NO 548
<211> LENGTH: 6
<212> TYPE: PRT
<213> ORGANISM: Artificial Sequence
<220> FEATURE:
<223> OTHER INFORMATION: Synthetic peptide

<400> SEQUENCE: 548

Lys Ser Ala Asn Pro Glu
1               5

<210> SEQ ID NO 549
<211> LENGTH: 6
<212> TYPE: PRT
<213> ORGANISM: Artificial Sequence
<220> FEATURE:
<223> OTHER INFORMATION: Synthetic peptide

<400> SEQUENCE: 549

Lys Ser Ile Asn Pro Glu
1               5

<210> SEQ ID NO 550
<211> LENGTH: 6
<212> TYPE: PRT
<213> ORGANISM: Artificial Sequence
<220> FEATURE:
<223> OTHER INFORMATION: Synthetic peptide

<400> SEQUENCE: 550

Lys Ala Ser Asn Pro His
1               5

<210> SEQ ID NO 551
<211> LENGTH: 6
<212> TYPE: PRT
<213> ORGANISM: Artificial Sequence
<220> FEATURE:
<223> OTHER INFORMATION: Synthetic peptide

<400> SEQUENCE: 551

Asn Ala Leu Pro His Glu
1               5

<210> SEQ ID NO 552
<211> LENGTH: 6
<212> TYPE: PRT
<213> ORGANISM: Artificial Sequence
<220> FEATURE:
<223> OTHER INFORMATION: Synthetic peptide

<400> SEQUENCE: 552

Asp Ala Leu Pro His Glu
1               5
```

```
<210> SEQ ID NO 553
<211> LENGTH: 6
<212> TYPE: PRT
<213> ORGANISM: Artificial Sequence
<220> FEATURE:
<223> OTHER INFORMATION: Synthetic peptide

<400> SEQUENCE: 553

Glu Pro Leu Pro His Glu
1               5

<210> SEQ ID NO 554
<211> LENGTH: 6
<212> TYPE: PRT
<213> ORGANISM: Artificial Sequence
<220> FEATURE:
<223> OTHER INFORMATION: Synthetic peptide

<400> SEQUENCE: 554

Glu Met Leu Pro His Glu
1               5

<210> SEQ ID NO 555
<211> LENGTH: 6
<212> TYPE: PRT
<213> ORGANISM: Artificial Sequence
<220> FEATURE:
<223> OTHER INFORMATION: Synthetic peptide

<400> SEQUENCE: 555

Gln Pro Leu Pro His Glu
1               5

<210> SEQ ID NO 556
<211> LENGTH: 5
<212> TYPE: PRT
<213> ORGANISM: Artificial Sequence
<220> FEATURE:
<223> OTHER INFORMATION: Synthetic peptide

<400> SEQUENCE: 556

Gly Gln Tyr Gly Val
1               5

<210> SEQ ID NO 557
<211> LENGTH: 9
<212> TYPE: PRT
<213> ORGANISM: Artificial Sequence
<220> FEATURE:
<223> OTHER INFORMATION: Synthetic peptide

<400> SEQUENCE: 557

Lys Ile Pro Asn Ile Gly Asp Lys Phe
1               5

<210> SEQ ID NO 558
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be M or L
<220> FEATURE:
<221> NAME/KEY: MISC_FEATURE
<222> LOCATION: (3)..(3)
```

```
<223> OTHER INFORMATION: Xaa can be A or S
<220> FEATURE:
<221> NAME/KEY: MISC_FEATURE
<222> LOCATION: (4)..(4)
<223> OTHER INFORMATION: Xaa can be T or A
<220> FEATURE:
<221> NAME/KEY: misc_feature
<222> LOCATION: (5)..(5)
<223> OTHER INFORMATION: Xaa can be any naturally occurring amino acid

<400> SEQUENCE: 558

Xaa Leu Xaa Xaa Xaa Lys
1               5

<210> SEQ ID NO 559
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or L
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be A or S
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 559

Xaa Xaa Xaa Xaa Asp Pro Xaa Xaa Pro
1               5

<210> SEQ ID NO 560
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be K or R
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be I or L
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be S or T
<220> FEATURE:
<221> NAME/KEY: MISC_FEATURE
<222> LOCATION: (6)..(6)
<223> OTHER INFORMATION: Xaa can be M, L or F
```

<400> SEQUENCE: 560

Xaa Xaa Xaa Xaa Xaa Xaa Asn
1               5

<210> SEQ ID NO 561
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be K or R
<220> FEATURE:
<221> NAME/KEY: misc_feature
<222> LOCATION: (5)..(8)
<223> OTHER INFORMATION: Xaa can be any naturally occurring amino acid

<400> SEQUENCE: 561

Thr Gly Xaa Met Xaa Xaa Xaa Xaa Gln
1               5

<210> SEQ ID NO 562
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be S, T or A
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be M or L

<400> SEQUENCE: 562

Gly Xaa Pro Tyr Xaa Xaa Xaa Xaa Xaa Xaa
1               5                   10

<210> SEQ ID NO 563
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be E, D or A
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be P or A

<400> SEQUENCE: 563

Trp Glu Xaa Xaa Xaa Ile

```
<210> SEQ ID NO 564
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I or V
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 564

Glu Xaa Xaa His Xaa Xaa Phe Xaa Arg
 1               5

<210> SEQ ID NO 565
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be T or S
<220> FEATURE:
<221> NAME/KEY: misc_feature
<222> LOCATION: (7)..(7)
<223> OTHER INFORMATION: Xaa can be any naturally occurring amino acid

<400> SEQUENCE: 565

Lys Xaa Xaa Xaa His Arg Xaa Lys
 1               5

<210> SEQ ID NO 566
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 566

Thr Phe Glu Xaa Gly Xaa Lys
 1               5

<210> SEQ ID NO 567
```

```
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be R or A
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be F or I

<400> SEQUENCE: 567

Trp Glu Asn Xaa Xaa Xaa Xaa Xaa Xaa
1               5

<210> SEQ ID NO 568
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be N or T
<220> FEATURE:
<221> NAME/KEY: MISC_FEATURE
<222> LOCATION: (2)..(2)
<223> OTHER INFORMATION: Xaa can be M or F
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 568

Xaa Xaa Phe Xaa Xaa Xaa Xaa Trp Xaa Asp
1               5                   10

<210> SEQ ID NO 569
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be P or A
<220> FEATURE:
<221> NAME/KEY: MISC_FEATURE
<222> LOCATION: (2)..(2)
<223> OTHER INFORMATION: Xaa can be G or A
<220> FEATURE:
<221> NAME/KEY: MISC_FEATURE
<222> LOCATION: (3)..(3)
<223> OTHER INFORMATION: Xaa can be I or V
<220> FEATURE:
<221> NAME/KEY: MISC_FEATURE
<222> LOCATION: (4)..(4)
<223> OTHER INFORMATION: Xaa can be M, I, T or V
```

```
<220> FEATURE:
<221> NAME/KEY: misc_feature
<222> LOCATION: (5)..(6)
<223> OTHER INFORMATION: Xaa can be any naturally occurring amino acid

<400> SEQUENCE: 569

Xaa Xaa Xaa Xaa Xaa Xaa Pro
1               5

<210> SEQ ID NO 570
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be Y, W or H

<400> SEQUENCE: 570

Lys Xaa Xaa Arg Xaa Ser Xaa Asp
1               5

<210> SEQ ID NO 571
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be Y or F
<220> FEATURE:
<221> NAME/KEY: MISC_FEATURE
<222> LOCATION: (9)..(9)
<223> OTHER INFORMATION: Xaa can be D or N

<400> SEQUENCE: 571

Glu Lys Xaa Xaa Arg Xaa Xaa Xaa Xaa
1               5

<210> SEQ ID NO 572
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 572

Asp Thr Xaa Thr Pro Xaa Glu
1               5

<210> SEQ ID NO 573
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be D or A

<400> SEQUENCE: 573

Trp Leu Xaa Gln Trp
1               5

<210> SEQ ID NO 574
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be E or N
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 574

Lys Xaa Xaa Xaa Asp Xaa Trp Asn
1               5

<210> SEQ ID NO 575
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be G or T

<400> SEQUENCE: 575

Xaa Gly Asn Gly Gly
1               5

<210> SEQ ID NO 576
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be Y,F or W
<220> FEATURE:
<221> NAME/KEY: misc_feature
<222> LOCATION: (4)..(5)
```

```
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be Q or T

<400> SEQUENCE: 576

Gly Xaa Asp Xaa Xaa Xaa Pro
1               5

<210> SEQ ID NO 577
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I or V
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be R or K
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be C or R

<400> SEQUENCE: 577

Xaa Gly Xaa Ser Xaa Xaa Xaa
1               5

<210> SEQ ID NO 578
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be S, A or T
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be M or L

<400> SEQUENCE: 578

Xaa Thr Pro Xaa Xaa Glu
1               5

<210> SEQ ID NO 579
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
```

```
<223> OTHER INFORMATION: Xaa can be D or Q
<220> FEATURE:
<221> NAME/KEY: misc_feature
<222> LOCATION: (4)..(4)
<223> OTHER INFORMATION: Xaa can be any naturally occurring amino acid

<400> SEQUENCE: 579

Ser Xaa Trp Xaa Trp Glu
1               5

<210> SEQ ID NO 580
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be I or T
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be H or F

<400> SEQUENCE: 580

Asp Xaa Xaa Tyr Xaa Xaa Xaa Xaa Lys
1               5

<210> SEQ ID NO 581
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be Y or F
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be I, V or T

<400> SEQUENCE: 581

Lys Xaa Xaa Xaa Xaa Leu Xaa Lys
1               5

<210> SEQ ID NO 582
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be V or I
<220> FEATURE:
<221> NAME/KEY: misc_feature
<222> LOCATION: (3)..(3)
```

```
<223> OTHER INFORMATION: Xaa can be any naturally occurring amino acid

<400> SEQUENCE: 582

Pro Xaa Xaa Tyr Met Gln
1               5

<210> SEQ ID NO 583
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be S or N

<400> SEQUENCE: 583

Trp Pro Thr Gly Xaa Xaa Xaa Xaa
1               5

<210> SEQ ID NO 584
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be I or M
<220> FEATURE:
<221> NAME/KEY: MISC_FEATURE
<222> LOCATION: (4)..(4)
<223> OTHER INFORMATION: Xaa can be V or N
<220> FEATURE:
<221> NAME/KEY: misc_feature
<222> LOCATION: (5)..(5)
<223> OTHER INFORMATION: Xaa can be any naturally occurring amino acid

<400> SEQUENCE: 584

Lys Xaa Xaa Xaa Xaa Trp Ala
1               5

<210> SEQ ID NO 585
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be A or P
<220> FEATURE:
<221> NAME/KEY: MISC_FEATURE
<222> LOCATION: (5)..(5)
<223> OTHER INFORMATION: Xaa can be K or R

<400> SEQUENCE: 585

Trp Xaa Thr Gly Xaa
1               5
```

```
<210> SEQ ID NO 586
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be I or V
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be K or R

<400> SEQUENCE: 586

Tyr Xaa Xaa Leu Xaa Xaa Pro Xaa
1               5

<210> SEQ ID NO 587
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be S or A
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be M or L

<400> SEQUENCE: 587

Xaa Asn Xaa Xaa Phe Tyr
1               5

<210> SEQ ID NO 588
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be I or V

<400> SEQUENCE: 588

Trp Asp Gly Ser Xaa Xaa
1               5

<210> SEQ ID NO 589
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be I or V

<400> SEQUENCE: 589

Pro Xaa Xaa Leu Xaa Lys Pro
1               5

<210> SEQ ID NO 590
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 590

Lys Xaa Asp Trp Asp Gly
1               5

<210> SEQ ID NO 591
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be H or Y

<400> SEQUENCE: 591

Arg Xaa Xaa Xaa Xaa Lys Xaa Asp Xaa Asp
1               5                   10

<210> SEQ ID NO 592
<211> LENGTH: 6
<212> TYPE: PRT
<213> ORGANISM: Artificial Sequence
<220> FEATURE:
<223> OTHER INFORMATION: Synthetic peptide

<400> SEQUENCE: 592

Val Asp Val Met Gly Asn
1               5

<210> SEQ ID NO 593
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be N or Q
<220> FEATURE:
<221> NAME/KEY: MISC_FEATURE
<222> LOCATION: (4)..(4)
<223> OTHER INFORMATION: Xaa can be Q or N
<220> FEATURE:
<221> NAME/KEY: misc_feature
<222> LOCATION: (5)..(5)
<223> OTHER INFORMATION: Xaa can be any naturally occurring amino acid

<400> SEQUENCE: 593

Glu Xaa Xaa Xaa Xaa Phe Tyr
1               5

<210> SEQ ID NO 594
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be T or S
<220> FEATURE:
<221> NAME/KEY: MISC_FEATURE
<222> LOCATION: (4)..(4)
<223> OTHER INFORMATION: Xaa can be T or S

<400> SEQUENCE: 594

Val Xaa Xaa Xaa Asn
1               5

<210> SEQ ID NO 595
<211> LENGTH: 5
<212> TYPE: PRT
<213> ORGANISM: Artificial Sequence
<220> FEATURE:
<223> OTHER INFORMATION: Synthetic peptide

<400> SEQUENCE: 595

Lys Leu His Asp Pro
1               5

<210> SEQ ID NO 596
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be G or N
```

```
<400> SEQUENCE: 596

Lys Xaa Asp Xaa Asp Thr Xaa
1               5

<210> SEQ ID NO 597
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be H or A
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be S, A or E

<400> SEQUENCE: 597

Tyr Xaa Gly Trp Xaa Xaa
1               5

<210> SEQ ID NO 598
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa can be D, T or E

<400> SEQUENCE: 598

Asn Pro Glu His Xaa
1               5

<210> SEQ ID NO 599
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be H or R

<400> SEQUENCE: 599

Asn Pro Ala Xaa Gln Xaa
1               5

<210> SEQ ID NO 600
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be K or R
```

```
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be T or P

<400> SEQUENCE: 600

Xaa Met Asn Lys Xaa Xaa Xaa
1               5

<210> SEQ ID NO 601
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be F or Y
<220> FEATURE:
<221> NAME/KEY: MISC_FEATURE
<222> LOCATION: (7)..(7)
<223> OTHER INFORMATION: Xaa can be V or K

<400> SEQUENCE: 601

Asp Trp Xaa Xaa Xaa Xaa Xaa Lys
1               5

<210> SEQ ID NO 602
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be A, P, T or S
<220> FEATURE:
<221> NAME/KEY: misc_feature
<222> LOCATION: (5)..(5)
<223> OTHER INFORMATION: Xaa can be any naturally occurring amino acid

<400> SEQUENCE: 602

Gly Val Asn Xaa Xaa Lys
1               5

<210> SEQ ID NO 603
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I or V
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be P or R
```

```
<220> FEATURE:
<221> NAME/KEY: misc_feature
<222> LOCATION: (6)..(6)
<223> OTHER INFORMATION: Xaa can be any naturally occurring amino acid

<400> SEQUENCE: 603

Xaa Xaa Xaa Glu Gly Xaa Lys
1               5

<210> SEQ ID NO 604
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be S or T
<220> FEATURE:
<221> NAME/KEY: MISC_FEATURE
<222> LOCATION: (5)..(5)
<223> OTHER INFORMATION: Xaa can be M or A

<400> SEQUENCE: 604

Arg Val Phe Xaa Xaa
1               5

<210> SEQ ID NO 605
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be V or I
<220> FEATURE:
<221> NAME/KEY: MISC_FEATURE
<222> LOCATION: (8)..(8)
<223> OTHER INFORMATION: Xaa can be Y or F

<400> SEQUENCE: 605

Asn Xaa Arg Xaa Xaa Xaa Trp Xaa
1               5

<210> SEQ ID NO 606
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be M, T or L
<220> FEATURE:
<221> NAME/KEY: misc_feature
<222> LOCATION: (5)..(5)
<223> OTHER INFORMATION: Xaa can be any naturally occurring amino acid
```

```
<400> SEQUENCE: 606

Tyr Xaa Xaa Xaa Xaa Tyr Asn Ala
1               5

<210> SEQ ID NO 607
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be V or I
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be N or D
<220> FEATURE:
<221> NAME/KEY: MISC_FEATURE
<222> LOCATION: (6)..(6)
<223> OTHER INFORMATION: Xaa can be I or V

<400> SEQUENCE: 607

Lys Xaa Xaa Xaa Xaa Xaa Trp
1               5

<210> SEQ ID NO 608
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be E or D
<220> FEATURE:
<221> NAME/KEY: MISC_FEATURE
<222> LOCATION: (2)..(2)
<223> OTHER INFORMATION: Xaa can be Y or F
<220> FEATURE:
<221> NAME/KEY: MISC_FEATURE
<222> LOCATION: (4)..(4)
<223> OTHER INFORMATION: Xaa can be L or Q

<400> SEQUENCE: 608

Xaa Xaa Gln Xaa His
1               5

<210> SEQ ID NO 609
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 609

Phe Gly Xaa Pro Ser Ile
```

```
<210> SEQ ID NO 610
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 610

Gln Leu Val Gly Xaa Xaa Lys
1               5

<210> SEQ ID NO 611
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be I or V
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be K or R

<400> SEQUENCE: 611

Tyr Xaa Xaa Leu Xaa Xaa Pro Xaa
1               5

<210> SEQ ID NO 612
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be Y or K
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be P or A

<400> SEQUENCE: 612

Trp Xaa Trp Xaa Xaa Lys
1               5

<210> SEQ ID NO 613
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be N or K

<400> SEQUENCE: 613

Lys Xaa Glu Xaa His Xaa Phe
1               5

<210> SEQ ID NO 614
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 614

Gln Xaa Xaa Xaa Trp Pro Tyr Xaa Lys
1               5

<210> SEQ ID NO 615
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 615

Tyr Xaa Phe Asp Xaa Asn Xaa Arg
1               5

<210> SEQ ID NO 616
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
```

```
<223> OTHER INFORMATION: Xaa can be V or I

<400> SEQUENCE: 616

Phe Xaa Trp Asn Xaa Pro
1               5

<210> SEQ ID NO 617
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be F or W
<220> FEATURE:
<221> NAME/KEY: MISC_FEATURE
<222> LOCATION: (2)..(2)
<223> OTHER INFORMATION: Xaa can be L or M
<220> FEATURE:
<221> NAME/KEY: misc_feature
<222> LOCATION: (4)..(4)
<223> OTHER INFORMATION: Xaa can be any naturally occurring amino acid

<400> SEQUENCE: 617

Xaa Xaa Glu Xaa Ala His
1               5

<210> SEQ ID NO 618
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be L or I
<220> FEATURE:
<221> NAME/KEY: misc_feature
<222> LOCATION: (4)..(4)
<223> OTHER INFORMATION: Xaa can be any naturally occurring amino acid

<400> SEQUENCE: 618

Asp Phe Xaa Xaa Ala Thr
1               5

<210> SEQ ID NO 619
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 619

Lys Xaa Met Ser Xaa Phe Val
1               5

<210> SEQ ID NO 620
<211> LENGTH: 6
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be Y or K
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be P or A

<400> SEQUENCE: 620

Trp Xaa Trp Xaa Xaa Lys
 1               5

<210> SEQ ID NO 621
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be N or K

<400> SEQUENCE: 621

Lys Xaa Glu Xaa His Xaa Phe
 1               5

<210> SEQ ID NO 622
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 622

Gln Xaa Xaa Xaa Trp Pro Tyr Xaa Lys
 1               5

<210> SEQ ID NO 623
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be S or F

<400> SEQUENCE: 623
```

```
Trp Pro Thr Xaa Thr
1               5

<210> SEQ ID NO 624
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be T or A

<400> SEQUENCE: 624

Trp Pro Xaa Gly Arg
1               5

<210> SEQ ID NO 625
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be G or F

<400> SEQUENCE: 625

Lys Asn Trp Pro Xaa Xaa
1               5

<210> SEQ ID NO 626
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be L or I

<400> SEQUENCE: 626

Lys Xaa Xaa Pro Xaa Phe Ala
1               5

<210> SEQ ID NO 627
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 627

Trp Pro Xaa Gly Gln Val
1               5
```

```
<210> SEQ ID NO 628
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or I
<220> FEATURE:
<221> NAME/KEY: MISC_FEATURE
<222> LOCATION: (2)..(2)
<223> OTHER INFORMATION: Xaa can be L or R

<400> SEQUENCE: 628

Xaa Xaa Lys Asp Phe
1               5

<210> SEQ ID NO 629
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be S or F

<400> SEQUENCE: 629

Trp Pro Thr Xaa Thr
1               5

<210> SEQ ID NO 630
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be I or M
<220> FEATURE:
<221> NAME/KEY: MISC_FEATURE
<222> LOCATION: (4)..(4)
<223> OTHER INFORMATION: Xaa can be V or N
<220> FEATURE:
<221> NAME/KEY: misc_feature
<222> LOCATION: (5)..(5)
<223> OTHER INFORMATION: Xaa can be any naturally occurring amino acid

<400> SEQUENCE: 630

Lys Xaa Xaa Xaa Xaa Trp Ala
1               5

<210> SEQ ID NO 631
<211> LENGTH: 6
<212> TYPE: PRT
<213> ORGANISM: Artificial Sequence
<220> FEATURE:
<223> OTHER INFORMATION: Sythentic peptide
<220> FEATURE:
<221> NAME/KEY: MISC_FEATURE
<222> LOCATION: (1)..(1)
<223> OTHER INFORMATION: Xaa can be Y or W
```

<220> FEATURE:
<221> NAME/KEY: misc_feature
<222> LOCATION: (3)..(3)
<223> OTHER INFORMATION: Xaa can be any naturally occurring amino acid

<400> SEQUENCE: 631

Xaa Thr Xaa Glu Pro Phe
1               5

<210> SEQ ID NO 632
<211> LENGTH: 6
<212> TYPE: PRT
<213> ORGANISM: Artificial Sequence
<220> FEATURE:
<223> OTHER INFORMATION: Sythentic peptide
<220> FEATURE:
<221> NAME/KEY: MISC_FEATURE
<222> LOCATION: (1)..(1)
<223> OTHER INFORMATION: Xaa can be A or M
<220> FEATURE:
<221> NAME/KEY: MISC_FEATURE
<222> LOCATION: (2)..(2)
<223> OTHER INFORMATION: Xaa can be P, T or S
<220> FEATURE:
<221> NAME/KEY: misc_feature
<222> LOCATION: (5)..(5)
<223> OTHER INFORMATION: Xaa can be any naturally occurring amino acid

<400> SEQUENCE: 632

Xaa Xaa Trp Glu Xaa Phe
1               5

<210> SEQ ID NO 633
<211> LENGTH: 5
<212> TYPE: PRT
<213> ORGANISM: Artificial Sequence
<220> FEATURE:
<223> OTHER INFORMATION: Sythentic peptide
<220> FEATURE:
<221> NAME/KEY: MISC_FEATURE
<222> LOCATION: (2)..(2)
<223> OTHER INFORMATION: Xaa can be P or T
<220> FEATURE:
<221> NAME/KEY: MISC_FEATURE
<222> LOCATION: (3)..(3)
<223> OTHER INFORMATION: Xaa can be R, T or K
<220> FEATURE:
<221> NAME/KEY: MISC_FEATURE
<222> LOCATION: (5)..(5)
<223> OTHER INFORMATION: Xaa can be N or S

<400> SEQUENCE: 633

Arg Xaa Xaa Phe Xaa
1               5

<210> SEQ ID NO 634
<211> LENGTH: 5
<212> TYPE: PRT
<213> ORGANISM: Artificial Sequence
<220> FEATURE:
<223> OTHER INFORMATION: Sythentic peptide
<220> FEATURE:
<221> NAME/KEY: MISC_FEATURE
<222> LOCATION: (3)..(3)
<223> OTHER INFORMATION: Xaa can be S or A

<400> SEQUENCE: 634

Val Tyr Xaa His Trp
1               5

<210> SEQ ID NO 635

```
<211> LENGTH: 10
<212> TYPE: PRT
<213> ORGANISM: Artificial Sequence
<220> FEATURE:
<223> OTHER INFORMATION: Sythentic peptide
<220> FEATURE:
<221> NAME/KEY: MISC_FEATURE
<222> LOCATION: (1)..(1)
<223> OTHER INFORMATION: Xaa can be W or F
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 635

Xaa Xaa Xaa Lys Pro Xaa Trp Xaa Xaa Met
1               5                   10

<210> SEQ ID NO 636
<211> LENGTH: 7
<212> TYPE: PRT
<213> ORGANISM: Artificial Sequence
<220> FEATURE:
<223> OTHER INFORMATION: Sythentic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be S or A
<220> FEATURE:
<221> NAME/KEY: misc_feature
<222> LOCATION: (6)..(6)
<223> OTHER INFORMATION: Xaa can be any naturally occurring amino acid

<400> SEQUENCE: 636

Lys Gly Xaa Xaa His Xaa Phe
1               5

<210> SEQ ID NO 637
<211> LENGTH: 7
<212> TYPE: PRT
<213> ORGANISM: Artificial Sequence
<220> FEATURE:
<223> OTHER INFORMATION: Sythentic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be A or S

<400> SEQUENCE: 637

Lys Gly Xaa Val Xaa Phe Xaa
1               5

<210> SEQ ID NO 638
```

```
<211> LENGTH: 7
<212> TYPE: PRT
<213> ORGANISM: Artificial Sequence
<220> FEATURE:
<223> OTHER INFORMATION: Sythentic peptide
<220> FEATURE:
<221> NAME/KEY: MISC_FEATURE
<222> LOCATION: (1)..(1)
<223> OTHER INFORMATION: Xaa can be I or V
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 638

Xaa Xaa His Xaa Thr Ile Asp
1               5

<210> SEQ ID NO 639
<211> LENGTH: 7
<212> TYPE: PRT
<213> ORGANISM: Artificial Sequence
<220> FEATURE:
<223> OTHER INFORMATION: Sythentic peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 639

Met Leu Ser Xaa Xaa Val Asn
1               5

<210> SEQ ID NO 640
<211> LENGTH: 8
<212> TYPE: PRT
<213> ORGANISM: Artificial Sequence
<220> FEATURE:
<223> OTHER INFORMATION: Sythentic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 640

Lys Xaa Tyr Ser Xaa Xaa Val Arg
1               5

<210> SEQ ID NO 641
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be V or K

<400> SEQUENCE: 641
```

```
Lys Xaa Xaa Val Asn Pro
1               5

<210> SEQ ID NO 642
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R, K or H

<400> SEQUENCE: 642

Xaa Glu Pro Gly Asp
1               5

<210> SEQ ID NO 643
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 643

Cys Xaa Xaa Ile Xaa Asn Glu Xaa Cys
1               5

<210> SEQ ID NO 644
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be S or N

<400> SEQUENCE: 644

Glu Ser Arg Xaa Ile
1               5

<210> SEQ ID NO 645
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Q or N

<400> SEQUENCE: 645
```

```
His Pro Asp Xaa Xaa Leu
1               5

<210> SEQ ID NO 646
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be F or Y
<220> FEATURE:
<221> NAME/KEY: MISC_FEATURE
<222> LOCATION: (6)..(6)
<223> OTHER INFORMATION: Xaa can be E or D

<400> SEQUENCE: 646

Arg Tyr Xaa His Xaa Xaa
1               5

<210> SEQ ID NO 647
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be A or S
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 647

Phe Xaa Xaa Arg Gln Xaa Pro
1               5

<210> SEQ ID NO 648
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be A or P

<400> SEQUENCE: 648

Gln Asp Xaa Arg Asn
1               5

<210> SEQ ID NO 649
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be I, L or M

<400> SEQUENCE: 649

Leu Xaa Xaa Xaa Asn Gln Gln
1               5

<210> SEQ ID NO 650
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or A
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be W or F

<400> SEQUENCE: 650

Xaa Xaa Asp Gly Ala Xaa
1               5

<210> SEQ ID NO 651
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be M, T or S

<400> SEQUENCE: 651

Cys Xaa Leu Pro Glu Xaa
1               5

<210> SEQ ID NO 652
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be T, H or S

<400> SEQUENCE: 652

Phe Xaa Xaa Met Gln Xaa Lys
1               5
```

<210> SEQ ID NO 653
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be G, A or S
<220> FEATURE:
<221> NAME/KEY: misc_feature
<222> LOCATION: (4)..(4)
<223> OTHER INFORMATION: Xaa can be any naturally occurring amino acid

<400> SEQUENCE: 653

Gly His Xaa Xaa Leu Arg
1               5

<210> SEQ ID NO 654
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be D or E
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be V or E

<400> SEQUENCE: 654

Trp Xaa Xaa Xaa Tyr Xaa Xaa Leu Xaa
1               5

<210> SEQ ID NO 655
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be H, N or D
<220> FEATURE:
<221> NAME/KEY: MISC_FEATURE
<222> LOCATION: (3)..(3)
<223> OTHER INFORMATION: Xaa can be Y or F

<400> SEQUENCE: 655

Phe Xaa Xaa Pro Arg
1               5

<210> SEQ ID NO 656
<211> LENGTH: 5
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<222> LOCATION: (3)..(3)
<223> OTHER INFORMATION: Xaa can be F or Y

<400> SEQUENCE: 656

Pro Glu Xaa Thr Ser
1               5

<210> SEQ ID NO 657
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 657

Cys Asp Xaa Pro Ser Xaa Xaa Xaa Cys
1               5

<210> SEQ ID NO 658
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be F or Y
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 658

Xaa Xaa Xaa Asn Gly His Xaa Phe
1               5

<210> SEQ ID NO 659
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 659

Tyr Xaa Ile Cys Xaa Glu Xaa Xaa Cys
```

```
<210> SEQ ID NO 660
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 660

Asp Cys Met Gly Xaa Xaa Cys
1               5

<210> SEQ ID NO 661
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be M or L
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be D or E

<400> SEQUENCE: 661

Xaa Xaa Thr Gly Leu Xaa Xaa
1               5

<210> SEQ ID NO 662
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 662

Met Xaa Leu Gly Tyr Tyr
1               5

<210> SEQ ID NO 663
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be L or T
<220> FEATURE:
<221> NAME/KEY: misc_feature
<222> LOCATION: (5)..(5)
```

```
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be Y or H

<400> SEQUENCE: 663

Met Pro Xaa Gly Xaa Xaa
1               5

<210> SEQ ID NO 664
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be F or L
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be I or L

<400> SEQUENCE: 664

Xaa Gln Thr Gly Xaa Xaa
1               5

<210> SEQ ID NO 665
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be T or S

<400> SEQUENCE: 665

Lys Xaa Xaa Cys Pro Cys
1               5

<210> SEQ ID NO 666
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be T, S or D

<400> SEQUENCE: 666

Cys Lys Asp Xaa Cys
1               5

<210> SEQ ID NO 667
<211> LENGTH: 5
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be V or A
<220> FEATURE:
<221> NAME/KEY: MISC_FEATURE
<222> LOCATION: (5)..(5)
<223> OTHER INFORMATION: Xaa can be E or Q

<400> SEQUENCE: 667

Cys Gly Xaa Phe Xaa
1               5

<210> SEQ ID NO 668
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be I, V, A or E
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be I, M or L

<400> SEQUENCE: 668

Ser Asn Xaa Xaa Ala Xaa Xaa Xaa
1               5

<210> SEQ ID NO 669
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be K or R

<400> SEQUENCE: 669

Pro Thr Xaa Leu Xaa His Xaa Xaa
1               5

<210> SEQ ID NO 670
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 670

Trp Pro Val Asn Asn
1               5

<210> SEQ ID NO 671
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V, I or A
<220> FEATURE:
<221> NAME/KEY: MISC_FEATURE
<222> LOCATION: (4)..(4)
<223> OTHER INFORMATION: Xaa can be G or D
<220> FEATURE:
<221> NAME/KEY: misc_feature
<222> LOCATION: (5)..(8)
<223> OTHER INFORMATION: Xaa can be any naturally occurring amino acid

<400> SEQUENCE: 671

Xaa Cys Asn Xaa Xaa Xaa Xaa Xaa Cys
1               5

<210> SEQ ID NO 672
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be K or R
<220> FEATURE:
<221> NAME/KEY: MISC_FEATURE
<222> LOCATION: (4)..(4)
<223> OTHER INFORMATION: Xaa can be Y or S

<400> SEQUENCE: 672

Xaa Asn Pro Xaa Leu
1               5

<210> SEQ ID NO 673
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 673

Cys Xaa Xaa Xaa Pro Met Xaa Val Xaa Cys
1               5                   10
```

```
<210> SEQ ID NO 674
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be L or M
<220> FEATURE:
<221> NAME/KEY: MISC_FEATURE
<222> LOCATION: (3)..(3)
<223> OTHER INFORMATION: Xaa can be K, Q or T
<220> FEATURE:
<221> NAME/KEY: misc_feature
<222> LOCATION: (5)..(6)
<223> OTHER INFORMATION: Xaa can be any naturally occurring amino acid

<400> SEQUENCE: 674

Gly Xaa Xaa Phe Xaa Xaa Asp
1               5

<210> SEQ ID NO 675
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I or A
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be P, A or K

<400> SEQUENCE: 675

Xaa Pro Met Xaa Xaa Asn
1               5

<210> SEQ ID NO 676
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be H or T
<220> FEATURE:
<221> NAME/KEY: misc_feature
<222> LOCATION: (7)..(9)
<223> OTHER INFORMATION: Xaa can be any naturally occurring amino acid

<400> SEQUENCE: 676

Trp Xaa Trp Cys Xaa Xaa Xaa Xaa Xaa Cys
1               5                   10
```

```
<210> SEQ ID NO 677
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Q, M, H or E
<220> FEATURE:
<221> NAME/KEY: MISC_FEATURE
<222> LOCATION: (6)..(6)
<223> OTHER INFORMATION: Xaa can be T or H

<400> SEQUENCE: 677

Phe Xaa Xaa Met Xaa Xaa Lys
1               5

<210> SEQ ID NO 678
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be V or I
<220> FEATURE:
<221> NAME/KEY: misc_feature
<222> LOCATION: (6)..(6)
<223> OTHER INFORMATION: Xaa can be any naturally occurring amino acid

<400> SEQUENCE: 678

Lys Xaa Glu Xaa Xaa Xaa Trp Arg
1               5

<210> SEQ ID NO 679
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be N or T
<220> FEATURE:
<221> NAME/KEY: misc_feature
<222> LOCATION: (5)..(5)
<223> OTHER INFORMATION: Xaa can be any naturally occurring amino acid

<400> SEQUENCE: 679

Cys His Xaa Gly Xaa Cys
1               5

<210> SEQ ID NO 680
<211> LENGTH: 5
<212> TYPE: PRT
```

```
<213> ORGANISM: Artificial Sequence
<220> FEATURE:
<223> OTHER INFORMATION: Synthetic peptide

<400> SEQUENCE: 680

His Glu Pro Gly Asp
1               5

<210> SEQ ID NO 681
<211> LENGTH: 5
<212> TYPE: PRT
<213> ORGANISM: Artificial Sequence
<220> FEATURE:
<223> OTHER INFORMATION: Synthetic peptide

<400> SEQUENCE: 681

Arg Glu Pro Gly Asp
1               5

<210> SEQ ID NO 682
<211> LENGTH: 5
<212> TYPE: PRT
<213> ORGANISM: Artificial Sequence
<220> FEATURE:
<223> OTHER INFORMATION: Synthetic peptide

<400> SEQUENCE: 682

Lys Glu Pro Gly Asp
1               5

<210> SEQ ID NO 683
<211> LENGTH: 5
<212> TYPE: PRT
<213> ORGANISM: Artificial Sequence
<220> FEATURE:
<223> OTHER INFORMATION: Synthetic peptide

<400> SEQUENCE: 683

Arg Glu Pro Gly Asp
1               5

<210> SEQ ID NO 684
<211> LENGTH: 9
<212> TYPE: PRT
<213> ORGANISM: Artificial Sequence
<220> FEATURE:
<223> OTHER INFORMATION: Synthetic peptide

<400> SEQUENCE: 684

Cys Lys Lys Ile Val Asn Glu Thr Cys
1               5

<210> SEQ ID NO 685
<211> LENGTH: 5
<212> TYPE: PRT
<213> ORGANISM: Artificial Sequence
<220> FEATURE:
<223> OTHER INFORMATION: Synthetic peptide

<400> SEQUENCE: 685

Glu Ser Arg Ser Ile
1               5

<210> SEQ ID NO 686
<211> LENGTH: 5
<212> TYPE: PRT
<213> ORGANISM: Artificial Sequence
```

<220> FEATURE:
<223> OTHER INFORMATION: Synthetic peptide

<400> SEQUENCE: 686

Glu Ser Arg Asn Ile
1               5

<210> SEQ ID NO 687
<211> LENGTH: 6
<212> TYPE: PRT
<213> ORGANISM: Artificial Sequence
<220> FEATURE:
<223> OTHER INFORMATION: Synthetic peptide

<400> SEQUENCE: 687

His Pro Asp Val Asn Leu
1               5

<210> SEQ ID NO 688
<211> LENGTH: 6
<212> TYPE: PRT
<213> ORGANISM: Artificial Sequence
<220> FEATURE:
<223> OTHER INFORMATION: Synthetic peptide

<400> SEQUENCE: 688

His Pro Asp Gly Asn Leu
1               5

<210> SEQ ID NO 689
<211> LENGTH: 6
<212> TYPE: PRT
<213> ORGANISM: Artificial Sequence
<220> FEATURE:
<223> OTHER INFORMATION: Synthetic peptide

<400> SEQUENCE: 689

His Pro Asp Lys Asn Leu
1               5

<210> SEQ ID NO 690
<211> LENGTH: 6
<212> TYPE: PRT
<213> ORGANISM: Artificial Sequence
<220> FEATURE:
<223> OTHER INFORMATION: Synthetic peptide

<400> SEQUENCE: 690

His Pro Asp Glu Gln Leu
1               5

<210> SEQ ID NO 691
<211> LENGTH: 6
<212> TYPE: PRT
<213> ORGANISM: Artificial Sequence
<220> FEATURE:
<223> OTHER INFORMATION: Synthetic peptide

<400> SEQUENCE: 691

His Pro Asp Thr Gln Leu
1               5

<210> SEQ ID NO 692
<211> LENGTH: 6
<212> TYPE: PRT
<213> ORGANISM: Artificial Sequence
<220> FEATURE:

<223> OTHER INFORMATION: Synthetic peptide

<400> SEQUENCE: 692

Arg Tyr Cys His Phe Asp
1               5

<210> SEQ ID NO 693
<211> LENGTH: 6
<212> TYPE: PRT
<213> ORGANISM: Artificial Sequence
<220> FEATURE:
<223> OTHER INFORMATION: Synthetic peptide

<400> SEQUENCE: 693

Arg Tyr Tyr His Tyr Asp
1               5

<210> SEQ ID NO 694
<211> LENGTH: 6
<212> TYPE: PRT
<213> ORGANISM: Artificial Sequence
<220> FEATURE:
<223> OTHER INFORMATION: Synthetic peptide

<400> SEQUENCE: 694

Arg Tyr Lys His Phe Asp
1               5

<210> SEQ ID NO 695
<211> LENGTH: 7
<212> TYPE: PRT
<213> ORGANISM: Artificial Sequence
<220> FEATURE:
<223> OTHER INFORMATION: Synthetic peptide

<400> SEQUENCE: 695

Phe Ser Phe Arg Gln Gln Pro
1               5

<210> SEQ ID NO 696
<211> LENGTH: 7
<212> TYPE: PRT
<213> ORGANISM: Artificial Sequence
<220> FEATURE:
<223> OTHER INFORMATION: Synthetic peptide

<400> SEQUENCE: 696

Phe Ala His Arg Gln Gln Pro
1               5

<210> SEQ ID NO 697
<211> LENGTH: 7
<212> TYPE: PRT
<213> ORGANISM: Artificial Sequence
<220> FEATURE:
<223> OTHER INFORMATION: Synthetic peptide

<400> SEQUENCE: 697

Phe Ala His Arg Gln Arg Pro
1               5

<210> SEQ ID NO 698
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 698

Phe Ala Thr Arg Gln Gly Pro
1               5

<210> SEQ ID NO 699
<211> LENGTH: 5
<212> TYPE: PRT
<213> ORGANISM: Artificial Sequence
<220> FEATURE:
<223> OTHER INFORMATION: Synthetic peptide

<400> SEQUENCE: 699

Gln Asp Pro Arg Asn
1               5

<210> SEQ ID NO 700
<211> LENGTH: 7
<212> TYPE: PRT
<213> ORGANISM: Artificial Sequence
<220> FEATURE:
<223> OTHER INFORMATION: Synthetic peptide

<400> SEQUENCE: 700

Leu Leu Gln Leu Asn Gln Gln
1               5

<210> SEQ ID NO 701
<211> LENGTH: 7
<212> TYPE: PRT
<213> ORGANISM: Artificial Sequence
<220> FEATURE:
<223> OTHER INFORMATION: Synthetic peptide

<400> SEQUENCE: 701

Leu Ser Leu Met Asn Gln Gln
1               5

<210> SEQ ID NO 702
<211> LENGTH: 7
<212> TYPE: PRT
<213> ORGANISM: Artificial Sequence
<220> FEATURE:
<223> OTHER INFORMATION: Synthetic peptide

<400> SEQUENCE: 702

Leu Phe Trp Ile Asn Gln Gln
1               5

<210> SEQ ID NO 703
<211> LENGTH: 7
<212> TYPE: PRT
<213> ORGANISM: Artificial Sequence
<220> FEATURE:
<223> OTHER INFORMATION: Synthetic peptide

<400> SEQUENCE: 703

Leu Gln Lys Leu Asn Gln Gln
1               5

<210> SEQ ID NO 704
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 704

Leu Ile Leu Leu Asn Gln Gln
1               5

<210> SEQ ID NO 705
<211> LENGTH: 6
<212> TYPE: PRT
<213> ORGANISM: Artificial Sequence
<220> FEATURE:
<223> OTHER INFORMATION: Synthetic peptide

<400> SEQUENCE: 705

Ala Pro Asp Gly Ala Phe
1               5

<210> SEQ ID NO 706
<211> LENGTH: 6
<212> TYPE: PRT
<213> ORGANISM: Artificial Sequence
<220> FEATURE:
<223> OTHER INFORMATION: Synthetic peptide

<400> SEQUENCE: 706

Val Gln Asp Gly Ala Phe
1               5

<210> SEQ ID NO 707
<211> LENGTH: 6
<212> TYPE: PRT
<213> ORGANISM: Artificial Sequence
<220> FEATURE:
<223> OTHER INFORMATION: Synthetic peptide

<400> SEQUENCE: 707

Ala Cys Asp Gly Ala Phe
1               5

<210> SEQ ID NO 708
<211> LENGTH: 6
<212> TYPE: PRT
<213> ORGANISM: Artificial Sequence
<220> FEATURE:
<223> OTHER INFORMATION: Synthetic peptide

<400> SEQUENCE: 708

Ala Ile Asp Gly Ala Phe
1               5

<210> SEQ ID NO 709
<211> LENGTH: 6
<212> TYPE: PRT
<213> ORGANISM: Artificial Sequence
<220> FEATURE:
<223> OTHER INFORMATION: Synthetic peptide

<400> SEQUENCE: 709

Ala Ile Asp Gly Ala Phe
1               5

<210> SEQ ID NO 710
<211> LENGTH: 6
<212> TYPE: PRT
<213> ORGANISM: Artificial Sequence
<220> FEATURE:
<223> OTHER INFORMATION: Synthetic peptide

<400> SEQUENCE: 710

Cys Ser Leu Pro Glu Ser
1               5

<210> SEQ ID NO 711
<211> LENGTH: 6
<212> TYPE: PRT
<213> ORGANISM: Artificial Sequence
<220> FEATURE:
<223> OTHER INFORMATION: Synthetic peptide

<400> SEQUENCE: 711

Cys Pro Leu Pro Glu Thr
1               5

<210> SEQ ID NO 712
<211> LENGTH: 6
<212> TYPE: PRT
<213> ORGANISM: Artificial Sequence
<220> FEATURE:
<223> OTHER INFORMATION: Synthetic peptide

<400> SEQUENCE: 712

Cys Val Leu Pro Glu Ser
1               5

<210> SEQ ID NO 713
<211> LENGTH: 6
<212> TYPE: PRT
<213> ORGANISM: Artificial Sequence
<220> FEATURE:
<223> OTHER INFORMATION: Synthetic peptide

<400> SEQUENCE: 713

Cys Arg Leu Pro Glu Thr
1               5

<210> SEQ ID NO 714
<211> LENGTH: 6
<212> TYPE: PRT
<213> ORGANISM: Artificial Sequence
<220> FEATURE:
<223> OTHER INFORMATION: Synthetic peptide

<400> SEQUENCE: 714

Cys Pro Leu Pro Glu Thr
1               5

<210> SEQ ID NO 715
<211> LENGTH: 6
<212> TYPE: PRT
<213> ORGANISM: Artificial Sequence
<220> FEATURE:
<223> OTHER INFORMATION: Synthetic peptide

<400> SEQUENCE: 715

Cys Asp Leu Pro Glu Thr
1               5

<210> SEQ ID NO 716
<211> LENGTH: 7
<212> TYPE: PRT
<213> ORGANISM: Artificial Sequence
<220> FEATURE:
<223> OTHER INFORMATION: Synthetic peptide

<400> SEQUENCE: 716

```
Phe Lys Lys Met Gln Ser Lys
1               5
```

<210> SEQ ID NO 717
<211> LENGTH: 7
<212> TYPE: PRT
<213> ORGANISM: Artificial Sequence
<220> FEATURE:
<223> OTHER INFORMATION: Synthetic peptide

<400> SEQUENCE: 717

```
Phe Leu Phe Met Gln His Lys
1               5
```

<210> SEQ ID NO 718
<211> LENGTH: 6
<212> TYPE: PRT
<213> ORGANISM: Artificial Sequence
<220> FEATURE:
<223> OTHER INFORMATION: Synthetic peptide

<400> SEQUENCE: 718

```
Gly His Ser Thr Leu Arg
1               5
```

<210> SEQ ID NO 719
<211> LENGTH: 6
<212> TYPE: PRT
<213> ORGANISM: Artificial Sequence
<220> FEATURE:
<223> OTHER INFORMATION: Synthetic peptide

<400> SEQUENCE: 719

```
Gly His Ser Ala Leu Arg
1               5
```

<210> SEQ ID NO 720
<211> LENGTH: 6
<212> TYPE: PRT
<213> ORGANISM: Artificial Sequence
<220> FEATURE:
<223> OTHER INFORMATION: Synthetic peptide

<400> SEQUENCE: 720

```
Gly His Gly Thr Leu Arg
1               5
```

<210> SEQ ID NO 721
<211> LENGTH: 6
<212> TYPE: PRT
<213> ORGANISM: Artificial Sequence
<220> FEATURE:
<223> OTHER INFORMATION: Synthetic peptide

<400> SEQUENCE: 721

```
Gly His Gly Arg Leu Arg
1               5
```

<210> SEQ ID NO 722
<211> LENGTH: 6
<212> TYPE: PRT
<213> ORGANISM: Artificial Sequence
<220> FEATURE:
<223> OTHER INFORMATION: Synthetic peptide

<400> SEQUENCE: 722

```
Gly His Gly Phe Leu Arg
```

```
1               5

<210> SEQ ID NO 723
<211> LENGTH: 9
<212> TYPE: PRT
<213> ORGANISM: Artificial Sequence
<220> FEATURE:
<223> OTHER INFORMATION: Synthetic peptide

<400> SEQUENCE: 723

Trp Gln Ile Asp Tyr Thr Ser Leu Val
1               5

<210> SEQ ID NO 724
<211> LENGTH: 5
<212> TYPE: PRT
<213> ORGANISM: Artificial Sequence
<220> FEATURE:
<223> OTHER INFORMATION: Synthetic peptide

<400> SEQUENCE: 724

Phe Asp Phe Pro Arg
1               5

<210> SEQ ID NO 725
<211> LENGTH: 5
<212> TYPE: PRT
<213> ORGANISM: Artificial Sequence
<220> FEATURE:
<223> OTHER INFORMATION: Synthetic peptide

<400> SEQUENCE: 725

Phe Asp Tyr Pro Arg
1               5

<210> SEQ ID NO 726
<211> LENGTH: 5
<212> TYPE: PRT
<213> ORGANISM: Artificial Sequence
<220> FEATURE:
<223> OTHER INFORMATION: Synthetic peptide

<400> SEQUENCE: 726

Phe Asn Tyr Pro Arg
1               5

<210> SEQ ID NO 727
<211> LENGTH: 5
<212> TYPE: PRT
<213> ORGANISM: Artificial Sequence
<220> FEATURE:
<223> OTHER INFORMATION: Synthetic peptide

<400> SEQUENCE: 727

Pro Glu Phe Thr Ser
1               5

<210> SEQ ID NO 728
<211> LENGTH: 8
<212> TYPE: PRT
<213> ORGANISM: Artificial Sequence
<220> FEATURE:
<223> OTHER INFORMATION: Synthetic peptide

<400> SEQUENCE: 728

Tyr Tyr Gln Asn Gly His Glu Phe
1               5
```

<210> SEQ ID NO 729
<211> LENGTH: 8
<212> TYPE: PRT
<213> ORGANISM: Artificial Sequence
<220> FEATURE:
<223> OTHER INFORMATION: Synthetic peptide

<400> SEQUENCE: 729

Tyr His Val Asn Gly His Arg Phe
1               5

<210> SEQ ID NO 730
<211> LENGTH: 7
<212> TYPE: PRT
<213> ORGANISM: Artificial Sequence
<220> FEATURE:
<223> OTHER INFORMATION: Synthetic peptide

<400> SEQUENCE: 730

Leu Ile Thr Gly Leu Pro Asp
1               5

<210> SEQ ID NO 731
<211> LENGTH: 7
<212> TYPE: PRT
<213> ORGANISM: Artificial Sequence
<220> FEATURE:
<223> OTHER INFORMATION: Synthetic peptide

<400> SEQUENCE: 731

Met Tyr Thr Gly Leu Pro Glu
1               5

<210> SEQ ID NO 732
<211> LENGTH: 7
<212> TYPE: PRT
<213> ORGANISM: Artificial Sequence
<220> FEATURE:
<223> OTHER INFORMATION: Synthetic peptide

<400> SEQUENCE: 732

Leu Trp Thr Gly Leu Glu Glu
1               5

<210> SEQ ID NO 733
<211> LENGTH: 7
<212> TYPE: PRT
<213> ORGANISM: Artificial Sequence
<220> FEATURE:
<223> OTHER INFORMATION: Synthetic peptide

<400> SEQUENCE: 733

Leu Leu Thr Gly Leu Ala Asp
1               5

<210> SEQ ID NO 734
<211> LENGTH: 7
<212> TYPE: PRT
<213> ORGANISM: Artificial Sequence
<220> FEATURE:
<223> OTHER INFORMATION: Synthetic peptide

<400> SEQUENCE: 734

Leu Leu Thr Gly Leu Leu Asp
1               5

<210> SEQ ID NO 735
<211> LENGTH: 7
<212> TYPE: PRT
<213> ORGANISM: Artificial Sequence
<220> FEATURE:
<223> OTHER INFORMATION: Synthetic peptide

<400> SEQUENCE: 735

Met Asp Thr Gly Leu Val Asp
1               5

<210> SEQ ID NO 736
<211> LENGTH: 6
<212> TYPE: PRT
<213> ORGANISM: Artificial Sequence
<220> FEATURE:
<223> OTHER INFORMATION: Synthetic peptide

<400> SEQUENCE: 736

Met Arg Leu Gly Tyr Tyr
1               5

<210> SEQ ID NO 737
<211> LENGTH: 6
<212> TYPE: PRT
<213> ORGANISM: Artificial Sequence
<220> FEATURE:
<223> OTHER INFORMATION: Synthetic peptide

<400> SEQUENCE: 737

Met Pro Thr Gly Gly His
1               5

<210> SEQ ID NO 738
<211> LENGTH: 6
<212> TYPE: PRT
<213> ORGANISM: Artificial Sequence
<220> FEATURE:
<223> OTHER INFORMATION: Synthetic peptide

<400> SEQUENCE: 738

Leu Gln Thr Gly Thr Leu
1               5

<210> SEQ ID NO 739
<211> LENGTH: 6
<212> TYPE: PRT
<213> ORGANISM: Artificial Sequence
<220> FEATURE:
<223> OTHER INFORMATION: Synthetic peptide

<400> SEQUENCE: 739

Leu Gln Thr Gly Lys Leu
1               5

<210> SEQ ID NO 740
<211> LENGTH: 6
<212> TYPE: PRT
<213> ORGANISM: Artificial Sequence
<220> FEATURE:
<223> OTHER INFORMATION: Synthetic peptide

<400> SEQUENCE: 740

Phe Gln Thr Gly Asp Ile
1               5

```
<210> SEQ ID NO 741
<211> LENGTH: 5
<212> TYPE: PRT
<213> ORGANISM: Artificial Sequence
<220> FEATURE:
<223> OTHER INFORMATION: Synthetic peptide

<400> SEQUENCE: 741

Cys Gly Ala Phe Glu
1               5

<210> SEQ ID NO 742
<211> LENGTH: 5
<212> TYPE: PRT
<213> ORGANISM: Artificial Sequence
<220> FEATURE:
<223> OTHER INFORMATION: Synthetic peptide

<400> SEQUENCE: 742

Cys Gly Val Phe Gln
1               5

<210> SEQ ID NO 743
<211> LENGTH: 8
<212> TYPE: PRT
<213> ORGANISM: Artificial Sequence
<220> FEATURE:
<223> OTHER INFORMATION: Synthetic peptide

<400> SEQUENCE: 743

Ser Asn Arg Val Ala Ser Phe Leu
1               5

<210> SEQ ID NO 744
<211> LENGTH: 8
<212> TYPE: PRT
<213> ORGANISM: Artificial Sequence
<220> FEATURE:
<223> OTHER INFORMATION: Synthetic peptide

<400> SEQUENCE: 744

Ser Asn Lys Ala Ala Arg Gln Met
1               5

<210> SEQ ID NO 745
<211> LENGTH: 8
<212> TYPE: PRT
<213> ORGANISM: Artificial Sequence
<220> FEATURE:
<223> OTHER INFORMATION: Synthetic peptide

<400> SEQUENCE: 745

Ser Asn Ser Ala Ala Val Asp Leu
1               5

<210> SEQ ID NO 746
<211> LENGTH: 8
<212> TYPE: PRT
<213> ORGANISM: Artificial Sequence
<220> FEATURE:
<223> OTHER INFORMATION: Synthetic peptide

<400> SEQUENCE: 746

Ser Asn Asp Val Ala Lys Ile Ile
1               5

<210> SEQ ID NO 747
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 747

Ser Asn Ala Val Ala Gln Val Leu
1               5

<210> SEQ ID NO 748
<211> LENGTH: 8
<212> TYPE: PRT
<213> ORGANISM: Artificial Sequence
<220> FEATURE:
<223> OTHER INFORMATION: Synthetic peptide

<400> SEQUENCE: 748

Ser Asn Asn Val Ala Phe Glu Ile
1               5

<210> SEQ ID NO 749
<211> LENGTH: 8
<212> TYPE: PRT
<213> ORGANISM: Artificial Sequence
<220> FEATURE:
<223> OTHER INFORMATION: Synthetic peptide

<400> SEQUENCE: 749

Pro Thr Gly Leu Asp His His Arg
1               5

<210> SEQ ID NO 750
<211> LENGTH: 8
<212> TYPE: PRT
<213> ORGANISM: Artificial Sequence
<220> FEATURE:
<223> OTHER INFORMATION: Synthetic peptide

<400> SEQUENCE: 750

Pro Thr Tyr Leu Ile His Glu Arg
1               5

<210> SEQ ID NO 751
<211> LENGTH: 9
<212> TYPE: PRT
<213> ORGANISM: Artificial Sequence
<220> FEATURE:
<223> OTHER INFORMATION: Synthetic peptide

<400> SEQUENCE: 751

Ile Cys Asn Asp Ser Ser Arg Arg Cys
1               5

<210> SEQ ID NO 752
<211> LENGTH: 9
<212> TYPE: PRT
<213> ORGANISM: Artificial Sequence
<220> FEATURE:
<223> OTHER INFORMATION: Synthetic peptide

<400> SEQUENCE: 752

Ala Cys Asn Gly His Ser Ile Thr Cys
1               5

<210> SEQ ID NO 753
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 753

Val Cys Asn Gly His Ala Asp Thr Cys
1               5

<210> SEQ ID NO 754
<211> LENGTH: 9
<212> TYPE: PRT
<213> ORGANISM: Artificial Sequence
<220> FEATURE:
<223> OTHER INFORMATION: Synthetic peptide

<400> SEQUENCE: 754

Ala Cys Asn Gly Glu His Ser Gln Cys
1               5

<210> SEQ ID NO 755
<211> LENGTH: 5
<212> TYPE: PRT
<213> ORGANISM: Artificial Sequence
<220> FEATURE:
<223> OTHER INFORMATION: Synthetic peptide

<400> SEQUENCE: 755

Arg Asn Pro Ser Leu
1               5

<210> SEQ ID NO 756
<211> LENGTH: 5
<212> TYPE: PRT
<213> ORGANISM: Artificial Sequence
<220> FEATURE:
<223> OTHER INFORMATION: Synthetic peptide

<400> SEQUENCE: 756

Lys Asn Pro Ser Leu
1               5

<210> SEQ ID NO 757
<211> LENGTH: 7
<212> TYPE: PRT
<213> ORGANISM: Artificial Sequence
<220> FEATURE:
<223> OTHER INFORMATION: Synthetic peptide

<400> SEQUENCE: 757

Gly Leu Thr Phe Gln Ala Asp
1               5

<210> SEQ ID NO 758
<211> LENGTH: 7
<212> TYPE: PRT
<213> ORGANISM: Artificial Sequence
<220> FEATURE:
<223> OTHER INFORMATION: Synthetic peptide

<400> SEQUENCE: 758

Gly Leu Gln Phe Ala Phe Asp
1               5

<210> SEQ ID NO 759
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 759

Gly Met Lys Phe Thr Arg Asp
1               5

<210> SEQ ID NO 760
<211> LENGTH: 7
<212> TYPE: PRT
<213> ORGANISM: Artificial Sequence
<220> FEATURE:
<223> OTHER INFORMATION: Synthetic peptide

<400> SEQUENCE: 760

Gly Leu Gln Phe Pro Ser Asp
1               5

<210> SEQ ID NO 761
<211> LENGTH: 7
<212> TYPE: PRT
<213> ORGANISM: Artificial Sequence
<220> FEATURE:
<223> OTHER INFORMATION: Synthetic peptide

<400> SEQUENCE: 761

Gly Leu Lys Phe Ser Pro Asp
1               5

<210> SEQ ID NO 762
<211> LENGTH: 7
<212> TYPE: PRT
<213> ORGANISM: Artificial Sequence
<220> FEATURE:
<223> OTHER INFORMATION: Synthetic peptide

<400> SEQUENCE: 762

Gly Leu Thr Phe Thr Pro Asp
1               5

<210> SEQ ID NO 763
<211> LENGTH: 6
<212> TYPE: PRT
<213> ORGANISM: Artificial Sequence
<220> FEATURE:
<223> OTHER INFORMATION: Synthetic peptide

<400> SEQUENCE: 763

Ala Pro Met Asp Ala Asn
1               5

<210> SEQ ID NO 764
<211> LENGTH: 6
<212> TYPE: PRT
<213> ORGANISM: Artificial Sequence
<220> FEATURE:
<223> OTHER INFORMATION: Synthetic peptide

<400> SEQUENCE: 764

Ile Pro Met Asp Pro Asn
1               5

<210> SEQ ID NO 765
<211> LENGTH: 6
<212> TYPE: PRT
<213> ORGANISM: Artificial Sequence
```

```
<220> FEATURE:
<223> OTHER INFORMATION: Synthetic peptide

<400> SEQUENCE: 765

Ala Pro Met Pro Lys Asn
1               5

<210> SEQ ID NO 766
<211> LENGTH: 6
<212> TYPE: PRT
<213> ORGANISM: Artificial Sequence
<220> FEATURE:
<223> OTHER INFORMATION: Synthetic peptide

<400> SEQUENCE: 766

Ala Pro Met Phe Lys Asn
1               5

<210> SEQ ID NO 767
<211> LENGTH: 7
<212> TYPE: PRT
<213> ORGANISM: Artificial Sequence
<220> FEATURE:
<223> OTHER INFORMATION: Synthetic peptide

<400> SEQUENCE: 767

Phe Leu Phe Met Gln His Lys
1               5

<210> SEQ ID NO 768
<211> LENGTH: 7
<212> TYPE: PRT
<213> ORGANISM: Artificial Sequence
<220> FEATURE:
<223> OTHER INFORMATION: Synthetic peptide

<400> SEQUENCE: 768

Phe Phe Asp Met Glu Thr Lys
1               5

<210> SEQ ID NO 769
<211> LENGTH: 7
<212> TYPE: PRT
<213> ORGANISM: Artificial Sequence
<220> FEATURE:
<223> OTHER INFORMATION: Synthetic peptide

<400> SEQUENCE: 769

Phe Glu Glu Met Gln Thr Lys
1               5

<210> SEQ ID NO 770
<211> LENGTH: 6
<212> TYPE: PRT
<213> ORGANISM: Artificial Sequence
<220> FEATURE:
<223> OTHER INFORMATION: Synthetic peptide

<400> SEQUENCE: 770

Cys His Thr Gly Pro Cys
1               5

<210> SEQ ID NO 771
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or I
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be S or A

<400> SEQUENCE: 771

Xaa Pro Glu Phe Xaa Gly Xaa
1               5

<210> SEQ ID NO 772
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I, V or M
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be L or M

<400> SEQUENCE: 772

Tyr Xaa Asp Xaa Xaa Xaa Asn
1               5

<210> SEQ ID NO 773
<211> LENGTH: 5
<212> TYPE: PRT
<213> ORGANISM: Artificial Sequence
<220> FEATURE:
<223> OTHER INFORMATION: Synthetic peptide

<400> SEQUENCE: 773

Asp Asp Lys Gly Lys
1               5

<210> SEQ ID NO 774
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 774

Lys Xaa Pro Glu Glu Pro
1               5

<210> SEQ ID NO 775
<211> LENGTH: 6
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L or M
<220> FEATURE:
<221> NAME/KEY: misc_feature
<222> LOCATION: (2)..(2)
<223> OTHER INFORMATION: Xaa can be any naturally occurring amino acid

<400> SEQUENCE: 775

Xaa Xaa Leu Pro Asp Lys
1               5

<210> SEQ ID NO 776
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I, V or Y
<220> FEATURE:
<221> NAME/KEY: misc_feature
<222> LOCATION: (3)..(4)
<223> OTHER INFORMATION: Xaa can be any naturally occurring amino acid

<400> SEQUENCE: 776

Xaa Asp Xaa Xaa Gly Asn
1               5

<210> SEQ ID NO 777
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be V or I
<220> FEATURE:
<221> NAME/KEY: MISC_FEATURE
<222> LOCATION: (3)..(3)
<223> OTHER INFORMATION: Xaa can be V or I
<220> FEATURE:
<221> NAME/KEY: MISC_FEATURE
<222> LOCATION: (4)..(4)
<223> OTHER INFORMATION: Xaa can be V or I

<400> SEQUENCE: 777

Glu Xaa Xaa Xaa Asp Lys
1               5

<210> SEQ ID NO 778
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be M or L
<220> FEATURE:
<221> NAME/KEY: MISC_FEATURE
<222> LOCATION: (2)..(2)
<223> OTHER INFORMATION: Xaa can be W or Y

<400> SEQUENCE: 778
```

```
Xaa Xaa Trp Met Asp Lys
1               5
```

<210> SEQ ID NO 779
<211> LENGTH: 4
<212> TYPE: PRT
<213> ORGANISM: Artificial Sequence
<220> FEATURE:
<223> OTHER INFORMATION: Synthetic peptide

<400> SEQUENCE: 779

```
Asn Pro Val Glu
1
```

<210> SEQ ID NO 780
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 780

```
Cys Met Asn Xaa Xaa Cys
1               5
```

<210> SEQ ID NO 781
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or K
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be M or L

<400> SEQUENCE: 781

```
Xaa Asp Xaa Xaa Gly Arg
1               5
```

<210> SEQ ID NO 782
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I or V
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:

```
<221> NAME/KEY: MISC_FEATURE
<222> LOCATION: (7)..(7)
<223> OTHER INFORMATION: Xaa can be D or E

<400> SEQUENCE: 782

Xaa Xaa Xaa Pro Xaa Tyr Xaa Lys
1               5

<210> SEQ ID NO 783
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be T or V
<220> FEATURE:
<221> NAME/KEY: misc_feature
<222> LOCATION: (6)..(6)
<223> OTHER INFORMATION: Xaa can be any naturally occurring amino acid

<400> SEQUENCE: 783

Pro Xaa Gly Xaa Leu Xaa Lys
1               5

<210> SEQ ID NO 784
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or I
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 784

Xaa Xaa Xaa Gln Pro Xaa Lys Pro
1               5

<210> SEQ ID NO 785
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be R or K

<400> SEQUENCE: 785

Asp Thr Xaa Pro Xaa
1               5
```

```
<210> SEQ ID NO 786
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 786

Cys Xaa Xaa Pro Trp Xaa Xaa Glu Xaa Cys
1               5                   10

<210> SEQ ID NO 787
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be W or F
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be Q, I or V

<400> SEQUENCE: 787

Trp Xaa Xaa Xaa Pro Asp Lys
1               5

<210> SEQ ID NO 788
<211> LENGTH: 4
<212> TYPE: PRT
<213> ORGANISM: Artificial Sequence
<220> FEATURE:
<223> OTHER INFORMATION: Synthetic peptide

<400> SEQUENCE: 788

Pro Pro Trp Trp
1

<210> SEQ ID NO 789
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L or I
<220> FEATURE:
<221> NAME/KEY: MISC_FEATURE
<222> LOCATION: (3)..(3)
<223> OTHER INFORMATION: Xaa can be K or R
```

<400> SEQUENCE: 789

Xaa Asn Xaa Pro
1

<210> SEQ ID NO 790
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I or L
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be H or P
<220> FEATURE:
<221> NAME/KEY: misc_feature
<222> LOCATION: (7)..(7)
<223> OTHER INFORMATION: Xaa can be any naturally occurring amino acid

<400> SEQUENCE: 790

Pro Xaa Xaa Asn Xaa Xaa Xaa Trp
1               5

<210> SEQ ID NO 791
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be F or Y
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be L, I or M

<400> SEQUENCE: 791

Xaa Xaa His Xaa Xaa Xaa Asn
1               5

<210> SEQ ID NO 792
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be P or W

```
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be D or N

<400> SEQUENCE: 792

Xaa Phe Xaa Xaa Met Xaa Lys Pro
1               5

<210> SEQ ID NO 793
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be F, Y or W

<400> SEQUENCE: 793

Lys Xaa Thr His Pro
1               5

<210> SEQ ID NO 794
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be W or Y

<400> SEQUENCE: 794

Tyr Xaa Pro Thr Xaa Xaa Xaa
1               5

<210> SEQ ID NO 795
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be L, M or I
<220> FEATURE:
<221> NAME/KEY: MISC_FEATURE
<222> LOCATION: (8)..(8)
<223> OTHER INFORMATION: Xaa can be L, V or I
```

<400> SEQUENCE: 795

Pro Xaa Ala Ile Xaa Asp Xaa Xaa
1               5

<210> SEQ ID NO 796
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be L or M

<400> SEQUENCE: 796

Tyr Xaa Asp Xaa Xaa Xaa Asn
1               5

<210> SEQ ID NO 797
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be W or N
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be W or R
<220> FEATURE:
<221> NAME/KEY: MISC_FEATURE
<222> LOCATION: (4)..(4)
<223> OTHER INFORMATION: Xaa can be W or R
<220> FEATURE:
<221> NAME/KEY: misc_feature
<222> LOCATION: (5)..(5)
<223> OTHER INFORMATION: Xaa can be any naturally occurring amino acid

<400> SEQUENCE: 797

Cys Xaa Xaa Xaa Xaa Cys
1               5

<210> SEQ ID NO 798
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

```
<400> SEQUENCE: 798

Lys Xaa Asp Pro Asp Xaa Xaa Trp
1               5

<210> SEQ ID NO 799
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or K
<220> FEATURE:
<221> NAME/KEY: MISC_FEATURE
<222> LOCATION: (3)..(3)
<223> OTHER INFORMATION: Xaa can be Y or F
<220> FEATURE:
<221> NAME/KEY: MISC_FEATURE
<222> LOCATION: (4)..(4)
<223> OTHER INFORMATION: Xaa can be L, I, V or M
<220> FEATURE:
<221> NAME/KEY: MISC_FEATURE
<222> LOCATION: (6)..(6)
<223> OTHER INFORMATION: Xaa can be E or D

<400> SEQUENCE: 799

Xaa Cys Xaa Xaa Cys Xaa
1               5

<210> SEQ ID NO 800
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa can be D or E

<400> SEQUENCE: 800

Trp Cys Trp Lys Xaa
1               5

<210> SEQ ID NO 801
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or I
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be L, F or M

<400> SEQUENCE: 801

Xaa Xaa Xaa Pro His Trp
1               5

<210> SEQ ID NO 802
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be S or T
<220> FEATURE:
<221> NAME/KEY: misc_feature
<222> LOCATION: (5)..(6)
<223> OTHER INFORMATION: Xaa can be any naturally occurring amino acid

<400> SEQUENCE: 802

Pro Xaa Leu Xaa Xaa Xaa Glu
1               5

<210> SEQ ID NO 803
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be I or V
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be F or W

<400> SEQUENCE: 803

Pro Xaa Xaa Xaa Glu Xaa Xaa Met Xaa
1               5

<210> SEQ ID NO 804
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be W or F

<400> SEQUENCE: 804

Asp Pro Tyr Gln Xaa Xaa Xaa
1               5

<210> SEQ ID NO 805
```

```
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or I
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 805

Xaa Pro Xaa Leu Xaa Xaa Xaa Glu
1               5

<210> SEQ ID NO 806
<211> LENGTH: 4
<212> TYPE: PRT
<213> ORGANISM: Artificial Sequence
<220> FEATURE:
<223> OTHER INFORMATION: Synthetic peptide

<400> SEQUENCE: 806

Tyr Asn Pro Phe
1

<210> SEQ ID NO 807
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be N or D

<400> SEQUENCE: 807

Pro Val Xaa Phe Xaa Lys
1               5

<210> SEQ ID NO 808
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 808

Pro Xaa Xaa Phe Tyr Asn
1               5

<210> SEQ ID NO 809
<211> LENGTH: 6
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 809

Pro Tyr Xaa Xaa Tyr Gln
1               5

<210> SEQ ID NO 810
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be R or H
<220> FEATURE:
<221> NAME/KEY: MISC_FEATURE
<222> LOCATION: (2)..(2)
<223> OTHER INFORMATION: Xaa can be R or K
<220> FEATURE:
<221> NAME/KEY: MISC_FEATURE
<222> LOCATION: (3)..(3)
<223> OTHER INFORMATION: Xaa can be P or W

<400> SEQUENCE: 810

Xaa Xaa Xaa Phe Phe
1               5

<210> SEQ ID NO 811
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 811

Lys Xaa Arg Pro Xaa Trp
1               5

<210> SEQ ID NO 812
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 812

Cys Xaa Asn Trp Xaa Xaa Xaa Cys
1               5
```

```
<210> SEQ ID NO 813
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be I, W, M or L
<220> FEATURE:
<221> NAME/KEY: misc_feature
<222> LOCATION: (4)..(5)
<223> OTHER INFORMATION: Xaa can be any naturally occurring amino acid

<400> SEQUENCE: 813

Cys Xaa Asn Xaa Xaa Asp Cys
1               5

<210> SEQ ID NO 814
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 814

Lys Xaa Asp Xaa Met Xaa Asn
1               5

<210> SEQ ID NO 815
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 815

Trp Xaa Lys Xaa Xaa Gly Xaa Trp
1               5

<210> SEQ ID NO 816
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be S or A

<400> SEQUENCE: 816

Pro Xaa Asp Thr Xaa Pro Arg
1               5

<210> SEQ ID NO 817
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be Y, F or W
<220> FEATURE:
<221> NAME/KEY: MISC_FEATURE
<222> LOCATION: (5)..(5)
<223> OTHER INFORMATION: Xaa can be L or M

<400> SEQUENCE: 817

Pro Pro Thr Xaa Xaa Gly
1               5

<210> SEQ ID NO 818
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be Y or F
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be Y or F
<220> FEATURE:
<221> NAME/KEY: misc_feature
<222> LOCATION: (4)..(5)
<223> OTHER INFORMATION: Xaa can be any naturally occurring amino acid

<400> SEQUENCE: 818

Xaa Xaa Xaa Xaa Xaa Phe Asn
1               5

<210> SEQ ID NO 819
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be L or M
<220> FEATURE:
<221> NAME/KEY: misc_feature
<222> LOCATION: (2)..(3)
<223> OTHER INFORMATION: Xaa can be any naturally occurring amino acid
<220> FEATURE:
```

```
<221> NAME/KEY: misc_feature
<222> LOCATION: (7)..(7)
<223> OTHER INFORMATION: Xaa can be any naturally occurring amino acid

<400> SEQUENCE: 819

Xaa Xaa Xaa Gly Trp Asn Xaa Lys Pro
1               5

<210> SEQ ID NO 820
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be I, V or F
<220> FEATURE:
<221> NAME/KEY: misc_feature
<222> LOCATION: (5)..(5)
<223> OTHER INFORMATION: Xaa can be any naturally occurring amino acid

<400> SEQUENCE: 820

Lys Xaa Xaa Pro Xaa Tyr Leu
1               5

<210> SEQ ID NO 821
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be I or V
<220> FEATURE:
<221> NAME/KEY: MISC_FEATURE
<222> LOCATION: (7)..(7)
<223> OTHER INFORMATION: Xaa can be M or L

<400> SEQUENCE: 821

Tyr Xaa Xaa Xaa Pro Trp Xaa
1               5

<210> SEQ ID NO 822
<211> LENGTH: 5
<212> TYPE: PRT
<213> ORGANISM: Artificial Sequence
<220> FEATURE:
<223> OTHER INFORMATION: Synthetic peptide

<400> SEQUENCE: 822

Gly Ala Gly Gly Gly
1               5

<210> SEQ ID NO 823
<211> LENGTH: 8
<212> TYPE: PRT
<213> ORGANISM: Artificial Sequence
<220> FEATURE:
<223> OTHER INFORMATION: Synthetic peptide
```

<220> FEATURE:
<221> NAME/KEY: misc_feature
<222> LOCATION: (2)..(2)
<223> OTHER INFORMATION: Xaa can be any na

```
1               5

<210> SEQ ID NO 827
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 827

Asp Met Asn Xaa His
1               5

<210> SEQ ID NO 828
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be K or R
<220> FEATURE:
<221> NAME/KEY: MISC_FEATURE
<222> LOCATION: (2)..(2)
<223> OTHER INFORMATION: Xaa can be L, M or I
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be S or N

<400> SEQUENCE: 828

Xaa Xaa Val Xaa Gln Ser Xaa
1               5

<210> SEQ ID NO 829
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 829

Trp Asp Xaa Xaa Asp Gly
1               5

<210> SEQ ID NO 830
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
```

```
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be L or I
<220> FEATURE:
<221> NAME/KEY: MISC_FEATURE
<222> LOCATION: (8)..(8)
<223> OTHER INFORMATION: Xaa can be T or S

<400> SEQUENCE: 830

Pro Xaa Xaa Asn Xaa Xaa Xaa Xaa
1               5

<210> SEQ ID NO 831
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V, M or I
<220> FEATURE:
<221> NAME/KEY: misc_feature
<222> LOCATION: (5)..(5)
<223> OTHER INFORMATION: Xaa can be any naturally occurring amino acid

<400> SEQUENCE: 831

Xaa Val Pro Glu Xaa Lys
1               5

<210> SEQ ID NO 832
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be V or I
<220> FEATURE:
<221> NAME/KEY: MISC_FEATURE
<222> LOCATION: (4)..(4)
<223> OTHER INFORMATION: Xaa can be F, Y or W
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 832

Pro Xaa Xaa Xaa Xaa Asn Xaa Pro
1               5

<210> SEQ ID NO 833
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
```

```
<223> OTHER INFORMATION: Xaa can be K or R
<220> FEATURE:
<221> NAME/KEY: MISC_FEATURE
<222> LOCATION: (5)..(5)
<223> OTHER INFORMATION: Xaa can be H or Y

<400> SEQUENCE: 833

Ser Gly Pro Xaa Xaa
1               5

<210> SEQ ID NO 834
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 834

Lys Xaa Xaa Phe Pro Gln
1               5

<210> SEQ ID NO 835
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 835

Pro Asp Xaa Xaa Trp Xaa Lys
1               5

<210> SEQ ID NO 836
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be L or M
<220> FEATURE:
<221> NAME/KEY: MISC_FEATURE
<222> LOCATION: (4)..(4)
<223> OTHER INFORMATION: Xaa can be F or M

<400> SEQUENCE: 836

Gln Pro Xaa Xaa Tyr
1               5

<210> SEQ ID NO 837
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: Xaa can be Y or F
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be F, Y or M

<400> SEQUENCE: 837

Xaa Xaa Cys Thr Xaa Met Cys
1               5

<210> SEQ ID NO 838
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be F or W
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be L, M or I
<220> FEATURE:
<221> NAME/KEY: MISC_FEATURE
<222> LOCATION: (7)..(7)
<223> OTHER INFORMATION: Xaa can be Q or N
<220> FEATURE:
<221> NAME/KEY: MISC_FEATURE
<222> LOCATION: (8)..(8)
<223> OTHER INFORMATION: Xaa can be R or K

<400> SEQUENCE: 838

Xaa Xaa Pro Xaa Xaa Xaa Xaa Xaa
1               5

<210> SEQ ID NO 839
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be I or V
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be P or C

<400> SEQUENCE: 839

Xaa Cys Trp Ser Xaa Xaa
1               5
```

```
<210> SEQ ID NO 840
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be V or I

<400> SEQUENCE: 840

Pro Asp Xaa Pro Xaa Ser
1               5

<210> SEQ ID NO 841
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be L or I
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 841

Pro Xaa Xaa Gly Xaa Pro Trp
1               5

<210> SEQ ID NO 842
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be Y, M or L

<400> SEQUENCE: 842

Glu Leu Pro Arg Xaa Xaa
1               5

<210> SEQ ID NO 843
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa can be D or W

<400> SEQUENCE: 843
```

```
Pro Glu Ser His Asn Xaa
1               5
```

<210> SEQ ID NO 844
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be Y or W

<400> SEQUENCE: 844

```
Tyr Xaa Xaa Thr Leu Xaa Xaa
1               5
```

<210> SEQ ID NO 845
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be V or I
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 845

```
Xaa Xaa Trp Asn Xaa Pro
1               5
```

<210> SEQ ID NO 846
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be W, Y or F
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be G or P

<400> SEQUENCE: 846

```
Gly Xaa Asp Xaa Xaa Asp Xaa
1               5
```

```
<210> SEQ ID NO 847
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be T,S or N
<220> FEATURE:
<221> NAME/KEY: MISC_FEATURE
<222> LOCATION: (7)..(7)
<223> OTHER INFORMATION: Xaa can be E or D

<400> SEQUENCE: 847

Lys Xaa Xaa His Pro Gly Xaa
1               5

<210> SEQ ID NO 848
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 848

Met Met Xaa His Ile
1               5

<210> SEQ ID NO 849
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be K or R

<400> SEQUENCE: 849

Lys Pro Xaa Leu Gly Xaa Xaa
1               5

<210> SEQ ID NO 850
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be S or D
```

```
-continued

<400> SEQUENCE: 850

Asn Xaa Ser Met Asn
1               5

<210> SEQ ID NO 851
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 851

Trp Xaa Xaa Trp Phe
1               5

<210> SEQ ID NO 852
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 852

Gly Glu Leu Xaa Gly Gln
1               5

<210> SEQ ID NO 853
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be M, L or F
<220> FEATURE:
<221> NAME/KEY: misc_feature
<222> LOCATION: (2)..(2)
<223> OTHER INFORMATION: Xaa can be any naturally occurring amino acid

<400> SEQUENCE: 853

Xaa Xaa Asn Pro Gln Gln
1               5

<210> SEQ ID NO 854
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 854

Thr Thr Glu Ser Xaa Val
1               5

<210> SEQ ID NO 855
```

```
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be G or A

<400> SEQUENCE: 855

Lys Asp Val Xaa Glu
1               5

<210> SEQ ID NO 856
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be F, W or M
<220> FEATURE:
<221> NAME/KEY: misc_feature
<222> LOCATION: (7)..(7)
<223> OTHER INFORMATION: Xaa can be any naturally occurring amino acid

<400> SEQUENCE: 856

Lys Pro Xaa Asp Xaa Gly Xaa Lys
1               5

<210> SEQ ID NO 857
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 857

Val Xaa Ala Asp Gly Thr
1               5

<210> SEQ ID NO 858
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be A or P
<220> FEATURE:
<221> NAME/KEY: MISC_FEATURE
<222> LOCATION: (3)..(3)
<223> OTHER INFORMATION: Xaa can be A or T

<400> SEQUENCE: 858

Met Xaa Xaa Ala Asp
1               5
```

```
<210> SEQ ID NO 859
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be D or G

<400> SEQUENCE: 859

Val Pro Xaa Pro Lys Xaa
1               5

<210> SEQ ID NO 860
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be T or S

<400> SEQUENCE: 860

Gln Xaa Lys Pro Xaa Asp
1               5

<210> SEQ ID NO 861
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be T or S
<220> FEATURE:
<221> NAME/KEY: misc_feature
<222> LOCATION: (3)..(3)
<223> OTHER INFORMATION: Xaa can be any naturally occurring amino acid

<400> SEQUENCE: 861

Phe Xaa Xaa Asp Gly Phe
1               5

<210> SEQ ID NO 862
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be R or K
<220> FEATURE:
<221> NAME/KEY: MISC_FEATURE
```

```
<222> LOCATION: (6)..(6)
<223> OTHER INFORMATION: Xaa can be V or A

<400> SEQUENCE: 862

Trp Xaa Xaa Val Tyr Xaa
1               5

<210> SEQ ID NO 863
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be C or S
<220> FEATURE:
<221> NAME/KEY: MISC_FEATURE
<222> LOCATION: (3)..(3)
<223> OTHER INFORMATION: Xaa can be T or S
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be Y or F

<400> SEQUENCE: 863

Xaa Thr Xaa Glu Xaa Xaa Xaa Xaa
1               5

<210> SEQ ID NO 864
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be T or I

<400> SEQUENCE: 864

Tyr Xaa Glu Thr Cys Xaa
1               5

<210> SEQ ID NO 865
<211> LENGTH: 7
<212> TYPE: PRT
<213> ORGANISM: Artificial Sequence
<220> FEATURE:
<223> OTHER INFORMATION: Synthetic peptide

<400> SEQUENCE: 865

Val Gln His Tyr Met His Arg
1               5

<210> SEQ ID NO 866
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 866

Arg Gln Pro Gln Gly Arg
1               5

<210> SEQ ID NO 867
<211> LENGTH: 7
<212> TYPE: PRT
<213> ORGANISM: Artificial Sequence
<220> FEATURE:
<223> OTHER INFORMATION: Synthetic peptide

<400> SEQUENCE: 867

Asp Cys Met Gly Thr Phe Cys
1               5

<210> SEQ ID NO 868
<211> LENGTH: 8
<212> TYPE: PRT
<213> ORGANISM: Artificial Sequence
<220> FEATURE:
<223> OTHER INFORMATION: Synthetic peptide

<400> SEQUENCE: 868

Lys Arg Glu Ile Val Phe Trp Arg
1               5

<210> SEQ ID NO 869
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 869

Pro Asp Xaa Gly Val Xaa Pro
1               5

<210> SEQ ID NO 870
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(38)
<223> OTHER INFORMATION: n is a, c, g, or t

<400> SEQUENCE: 870
tcgtcggcag cgtcagatgt gtataagaga cagnnnnncc agtctggcca ggg         53

<210> SEQ ID NO 871
<211> LENGTH: 54
<212> TYPE: DNA
<213> ORGANISM: Artificial Sequence
<220> FEATURE:
<223> OTHER INFORMATION: Synthetic

<400> SEQUENCE: 871
ccagtactac ggcatcactg ctgtctctta tacacatctc cgagcccacg agac        54
```

<210> SEQ ID NO 872
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 872

Ser Ala Arg Gln Pro Glu Phe Arg Gly Ser Leu Pro
1               5                   10

<210> SEQ ID NO 873
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 873

Val Ala Gly Leu Gly Thr Val Pro Glu Phe Ala Gly
1               5                   10

<210> SEQ ID NO 874
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874

Leu Asn Ala Gln Val Pro Glu Phe Asn Gly Ala Phe
1               5                   10

<210> SEQ ID NO 875
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Ala Gln Leu Pro Ala Leu Thr Ala Ala Leu Thr Ala
1               5                   10

<210> SEQ ID NO 876
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 876

Ser Gly Phe Leu Lys Pro Val Glu Phe Tyr Gly Ser
1               5                   10

<210> SEQ ID NO 877
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 877

Ser Ala Arg Gln Pro Glu Phe Arg Gly Ser Leu Pro Ala Lys Val
1               5                   10                  15

<210> SEQ ID NO 878
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 878

Val Ala Gly Leu Gly Thr Val Pro Glu Phe Ala Gly Ser Tyr Val
1               5                   10                  15

<210> SEQ ID NO 879
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 879

Leu Asn Ala Gln Val Pro Glu Phe Asn Gly Ala Phe Thr Gly Ala
1               5                   10                  15

<210> SEQ ID NO 880
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 880

Val Gly Leu Ser Ala Ser Glu Gln Gly Ala Leu Arg Asp Lys Arg
1               5                   10                  15

<210> SEQ ID NO 881
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 881

Asp Val Leu Thr Tyr Gly Ala Arg Arg Pro Phe Trp Thr Gly Ser
1               5                   10                  15

<210> SEQ ID NO 882
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 882

Cys Ser Glu Val Asn Gly Arg Arg Pro Phe Phe Gly Gly Pro Arg
1               5                   10                  15

<210> SEQ ID NO 883
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883

Arg Leu Ala Gly Cys Asp Gly Gly Ser Arg Ser Ala Cys Ser Met
1               5                   10                  15

<210> SEQ ID NO 884
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

Asp Phe Val Gly Lys Pro Glu Tyr Ala Ser Leu Leu Lys Glu Trp
1               5                   10                  15

<210> SEQ ID NO 885
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 885

Asn Ala Trp Ser Leu Thr Gly Arg Arg Pro Phe Trp Asp Met Leu
1               5                   10                  15

<210> SEQ ID NO 886
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 886

Gly Pro Ala Arg Asp His Gly Arg Arg Pro Trp Phe Ser Gln Ala
1               5                   10                  15

<210> SEQ ID NO 887
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 887

Lys Pro Pro Val Lys Pro Ala Thr Arg Gly Ser Glu Thr Lys Met
1               5                   10                  15

<210> SEQ ID NO 888
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 888

Ser Ser Gly Arg Arg Pro Phe Phe Gly Tyr Gln Ser Thr Tyr Val
```

```
<210> SEQ ID NO 889
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 889

Val Phe Arg Arg Pro Phe Phe Met Glu Gly Ser Gln Val Ser Met
1               5                   10                  15

<210> SEQ ID NO 890
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 890

Gly Arg Cys Val Gly Asp Gly Glu Arg Arg Pro Phe Phe Gly Ser
1               5                   10                  15

<210> SEQ ID NO 891
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 891

Leu Pro Gly Arg Arg Pro Phe Trp Cys Phe Asn Ala Tyr Gly Thr
1               5                   10                  15

<210> SEQ ID NO 892
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 892

Lys Arg Thr Ser Ser Gly Gly Ala Gly Pro Leu Met Asn Ala Lys
1               5                   10                  15

<210> SEQ ID NO 893
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

Ala Gln Leu Pro Ala Leu Thr Ala Ala Leu Thr Ala Phe Gly Arg
1               5                   10                  15

<210> SEQ ID NO 894
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 894

Ser Gly Phe Leu Lys Pro Val Glu Phe Tyr Gly Ser Leu Ala Ser
1               5                   10                  15

<210> SEQ ID NO 895
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile, Val, or Met
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 895

Xaa Xaa Leu Xaa Gly Met Xaa Asp
1               5

<210> SEQ ID NO 896
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (6)..(6)
<223> OTHER INFORMATION: Thr, Val, or Ser
<220> FEATURE:
<221> NAME/KEY: MOD_RES
<222> LOCATION: (7)..(7)
<223> OTHER INFORMATION: Glu or Asp

<400> SEQUENCE: 896

Arg Gly Leu Xaa Xaa Xaa Xaa
1               5

<210> SEQ ID NO 897
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 897

Gly Glu Xaa Glu Asp Lys

<210> SEQ ID NO 898
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 898

Ala Leu Xaa Leu Xaa Glu Xaa Val Ile
1               5

<210> SEQ ID NO 899
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Gly or Ala

<400> SEQUENCE: 899

Xaa Asn Cys Xaa Ile Cys Xaa
1               5

<210> SEQ ID NO 900
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid

<400> SEQUENCE: 900

Lys Asp Arg Xaa Xaa Asp Glu
1               5

<210> SEQ ID NO 901
<211> LENGTH: 7
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (3)..(3)
<223> OTHER INFORMATION: Leu or Val
<220> FEATURE:
<221> NAME/KEY: MOD_RES
<222> LOCATION: (4)..(4)
<223> OTHER INFORMATION: Met, Leu, or Phe
<220> FEATURE:
<221> NAME/KEY: MOD_RES
<222> LOCATION: (5)..(6)
<223> OTHER INFORMATION: Any amino acid

<400> SEQUENCE: 901

Thr Thr Xaa Xaa Xaa Xaa Gly
1               5

<210> SEQ ID NO 902
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Any amino acid

<400> SEQUENCE: 902

Asp Leu Asp Xaa Xaa Xaa Leu Glu
1               5

<210> SEQ ID NO 903
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid

<400> SEQUENCE: 903

Arg Xaa Xaa Xaa Arg Cys Arg Gly Cys
1               5

<210> SEQ ID NO 904
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 904

Thr Glu Glu Asp Gln
1               5

<210> SEQ ID NO 905
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(5)
<223> OTHER INFORMATION: Any amino acid

<400> SEQUENCE: 905

Met Met His Xaa Xaa Glu His Lys
1               5

<210> SEQ ID NO 906
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Glu
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 906

Xaa Arg Ile Thr Xaa Xaa Met Xaa Glu
1               5

<210> SEQ ID NO 907
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(10)
<223> OTHER INFORMATION: Any amino acid

<400> SEQUENCE: 907

Leu Leu Ala Xaa Xaa Ala Xaa Xaa Xaa Xaa Arg
1               5                   10

<210> SEQ ID NO 908
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 908

Asp Glu Ser Thr Lys
1               5

<210> SEQ ID NO 909
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Phe, Tyr, or Leu
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Ile or Leu

<400> SEQUENCE: 909

Phe Xaa Xaa Xaa Xaa Glu Arg
1               5

<210> SEQ ID NO 910
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu, Asp, or Gln
<220> FEATURE:
<221> NAME/KEY: MOD_RES
<222> LOCATION: (4)..(4)
<223> OTHER INFORMATION: Any amino acid

<400> SEQUENCE: 910

Asp Xaa Arg Xaa Thr
1               5

<210> SEQ ID NO 911
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu or Val
<220> FEATURE:
<221> NAME/KEY: MOD_RES
<222> LOCATION: (3)..(3)
<223> OTHER INFORMATION: Leu, Val, or Pro
<220> FEATURE:
<221> NAME/KEY: MOD_RES
<222> LOCATION: (4)..(4)
<223> OTHER INFORMATION: Any amino acid

<400> SEQUENCE: 911

Glu Xaa Xaa Xaa Ile
1               5

<210> SEQ ID NO 912
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
```

```
<222> LOCATION: (6)..(6)
<223> OTHER INFORMATION: Any amino acid

<400> SEQUENCE: 912

Gly Gly Xaa Gly Thr Xaa Ala Gly
1               5

<210> SEQ ID NO 913
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(8)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 913

Arg Xaa Xaa Xaa Arg Xaa Xaa Xaa Ile Thr Xaa Glu
1               5                   10

<210> SEQ ID NO 914
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe or Tyr
<220> FEATURE:
<221> NAME/KEY: MOD_RES
<222> LOCATION: (2)..(2)
<223> OTHER INFORMATION: Leu, Ile, or Val
<220> FEATURE:
<221> NAME/KEY: MOD_RES
<222> LOCATION: (4)..(5)
<223> OTHER INFORMATION: Any amino acid

<400> SEQUENCE: 914

Xaa Xaa Gly Xaa Xaa His Gly
1               5

<210> SEQ ID NO 915
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 915

Val Gly Leu Ser Leu Ser Gly Met Gly Asp Leu Arg
1               5                   10

<210> SEQ ID NO 916
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 916

Asp Val Leu Thr Tyr Gly Ala Arg Arg Pro Phe Trp
1               5                   10

<210> SEQ ID NO 917
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 917

Cys Ser Glu Val Asn Gly Arg Arg Pro Phe Phe Gly
1               5                   10

<210> SEQ ID NO 918
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 918

Arg Leu Ala Gly Cys Asp Gly Gly Ser Arg Ser Ala
1               5                   10

<210> SEQ ID NO 919
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Asp Phe Val Gly Lys Pro Glu Tyr Ala Ser Leu Leu
1               5                   10

<210> SEQ ID NO 920
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 920

Asn Ala Trp Ser Leu Thr Gly Arg Arg Pro Phe Trp
1               5                   10

<210> SEQ ID NO 921
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 921

Gly Pro Ala Arg Asp His Gly Arg Arg Pro Trp Phe
1               5                   10
```

<210> SEQ ID NO 922
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 922

Lys Pro Pro Val Lys Pro Ala Thr Arg Gly Ser Glu
1               5                   10

<210> SEQ ID NO 923
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 923

Ser Ser Gly Arg Arg Pro Phe Phe Gly Tyr Gln Ser
1               5                   10

<210> SEQ ID NO 924
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

Lys Arg Thr Ser Ser Gly Gly Ala Gly Pro Leu Met
1               5                   10

<210> SEQ ID NO 925
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Gly Gly Pro Ala Ile Thr Leu Ala Gly Met Ala Asp
1               5                   10

<210> SEQ ID NO 926
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 926

Lys Thr Leu Phe Phe Ala Glu Asp Tyr Thr Met Asn
1               5                   10

<210> SEQ ID NO 927
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 927

Ile Asp Asp Asn Gly Gly Ala Gly Thr Glu Trp Trp
1               5                   10

<210> SEQ ID NO 928
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 928

Arg Arg Glu Gln Gln Ala Ser Thr Ala Gly Gly Ala
1               5                   10

<210> SEQ ID NO 929
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 929

Lys Pro Xaa Phe Xaa Gly Xaa Lys
1               5

<210> SEQ ID NO 930
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or His
<220> FEATURE:
<221> NAME/KEY: MOD_RES
<222> LOCATION: (3)..(3)
<223> OTHER INFORMATION: Pro or Trp

<400> SEQUENCE: 930

Xaa Arg Xaa Phe Phe
1               5

<210> SEQ ID NO 931
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
```

```
<220> FEATURE:
<221> NAME/KEY: MOD_RES
<222> LOCATION: (3)..(3)
<223> OTHER INFORMATION: Ile, Leu, or Val
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Asp or Glu
<220> FEATURE:
<221> NAME/KEY: MOD_RES
<222> LOCATION: (6)..(6)
<223> OTHER INFORMATION: Leu, Met, or Val

<400> SEQUENCE: 931

Xaa Gly Xaa Xaa Xaa Xaa
1               5

<210> SEQ ID NO 932
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys

<400> SEQUENCE: 932

Xaa Lys Arg Asp
1

<210> SEQ ID NO 933
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 933

Gln Pro Glu Gln Pro Phe Pro Glu
1               5

<210> SEQ ID NO 934
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 934

Lys Ile Arg Ala Glu Phe
1               5

<210> SEQ ID NO 935
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 935

Cys Asp Ala Pro Ser Thr Arg Ser Cys
1               5

<210> SEQ ID NO 936
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 936

Lys Thr Asp Lys Thr Asn Asp Phe
1               5

<210> SEQ ID NO 937
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 937

Arg Arg Pro Phe Phe
1               5
```